US011898173B2

United States Patent
Park et al.

(10) Patent No.: US 11,898,173 B2
(45) Date of Patent: *Feb. 13, 2024

(54) RECOMBINANT ACID-RESISTANT YEAST HAVING IMPROVED LACTIC-ACID-PRODUCING ABILITY

(71) Applicant: SK INNOVATION CO., LTD., Seoul (KR)

(72) Inventors: Jae Yeon Park, Daejeon (KR); Tae Young Lee, Daejeon (KR); Ki Sung Lee, Daejeon (KR)

(73) Assignee: SK Innovation Co., Ltd., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 17/353,323

(22) Filed: Jun. 21, 2021

(65) Prior Publication Data

US 2021/0403882 A1   Dec. 30, 2021

(30) Foreign Application Priority Data

Jun. 24, 2020   (KR) .......................... 10-2020-0077331

(51) Int. Cl.
  *C12P 7/56*     (2006.01)
  *C12N 9/04*     (2006.01)

(52) U.S. Cl.
  CPC .............. *C12N 9/0006* (2013.01); *C12P 7/56* (2013.01); *C12Y 101/01027* (2013.01)

(58) Field of Classification Search
  CPC ........ C12N 9/0006; C12N 1/16; C12N 1/165; C12N 1/36; C12N 9/0008; C12N 9/88; C12N 15/52; C12N 15/81; C12P 7/56; C12Y 101/01027; C12Y 101/01008; C12Y 101/02003; C12Y 401/01001; C12Y 101/01001; C12Y 101/01028; C12R 2001/645
  See application file for complete search history.

(56) References Cited

U.S. PATENT DOCUMENTS

| | | | |
|---|---|---|---|
| 7,049,108 B2 | 5/2006 | Porro et al. | |
| 7,141,410 B2 | 11/2006 | Rajgarhia et al. | |
| 7,232,664 B2 | 6/2007 | Van Hoek et al. | |
| 7,534,597 B2 | 5/2009 | Hause et al. | |
| 8,137,953 B2 | 3/2012 | Miller et al. | |
| 9,353,388 B2 | 5/2016 | Kim et al. | |
| 9,617,570 B2 | 4/2017 | Lim et al. | |
| 9,758,770 B2 | 9/2017 | Lim et al. | |
| 2003/0032152 A1 | 2/2003 | Porro et al. | |
| 2003/0190630 A1 | 10/2003 | Rajgarhia et al. | |
| 2009/0053782 A1 | 2/2009 | Dundon et al. | |
| 2012/0058529 A1 | 3/2012 | Ikushima et al. | |
| 2012/0214214 A1 | 8/2012 | Hara et al. | |
| 2012/0295319 A1 | 11/2012 | Nevoigt et al. | |
| 2013/0071893 A1 | 3/2013 | Lynch et al. | |
| 2015/0064752 A1 | 3/2015 | Lee | |
| 2015/0152447 A1 | 6/2015 | Kim et al. | |
| 2016/0002678 A1 | 1/2016 | Song et al. | |
| 2016/0024484 A1 | 1/2016 | Lim et al. | |
| 2016/0333380 A1 | 11/2016 | Chung et al. | |
| 2021/0155945 A1 | 5/2021 | Park et al. | |
| 2021/0324346 A1* | 10/2021 | Park .......................... | C12N 9/88 |
| 2021/0403882 A1* | 12/2021 | Park ............... | C12Y 101/01008 |
| 2022/0049262 A1 | 2/2022 | Park et al. | |
| 2022/0056459 A1* | 2/2022 | Park ....................... | C12N 15/52 |

FOREIGN PATENT DOCUMENTS

| | | |
|---|---|---|
| CN | 106459881 A | 2/2017 |
| EP | 2873725 A1 | 5/2015 |
| EP | 3795689 A1 | 3/2021 |
| EP | 3808852 A1 | 4/2021 |
| EP | 3865577 A2 | 8/2021 |
| EP | 3896166 A1 | 10/2021 |
| JP | 2001204464 A | 7/2001 |
| JP | 2005137306 A | 6/2005 |
| JP | 4095889 B2 | 6/2008 |
| JP | 4692173 B2 | 6/2011 |
| JP | 4700395 B2 | 6/2011 |
| JP | 201261006 A | 3/2012 |
| JP | 2018518175 A | 7/2018 |
| KR | 101576186 B1 | 12/2015 |
| KR | 1020160012561 A | 2/2016 |
| KR | 1020160133308 A | 11/2016 |

(Continued)

OTHER PUBLICATIONS

GenEmbl Accession No. CP024408, published Nov. 3, 2017 (Year: 2017).*
Zhou et al., Cell Mol Life Sci 63(19-20):2260-2290, 2006.*
Kozak, M., Gene 234:187-208, 1999.*
Ellen I. Garvie, Bacterial Lactate Dehydrogenases, Microbiological Reviews, 106-139, 1980.
Michael Sauer et al., Biotechnology and Genetic Engineering Reviews, 27:229-256, 2010.
Zhengming Zhu et al., Applied Microbiology and Biotechnology, 102:4615-4627,2018.
Eugene Fletcher et al., Metabolic Engineering 39 (2017) 19-28, 2017.
Christopher P. Long, Current opinion in Chemical Engineering, 22:209-215, 2018.
Derek A. Abbott et al., Applied and Environmental Microbiology, 2320-2325, 2009.
B. Gao et al., Cell Death and Disease, 5:e1334, 2014.
Ananda S. Prasad and Bin Bao, Antioxidants 8:164, 2019.

(Continued)

*Primary Examiner* — Delia M Ramirez
(74) *Attorney, Agent, or Firm* — The Webb Law Firm

(57) ABSTRACT

Disclosed are a recombinant acid-resistant yeast having improved lactic-acid-producing ability and a method of preparing lactic acid using the same. When producing lactic acid using the recombinant acid-resistant yeast according to the present invention, not only lactic-acid fermentation can be performed with lactic-acid-producing ability similar to that of bacterial fermentation using a remarkably smaller amount of a neutralizing agent than in the case of conventional bacterial fermentation, but also the production of ethanol and glycerol which are byproducts can be reduced. Thus, fermentation costs can be greatly reduced and the cost of subsequent purification processes can be reduced.

11 Claims, 7 Drawing Sheets

Specification includes a Sequence Listing.

(56) References Cited

FOREIGN PATENT DOCUMENTS

| KR | 101686900 B1 | 12/2016 |
|---|---|---|
| KR | 1020170008151 A | 1/2017 |
| KR | 1020170025315 A | 3/2017 |
| KR | 1020170077599 A | 7/2017 |
| KR | 1020180015591 A | 2/2018 |
| KR | 1020180044509 | 4/2018 |
| KR | 1020190121030 A | 10/2019 |
| KR | 1020190124701 | 10/2019 |
| KR | 102140596 B1 | 8/2020 |
| KR | 10-2021-0128742 A | 10/2021 |
| WO | 9914335 A1 | 3/1999 |
| WO | 2005052174 A3 | 6/2005 |
| WO | 2007117282 A2 | 10/2007 |
| WO | 2016056566 A1 | 4/2016 |
| WO | 2019203436 A1 | 10/2019 |
| WO | 2020075986 A2 | 4/2020 |

OTHER PUBLICATIONS

Jae Won Lee et al., Co-expression of two heterologous lactate dehydrogenases genes in Kluyveromyces marxianus for L-lactic acid production, J. Biotechnology 241, 2017.
Antonius J. A. Van Maris et al., Appl. Environ. Microbiol., 70;2898, 2004.
Xixi Zhou et al., The Journal of Biological Chemistry, 290:18361-18369, 2015.
Partial European Search Report, dated Nov. 10, 2021 for corresponding EP Application 21180788.8.
Abbott et al., "Metabolic engineering of Saccharomyces cerevisiae for production of carboxylic acids: current status and challenges", FEMS Yeast Research, 2009, pp. 1123-1136, vol. 9.
Baek et al., "Metabolic engineering and adaptive evolution for efficient production of D-lactic acid in Saccharomyces cerevisiae", Applied Microbiology and Biotechnology, 2016, pp. 2737-2748, vol. 100.
Devos et al., "Practical Limits of Function Prediction" Proteins: Structure, Function and Genetics, 2000, pp. 98-107, vol. 41.
Feldman-Salit et al., "Regulation of the activity of lactate dehydrogenases from four lactic acid bacteria" Journal of Biological Chemistry 288.29 (2013): pp. 21295-21306.
Guiard, B., "Structure, expression and regulation of a nuclear gene encoding a mitochondrial protein: the yeast L(+)-lactate cytochrome c oxidoreductase (cytochrome b2)," EMBO J., 1985, pp. 3265-3272, vol. 12.
Halestrap, A.P., The monocarboxylate transporter family - Structure and Functional Characterization, IUBMB Life, 2012, pp. 1-9, vol. 64, No. 1.
Hoppner et al., "Purification and kinetic characteristics of pyruvate decarboxylase and ethanol dehydrogenase from Zymomonas mobilis in relation to ethanol production", European Journal of Applied Microbiology and Biotechnology, 1983, pp. 152-157, vol. 17.
Ishida et al., "Efficient production of L-lactic acid by metabolically engineered Saccharomyces cerevisiae with a genome-integrated L-lactate dehydrogenase gene", Applied and Environmental Microbiology, 2005, pp. 1964-1970, vol. 71, No. 4.
Kisselev, L., "Polypeptide Release Factors in Prokaryotes and Eukaryotes: Same Function, Different Structure" Structure, 2002, pp. 8-9, vol. 10.
Lodi et al., "Isolation of the DLD gene of Saccharomyces cerevisiae encoding the mitochondrial enzyme D-lactate ferricytochrome c oxidoreductase", Mol. Gen. Genet., 1993, pp. 315-324, vol. 238.
NCBI, GenBank Accession No. SMN19920.1, similar to Saccharomyces cerevisiae YLR044C PDC1 Major of three pyruvate decarboxylase isozymes, key enzyme in alcoholic fermentation, decarboxylates pyruvate to acetaldehyde [Kazachstania saulgeensis], 2017.
Ookubo et al., "Improvement of L-lactate production by CYB2 gene disruption in a Recombinant Saccharomyces cerevisiae Strain under low pH condition", Biosci. Biotechnol. Biochem., 2008, pp. 3063-3066, vol. 72, No. 11.

Pacheco et al., Lactic Acid production in Saccharomyces cerevisiae is modulated by expression of the monocarxboxylate transporter Jen1 and Ady2, FEMS Yeast Res, 2012, pp. 375-381, vol. 12.
Park et al., "Low-pH production of D-lactic acid using newly isolated acid tolerant yeast Pichia kudriavzevii NG7", Biotechnology and Bioengineering, 2018, pp. 2232-2242, vol. 115.
Savijoki et al., "Molecular genetic characterization of the L-lactate dehydrogenase gene (IdhL) of Lactobacillus helveticus and biochemical characterization of the enzyme" Applied and Environmental Microbiology 63.7 (1997): pp. 2850-2856.
Skory et al., "Inhibition of Rhizopus lactate dehydrogenase by fructose 1,6-bisphosphate" Enzyme and Microbial Technology 44 (2009): pp. 242-247.
Skory et al., "Lactic acid production by Saccharomyces cerevisiae expressing a Rhizopus oryzae lactate dehydrogenase gene", Journal of Industrial Microbiology and Biotechnology, 2003, pp. 22-27, vol. 30, No. 1.
Tokuhiro et al., "Double mutation of the PDC1 and ADH1 genes improves lactate production in the yeast Saccharomyces cerevisiae expressing the bovine lactate dehydrogenase gene" Applied Microbiology and Biotechnology 82.5 (2009): pp. 883-890.
Valli et al., "Improvement of Lactic acid production in Saccharomyces cerevisiae by cell sorting for high intracellular OH", Appl Environ Microbiol, 2006, pp. 5492-5499, vol. 72, No. 8.
Van Maris et al., "Mini-review Microbial export of lactic and 3-hydroxypropanoic acid: implication for industrial fermentation processes", Metabolic Engineering, 2004, pp. 245-255, vol. 6.
Whisstock et al., "Prediction of protein function from protein sequence and structure" Quarterly Reviews of Biophysics, 2003, pp. 307-340, vol. 36, No. (3).
Witkowski et al., "Conversion of a Beta-Ketoacyl Synthase to a Malonyl Decarboxylase by Replacement of the Active-Site Cysteine with Glutamine" Biochemistry, 1999, pp. 11643-11650, vol. 38.
Zhang et al., "Adaptive mutations in sugar metabolism restore growth on glucose in a pyruvate decarboxylase negative yeast strain" Microbial Cell Factories 14.1 (2015): article 116, 11 pages.
Albertyn et al., "GPD1, which encodes glycerol-3-phosphate dehydrogenase, is essential for growth under osmotic stress in Saccharomyces cerevisiae, and its expression is regulated by the high osmolarity glycerol response pathway", Molecular and cellular biology, 1994, pp. 4135-4144.
Costenoble et al., "Microaerobic glycerol formation in Saccharomyces cervisiae", Yeast, 2000, pp. 1483-1495, vol. 16.
Dexter et al., "Robust network structure of the SIn1-Ypd1-Ssk1 three-component phospho-relay prevents unintended activation of the HOG MAPK pathway in Saccharomyces cerevisiae", BMC Systems Biology, 2015, pp. 1-15, vol. 9, No. 17.
Hubmann et al., "Identification of multiple interacting alleles conferring low glycerol and high ethanol yield in Saccharomyces cerevisiae ethanolic fermentation", Biotechnology for Biofuels, 2013,pp. 1-17, vol. 6, No. 87.
Hubmann et al., "Quantitative trait analysis of yeast biodeversity yields novel gene tools for metabolic engineering," Metabolic Engineering, 2013, pp. 68-81, vol. 17.
Nevoigt et al., "Osmoregulation and glycerol metabolism in the yeast Saccharomyces cerevisiae", FEMS Microbiology Reviews, 1997, pp. 231-241, vol. 21.
Pearson, "Effective protein sequence comparison", Methods Enzymology, 1996, pp. 227-258, vol. 266.
Uniprot, Accession No. A0A1X7R452, 2019.
Shen, et al. "Effect on electrospun fibres by synthesis of high branching polylactic acid," R. Soc. Open Sci., 2018, pp. 1-13, vol. 5.
Hyland, P., "Development of a Platform Strain for Production of Adipic Acid Yields Insights into the Localized Redox of Metabolism of S. cerevisiae", Dissertation, University of Toronto, 2013.
Jiang et al., "Progress of succinic acid production from renewable resources: metabolic and fermentative strategies", Bioresource Technology, 2017, pp. 1-38.
Karlin et al., "Applications and statistics for multiple high-scoring segments in molecular sequences", Proceedings of the National Academy of Sciences, 1993, pp. 5873-5877, vol. 90, No. 12.

(56) References Cited

OTHER PUBLICATIONS

Nishant et al., "The baker's yeast diploid genome is remarkably stable in vegetative growth and meiosis", PLoS Genet, 2010, pp. 1-15, vol. 6, No. 9 e1001109.

Steiger et al., "Biochemistry of microbial itaconic acid production", Frontiers in Microbiology, 2013, pp. 1-5, vol. 4, No. 23.

Storchova, Z., "Ploidy changes and genome stability in yeast", Yeast, 2014, pp. 421-430, vol. 31, No. 11.

Zhang et al., "A synthetic metabolic pathway for production of the platform chemical isobutyric acid", ChemSusChem, 2011, pp. 1068-1070, vol. 4, No. 8.

Zelle et al., "Malic acid production by *Saccharomyces cerevisiae*: engineering of pyruvate carboxylation, oxaloacetate reduction, and malate export", Applied and Environmental Microbiology, 2008, pp. 2766-2777, vol. 74, No. 9.

Bon et al., "Genomic Exploration of the Hemiascomycetous Yeasts: 6. *Saccharomyces exiguus*", FEBS Letters, 2000, pp. 42-46, vol. 487.

Chen et al., "Cloning and characterization of a NAD+-dependent glycerol-3-phosphate dehydrogenase gene from Candida glycerinogenes, an industrial glycerol producer", FEMS Yeast Research, 2008, pp. 725-734, vol. 8.

Genbank, Accession No. AL409647.1, 2001.
Genbank, Accession No. AL409824.1, 2001.
Genbank, Accession No. AL409367.1, 2001.

* cited by examiner

RECOMBINANT ACID-RESISTANT YEAST HAVING IMPROVED LACTIC-ACID-PRODUCING ABILITY

CROSS REFERENCE TO RELATED APPLICATION

This application claims priority to KR patent application No. 10-2020-0077331, filed Jun. 24, 2020, the contents of which are herein incorporated by reference in their entirety.

SEQUENCE LISTING

The instant application contains a Sequence Listing which has been submitted in ASCII format via EFS-Web and is hereby incorporated by reference in its entirety. Said ASCII copy, created on May 25, 2021, is named PF-82588_ST25.txt, and is 215,129 bytes in size.

BACKGROUND OF THE INVENTION

Field of the Invention

The present invention relates to a recombinant acid-resistant yeast having improved lactic-acid-producing ability and a method of preparing lactic acid using the same. More particularly, the present invention relates to a recombinant acid-resistant yeast in which a specific bacterial-derived lactate dehydrogenase gene is introduced at a site from which a gene encoding pyruvate decarboxylase has been deleted, and a method of preparing lactic acid using the same.

Description of the Related Art

Polylactic acid (PLA) is a biodegradable polymer that is prepared by converting lactic acid into lactide and conducting ring-opening polymerization thereon. The raw material thereof, lactic acid, is produced through fermentation. PLA is widely used in disposable food containers, and has an advantage in that it is capable of being used alone or in the form of a composition or a copolymer in plastics for a variety of industries including the automobile and fiber industries. In addition, it is a representative example of polymers that have come to be used in 3D printing in recent years, and is an eco-friendly polymer that generates lower amounts of harmful gases and odors when used for 3D printers.

A traditional lactic-acid production process is performed using lactic acid bacteria, and includes conducting fermentation while maintaining a neutral pH of 6 to 8 using various forms of Ca salt/Ma salt or a neutralizing agent such as ammonia in order to prevent bacterial death or slowing of growth thereof due to the lactic acid produced and accumulated by lactic acid bacteria. When fermentation is complete, microorganisms are separated, and sulfuric acid is added to convert lactate to lactic acid while Ca salt is removed in the form of $CaSO_4$ due to the difficulty of separation of salt from water and conversion thereof to lactide. In this process, $CaSO_4$, a byproduct, is produced in an amount greater than the amount of lactic acid, thus deteriorating process efficiency.

In general, PLA produces lactic acid through fermentation and then converts the produced lactic acid into lactide through a purification process. For conversion to lactide, a process of converting lactic acid into a hydrogenated form is required, and the pH for neutral fermentation is generally 6 to 7, and the neutral pH is thus changed to an acidic pH using a large amount of sulfuric acid. In this process, large amounts of neutralization salts are generated, and economic feasibility is deteriorated due to the low value of the neutralization salts along with the cost of investing in processes to remove the neutralization salts.

Meanwhile, lactic acid has L- and D-type optical isomers. There are a variety of microbial populations. For example, lactic acid bacteria that mainly produce L-type optical isomers often also produce about 5-10% D-type optical isomers, and strains that mainly produce D-type optical isomers include strains that produce both D-type and L-type optical isomers, strains that produce both D-type optical isomers and ethanol, and the like (Ellen I. Garvie, Microbiological Reviews, 106-139, 1980).

Meanwhile, in the case of *Lactobacillus*, which produces lactic acid in nature, a large amount of expensive nutrients must be used as a medium in order to commercially produce lactic acid. This excess of nutrient components greatly inhibits a downstream polymerization process or a lactide conversion process in which lactide is used as an intermediate, costs are incurred for purification processes such as adsorption, distillation and ion exchange in order to obtain high-yield and high-purity polymers or precursors thereof, thus further increasing production costs. Research on the use of yeast has been suggested in order to solve these problems. Yeast is known to conduct growth/fermentation even when inexpensive nutrients are used, and to be highly resistant to acidic conditions.

When lactic acid is produced using yeast that grows well in acid (hereinafter referred to as "acid-resistant yeast"), it is not necessary to maintain the medium at a pH of 6 to 7 using a neutralizing agent during fermentation, so the fermentation process is simplified and a downstream purification process for removing the neutralizing agent is not required. In addition, yeast itself produces many components that it requires for metabolism, and thus can be cultured in a medium with a relatively low nutrient level compared to bacteria, particularly *Lactobacillus*, thus obviating downstream purification processes and greatly lowering production costs.

However, there is a requirement for technology for producing lactic acid using yeast. The requirement is that the yield, productivity, and concentration of lactic acid, which are indicators of strain fermentation performance, must be maintained at high levels similar to the performance of lactic acid bacteria in order for the technology to be commercially applied.

Although acid-resistant lactic acid technology using yeast has been developed, in practice, in many cases, high-performance fermentation capability is realized only when fermentation is performed while maintaining a pH of at least 3.7, which is not less than the pKa value of lactic acid, by performing a neutralization reaction during the fermentation. For this reason, the technology cannot reasonably be considered a practical method for achieving acid resistance, and it is difficult to anticipate an effect of reducing production costs when applied to a process (Michael Sauer et al., *Biotechnology and Genetic Engineering Reviews*, 27:229-256, 2010).

Therefore, acid-resistant yeasts capable of reducing processing costs can be commercially applied only when they are capable of completing fermentation at a fermentation solution pH not more than the pKa value with minimal or no use of a neutralizing agent, and when three major fermentation indicators reach levels similar to those for lactic acid bacteria.

In general, when glucose is fermented, yeast produces ethanol as a main product, glycerol as a byproduct, and hardly any lactic acid. In addition, since the likelihood of obtaining a strain that produces lactic acid from microorganisms having high acid resistance is very low, the present inventors selected a yeast strain having excellent acid resistance, and attempted to construct a strain imparted with lactic-acid-producing ability and reduced ethanol- and glycerol-producing ability from the selected strain through a genetic engineering method.

Accordingly, as a result of intensive efforts to produce a yeast strain having strong acid resistance while exhibiting lactic-acid-producing ability (lactic-acid production rate and concentration) similar to that of a bacterial strain, as well as reduced ability to produce ethanol and glycerol, which are byproducts, the present inventors have found that the lactic acid yield was improved due to the increased activity of lactate dehydrogenase by introducing a lactate dehydrogenase gene derived from *S. epidermidis* at the position of a gene coding a pyruvate conversion enzyme in an acid-resistant yeast. Based on this finding, the present invention was completed.

SUMMARY OF THE INVENTION

Therefore, the present invention has been made in view of the above problems, and it is one object of the present invention to provide a recombinant strain having an increased lactic acid production rate and concentration that is constructed by imparting an increased resistance to high-concentration lactic acid to a recombinant acid-resistant yeast strain having lactic-acid-producing ability.

It is another object of the present invention to provide a method for producing a recombinant yeast strain having lactic-acid-producing ability and increased lactic-acid resistance using an adaptive evolution method.

It is another object of the present invention to provide a recombinant yeast strain having improved lactic-acid-producing ability in a high-concentration lactic acid medium produced by the method.

In accordance with one aspect of the present invention, the above and other objects can be accomplished by the provision of a recombinant strain having lactic-acid-producing ability, the recombinant strain constructed by deleting a gene encoding pyruvate decarboxylase from an acid-resistant yeast YBC strain (KCTC13508BP) and introducing a gene encoding lactate dehydrogenase derived from *Staphylococcus epidermidis* at the position of the gene encoding pyruvate decarboxylase.

In accordance with another aspect of the present invention, there is provided a recombinant strain having lactic-acid-producing ability, the recombinant strain constructed by deleting a GPD1 gene, which is a gene encoding an enzyme that converts dihydroxyacetone phosphate to glycerol-3-phosphate, a CYB2 gene, which is a gene encoding an enzyme that converts lactate into pyruvate, an ADH gene, which is a gene encoding alcohol dehydrogenase, and a PDC gene, which is a gene encoding pyruvate decarboxylase from an acid-resistant yeast YBC strain (KCTC13508BP), and introducing the gene encoding lactate dehydrogenase into the acid-resistant yeast YBC strain, wherein the gene encoding the lactate dehydrogenase is introduced at the positions of the deleted ADH gene, PDC gene and GPD1 gene, and the gene encoding lactate dehydrogenase introduced at the position of the PDC gene is a gene encoding lactate dehydrogenase derived from *Staphylococcus epidermidis*.

In accordance with another aspect of the present invention, there is provided a method for producing a recombinant yeast strain having improved lactic acid resistance and lactic-acid-producing ability, the method comprising: (a) inducing adaptive evolution of the recombinant yeast strain to a high-lactic-acid concentration by sequentially culturing a recombinant yeast strain having lactic-acid-producing ability from in a low-concentration lactic acid medium to in a high-concentration lactic acid medium; (b) selecting a recombinant yeast strain having improved lactic-acid-producing ability in the high-concentration lactic acid medium; and (c) introducing a gene encoding a lactate dehydrogenase derived from *Staphylococcus epidermidis* at the position of the PDC gene of the genome of the selected strain.

In accordance with another aspect of the present invention, there is provided a recombinant strain #26-5 (Accession No.: KCTC 14215BP) obtained by adaptive evolution at a high lactic-acid concentration of a recombinant strain having lactic-acid-producing ability constructed by deleting a GPD1 gene, which is a gene encoding an enzyme that converts dihydroxyacetone phosphate to glycerol-3-phosphate, a CYB2 gene, which is a gene encoding an enzyme that converts lactate to pyruvate, an ADH gene, which is a gene encoding alcohol dehydrogenase, and a PDC gene, which is a gene encoding pyruvate decarboxylase from an acid-resistant yeast YBC strain (KCTC13508BP), and introducing the gene encoding lactate dehydrogenase into the acid-resistant yeast YBC strain.

In accordance with another aspect of the present invention, there is provided a recombinant yeast YBC6 strain constructed by introducing a gene encoding a lactate dehydrogenase derived from *Staphylococcus epidermidis* at the position of the PDC gene of the genome of a recombinant strain #26-5 (Accession No.: KCTC 14215BP), wherein the recombinant yeast YBC6 strain has improved lactic-acid-producing ability at a high lactic-acid concentration and reduced ethanol- and glycerol-producing ability compared to a YBC strain (KCTC13508BP) or a YBC5 strain.

In accordance with another aspect of the present invention, there is provided a method for producing lactic acid comprising: (a) culturing the strain to produce lactic acid; and (b) collecting the produced lactic acid.

Effects of the Invention

When producing lactic acid using the recombinant acid-resistant yeast according to the present invention, lactic-acid fermentation can be performed with lactic-acid-producing ability similar to that of bacterial fermentation using a remarkably smaller amount of a neutralizing agent than in the case of conventional bacterial fermentation, so fermentation costs can be greatly reduced. Also, the production of ethanol and glycerol, which are byproducts, can be reduced, and thus the cost of subsequent purification processes can be reduced.

BRIEF DESCRIPTION OF THE DRAWINGS

The above and other objects, features and other advantages of the present invention will be more clearly understood from the following detailed description taken in conjunction with the accompanying drawings, in which:

FIG. 1(b) shows the growth of the cells during the subculture in the 3$^{rd}$ round-adaptive evolution at a lactic-acid concentration of 70 to 80 g/L to further increase resistance to lactic acid;

DETAILED DESCRIPTION OF THE INVENTION

Figure 1:
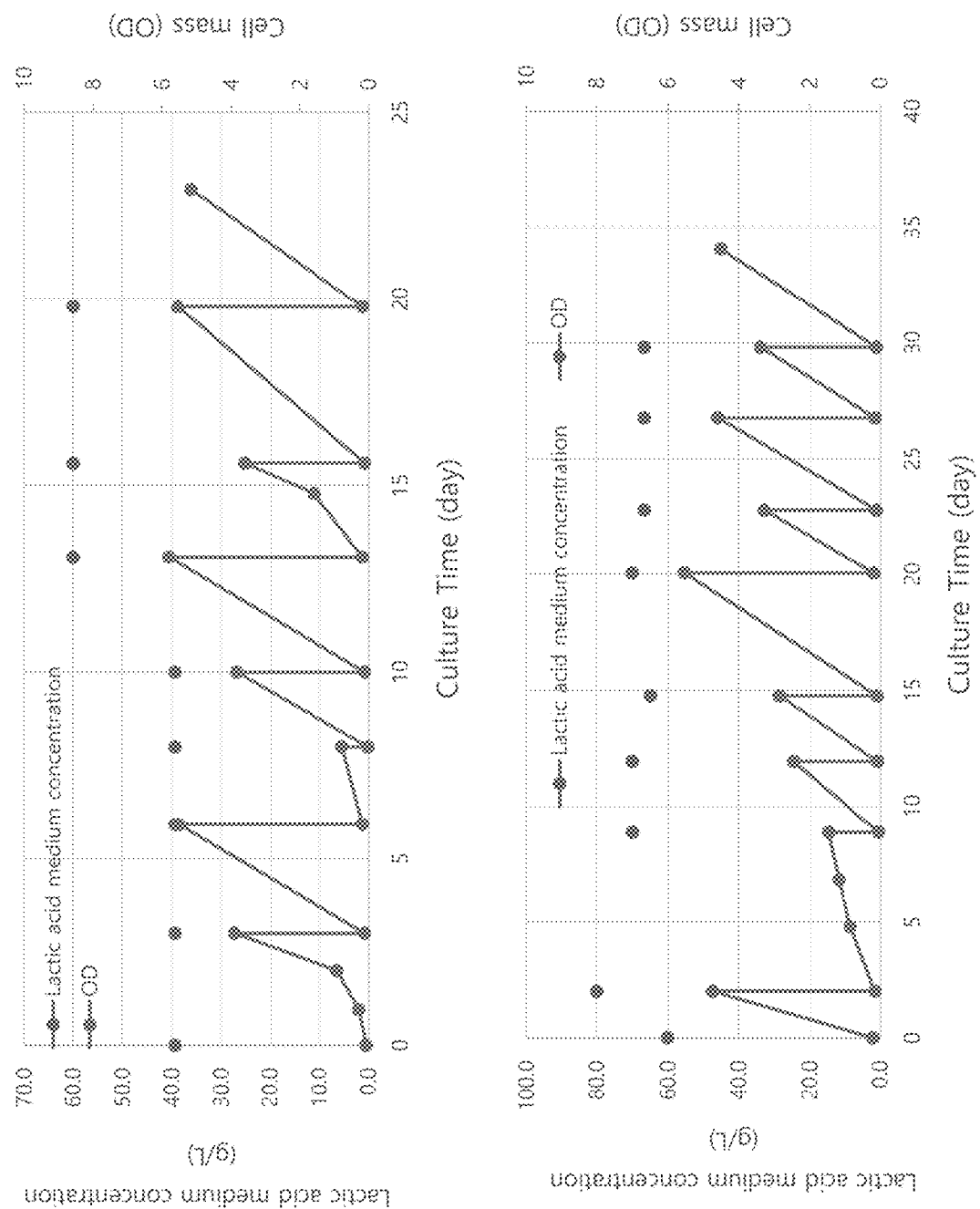
FIG. 1 is a schematic diagram illustrating a process of forcibly inducing adaptation of the YBC5 strain according to the present invention at a various lactic-acid concentration to increase resistance to lactic acid, specifically, FIG. 1(*a*) shows the growth of cells during subculture in the $2^{nd}$-round adaptive evolution to secure strain #26-5, selected during the lactic-acid concentration adaptation process.

Unless defined otherwise, all technical and scientific terms used herein have the same meanings as appreciated by those skilled in the field to which the present invention pertains. In general, the nomenclature used herein is well-known in the art and is ordinarily used.

Acid-resistant yeast is characterized by consuming sugar at a high rate even at an acidic pH, exhibiting a high growth rate, and converting the consumed sugar into a desired product under fermentation conditions. In previous research by the present inventors, an acid-resistant yeast strain (KCTC13508BP) was selected from yeasts having these characteristics in several yeast libraries, and the acid-resistant yeast strain (KCTC13508BP) had a high growth rate and a high sugar consumption rate even at a lactic-acid concentration of 40 g/L to 80 g/L (Korean Patent Application No. 10-2018-0044509).

In the previous patent application by the present inventors, by controlling the metabolic circuit to improve the lactic-acid-producing ability and suppress the ethanol-producing ability of the acid-resistant yeast YBC strain, the present inventors produced a recombinant strain by deleting a gene encoding the cytochrome b2 enzyme, which converts lactate to pyruvate, from a strain obtained by deleting a gene encoding alcohol dehydrogenase and a gene encoding pyruvate decarboxylase from the YBC strain and introducing a lactate dehydrogenase gene into the YBC strain.

In addition, in order to suppress glycerol production in the constructed strain, the present inventors constructed a recombinant strain by deleting a gene encoding a glycerol-3-phosphate dehydrogenase, which converts hydroxyacetone phosphate to glycerol 3-phosphate, from the strain.

In the present invention, in order to restore the lactic-acid resistance of the recombinant strain, the recombinant strain was subcultured in a medium containing lactic acid at various concentrations up to 80 g/L, a strain having excellent lactic-acid resistance was selected therefrom and a foreign lactate dehydrogenase gene that had been substituted at the position of the PDC genome of the selected strain was replaced with a lactate dehydrogenase gene derived from *S. epidermidis* to construct a novel recombinant strain, and the recombinant strain was found to have high lactic-acid resistance, high lactic-acid-producing ability, and suppressed ethanol- and glycerol-producing ability.

Therefore, in one aspect, the present invention is directed to a recombinant strain having lactic-acid-producing ability, the recombinant strain constructed by deleting a gene encoding pyruvate decarboxylase from an acid-resistant yeast YBC strain (KCTC13508BP) and introducing a gene encoding lactate dehydrogenase derived from *Staphylococcus epidermidis* at the position of the gene encoding pyruvate decarboxylase.

In the present invention, the gene encoding the lactate dehydrogenase derived from *Staphylococcus epidermidis* may be represented by SEQ ID NO: 1.

In the present invention, the recombinant strain may be characterized in that a gene encoding alcohol dehydrogenase is further deleted or inactivated and in that a gene encoding an enzyme that converts dihydroxyacetone phosphate to glycerol-3-phosphate is further deleted or inactivated.

In the present invention, the recombinant strain may be characterized in that a gene encoding an enzyme that converts lactate to pyruvate is further deleted or inactivated.

In another aspect, the present invention is directed to a recombinant strain having lactic-acid-producing ability, the recombinant strain constructed by deleting a GPD1 gene, which is a gene encoding an enzyme that converts dihydroxyacetone phosphate to glycerol-3-phosphate, a CYB2 gene, which is a gene encoding an enzyme that converts lactate into pyruvate, an ADH gene, which is a gene encoding alcohol dehydrogenase, and a PDC gene, which is a gene encoding pyruvate decarboxylase from an acid-resistant yeast YBC strain (KCTC13508BP), and introducing the gene encoding lactate dehydrogenase into the acid-resistant yeast YBC strain, wherein the gene encoding the lactate dehydrogenase is introduced at the positions of the deleted ADH gene, PDC gene and GPD1 gene, and the gene encoding lactate dehydrogenase introduced at the position of the PDC gene is a gene encoding lactate dehydrogenase derived from *Staphylococcus epidermidis*.

In the present invention, the gene encoding the lactate dehydrogenase derived from *Staphylococcus epidermidis* is represented by SEQ ID NO: 1, and the protein sequence thereof is represented by SEQ ID NO: 2, wherein a codon usage is regulated for expression of the gene in the acid-resistant YBC strain.

In the present invention, the gene encoding lactate dehydrogenase introduced at the positions of the deleted ADH gene and GPD1 gene may be derived from *Staphylococcus epidermidis* or *Lactobacillus plantarum*.

Recombinant strains having lactic-acid-producing ability exhibit a high lactic acid yield. However, lactic acid produced in large amounts inside the cells and large changes in carbon flux within cells affect the redox balance and cell growth and regulatory mechanisms, resulting in changes such that the cell growth rate and sugar consumption rate (and ultimately the lactic-acid production rate) are reduced. The reasons for the reduced lactic-acid resistance induced by genetic engineering are as follows. Conventional wild-type microorganisms are strains that grow well even under the environment that lactic acid is present at a high concentration (40~80 g/L) outside the cells, and at pH of 2 to 3, which is lower than pKa. This strain actively produces lactic acid inside cells after genetic engineering, so lactic acid production is inhibited by both lactic acid produced inside the cells and lactic acid that has penetrated the cell membrane (via mass transfer) from the outside of the cells. The increased intracellular lactic-acid concentration decreases the pH of the cells, thus exhibiting an effect of inhibiting various intracellular activities, including gene replication and protein production, resulting in lower lactic-acid resistance.

In addition, this effect becomes stronger when the extracellular lactic-acid concentration is increased or the external pH is more acidic and thus a large fraction of the total lactic acid is present in a hydrated form. In order to solve the problem caused by recombinant strains, the strains are continuously cultured in the target environment, such as adaptive evolution/forced evolution, and cells that are modified while adapting to the environment are continuously selected to improve performance (Zhengming Zhu et al., Applied Microbiology and Biotechnology, 102:4615-4627, 2018; Eugene Fletcher et al., Metabolic Engineering 39 (2017) 19-28, 2017; Christopher P Long, Current Opinions in Chemical Engineering, 22:209-215, 2018). Compounds causing mutation or physical mutation-causing factors such as UV may be used for such forced evolution (Zhengming Zhu et al., Applied Microbiology and Biotechnology (2018) 102:4615-4627). Initially, it was attempted to apply other methods rather than the adaptive evolution described above in the present invention. However, random mutations that simultaneously increase a desired aspect of performance (e.g., acid resistance) and other aspects of performance (e.g., productivity) are very rare. Although about 100 strains were individually monitored, it was difficult to select useful strains therefrom. It was difficult to expand the group from which to perform selection in consideration of the need to develop an automated high-throughput system capable of selecting excellent colonies and a gene system (for example, a fluorescent reporter proportional to the expression level of LDH) capable of detecting excellent colonies from the group of cells that were cultured and mutated to $10^8$ colony/ml or more.

Therefore, the adaptive evolution method was used, rather than a method using mutants, the cells of the recombinant yeast strain were continuously cultured at high sugar and lactic-acid concentrations, and the lactic-acid concentration was increased when cells grew well. In addition, a process including plating the corresponding cells on a solid medium containing lactic acid in the intermediate stage of culture, selecting colonies having a high growth rate (having a large size) from the solid medium, and separately flask-testing the lactic acid production ability of the colony was repeated. The selected strain was directly compared with the parent strain of the culture. This operation, when repeated, enables selection of strains having increased lactic-acid-producing ability and the desired lactic-acid resistance. The improved fermentation performance was detected through fermenter-based culture (see FIG. 7).

In another aspect, the present invention is directed to a method for producing a recombinant yeast strain having improved lactic acid resistance and lactic-acid-producing ability, the method comprising: (a) inducing adaptive evolution of the recombinant yeast strain to a high-lactic-acid concentration by sequentially culturing a recombinant yeast strain having lactic-acid-producing ability from in a low-concentration lactic acid medium to in a high-concentration lactic acid medium to; (b) selecting a recombinant yeast strain having improved lactic-acid-producing ability in the high-concentration lactic acid medium; and (c) introducing a gene encoding a lactate dehydrogenase derived from *Staphylococcus epidermidis* at the position of the PDC gene of the genome of the selected strain.

In the present invention, the recombinant yeast strain having lactic-acid-producing ability in step (a) is a YBC5 strain constructed by deleting a GPD1 gene, which is a gene encoding an enzyme that converts dihydroxyacetone phosphate to glycerol-3-phosphate, a CYB2 gene, which is a gene encoding an enzyme that converts lactate into pyruvate, an ADH gene, which is a gene encoding alcohol dehydrogenase, and a PDC gene, which is a gene encoding pyruvate decarboxylase from an acid-resistant yeast YBC strain (KCTC13508BP), and introducing the gene encoding lactate dehydrogenase into the acid-resistant yeast YBC strain, wherein the gene encoding the lactate dehydrogenase is introduced at the positions of the deleted ADH gene, PDC gene and GPD1 gene.

In another aspect, the present invention is directed to a recombinant strain #26-5 (Accession No.: KCTC 14215BP) obtained by adaptive evolution at a high lactic-acid concentration of the recombinant strain having lactic-acid-producing ability constructed by deleting a GPD1 gene, which is a gene encoding an enzyme that converts dihydroxyacetone phosphate to glycerol-3-phosphate, a CYB2 gene, which is a gene encoding an enzyme that converts lactate into pyruvate, an ADH gene, which is a gene encoding alcohol dehydrogenase, and a PDC gene, which is a gene encoding pyruvate decarboxylase from an acid-resistant yeast YBC strain (KCTC13508BP), and introducing the gene encoding lactate dehydrogenase into the acid-resistant yeast YBC strain.

In another aspect, the present invention is directed to a recombinant yeast YBC6 strain constructed by introducing a gene encoding a lactate dehydrogenase derived from *Staphylococcus epidermidis* at the position of the PDC gene of the genome of a recombinant strain #26-5 (Accession No.: KCTC 14215BP), wherein the recombinant yeast YBC6 strain has improved lactic-acid-producing ability at a high lactic-acid concentration and suppressed ethanol- and glycerol-producing ability compared to the YBC strain (KCTC13508BP) or the YBC5 strain.

Adaptive evolution is a very powerful tool, but causes side effects. The adaptive evolution performed in the present invention is the selection of strains adapted to grow well in the presence of high concentrations of lactic acid. The adaptive microorganism selected in this process can grow even when the concentration of free lactic acid is high, and a strain which has a defense mechanism against lactic-acid concentration and facilitates sugar metabolism even in the presence of lactic acid is obtained, because a strain having high lactic-acid-producing ability is selected during the selection process. This feature of the selected strain can increase the concentration of microorganisms in the reactor even when the concentration of lactic acid in the reactor increases during fermentation culture, and such a high concentration of microorganisms can increase the overall lactic-acid production rate. In particular, the parent strain used in the present invention is a strain that grows at a very fast rate and has a high glucose consumption rate at a high concentration of lactic acid, which is a characteristic before genetic manipulation. Thus, adaptive evolution can restore the reduced lactic acid resistance and consequent reduced growth rate in the presence of lactic acid during the process of converting carbon flux from ethanol to lactic acid through genetic manipulation. However, considering this adaptive evolution process from the perspective of microorganisms, there are several directions that microorganisms necessarily select. From the point of view of microorganisms, in an acidic pH lower than pKa, when the external concentration of lactic acid increases, unionized hydrated lactic acid is transferred to and penetrates the cells, which lowers the pH inside the cells. In a state where the effect of such lactic acid is great, in selecting a fermentation product (carbon flow) that can produce ATP and NADH while converting sugar, which is a growth substrate, while performing DNA replication and protein production, the direction of evolution in which growth is promoted and sugar metabolism is accelerated while enhancing the lactic acid production performance (for example, the production rate), which has the same effect as external stress, cannot be the direction of natural selection but it is natural for the organisms to select a direction in which fermentation products that have less effect on the current stressors than lactic acid are induced. In addition, the lactic-acid production pathway in the parent strain used in the present invention is a pathway introduced from the outside, and the wild-type microorganism was originally a microorganism that grew while producing ethanol as a main byproduct, so a carbon pathway that was strengthened to promote growth and increase the resistance of lactic acid is obviously ethanol, and it was identified that ethanol, a byproduct of the lactic-acid production process, was increased.

In order to analyze the genetic factors that promoted the increase in lactic acid resistance and the increase in by-products induced by adaptive evolution, qPCR analysis (transcriptome analysis) was performed on microorganisms before and after adaptive evolution. An analysis on the entire genome other than qPCR analysis may be performed to detect the difference therebetween. However, there are many genes that have been modified by mutations in the genome, but in fact, only some of these genes are factors appearing as phenotypes through protein expression or regulatory mechanisms thereof. For this reason, it was considered that qPCR analysis would be more appropriate to find phenotypic genetic factors such as increased resistance and increased growth rate.

In order to identify genes with differences in expression in the transcriptome analysis, genes in which the fold change in the expression in the adaptive evolutionary strain compared to the expression rate in the wild-type strain was reduced or increased by two time or less, or two times or more are screened among all analyzed RNA sequences and then the corresponding genes were analyzed using annotation (see Table 6).

Among the gene pools with reduced expression, a specific gene is the LDH gene encoding lactate dehydrogenase. As described above, microorganisms that increase the lactic acid concentration, and the fastest growth rate and lactic acid production rate (in some cases, the highest lactic acid production concentration) are selected, but the preferred response of microorganisms capable of responding to inhibition by oxidative pressure or acidic pH due to lactic acid is to reduce the amount of lactic acid produced internally. The reduction in expression is accumulated in the microorganism during the adaptive evolution process. Of course, the selected strain also has excellent lactic acid-producing ability, but this is mainly considered to be due to rapidly increased concentration of microorganisms resulting from the fast growth rate and the increased sugar consumption rate or sugar transfer rate in cells. It is believed that the lactic acid-producing ability per cell is decreased due to such a decrease in expression.

As a result of analyzing the gene pool with increased expression, it was observed that the expression of several gene groups performing the same functions increased together. These are categorized as follows.

Category A is related to fermentation products and is a group of genes related to the production of ethanol occurring for the purpose of enhancing the carbon flux to achieve the growth rate, in addition to the decrease in the expression of lactate dehydrogenase. In particular, when detecting the conventional PDC (gene encoding pyruvate decarboxylase) and ADH (alcohol dehydrogenase) activity, genes which were tested as candidates but the predicted activity of which could not detected were found to be enhanced in the present adaptive evolution. Category E is related to a hexose transporter and is a group of genes associated with proteins that initially act on C6 sugars, i.e., sugars such as glucose and mannose outside, and transport the same into cells. Category B is a group of zinc finger proteins. Studies reported that oxidative stress induced by lactic acid affects functional groups related to zinc finger proteins, or enhancement related to zinc finger proteins involves in alleviation of reactive oxygen species (ROS) (Derek A. Abbott et al., *Applied and Environmental Microbiology*, 2320-2325, 2009), and the relationship between oxidative stress including lactic acid and zinc finger proteins is very high (Xixi Zhou et al, *The journal of biological chemistry*, 290:18361-18369, 2015; B Gao et al., *Cell Death and Disease*, 5:e1334, 2014; Ananda S. Prasad and Bin Bao, *Antioxidants* 8:164, 2019), the acid resistance of the selected strains is predicted to be partially related to these Zinc finger proteins. Category D is a group of genes related to sulfate/sulfite, and in particular, an increase in the expression of sulfate/sulfite reductase was observed, which is presumed to be due to a mechanism to relieve sulfate/sulfite-mediated oxidative stress through lactic acid-mediated oxidative stress. In addition, the expression of genes to support gene structures and cell structures against external stress was identified and were collectively referred to as Category D stress response.

Through transcriptome analysis, various characteristics of the strains of the present invention were determined, and when the characteristics of each gene were studied in the further research including reverse engineering in the future, an additional development method can be designed.

In the transcriptome analysis, the increase in the expression of genes related to glycerol production could not be detected, but it was detected from the phenotype identified by fermentation culture that the strain selected through adaptive evolution also exhibited increased glycerol-producing ability compared to the parent strain. Therefore, it was considered that the increased glycerol was caused by NADH regeneration through the glycerol production pathway due to deficient NADH regeneration resulting from the inactivation of LDH rather than the expression of related genes and thus glycerol would decrease again when LDH was activated (enhanced).

In conclusion, more microorganisms can be acquired in the fermentor for the same period of time due to the increased lactic acid resistance, and the fermentation rate increased due to the increased sugar metabolism rate. However, at the same time, an increase in the by-products of the lactic acid process was observed due to the increased lactic acid resistance. This was a phenomenon which is due to the decrease in the expression of LDH and thus the increase in glycerol and the expression of genes related to ethanol production, resulting from the increase in resistance. As a solution to this problem, the enhancement of LDH and removal of the ethanol production-related genes may be considered. In the present invention, first, by performing further expression of LDH, the production rate in each cell was increased to further increase the overall production rate, by performing the reduction of the coenzyme, NADH with LDH, reduction of NADH responsible for the glycerol pathway, was decreased and consequently, the level of the increase of glycerol was lowered, and by enhancing lactic acid-producing ability that directly competes with ethanol-producing ability using pyruvic acid as a precursor node in the metabolic pathway, the production of ethanol was reduced. Thereafter, if necessary, the additionally expressed ethanol-producing gene may be removed.

In one aspect of the present invention, the strain that has undergone adaptive evolution is the YBC5 strain, wherein an LDH gene derived from *L. plantarum* is substituted at the sites of g4423 (ADH), g3002-1 (PDC), and g2947 (CYB2) of the genome thereof, and a total of 6 copies of the gene are inserted due to the characteristics of the diploid YBC strain. In many cases, when the many copies of same genes are inserted, the expression of the same genes is suppressed due to the feedback inhibition of the cell, so the effect increasing in proportion to the number of copies is not exerted, and the presence of the same gene may affect the stability of the genome. For this reason, the present invention has found a novel method to enhance LDH. As described in the prior patent applications (Korean Patent Application No. 2018-0044509 and Korean Patent Application No. 2019-0124701) of present inventors, LDH inserted at the g4423 (ADH) site of the YBC5 strain exhibited very high activity, and LDH inserted at the g2947 (CYB2) site also exhibited sustained activity in the late fermentation due to the influence of the g2947 promoter. However, the LDH inserted at the g3002-1 (PDC) site exhibited a relatively low effect of increasing lactic acid-producing ability in the phenotype. In particular, qPCR showed that the inherent PDC of YBC exhibited a high expression rate through the highly active promoter of the g3002-1 (PDC). Thus, further studies were conducted on related phenomena.

First, lactic acid-producing ability was determined by removing g3002-1 from the wild-type YBC strain and introducing LDH derived from *L. plantarum* into the strain. It was observed that the strain well exhibited a phenotype by the removal of PDC, but produced a very small amount of lactic acid. Considering that LDH derived from *L. plantarum* was strongly expressed due to g4423, the extreme difference in expression of the same gene at different genomic locations within the same strain was not a general phenomenon. When the LDH is expressed in RNA, it is expected that the translation to protein will proceed smoothly, and in conclusion, it is presumed that the same gene was not transcribed at the corresponding PDC site. In order to solve this phenomenon, the present inventors tried to establish various hypotheses, but could not find a hypothesis to solve this. Accordingly, the present inventors hypothesized that smooth expression is suppressed depending on the genomic site and the genetic structural problem of LDH derived from *L. plantarum*. To solve this, LDH derived from another strain was introduced to change the genomic structure and thereby to promote LDH expression.

For the target LDH to be introduced, genes that have optimum acidic pH and excellent expression in yeast to suit the characteristics of the acid-resistant strain was selected. Finding these genes among the numerous genes present in nature using screening alone is almost impossible in consideration of the necessary resources, and is a task that requires genome mining and experimental verification along with many assumptions. The present inventors first tried to select genes having similar characteristics from the literature rather than such genome mining, inject into the g3002-1 site of the corresponding acid-resistant strain and then determine the activity thereof. The present inventors tried to find genes that were previously verified under similar conditions through a literature search, and targeted LDH derived from *Staphylococcus epidermidis* and LDH derived from *Bos taurus*, which were found to be effective among the genes tested in the subject literature (Jae Won Lee et al, J. Biotechnology 241, 2017).

After introducing the target three genes into the g3002-1 site of the wild-type YBC strain (KCTC13508BP), the lactic acid-producing ability was compared therebetween. As a result, a very interesting fact was detected. The difference in the activity between the three genes was very great, among which the *S. epidermidis*-derived LDH (SeLDH) gene was found to exhibit a 39-fold increase in activity based on the lactic acid yield compared to *L. plantarum*-derived LDH (LpLDH), and as a result, the SeLDH gene alone achieved a yield of 0.39 g/g at the site of g3002-1, which is activity comparable to that of the LpLDH previously inserted at the g4423 site. As a result, the present inventors acquired a method capable of securing high activity at the g3002-1 site and restoring the LDH activity of the adaptively evolved strain.

However, the LDH gene of *S. epidermidis* is in the form of FDP-activated LDH which requires FDP as a coenzyme among various LDHs (E. I Garvie, Bacterial Lactate Dehydrogenases, Microbiological Reviews, 1980), and this FDP is an intermediate product of glycolysis. Therefore, the activity of the LpLDH gene is highly likely to be affected by the availability of FDP, and the activity thereof is likely to be affected thereby, compared to when general sugars such as glucose, fructose, and sucrose are used as substrates, when other sugars are used. However, such restrictions are minimized, because the substrates mainly used in commercial processes are corn starch, which is mainly composed of glucose, fructose, and sucrose, and saccharification products thereof, sugarcane juice and by-products thereof.

In one aspect of the present invention, the SeLDH gene was inserted into the strain selected through adaptive evolution, and the result showed that the strain exhibited further increased yield from 0.67 g/g to 0.75 g/g and showed great reduction of by-products as expected while attaining further increase in productivity from 2.54 g/L/h to 2.56 g/L/h and increase in concentration from 123 g/L to 130 g/L.

The ATP-associated requirement for fermentation of the acid-resistant strain was found in the culture of the strain acquired by the present invention, as described in the existing literature (Antonius J. A. van Maris et al., *Appl. Environ. Microbiol.*, 70; 2898, 2004). In order words, as extracellular lactic acid concentration increased, energy was required to transfer the intracellular lactic acid to the outside, and ATP supply was required for fermentation due to consumption of ATP. The consumption of ATP is due to the production of acid-resistant lactic acid when adding 2ATP/glucose that can be secured by forcing the production strain to produce lactic acid while blocking oxygen thereto in general fermentation. For this reason, energy required for cell maintenance is insufficient under the anaerobic conditions of general fermentation. Oxygen supply is required to supplement the energy, and supplied oxygen completely oxidizes the substrate in the TCA pathway to supply energy, ATP, but at the same time, some substrates are converted to $CO_2$, rather than lactic acid, resulting in a decrease in lactic acid yield. Therefore, it is necessary to set optimal aeration conditions that minimize the loss of lactic acid yield while maintaining cell activity.

In addition, the strain of the present invention is both a yeast and a gram-positive strain and thus this should be considered to set a fermentation method. As is well known, in the presence of high sugar concentration, gram-positive strains undergo anaerobic fermentation reactions such as ethanol fermentation or lactic acid fermentation other than TCA even under aerobic conditions. In contrast, gram-negative strains can inhibit the production of fermentation products under aerobic conditions, so only the cells can be increased, and the cell growth period and the fermentation product production period may be performed separately. However, these gram-negative strains cause cell growth under aerobic conditions and can secure a high cell concentration in the fermentor, but cells cannot be increased indefinitely in order to increase the fermentation rate, since many substrates consumed under aerobic conditions are converted to $CO_2$ along with cell growth (in addition, it is natural that the cell concentration is limited depending on the nutrients and the limit substrate of the medium). On the other hand, gram-positive strains grow cells under aerobic conditions and also yield fermented products. Therefore, when the fermentation product is lactic acid, NAD required for the glycolysis process can be supplied by the NADH consumed by LDH, gram-positive strains are relatively advantageous in lactic acid yield because lactic acid can be increased while reducing carbon loss to $CO_2$ compared to gram-negative strains in which NAD is supplied by converting (oxidizing) substrates to $CO_2$ through respiration. However, rapid accumulation of fermentation products in the reactor may quickly reach the lactic acid concentration where growth inhibition occurs, and there may be limitations in proliferation to the desired cell concentration. Therefore, in order to overcome this, adjustment of the optimal oxygen supply rate is required to maximize the optimal seed concentration and the initial growth rate of fermentation, and to prevent excessive conversion of the substrate to $CO_2$ due to excess oxygen. In addition, as soon as the concentration of lactic acid at which growth stops is reached, it is necessary to adjust the oxygen supply rate by reducing oxygen supply rate so as to maintain a microaerobic state in which excessive $CO_2$ loss does not occur, while supplying ATP, which is the energy to discharge lactic acid to the outside of the cell, as described above. Therefore, the present fermentation does not need to maintain a high mixing rate in the fermentor for the addition of the compound for neutralization and mixing the compound, but it is necessary to control the minimum oxygen supply rate at which sufficient cell growth occurs in the early stage of fermentation and sufficient ATP supply can occur at the late stage of fermentation, while reducing $CO_2$ loss due to excess oxygen, which is an important scale-up factor. Based on the optimization of the oxygen supply rate, an appropriate aeration rate and mixing rate can be found through many experiments, and an optimum value can also be found using parameters known in the art such as OUR and OTR.

In one aspect of the present invention, the strain selected by adaptive evolution can achieve high cell concentration and fast lactic acid production rate due to increased resistance to lactic acid compared to the parent strain YBC strain (KCTC13508BP) or the mutant strains (YBC1, YBC2/YBC3/YBC4/YBC5) derived from the parent strain due to increased resistance to lactic acid. In another aspect of the present invention, LDH was enhanced in the strains selected by the adaptive evolution to achieve reduction of ethanol and glycerol production.

In another aspect of the present invention, compared to the lactic acid-producing ability acquired by introducing the LDH gene derived from *L. plantarum* at the position of the PDC (g3002-1) gene of the genome of the parent strain YBC strain, the lactic acid-producing ability acquired by introducing the LDH gene derived from *S. epidermidis* at the position was found to be increased 30 times or more on a yiled basis.

In the present invention, the gene encoding lactate dehydrogenase that is introduced is preferably an LDH gene derived from *L. helveticus*, an LDH gene derived from *R. oryzae* or an LDH gene derived from *L. plantarum*, an LDH gene derived from *B. taurus*, and an LDH gene derived from *S. epidermidis*. More preferably, the *L. plantarum*-derived LDH gene is introduced at the site of g4423 (ADH), and the *S. epidermidis*-derived LDH gene is introduced at the site of g3002-1 (PDC).

In one aspect of the present invention, the strain #26-5 having remarkably increased lactic acid resistance obtained through adaptive evolution of the YBC5 strain (Δg4423::ldh/Δg3002-1::ldh/Δg2947::ldh/Δg1544) exhibits high lactic acid productivity and high lactic acid production concentration, thus remarkably improving an economic efficiency of the process. In addition, the YBC6 strain (Δg4423::LpLDH/Δg3002-1::SeLDH/Δg2947::LpLDH/Δg1544) constructed by substituting the LDH of g3002-1 of the #26-5 strain with LDH derived from *S. epidermidis* exhibits increased lactic acid production rate and production concentration, and suppressed production of ethanol and glycerol, thus increased yield, compared to YBC5 and #26-5. The fermentation properties of YBC6 exhibited the yield, production rate, and production concentration that have reached a level that can be commercialized as acid-resistant strains.

Accordingly, in another aspect, the present invention is directed to a method of producing lactic acid comprising (a) culturing the recombinant strain to produce lactic acid, and (b) collecting the produced lactic acid.

The present invention is capable of realizing an excellent acid-resistant strain having greatly increased lactate productivity, concentration and yield, which reach a level of commercialization, greatly reduced ethanol production, and greatly reduced glycerol byproducts.

As used herein, the term "acid-resistant yeast" is defined as a yeast that can maintain a biomass consumption rate (such as a sugar consumption rate) of at least 10% or a specific growth rate of at least 10%, at a pH less than a pKa value of an organic acid when the medium contains an organic acid (particularly lactic acid) at a concentration of at least 1M, compared to when the medium does not contain an organic acid. More specifically, the term "acid-resistant yeast" is defined as yeast that can maintain a biomass consumption rate (such as a sugar consumption rate) of at least 10% or a specific growth rate of at least 10% at a pH of 2 to 4 compared to a pH of 5 or higher.

The recombinant yeast according to the present invention can be produced by inserting the gene into a chromosome of a host yeast according to a conventional method, or by introducing a vector including the gene into the host yeast.

As the host yeast, a host cell having high DNA introduction efficiency and high expression efficiency of the introduced DNA is commonly used. In one embodiment of the present invention, an acid-resistant yeast is used, but the present invention is not limited thereto and any type of yeast may be used as long as it can sufficiently express the target DNA.

The recombinant yeast can be prepared according to any transformation method. The term "transformation" refers to a phenomenon in which DNA is introduced into a host to enable DNA to be replicated as a factor of chromosomes or by chromosomal integration, and means a phenomenon in which genetic changes are artificially induced by introducing external DNA into a cell. General transformation methods include electroporation, lithium acetate-PEG, and the like.

In addition, in the present invention, any commonly known genetically engineering method can be used as a method of inserting genes into the chromosomes of host microorganisms. For example, there are methods using retroviral vectors, adenoviral vectors, adeno-associated virus vectors, herpes simplex viral vectors, pox viral vectors, lentiviral vectors, non-viral vectors and the like. The "vector" means a DNA product containing a DNA sequence operably linked to a suitable regulatory sequence capable of expressing the DNA in a suitable host. Vectors may be plasmids, phage particles or simply potential genomic inserts. When transformed into a suitable host, vectors may be replicated or perform functions independent of the host genomes, or some thereof may be integrated with the genomes. Plasmids are currently the most commonly used forms of vector, but linear DNA is also a commonly used form for genomic integration of yeast.

Typical plasmid vectors include (a) a replication origin to efficiently conduct replication so as to include a predetermined amount of plasmid vector in each host cell, (b) an antibiotic resistance gene or auxotrophic marker gene to screen host cells transformed with plasmid vectors, and (c) a restriction enzyme cleavage site into which a foreign DNA fragment is inserted. Even if an appropriate restriction enzyme cleavage site is not present, the vector and foreign DNA can be easily ligated using a synthetic oligonucleotide adaptor or a linker according to a conventional method (Gibson assembly). If necessary, a method of synthesizing and using the entire desired sequence is also commonly used.

Furthermore, when a nucleic acid sequence is aligned with another nucleic acid sequence based on a functional relationship therebetween, it is said to be "operably linked" thereto. This may be gene(s) and control sequence(s) linked in such a way so as to enable gene expression when a suitable molecule (e.g., a transcriptional activator protein) is linked to the control sequence(s). For example, DNA for a pre-sequence or secretory leader is operably linked to DNA for a polypeptide when expressed as a pre-protein involved in the secretion of the polypeptide; a promoter or enhancer is operably linked to a coding sequence when it affects the transcription of the sequence; a ribosome-binding site is operably linked to a coding sequence when it affects the transcription of the sequence; or the ribosome-binding site is operably linked to a coding sequence when positioned to facilitate translation.

Generally, the term "operably linked" means that the linked DNA sequence is in contact therewith, or that a secretory leader is in contact therewith and is present in the reading frame. However, the enhancer need not be in contact therewith. The linkage of these sequences is carried out by ligation (linkage) at convenient restriction enzyme sites. When no such site exists, a synthetic oligonucleotide adaptor or a linker according to a conventional method is used.

It should be understood that not all vectors function identically in expressing the DNA sequences of the present invention. Likewise, not all hosts function identically for the same expression system. However, those skilled in the art will be able to make appropriate selections from among a variety of vectors, expression control sequences and hosts without excessive burden of experimentation and without departing from the scope of the present invention. For example, selection of a vector should be carried out in consideration of a host because the vector should be replicated therein. The number of times the vector replicates, the ability to control the number of times the vector replicates, and the expression of other proteins encoded by the corresponding vector, such as the expression of antibiotic markers, should also be considered.

In the present invention, the carbon source may include, but is not limited to, one or more selected from the group consisting of glucose, xylose, arabinose, sucrose, fructose, cellulose, galactose, glucose oligomer, and glycerol.

In the present invention, the culture may be performed under conditions such that microorganisms, for example, $E.$ $coli$, and the like no longer act (for example, cannot produce metabolites). For example, the culture may be carried out at a pH of 1.0 to 6.5, preferably a pH of 1.0 to 6.0, and more preferably a pH of 2.6 to 4.0, but is not limited thereto.

Hereinafter, the present invention will be described in more detail with reference to examples. However, it will be obvious to those skilled in the art that these examples are provided only for illustration of the present invention and should not be construed as limiting the scope of the present invention.

Example 1: Adaptive Evolution #1 of Acid-Resistant Strain YBC

In the previous research, the present inventors selected strains having acid resistance through testing on various yeast strains and determined the strain having the best acid resistance, namely, the YBC strain, by adding lactic acid to a medium at the beginning of the culture of yeast strains and monitoring the growth and sugar consumption rate of microorganisms, and deposited the strain with the accession number KCTC13508BP with the Biological Resource Center in the Korea Research Institute of Bioscience and Biotechnology.

Phylogenetic analysis showed that the YBC strain (KCTC13508BP) is a strain similar to $S.$ $cerevisiae$, is diploid, and is Crabtree-positive.

The YBC5 strain genetically modified from the corresponding YBC strain achieved a yield that could be commercialized by suppressing the consumption of lactic acid and suppressing glycerol production while minimizing inhibition of ethanol production (Korean Patent Application No. 10-2020-0046779).

The YBC5 strain was obtained by deleting an ADH (alcohol dehydrogenase) from the YBC strain and introducing an LDH gene into the strain to construct a YBC1 strain, removing the g3002-1 gene (PDC gene) from the YBC1 strain and expressing LDH therein to construct a YBC2 strain capable of producing lactic acid at high efficiency and having suppressed ethanol production, introducing an LDH gene into the YBC2 strain and removing g2947, a gene that consumes lactate to construct a YBC4 strain having removed lactic acid consumption ability and removing the GPD1 (g1544) gene (removing both allele 1 and allele 2, as a diploid strain) from the YBC4 strain to construct the YBC5 strain.

The method of constructing the strain is as follows:

The YBC1 strain is a strain obtained by removing the g4423 gene, which is the main ADH gene of the YBC strain, from the YBC strain and introducing the LDH gene of SEQ ID NO: 3 derived from Lactobacillus plantarum at the position of g4423. A gene cassette from which the ORF of each gene was removed and which contains 5' and 3' UTR was constructed based on the information of g4423 and UTR thereof and used as donor DNA. For each allele of g4423, the corresponding 5' UTR is represented by SEQ ID NO: 4 and SEQ ID NO: 5, and the 3' UTR is represented by SEQ ID NO: 6 and SEQ ID NO: 7. The donor DNA was produced using a cloning method using a restriction enzyme, Gibson assembly, and a method using gene synthesis as described above. The LDH of SEQ ID NO: 3 was synthesized and then introduced at the ORF site of g4423 to produce donor DNA, and the donor DNA was introduced into YBC to construct a recombinant strain YBC1.

In addition, the g3002-1 gene is a gene that is positioned at the scaffold 72 in the genome sequencing of the YBC strain and acts as a PDC gene. The g3002-1 gene (gene positioned at the scaffold 72) was removed from the YBC1 strain and the LDH gene of SEQ ID NO: 3 was introduced thereinto to construct a recombinant strain YBC2.

The cassette for substituting the gene of g3002 was constructed using the corresponding UTR as a recombination site. Similar to the method of introducing LDH into the site of the g4423 gene (ADH) of YBC1 described above, the cassette was constructed using the UTR of g3002-1. However, in order to simplify the process of gene substitution, a donor cassette for one allele was produced without considering allele variation, but it is also possible to produce a donor cassette for each allele. In addition, for the primers used for gene substitution, in addition to the primers used to produce the deletion strain, a pair of primers capable of detecting both LDH and the UTR of g3002-1 were separately used as follows to increase the accuracy of gene substitution verification.

```
g3002-1 UTR-LDH-fwd:
                              (SEQ ID NO: 8)
GCAGGATATCAGTTGTTTG g3002-1 UTR-LDH-rev:
                              (SEQ ID NO: 9)
AATACCTTGTTGAGCCATAG
```

In addition, the YBC4 strain is a strain constructed by deleting the g2947 gene, which is the main CYB2 gene of the YBC2 strain, from the YBC2 strain and introducing the LDH gene of SEQ ID NO: 3, derived from Lactobacillus plantarum, at the position of g2947. The g2947 gene is a gene positioned at scaffold 41 in the genome sequencing of the YBC strain. A gene cassette from which the ORF of each gene was removed and which contains 5' and 3' UTR was constructed based on the information of g2947 and UTR thereof and used as donor DNA. For each allele of g2947, the corresponding 5' UTR is represented by SEQ ID NO: 10 and SEQ ID NO: 11, and the 3' UTR is represented by SEQ ID NO: 12 and SEQ ID NO: 13. The donor DNA was produced using a cloning method using a restriction enzyme, Gibson assembly, and a method using gene synthesis, as described above.

However, in order to simplify the process of gene substitution, a donor cassette for one allele was produced without considering allele variation, but it is also possible to produce a donor cassette for each allele.

The YBC5 strain is a strain constructed by deleting the g1544 gene, which is the GPD1 gene of the YBC4 strain, from the YBC4 strain. The g1544 gene is a gene positioned at scaffold 19 in the genome sequencing of the YBC strain. A gene cassette from which the ORF of each gene was removed and which contains 5' and 3' UTR and antibiotic markers was constructed based on the information of g1544 and UTR thereof and used as donor DNA. For each allele of g1544, the corresponding 5' UTR is represented by SEQ ID NO: 14 and SEQ ID NO: 15, and the 3' UTR is represented by SEQ ID NO: 16 and SEQ ID NO: 17. The donor DNA was produced using a cloning method using a restriction enzyme, Gibson assembly, and a method using gene synthesis, as described above.

In order to simplify the process of gene substitution, a donor cassette for one allele was produced without considering allele variation, but it is also possible to produce a donor cassette for each allele. In addition, the donor cassette may be produced and applied without using antibiotic markers when a currently commercialized genetic engineering technology (CRISPR) is used.

The genotypes of the produced recombinant strains are as follows:

YBC2 Δg4423::ldh/Δg3002-1::ldh

YBC4 Δg4423::ldh/Δg3002-1::ldh/Δg2947::ldh

YBC5 Δg4423::ldh/Δg3002-1::ldh/Δg2947::ldh/Δg1544

However, in order to secure economic feasibility upon commercialization, the recombinant strain must achieve a production rate of 2.5 g/L/hr or more and a lactic acid concentration of 120 g/L or more at a pH of 3.7 or less. Therefore, in the following examples, treatment to increase the resistance to lactic acid was performed in order to increase the lactic acid production rate of the YBC5 strain.

As shown in Table 1, the YBC5 strain was subcultured while gradually increasing the lactic acid concentration from 10 g/L to 80 g/L. During subculture, mutants occur in the cells through natural mutations, and strains that are highly adaptable to high concentrations of lactic acid grow relatively quickly and gradually become dominant species within the entire strain flora. This process was repeated while increasing the lactic acid concentration, and the growth rate of the entire strain flora was detected. In addition, the strain flora were plated on an agar plate containing lactic acid at an appropriate time point and colonies that are produced were separated. At this time, the selected colony was the largest colony due to rapid growth on a solid medium containing lactic acid. Through this process, 42 colonies were selected from colonies grown at liquid concentrations of 40, 50, 60, 70, and 80 g/L.

TABLE 1

| mYP Component | Concentration (g/L) |
|---|---|
| Peptone | 5 |
| Yeast extract | 4 |
| KH2PO4 | 5 |
| MgSO4—7H2O | 2 |
| Uracil | 0.15 |
| Glucose | 50 |
| Lactic acid | variable |

TABLE 1-continued

| | Round | | | | | | | |
|---|---|---|---|---|---|---|---|---|
| LA(g/L) | 1<br>10 | 2<br>20 | 3<br>30 | 4<br>40 | 5<br>50 | 6<br>60 | 7<br>70 | 8<br>80 |
| m-YP(80%) | 40.0 | 40.0 | 40.0 | 40.0 | 40.0 | 40.0 | 40.0 | 40.0 |
| Glu(600 g/L) | 5 | 5 | 5 | 5 | 5 | 5 | 5 | 5 |
| LA(40%) | 1.5 | 3.0 | 4.5 | 6.0 | 7.5 | 9.0 | 10.5 | 12.0 |
| Seed(ml) | 2 | 2 | 2 | 2 | 2 | 2 | 2 | 2 |
| DW(ml) | 11.5 | 10.0 | 8.5 | 7.0 | 5.5 | 4.0 | 2.5 | 1.0 |
| Total (ml) | 60.0 | 60.0 | 60.0 | 60.0 | 60.0 | 60.0 | 60.0 | 60.0 |

Changes in the concentration of lactic acid produced by the strain
flora in each lactic acid-containing culture medium in this process
are shown in Table 2.

TABLE 2

| | Culture period (h) | OD(A600) | pH | Glucose | Lactate | Ethanol | Glycerol |
|---|---|---|---|---|---|---|---|
| 10/1, 14:00 | 0 | 0.20 | 4.34 | 54.5 | 1.0 | 0.0 | 0.0 |
| 10/2, 15:00 | 25 | 6.72 | 2.52 | 9.2 | 38.0 | 0.8 | 0.0 |
| LA10 | | | | | | | |
| 10/1, 14:00 | 0 | 0.20 | 3.10 | 54.2 | 11.4 | 0.0 | 0.6 |
| 10/2, 15:00 | 25 | 5.72 | 2.56 | 13.9 | 42.5 | 0.8 | 0.6 |
| LA20 | | | | | | | |
| 10/2, 15:00 | 0 | 0.17 | 2.94 | 55.2 | 21.7 | 0.0 | 0.9 |
| 10/4, 09:00 | 42 | 6.50 | 2.53 | 6.8 | 58.0 | 0.0 | 1.3 |
| LA30 | | | | | | | |
| 10/4, 09:00 | 0 | 0.21 | 2.83 | 52.0 | 32.6 | 0.0 | 1.5 |
| 10/5, 10:00 | 25 | 4.06 | 2.76 | 43.4 | 37.3 | 0.0 | 1.6 |
| LA40 | | | | | | | |
| 10/5, 10:00 | 0 | 0.10 | 2.78 | 54.5 | 41.9 | 0.0 | 2.6 |
| 10/7, 9:00 | 47 | 5.40 | 2.56 | 21.6 | 64.4 | 1.1 | 3.4 |
| LA50 | | | | | | | |
| 10/7, 11:00 | 0 | 0.22 | 2.75 | 54.6 | 51.9 | 0.0 | 2.5 |
| 10/9, 8:00 | 45 | 1.34 | 2.75 | 53.6 | 55.4 | 0.0 | 2.8 |
| 10/10, 9:00 | 70 | 5.92 | 2.64 | 29.5 | 65.7 | 0.0 | 3.3 |
| LA60 | | | | | | | |
| 10/9, 8:00 | 0 | 0.07 | 2.73 | 54.6 | 61.6 | 0.0 | 3.1 |
| 3 d | 72 | 0.25 | 2.72 | 51.0 | 60.6 | 0.0 | 3.4 |
| 5 d | 120 | 6.23 | 3.43 | 18.1 | 81.2 | 0.0 | 3.7 |
| LA70 | | | | | | | |
| 10/12, 09:00 | 0 | 0.05 | 2.73 | 51.7 | 68.7 | 0.0 | 3.8 |
| 6 d | 144 | 4.70 | 3.52 | 30.9 | 83.1 | 0.0 | 5.5 |
| LA80_1 | | | | | | | |
| 10/18, 09:00 | 0 | NA | 3.55 | 53.7 | 79.2 | 0.0 | 5.9 |
| 10/22, 15:00 | 102 | 6.14 | 3.37 | 5.4 | 105.6 | 1.0 | 8.5 |

The 42 selected colonies were inoculated into 5 ml of conical tubes. Because it is a small-scale culture, was the most uniform amount derived from the colony was inoculated for a uniform inoculation OD. The medium used herein was m-YP medium (5 g/L of peptone, 4 g/L yeast extract, 5 g/L of KH$_2$PO$_4$, 2 g/L of MgSO$_4$.7H$_2$O, 0.15 g/L of uracil) supplemented with 6% (primary) or 12% (secondary) glucose and cultured at 30° C. and 150 rpm for 96 hours.

Table 3 shows the result of 5 ml culture. In this culture, 15 colonies having high lactic acid production concentration, cell concentration, or lactic acid production yield were selected, and the following flask culture evaluation therefor was performed.

The selected colonies are as follows: 3, 5, 6, 8, 10, 22, 24, 26, 27, 31, 32, 35, 37, 38, 41.

TABLE 3

| Colony # | pH @3 d | OD | Glucose | Lactate | Ethanol | Glycerol | YLA |
|---|---|---|---|---|---|---|---|
| 1 | 2.22 | 5.28 | 8.5 | 45.0 | 1.86 | 0.40 | 0.817 |
| 2 | 2.24 | 5.96 | 11.4 | 41.8 | 1.75 | 0.34 | 0.802 |
| 3 | 2.14 | 9.06 | 0.0 | 49.8 | 0.73 | 0.61 | 0.784 |
| 4 | 2.20 | 6.96 | 7.4 | 44.4 | 1.81 | 0.41 | 0.790 |
| 5 | 2.16 | 10.32 | 1.3 | 49.2 | 0.58 | 0.67 | 0.791 |
| 6 | 2.15 | 9.58 | 3.3 | 48.0 | 0.63 | 0.50 | 0.797 |
| 7 | 2.19 | 7.06 | 7.5 | 45.3 | 1.76 | 0.38 | 0.810 |
| 8 | 2.21 | 6.06 | 10.8 | 42.8 | 1.71 | 0.32 | 0.812 |
| 9 | 2.19 | 6.50 | 8.9 | 43.9 | 1.71 | 0.36 | 0.803 |
| 10 | 2.14 | 8.96 | 4.4 | 48.0 | 0.63 | 0.53 | 0.812 |
| 11 | 2.21 | 4.30 | 12.9 | 40.2 | 1.96 | 0.32 | 0.796 |
| 12 | 2.18 | 4.08 | 10.0 | 43.8 | 1.72 | 0.38 | 0.818 |
| 13 | 2.20 | 6.04 | 12.8 | 42.0 | 1.60 | 0.33 | 0.828 |
| 14 | 2.18 | 7.26 | 7.8 | 44.3 | 2.28 | 0.35 | 0.794 |
| 15 | 2.19 | 5.22 | 12.6 | 42.6 | 1.63 | 0.34 | 0.838 |
| 16 | 2.18 | 5.72 | 10.5 | 44.1 | 1.64 | 0.35 | 0.833 |
| 17 | 2.18 | 6.20 | 11.6 | 43.3 | 1.70 | 0.33 | 0.836 |
| 18 | 2.17 | 6.70 | 9.8 | 45.3 | 1.71 | 0.38 | 0.843 |
| 19 | 2.19 | 6.18 | 13.4 | 44.0 | 1.51 | 0.34 | 0.877 |
| 20 | 2.16 | 6.32 | 8.2 | 45.2 | 1.54 | 0.35 | 0.817 |
| 21 | 2.18 | 5.74 | 10.0 | 44.0 | 1.57 | 0.25 | 0.822 |
| 22 | 2.17 | 8.80 | 8.0 | 43.3 | 1.87 | 0.49 | 0.780 |
| 23 | 2.19 | 7.46 | 13.5 | 40.4 | 1.81 | 0.37 | 0.808 |
| 24 | 2.12 | 9.02 | 3.6 | 48.1 | 0.86 | 0.53 | 0.802 |
| 25 | 2.20 | 7.82 | 13.2 | 40.6 | 1.81 | 0.34 | 0.807 |
| 26 | 2.12 | 9.04 | 2.6 | 48.3 | 1.21 | 0.59 | 0.793 |
| 27 | 2.17 | 6.00 | 10.8 | 43.2 | 1.76 | 0.34 | 0.820 |
| 28 | 2.17 | 6.38 | 9.4 | 42.4 | 2.17 | 0.44 | 0.784 |
| 29 | 2.17 | 6.14 | 10.9 | 43.3 | 1.71 | 0.35 | 0.823 |
| 30 | 2.12 | 7.72 | 6.2 | 45.2 | 0.64 | 0.40 | 0.790 |
| 31 | 2.12 | 9.48 | 4.6 | 46.4 | 0.98 | 0.49 | 0.789 |
| 32 | 2.11 | 9.54 | 0.7 | 49.2 | 0.69 | 0.52 | 0.782 |
| 33 | 2.12 | 8.66 | 3.1 | 46.9 | 1.19 | 0.49 | 0.777 |
| 34 | 2.15 | 8.14 | 5.4 | 44.8 | 2.06 | 0.41 | 0.771 |
| 35 | 2.20 | 7.02 | 5.1 | 38.5 | 4.26 | 1.61 | 0.658 |
| 36 | 2.15 | 6.48 | 6.5 | 43.8 | 1.97 | 0.48 | 0.769 |
| 37 | 2.15 | 7.36 | 6.1 | 45.2 | 1.93 | 0.35 | 0.787 |
| 38 | 2.15 | 6.48 | 8.5 | 44.8 | 1.83 | 0.37 | 0.815 |
| 39 | 2.14 | 6.24 | 4.7 | 45.9 | 2.07 | 0.50 | 0.781 |
| 40 | 2.17 | 5.54 | 9.9 | 42.6 | 1.88 | 0.37 | 0.795 |
| 41 | 2.10 | 8.98 | 1.5 | 50.2 | 0.87 | 0.57 | 0.809 |
| 42 | 2.15 | 7.24 | 6.0 | 44.0 | 2.11 | 0.48 | 0.764 |

| Colony # | pH @4 d | OD | Glucose | Lactate | Ethanol | Glycerol | YLA |
|---|---|---|---|---|---|---|---|
| 1 | 2.22 | 4.10 | 76.1 | 31.6 | 0.8 | 0.61 | 0.721 |
| 2 | 2.11 | 5.98 | 56.2 | 42.5 | 2.6 | 1.51 | 0.666 |
| 3 | 1.97 | 16.38 | 43.1 | 62.5 | 0.0 | 2.79 | 0.814 |
| 4 | 2.24 | 3.54 | 80.6 | 30.6 | 0.7 | 0.27 | 0.778 |
| 5 | 2.23 | 4.60 | 79.3 | 31.7 | 0.8 | 0.37 | 0.780 |
| 6 | 2.24 | 3.92 | 78.6 | 30.3 | 0.8 | 0.38 | 0.732 |
| 7 | 2.24 | 4.36 | 79.4 | 29.4 | 0.7 | 0.30 | 0.724 |
| 8 | 2.04 | 11.40 | 66.2 | 58.3 | 0.0 | 2.56 | 1.084 |
| 9 | 2.08 | 14.30 | 83.6 | 56.6 | 0.0 | 1.98 | 1.553 |
| 10 | 2.29 | 2.82 | 86.0 | 26.3 | 0.5 | -0.06 | 0.773 |
| 11 | 2.24 | 3.72 | 78.2 | 30.1 | 0.7 | 0.51 | 0.720 |
| 12 | 2.25 | 3.66 | 80.9 | 29.6 | 0.7 | 0.46 | 0.757 |
| 13 | 2.25 | 3.62 | 81.4 | 29.7 | 0.7 | 1.21 | 0.769 |
| 14 | 2.07 | 6.42 | 46.2 | 47.6 | 4.4 | 1.62 | 0.645 |
| 15 | 2.24 | 3.58 | 80.7 | 30.5 | 0.7 | 0.47 | 0.776 |
| 16 | 2.22 | 3.92 | 76.8 | 31.5 | 0.8 | 0.64 | 0.729 |
| 17 | 2.24 | 3.38 | 78.6 | 29.4 | 0.7 | 0.46 | 0.710 |
| 18 | 1.99 | 7.06 | 43.7 | 56.3 | 0.0 | 1.07 | 0.737 |
| 19 | 2.27 | 3.04 | 83.1 | 27.4 | 0.5 | 0.10 | 0.743 |
| 20 | 2.27 | 2.86 | 83.5 | 28.0 | 0.5 | 0.16 | 0.767 |
| 21 | 2.25 | 3.82 | 81.0 | 29.6 | 0.7 | 0.46 | 0.761 |
| 22 | 1.93 | 11.30 | 22.6 | 64.0 | 2.0 | 2.06 | 0.827 |
| 23 | 2.23 | 3.48 | 79.2 | 31.0 | 0.8 | 0.51 | 0.758 |
| 24 | 2.24 | 3.58 | 80.0 | 29.7 | 0.7 | 0.48 | 0.743 |
| 25 | 2.26 | 4.02 | 81.9 | 29.3 | 0.7 | 0.42 | 0.768 |
| 26 | 2.25 | 3.82 | 80.6 | 29.9 | 0.7 | 0.40 | 0.758 |
| 27 | 1.94 | 11.24 | 29.7 | 63.6 | 0.1 | 1.75 | 0.704 |

TABLE 3-continued

| 28 | 1.99 | 8.16 | 38.7 | 59.6 | 0.1 | 1.16 | 0.733 |
| --- | --- | --- | --- | --- | --- | --- | --- |
| 29 | 2.28 | 3.22 | 83.9 | 28.9 | 0.6 | 0.27 | 0.802 |
| 30 | 2.27 | 3.66 | 81.5 | 29.4 | 0.77 | 0.30 | 0.763 |
| 31 | 2.00 | 11.44 | 39.3 | 60.1 | 0.04 | 2.39 | 0.745 |
| 32 | 1.95 | 11.88 | 24.2 | 66.0 | 2.09 | 1.90 | 0.689 |
| 33 | 2.11 | 6.06 | 55.7 | 45.4 | 2.73 | 1.28 | 0.706 |
| 34 | 2.26 | 3.44 | 81.0 | 30.1 | 0.70 | 0.42 | 0.771 |
| 35 | 1.99 | 12.94 | 14.0 | 59.8 | 8.09 | 4.10 | 0.564 |
| 36 | 2.08 | 6.26 | 51.8 | 47.9 | 2.63 | 1.14 | 0.702 |
| 37 | 1.99 | 9.86 | 34.5 | 58.1 | 2.44 | 1.45 | 0.679 |
| 38 | 2.01 | 11.16 | 55.7 | 61.9 | 0.57 | 1.70 | 0.962 |
| 39 | 2.19 | 4.34 | 73.9 | 34.7 | 1.14 | 0.43 | 0.752 |
| 40 | 2.27 | 3.62 | 82.7 | 29.2 | 0.64 | 0.32 | 0.784 |
| 41 | 2.25 | 4.16 | 81.9 | 30.8 | 0.77 | 0.52 | 0.807 |
| 42 | 2.20 | 4.42 | 75.7 | 34.4 | 0.95 | 0.68 | 0.777 |

Flask culture evaluation was performed on the selected colonies and the culture conditions are as follows. 10% glucose (primary) was added to m-YP medium (5 g/L peptone, 4 g/L yeast extract, 5 g/L $KH_2PO_4$, 2 g/L $MgSO_4.7H_2O$, 0.15 g/L uracil) to adjust a total volume of 50 ml. Microorganisms were inoculated into the medium and cultured at 30° C. and 150 rpm for 72 hours. In addition, 1 day after incubation, a $CaCO_3$ solution was added in an amount of 20% of the sugar injection concentration.

The analysis results of the flask culture are shown in Table 4.

The result of flask culture was analyzed based on an evaluation logic introduced for comprehensive judgment. First, the top five colonies were selected for each item of production rate, lactic acid yield, growth rate, ethanol concentration (in low order), and glycerol concentration (in low order), and scores and weights in each item were assigned to the selected colonies and were summed up. As for the weights, for the purpose of adaptive evolution, the lactic acid production rate was given priority, and colonies having fast growth rate, but low lactic acid-producing ability were excluded. Table 5 shows the evaluation process and results thereof.

TABLE 4

| 30% Lactic acid productivity (g/L/h) | | | |
| --- | --- | --- | --- |
| Colony | 1 | 2 | 3 |
| 3 | 1.36 | 1.74 | 1.11 |
| 26 | 0.89 | 1.70 | 1.14 |
| 8 | 1.42 | 1.69 | 1.08 |
| 32 | 1.35 | 1.69 | 1.10 |
| 5 | 1.35 | 1.67 | 1.10 |
| 31 | 1.22 | 1.67 | 1.12 |
| YBC5 | 1.50 | 1.66 | 1.08 |
| 6 | 1.51 | 1.66 | 1.08 |
| 24 | 1.41 | 1.66 | 1.07 |
| 22 | 1.41 | 1.65 | 1.17 |
| 38 | 1.46 | 1.63 | 1.10 |
| 10 | 1.45 | 1.62 | 1.12 |
| 27 | 0.84 | 1.59 | 1.18 |
| 41 | 1.37 | 1.56 | 1.08 |
| 48 | 1.43 | 1.56 | 1.06 |
| 37 | 1.35 | 1.41 | 1.09 |
| 23 | 1.34 | 1.39 | 1.02 |
| 35 | 1.44 | 1.17 | 0.90 |

| 25% Lactic acid yield on Glucose (g/g) | | | |
| --- | --- | --- | --- |
| Colony | 1 | 2 | 3 |
| 3 | 0.78 | 0.80 | 0.77 |
| 26 | 0.75 | 0.80 | 0.79 |
| 22 | 0.74 | 0.79 | 0.81 |
| 27 | 0.73 | 0.79 | 0.81 |
| 8 | 0.74 | 0.78 | 0.75 |
| 32 | 0.71 | 0.78 | 0.76 |
| 5 | 0.69 | 0.77 | 0.76 |
| 31 | 0.75 | 0.77 | 0.77 |
| YBC5 | 0.72 | 0.76 | 0.75 |
| 6 | 0.75 | 0.76 | 0.75 |
| 10 | 0.73 | 0.76 | 0.77 |
| 24 | 0.72 | 0.76 | 0.74 |
| 48 | 0.76 | 0.75 | 0.73 |
| 38 | 0.72 | 0.75 | 0.76 |
| 41 | 0.71 | 0.73 | 0.75 |
| 23 | 0.70 | 0.71 | 0.71 |
| 37 | 0.72 | 0.65 | 0.75 |
| 35 | 0.63 | 0.63 | 0.63 |

| Growth rate (20%) | |
| --- | --- |
| Colony # | μ (1/h) |
| 27 | 0.170 |
| 26 | 0.169 |
| 31 | 0.159 |
| 5 | 0.144 |
| 32 | 0.141 |
| 3 | 0.141 |
| 37 | 0.138 |
| 8 | 0.136 |
| 6 | 0.134 |
| 24 | 0.134 |
| 38 | 0.129 |
| YBC5 | 0.126 |
| 10 | 0.124 |
| 41 | 0.122 |
| 22 | 0.120 |
| 48 | 0.113 |
| 23 | 0.104 |
| 35 | 0.094 |

| 15% Ethanol/LA | | | |
| --- | --- | --- | --- |
| Colony | 1 | 2 | 3 |
| 27 | 0.016 | 0.024 | 0.012 |
| 31 | 0.022 | 0.025 | 0.002 |
| 26 | 0.023 | 0.026 | 0.001 |
| 8 | 0.023 | 0.027 | 0.003 |
| 5 | 0.035 | 0.027 | 0.001 |
| YBC5 | 0.030 | 0.028 | 0.005 |
| 37 | 0.030 | 0.029 | 0.014 |
| 22 | 0.024 | 0.029 | 0.010 |
| 32 | 0.027 | 0.029 | 0.008 |
| 3 | 0.026 | 0.030 | 0.009 |
| 6 | 0.035 | 0.035 | 0.009 |
| 38 | 0.047 | 0.035 | 0.025 |
| 24 | 0.035 | 0.039 | 0.024 |
| 10 | 0.032 | 0.040 | 0.036 |
| 48 | 0.035 | 0.054 | 0.030 |
| 41 | 0.048 | 0.061 | 0.057 |
| 23 | 0.069 | 0.074 | 0.070 |
| 35 | 0.094 | 0.097 | 0.099 |

| 10% Glycerol/LA | | | |
| --- | --- | --- | --- |
| Colony | 1 | 2 | 3 |
| 26 | 0.006 | 0.008 | 0.011 |
| 27 | 0.007 | 0.009 | 0.010 |
| 22 | 0.007 | 0.009 | 0.012 |
| 37 | 0.010 | 0.010 | 0.011 |
| 3 | 0.011 | 0.011 | 0.015 |
| 32 | 0.011 | 0.011 | 0.015 |
| 31 | 0.007 | 0.012 | 0.013 |
| 8 | 0.006 | 0.012 | 0.013 |
| 10 | 0.012 | 0.012 | 0.013 |
| 6 | 0.008 | 0.012 | 0.015 |
| 23 | 0.016 | 0.013 | 0.012 |

TABLE 4-continued

| | | | |
|---|---|---|---|
| 48 | 0.013 | 0.013 | 0.015 |
| YBC5 | 0.011 | 0.013 | 0.016 |
| 5 | 0.011 | 0.013 | 0.015 |
| 41 | 0.016 | 0.014 | 0.014 |
| 24 | 0.010 | 0.014 | 0.015 |
| 38 | 0.015 | 0.014 | 0.015 |
| 35 | 0.050 | 0.044 | 0.034 |

TABLE 5

| | Colony # | Grade | Weights(%) | Score |
|---|---|---|---|---|
| Productivity | 3 | 5 | 30 | 1.50 |
| | 26 | 4 | 30 | 1.20 |
| | 8 | 3 | 30 | 0.90 |
| | 32 | 2 | 30 | 0.60 |
| | 5 | 1 | 30 | 0.30 |
| Yield | 3 | 5 | 25 | 1.25 |
| | 26 | 4 | 25 | 1.00 |
| | 22 | 3 | 25 | 0.75 |
| | 27 | 2 | 25 | 0.50 |
| | 8 | 1 | 25 | 0.25 |
| Growth rate | 27 | 5 | 20 | 1.00 |
| | 26 | 4 | 20 | 0.80 |
| | 31 | 3 | 20 | 0.60 |
| | 5 | 2 | 20 | 0.40 |
| | 32 | 1 | 20 | 0.20 |
| EtOH/LA | 27 | 5 | 15 | 0.75 |
| | 31 | 4 | 15 | 0.60 |
| | 26 | 3 | 15 | 0.45 |
| | 8 | 2 | 15 | 0.30 |
| | 5 | 1 | 15 | 0.15 |
| Glycerol/LA | 26 | 5 | 10 | 0.50 |
| | 27 | 4 | 10 | 0.40 |
| | 22 | 3 | 10 | 0.30 |
| | 37 | 2 | 10 | 0.20 |
| | 3 | 1 | 10 | 0.10 |

| Colony # | Grade | Weights(%) | Score | Total |
|---|---|---|---|---|
| 26 | 5 | 10 | 0.50 | 3.95 |
| 26 | 4 | 30 | 1.20 | |
| 26 | 4 | 25 | 1.00 | |
| 26 | 4 | 20 | 0.80 | |
| 26 | 3 | 15 | 0.45 | |
| 3 | 5 | 30 | 1.50 | 2.85 |
| 3 | 5 | 25 | 1.25 | |
| 3 | 1 | 10 | 0.10 | |
| 27 | 5 | 20 | 1.00 | 2.65 |
| 27 | 5 | 15 | 0.75 | |
| 27 | 4 | 10 | 0.40 | |
| 27 | 2 | 25 | 0.50 | |
| 8 | 3 | 30 | 0.90 | 1.45 |
| 8 | 2 | 15 | 0.30 | |
| 8 | 1 | 25 | 0.25 | |
| 31 | 4 | 15 | 0.60 | 1.20 |
| 31 | 3 | 20 | 0.60 | |
| 22 | 3 | 25 | 0.75 | 1.05 |
| 22 | 3 | 10 | 0.30 | |
| 5 | 2 | 20 | 0.40 | 0.85 |
| 5 | 1 | 30 | 0.30 | |
| 5 | 1 | 15 | 0.15 | |
| 32 | 2 | 30 | 0.60 | 0.80 |
| 32 | 1 | 20 | 0.20 | |
| 37 | 2 | 10 | 0.20 | 0.20 |

| Priority | Colony# | Total |
|---|---|---|
| 1 | 26 | 3.95 |
| 2 | 3 | 2.85 |
| 3 | 27 | 2.65 |
| 4 | 8 | 1.45 |
| 5 | 31 | 1.20 |

As shown in Table 5, colony No. 26 (hereinafter referred to as "#26 strain") was selected, and the main reason for the selection is that it is a colony in which the increase of by-products is minimized compared to the increase in lactic acid-producing ability. When only the lactic acid-producing ability and yield were considered, while excluding the increase in by-products, colony No. 3 showed better results, but the overall performance was first considered in the $1^{st}$ round. The increasing trend of these by-products was also observed in the subsequent adaptive evolution.

Example 2: Adaptive Evolution #2 of Acid-Resistant Yeast Strain YBC

The #26 strain selected in the $1^{st}$ round of adaptive evolution of Example 1 had an increase in performance compared to YBC5 (refer to the result of comparison with YBC5 in Table 4), but did not reach the performance to suit commercialization, so further operation for improvement was performed.

Since the #26 strain had an increase in resistance to lactic acid concentration, the culture was started at a high concentration of lactic acid and the number of subcultures at each concentration increased. The culture was performed without the addition of $CaCO_3$, a neutralizing agent, in order to improve the growth properties under extreme conditions.

The lactic acid that is used was prepared by removing impurities from a medium actually produced through fermentation with a 0.2 μm filter, and then performing concentration to prepare a 40-50% solution, and then mixed with an YP medium (20 g/L peptone, 10 g/L yeast extract) depending on the desired lactic acid concentration. The sugar concentration was 10%, and the subculture medium was inoculated in an amount of 10% of the total volume of the fresh medium and culture was performed.

FIG. 1 (a) shows the result of the subculture of #26 strain. Even at a lactic acid concentration of 60 g/L, smooth growth of the strain flora was observed. The strain flora were cultured in YP medium diluted with the $23^{rd}$-day medium and then 12 colonies were separated. The colonies were selected based on size.

Figure 2:
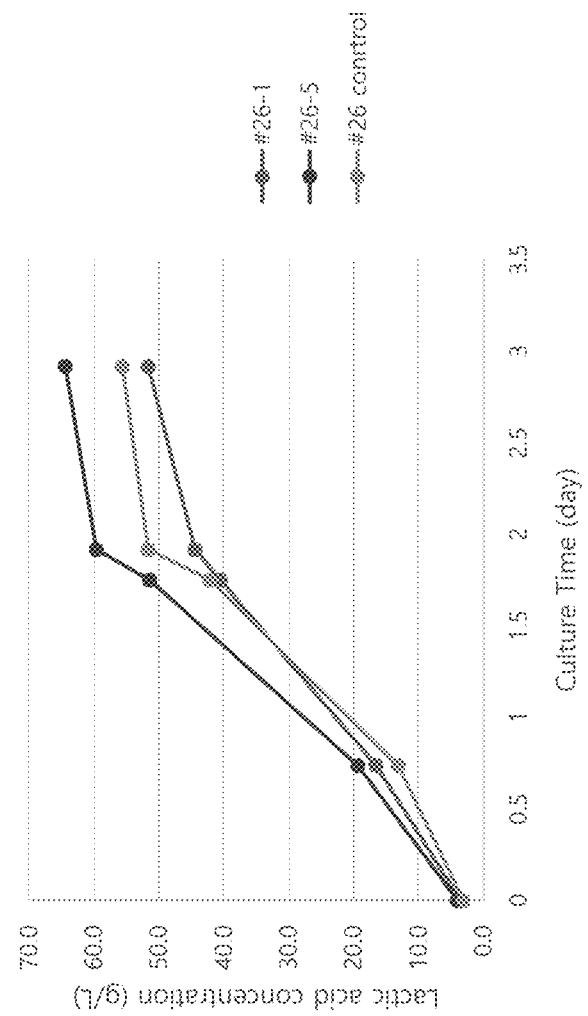
FIG. 2 shows the results of a comparison of the lactic-acid production profile among the strains #26-1 and #26-5, which are two strains selected in the 2$^{nd}$-round adaptive evolution according to the present invention, and the #26 strain selected in the 1$^{st}$-round adaptive evolution.

Flask culture was performed on the selected colonies under the same conditions as in Example 1. The reference performance at this time was the performance of the #26 strain. Colony No. 5 was selected through a selection process similar to that of Example 1, and it was named designated as the #26-5 strain for distinction from the $1^{st}$ round result. The result of culture of #26-5 is shown in FIG. 2.

The $3^{rd}$ round of adaptive evolution was conducted in order to further increase resistance compared to the strain #26-5. The target strains used herein were strain #26-5 and the strain flora cultured in the $2^{nd}$ round. The growth in the two flasks was compared at the beginning of the $3^{rd}$ round. As a result, the growth of the strain flora continuously grown from the $2^{nd}$ round was more excellent. The adaptive evolution using strain #26-5 as the starting culture strain was stopped due to the high possibility of the presence of a mutant with stronger resistance than the #26-5 strain selected within the strain flora. The result of the $3^{rd}$ round is shown in (b) of FIG. 1. The lactic acid concentration was increased to 80 g/L and the growth of the cells was observed, but it was observed that the growth rate was remarkably reduced compared to lactic acid concentration of 60 g/L. Therefore, subculture was performed at a decreased lactic acid concentration of 70 g/L, which provides a smooth growth rate. After the $3^{rd}$ round was completed, the corresponding strain flora were plated on an agar plate and colonies were then selected. At this time, a YPDU agar plate containing lactic acid at a concentration of 45 g/L and plates each having lactic acid concentrations of 50 g/L and 60 g/L were prepared and strain flora were plated thereon, and colonies were also produced on the agar plate containing the lactic acid.

Although the colonies produced in the additional $3^{rd}$ round have higher lactic acid resistance than #26-5 and thus can grow more at a high lactic acid concentration, compared to #26-5, the ratio of lactic acid in the fermentation product further decreases, and production of ethanol and glycerol as by-products was further increased. Here, any one of the strain #26-5 and the strain isolated in the $3^{rd}$ round should be selected as a target strain for commercialization which will be further developed in the future. It was necessary to make a decision to choose either further development (research on restoration of lactic acid-producing ability and high by-product reduction) on strains having high lactic acid resistance in the mid- to long-term, or #26-5 having relatively low lactic acid resistance but still good lactic acid resistance.

In the present invention, further research was conducted on #26-5, which was expected to be developed within a shorter period.

Example 3: Comparison of Gene Expression Before and after Adaptive Evolution

In this example, changes in gene expression for YBC5 and #26-5 due to adaptive evolution were observed based on qPCR. Total RNA was extracted from samples cultured in each YPDU medium at 30° C. and 200 rpm for 24 hours, the RNA was analyzed through NGS, and then the change in the expression level of the same gene was analyzed and shown in Table 6.

[Table 6]

Changes in gene expression of YBC5 and #26-5 strains and corresponding genes, Category A: Product related, Category B: Zinc finger protein, Category C: Sulfate/Sulfite related protein, Category D: Stress response, Category E: Hexose transporter

| Contig ID | Fold Change* | Uniprot annotation result of Contig | SEQ ID NO: | Category |
|---|---|---|---|---|
| c2862_g1_i1 | −17.8 | sp\|P56511\|LDH_LACPE L-lactate dehydrogenase OS = Lactobacillus pentosus GN = ldh PE = 1 SV = 1 | 18 | A |
| c4821_g17_i3 | 2.00 | sp\|P32467\|HXT4_YEAST Low-affinity glucose transporter HXT4 OS = Saccharomyces cerevisiae (strain ATCC 204508/S288c) GN = HXT4 PE = 1 SV = 1 | 19 | E |
| c4795_g1_i1 | 2.01 | sp\|P29496\|MCM5_YEAST Minichromosome maintenance protein 5 OS = Saccharomyces cerevisiae (strain ATCC 204508/S288c) GN = MCM5 PE = 1 SV = 1 | 20 | D |
| c4321_g4_i2 | 2.04 | sp\|Q12531\|YP015_YEAST Zinc finger protein YPR015C OS = Saccharomyces cerevisiae (strain ATCC 204508/S288c) GN = YPR015C PE = 4 SV = 1 | 21 | B |
| c144_g1_i1 | 2.06 | sp\|P53631\|HXT17_YEAST Hexose transporter HXT17 OS = Saccharomyces cerevisiae (strain ATCC 204508/S288c) GN = HXT17 PE = 3 SV = 1 | 22 | E |
| c2309_g1_i1 | 2.09 | sp\|Q02685\|RMI1_YEAST RecQ-mediated genome instability protein 1 OS = Saccharomyces cerevisiae (strain ATCC 204508/S288c) GN = RMI1 PE = 1 SV = 1 | 23 | D |
| c3558_g1_i1 | 2.09 | sp\|Q12145\|YP013_YEAST Zinc finger protein YPR013C OS = Saccharomyces cerevisiae (strain ATCC 204508/S288c) GN = YPR013C PE = 1 SV = 1 | 24 | B |
| c1715_g1_i1 | 2.10 | sp\|P40352\|RAD26_YEAST DNA repair and recombination protein RAD26 OS = Saccharomyces cerevisiae (strain ATCC 204508/S288c) GN = RAD26 PE = 1 SV = 1 | 25 | D |
| c4733_g1_i1 | 2.16 | sp\|P39692\|MET10_YEAST Sulfite reductase [NADPH] flavoprotein component OS = Saccharomyces cerevisiae (strain ATCC 204508/S288c) GN = MET10 PE = 1 SV = 2 | 26 | C |
| c4679_g6_i1 | 2.23 | sp\|P39959\|YEW0_YEAST Zinc finger protein YER130C OS = Saccharomyces cerevisiae (strain ATCC 204508/S288c) GN = YER130C PE = 4 SV = 2 | 27 | B |
| c4955_g2_i1 | 2.28 | sp\|P33400\|PACC_YEAST pH-response transcription factor pacC/RIM101 OS = Saccharomyces cerevisiae (strain ATCC 204508/S288c) GN = RIM101 PE = 1 SV = 2 | 28 | D |
| c8855_g1_i1 | 2.39 | sp\|Q08032\|CDC45_YEAST Cell division control protein 45 OS = Saccharomyces cerevisiae (strain ATCC 204508/S288c) GN = CDC45 PE = 1 SV = 1 | 29 | D |
| c7636_g1_i1 | 2.42 | sp\|Q12749\|SMC6_YEAST Structural maintenance of chromosomes protein 6 OS = Saccharomyces cerevisiae (strain ATCC 204508/S288c) GN = SMC6 PE = 1 SV = 1 | 30 | D |

-continued

| Contig ID | Fold Change* | Uniprot annotation result of Contig | SEQ ID NO: | Category |
|---|---|---|---|---|
| c4682_g2_i1 | 2.50 | sp|Q02805|ROD1_YEAST Protein ROD1 OS = Saccharomyces cerevisiae (strain ATCC 204508/S288c) GN = ROD1 PE = 1 SV = 1 | 31 | D |
| c4154_g1_i1 | 2.50 | sp|P18408|MET16_YEAST Phosphoadenosine phosphosulfate reductase OS = Saccharomyces cerevisiae (strain ATCC 204508/S288c) GN = MET16 PE = 1 SV = 2 | 32 | C |
| c422_g1_i1 | 2.50 | sp|P47169|MET5_YEAST Sulfite reductase [NADPH] subunit beta OS = Saccharomyces cerevisiae (strain ATCC 204508/S288c) GN = MET5 PE = 1 SV = 1 | 33 | C |
| c3775_g2_i1 | 2.57 | sp|Q6FJA3|PDC1_CANGA Pyruvate decarboxylase OS = Candida glabrata (strain ATCC 2001/CBS 138/JCM 3761/NBRC 0622/NRRL Y-65) GN = PDC1 PE = 3 SV = 1 | 34 | A |
| c4997_g1_i1 | 2.62 | sp|Q12139|YP022_YEAST Zinc finger protein YPR022C OS = Saccharomyces cerevisiae (strain ATCC 204508/S288c) GN = YPR022C PE = 1 SV = 1 | 35 | B |
| c7526_g1_i1 | 2.63 | sp|P47169|MET5_YEAST Sulfite reductase [NADPH] subunit beta OS = Saccharomyces cerevisiae (strain ATCC 204508/S288c) GN = MET5 PE = 1 SV = 1 | 36 | C |
| c10116_g1_i1 | 2.83 | sp|P53721|RCF2_YEAST Respiratory supercomplex factor 2, mitochondrial OS = Saccharomyces cerevisiae (strain ATCC 204508/S288c) GN = RCF2 PE = 1 SV = 1 | 37 | D |
| c2453_g4_i1 | 2.86 | sp|P53035|MIG2_YEAST Regulatory protein MIG2 OS = Saccharomyces cerevisiae (strain ATCC 204508/S288c) GN = MIG2 PE = 1 SV = 1 | 38 | A, B, D |
| c8818_g1_i1 | 2.88 | sp|Q05937|STP3_YEAST Zinc finger protein STP3 OS = Saccharomyces cerevisiae (strain ATCC 204508/288c) GN = STP3 PE = 1 SV = 1 | 39 | B |
| c4613_g5_i1 | 2.89 | sp|P39005|KRE9_YEAST Cell wall synthesis protein KRE9 OS = Saccharomyces cerevisiae (strain ATCC 204508/S288c) GN = KRE9 PE = 3 SV = 1 | 40 | D |
| c4552_g7_i1 | 2.92 | sp|P30624|LCF1_YEAST Long-chain-fatty-acid--CoA ligase 1 OS = Saccharomyces cerevisiae (strain ATCC 204508/S288c) GN = FAA1 PE = 1 SV = 1 | 41 | D |
| c5170_g1_i1 | 2.94 | sp|P39003|HXT6_YEAST High-affinity hexose transporter HXT6 OS = Saccharomyces cerevisiae (strain ATCC 204508/S288c) GN = HXT6 PE = 1 SV = 2 | 42 | E |
| c2749_g2_i1 | 3.11 | sp|Q04894|ADH6_YEAST NADP-dependent alcohol dehydrogenase 6 OS = Saccharomyces cerevisiae (strain ATCC 204508/S288c) GN = ADH6 PE = 1 SV = 1 | 43 | A |
| c2564_g1_i1 | 3.16 | sp|P38079|YRO2_YEAST Protein YR02 OS = Saccharomyces cerevisiae (strain ATCC 204508/S288c) GN = YRO2 PE = 1 SV = 1 | 44 | D |
| c2992_g1_i1 | 3.33 | sp|Q12117|MRH1_YEAST Protein MRH1 OS = Saccharomyces cerevisiae (strain ATCC 204508/S288c) GN = MRH1 PE = 1 SV = 1 | 45 | D |
| c4074_g1_i1 | 3.56 | sp|Q6FXQ8|MET3_CANGA Sulfate adenylyltransferase OS = Candida glabrata (strain ATCC 2001/CBS 138/JCM 3761/NBRC 0622/NRRL Y-65) GN = MET3 PE = 3 SV = 1 | 46 | C |
| c4925_g1_i1 | 3.84 | sp|Q12531|YP015_YEAST Zinc finger protein YPR015C OS = Saccharomyces cerevisiae (strain ATCC 204508/S288c) GN = YPR015C PE = 4 SV = 1 | 47 | B |
| c4569_g1_i1 | 3.97 | sp|Q99252|ECM3_YEAST Protein ECM3 OS = Saccharomyces cerevisiae (strain ATCC 204508/S288c) GN = ECM3 PE = 1 SV = 1 | 48 | D |
| cl919_g1_i1 | 4.14 | sp|P40489|XBP1_YEAST Transcriptional repressor XBP1 OS = Saccharomyces cerevisiae (strain ATCC 204508/S288c) GN = XBP1 PE = 1 SV = 1 | 49 | D |
| c2966_g3_i1 | 4.76 | sp|P39003|HXT6_YEAST High-affinity hexose transporter HXT6 OS = Saccharomyces cerevisiae (strain ATCC 204508/S288c) GN = HXT6 PE = 1 SV = 2 | 50 | E |

| Contig ID | Fold Change* | Uniprot annotation result of Contig | SEQ ID NO: | Category |
|---|---|---|---|---|
| c6180_g1_i1 | 5.05 | sp|Q12340|YRM1__YEAST Zinc finger transcription factor YRM1 OS = Saccharomyces cerevisiae (strain ATCC 204508/S288c) GN = YRM1 PE = 1 SV = 1 | 51 | B |
| c494_g1_i1 | 5.31 | sp|Q12325|SUL2__YEAST Sulfate permease 2 OS = Saccharomyces cerevisiae (strain ATCC 204508/S288c) GN = SUL2 PE = 1 SV = 1 | 52 | C |
| c2966_g2_i1 | 5.34 | sp|P39003|HXT6__YEAST High-affinity hexose transporter HXT6 OS = Saccharomyces cerevisiae (strain ATCC 204508/S288c) GN = HXT6 PE = 1 SV = 2 | 53 | E |
| c849_g1_i1 | 5.36 | sp|Q12145|YP013__YEAST Zinc finger protein YPR013C OS = Saccharomyces cerevisiae (strain ATCC 204508/S288c) GN = YPR013C PE = 1 SV = 1 | 54 | B |
| c2966_g1_i1 | 6.09 | sp|A6ZT02|HXT4__YEAS7 Low-affinity glucose transporter HXT4 OS = Saccharomyces cerevisiae (strain YJM789) GN = HXT4 PE = 3 SV = 1 | 55 | E |
| c2749_g1_i1 | 6.51 | sp|Q04894|ADH6__YEAST NADP-dependent alcohol dehydrogenase 6 OS = Saccharomyces cerevisiae (strain ATCC 204508/S288c) GN = ADH6 PE = 1 SV = 1 | 56 | A |
| c7728_g1_i1 | 7.51 | sp|Q12442|IZH2__YEAST ADIPOR-like receptor IZH2 OS = Saccharomyces cerevisiae (strain ATCC 204508/S288c) GN = IZH2 PE = 1 SV = 2 | 57 | D |

*Evolution strain/origin strain fold change − means expression decrease, and evolution strain/origin strain fold change + means expression increase Expression levels of various genes were increased or decreased in the strains of the selected colonies through adaptive evolution, but the most striking difference is the weakened part of LpLDH (LDH derived from *Lactobacillus plantarum*), which is responsible for lactic acid production. It has clearly shown that the LDH enhancement study is needed. However, despite the weakening of LDH, as a result of selection of only strains that produce rapidly lactic acid by the present inventors, it was found that the expression of several transporter genes that transport sugar into cells from the outside was enhanced in the strain #26-5. This is considered to be the main reason for acquiring rapid lactic acid-producing ability, despite the weakening of LpLDH.

Acid-resistant recombinant #26-5 strain was deposited with KCTC on Jun. 15, 2020 (Accession No. KCTC 14215).

Example 4: Fermenter Operation Using Selected Adaptive Evolution Strain

In this example, the #26-5 strain selected as adaptive evolution in Example 3 was cultured in a bioreactor and the lactic acid fermentation performance thereof was determined.

The #26-5 strain was primarily and secondarily seeded in 40 ml and 380 ml, respectively, in mYP medium (10 g/L peptone, 5 g/L yeast extract, 5 g/L $KH_2PO_4$, 2 g/L $MgSO_4.7H_2O$, 0.3 g/L uracil), cultured at 30° C. at 200 rpm for 2 days, and all cells were harvested. The cells were inoculated in 1.18 L mYP medium and then cultured at 30° C. At this time, the concentration of each of the components of the mYP medium was adjusted with respect to a volume of 1.7 L including both the additional sugar solution and $CaCO_3$ solution. The culture was initiated at an inoculation OD of 1.73, and 100 ml of 42.33% $CaCO_3$ was mixed with 450 ml of 62.5% sugar solution in separate feeding bottles, and the mixture of sugar and $CaCO_3$ was injected into a bioreactor while the bottle was continuously mixed at 400 rpm with a magnetic stirrer such that $CaCO_3$ was homogenized in the solution. In addition to this method of injecting a mixture of $CaCO_3$ with a sugar solution, in some fermentations, $CaCO_3$ may be injected in a predetermined amount (5-10 ml) once every 2 hours, separately from the sugar solution. However, the mixture of $CaCO_3$ with a sugar solution was injected in consideration of the fact that it is possible to minimize the increase in $CO_2$ concentration due to the introduction of $CaCO_3$ and thereby to improve fermentation performance when injecting small amounts as evenly as possible. In commercial fermentation, $CaCO_3$ may be directly injected without mixing with water, so a decrease in lactic acid concentration due to additional water can be avoided. However, in a laboratory scale, sterilized $CaCO_3$ was injected as a solution phase. In addition, $CaCO_3$ may be injected at a uniform mix ratio of the sugar and $CaCO_3$ during the entire fermentation process. In some cases, most of $CaCO_3$ was added within 24 hours after inoculation at which initial strain growth actively occurs, and only sugar solution was injected thereafter (based on fermentation ID 60). The injection rate and aeration rate of the sugar and $CaCO_3$ mixture were different in respective batches, but based on the fermentation ID F60 in Table 7, the injection rate of the mixed solution was 13.5 ml/hr during the initial 2 hours, and was 15.3 ml/hr thereafter. Based on F60, the culture was performed at an aeration rate of 0.7 lpm and at a stirring rate of 700 rpm during the cell growth phase. After 20 hours, the culture condition was gradually changed therefrom to an aeration rate of 0.35 lpm and a stirring rate of 600 rpm.

Figure 3:
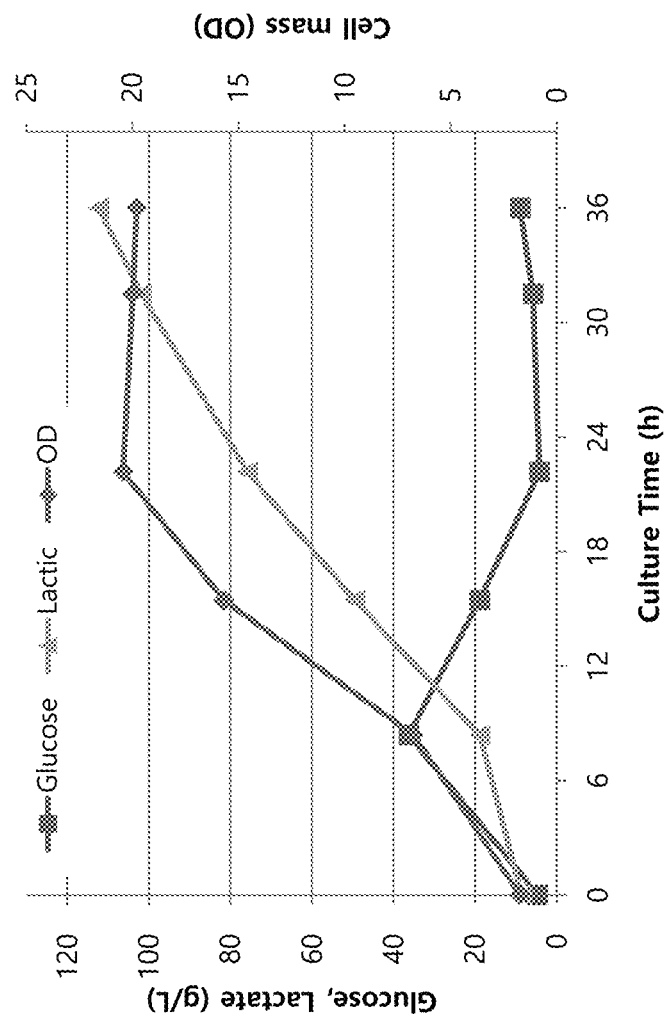
FIG. 3 shows a fermentation profile of strain #26-5, selected from a colony imparted with increased lactic-acid resistance by adaptive evolution of the YBC5 strain according to the present invention.

The results of fermentation culture using strain #26-5 are shown in FIG. 3.

The result of #26-5 strain fermentation showed that the production rate of lactic acid is 2.54 g/L/hr, the yield is 0.67 g/g, and the lactic acid concentration is 123 g/L. That is, lactic acid production rate and concentration are excellent, but there is a problem of a decrease in yield compared to YBC5. This problem is caused by production of each of ethanol and glycerol at 7 g/L during the fermentation. This problem is due to the LDH weakening and ethanol-producing gene expression that occurred as side effects of adaptive evolution, which has the effects of increasing the fermentation rate and resistance to lactic acid. The method to offset these side effects is to enhance LDH and remove the corresponding ethanol-producing gene, among which the method of enhancing LDH was performed in Examples 5 to 7. The concentration of sugar shown in FIG. 3 is the concentration of sugar in the reactor during the process of injecting a mixture of sugar and $CaCO_3$ in a fed-batch manner. Commercial fermentation may be performed in a batch manner in which the total amount of sugar is injected in the initial stage, while $CaCO_3$ is separately injected. In the same way, it is possible to operate and optimize fermentation in a fed-batch or a semi-fed batch manner, in which a part of sugar is injected during fermentation as an appropriate combination with the fed-batch.

Figure 4:
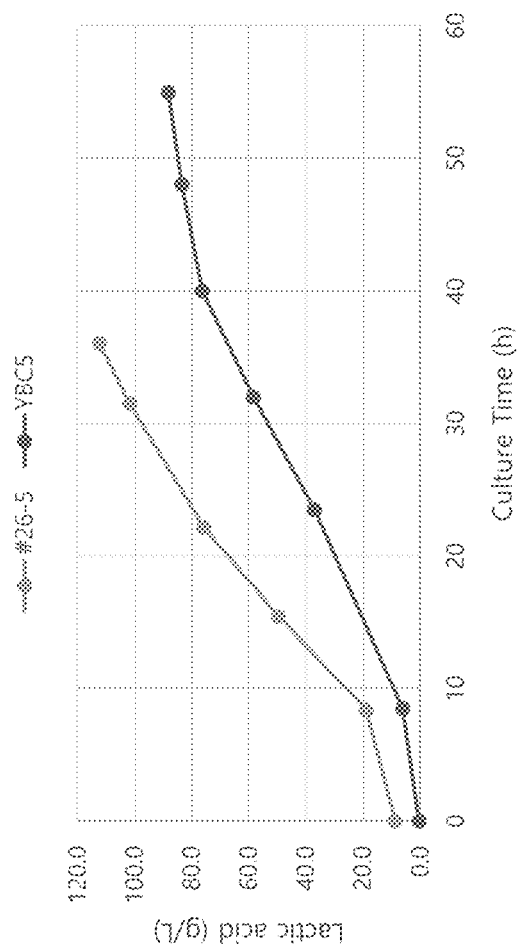
FIG. 4 shows the result of a comparison of the fermentation profile between the strains #26-5 and YBC5 according to the present invention.

FIG. 4 shows the results of comparison only in the lactic acid concentration between strain #26-5 and strain YBC5 during fermentation. The strain #26-5 exhibited increases in fermentation rate and lactic acid production concentration The functions and importance of aeration in acid-resistant fermentation have already been described above, and aeration should be maximized until 24 hours, which is the cell growth period, and maintained at a minimum value thereafter. However, even during the cell growth phase, excessive aeration caused a decrease in the lactic acid yield (refer to F57 fermentation in Table 7). The effect of the aeration rate for maintaining cell activity after 24 hours on the yield were very sensitive, so in the case of lowering to 0.3 lpm or less from the optimal aeration rate of 0.35 lpm, based on 2 L culture, the lactic acid production rate was remarkably lowered or in serious cases, the lactic acid production stopped, and the yield decreased in inverse proportion with the aeration rate when aeration rate is 0.4 lpm or more. The aeration rate may be expressed as the oxygen transfer rate or the oxygen inflow rate into the cells. However, the aeration rate is affected by the structure of the reactor, the shape of the stirrer, and the air discharge form of the sparger and thus should be re-optimized when these factors are changed. This is not very difficult for those who have knowledge associated with microbial cell culture to perform the re-optimization.

The fermentation results for various condition changes are shown in Table 7 below.

TABLE 7

Results of optimization of conditions including sugar injection and aeration in culture using #26-5 strains

| Culture ID | Fermentation conditions | Final pH | Lactic acid yield (g/g) | Lactic acid production rate (g/L/hr) | Lactic acid production concentration (g/L) |
|---|---|---|---|---|---|
| F55 | Seed 188 ml, total volume 1.68 L, intermittent injection of 20% $CaCO_3$ compared to sugar separately from sugar solution, Aeration 1.0 lpm --> 0.3 lpm, Stirring rate 600 rpm--> 500 rpm | 3.46 | 0.74 | 2.23 | 106 |
| F56 | Seed 188 ml, total volume 1.65 L, intermittent injection of 20% $CaCO_3$ compared to sugar separately from sugar solution (reduced injection interval), Aeration 1.0 lpm --> 0.3 lpm, Stirring rate 600 rpm--> 500 rpm | 3.4 | 0.72 | 2.25 | 107 |
| F57 | Seed 188 ml, total volume 1.65 L, intermittent injection of 20% $CaCO_3$ compared to sugar separately from sugar solution (reduced injection interval), Aeration 1.0 lpm --> 2.0 lpm --> 0.6 lpm, Stirring rate 600 rpm--> 900 rpm | 3.52 | 0.63 | 2.11 | 102 |
| F58 | Seed 188 ml, total volume 1.53 L, consecutive injection by mixing with 20% $CaCO_3$ sugar solution compared to sugar, Aeration 1.0 lpm --> 0.4 lpm, Stirring rate 600 rpm--> 800 rpm --> 500 rpm | 3.42 | 0.65 | 2.19 | 105 |
| F59 | Seed 384 ml, total volume 1.73 L, consecutive injection by mixing with 15% $CaCO_3$ sugar solution compared to sugar, Aeration 1.0 lpm --> 1.1 lpm ---> 0.4 lpm, Stirring rate 600 rpm--> 700 rpm --> 500 rpm | 3.23 | 0.68 | 2.39 | 116 |
| F60 | Seed 380 ml, total volume 1.73 L, consecutive injection by mixing with 15% $CaCO_3$ sugar solution compared to sugar, Aeration 0.7 lpm --> 0.35 lpm, Stirring rate 700 rpm--> 600 rpm | 3.14 | 0.67 | 2.54 | 123 | compared to YBC5 strain, which is considered to be due to increased lactic acid resistance. However, as described above, the lactic acid yield of the YBC5 strain was 0.81 to 0.83 g/g, whereas the lactic acid yield of the #26-5 strain was 0.63 to 0.72 g/g, and the yield in the vicinity of pH 3 was 0.67 to 0.68 g/g (refer to F59 and F60 in Table 6).

Example 5: Comparison of Effect of LDH Introduced at Site g3002-1 of YBC Strain 2 copies of each of LpLDH derived from *L. plantarum* (SEQ ID NO: 3), LDH derived from *Bos taurus* (BtLDH)

(SEQ ID NO: 58) or LDH derived from *S. epidermidis* (SeLDH) (SEQ ID NO: 1) were introduced at the PDC (g3002-1) site of the YBC strain.

Figure 5:
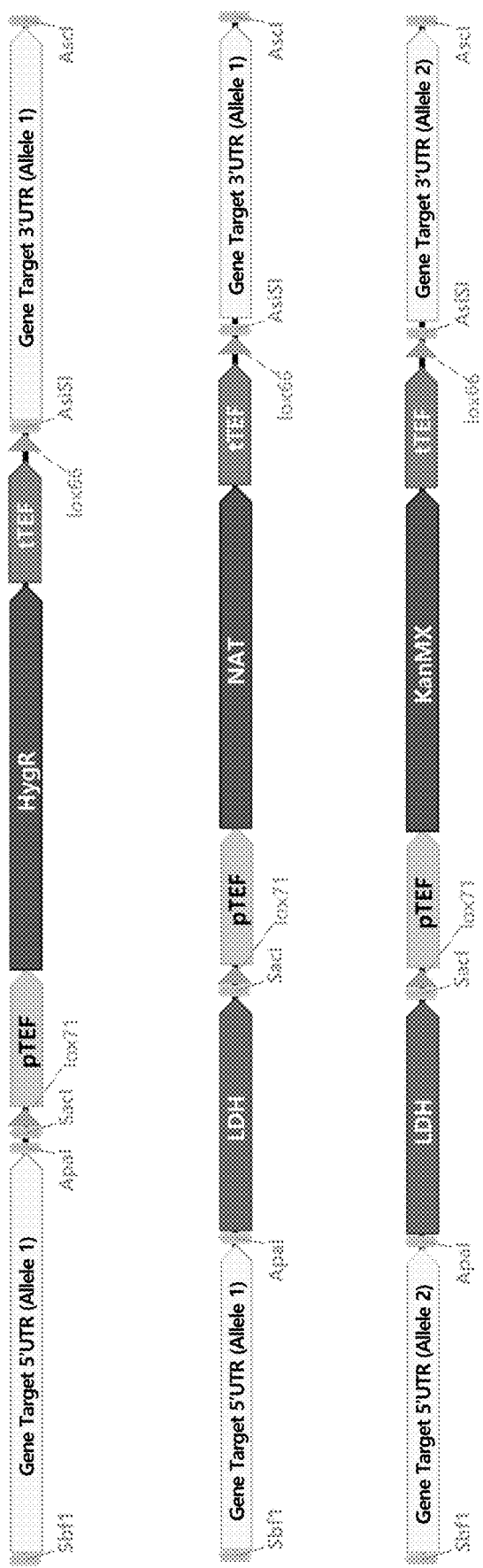
FIG. 5 shows an example of a cassette used for the deletion of the PDC1 (g3002-1) gene from the genome of strain #26-5, which is an improved variant of the YBC strain, YBC1 strain, and YBC5 strain, for insertion of the LDH gene at the position where the corresponding gene was deleted, or for exchange of the already inserted LDH gene with another LDH gene.

The method of constructing the strain is as follows:

The g3002-1 gene, the main PDC gene of the YBC strain, was removed and the yeast codon-optimized LDH gene of SEQ ID NO: 3 derived from *Lactobacillus plantarum* was introduced at the site of g3002-1 to obtain a strain. Based on the information of g3002-1 and UTR thereof, the ORF of each gene was removed, LpLDH was introduced at the site thereof, and a gene cassette containing the 5' and 3' UTRs of g3002-1 was produced and used as donor DNA (see an example of gene cassette in FIG. 5). In addition, the g3002-1 gene is a gene that is located at the scaffold 72 in the genome sequencing of the YBC strain and acts as a PDC gene. For simplification of the gene substitution process, the donor cassette was produced for one allele without considering allele variation, but may be produced for each of alleles. For each allele of g3002-1, the corresponding 5' UTR is shown in SEQ ID NO: 59 and SEQ ID NO: 60, and the 3' UTR is shown in SEQ ID NO: 61 and SEQ ID NO: 62. As described above, cloning method using a restriction enzyme and a method using Gibson assembly may be used for the production of donor DNA, but the overall gene sequence may be synthesized and used. This recombinant strain was designated as "YBClp".

In order to verify the correct execution of the genetic manipulation, the transformant was identified using the following primers, and if necessary, the correct transformant was identified through sequencing of the genome part.

Similarly, the strain introduced with the BtLDH gene was designated as "YBCbt", the strain introduced with the SeLDH gene was designated as "YBCse", and the primers used to identify the genome are as follows.

```
Forward for identifying 3002-1 ORF:
                                  (SEQ ID NO: 63)
GCAGGATATCAGTTGTTTG Reverse for identifying 3002-1 ORF:
                                  (SEQ ID NO: 64)
ATAGAGAAGCTGGAACAG Forward for identifying 3002-1 UTR:
                                  (SEQ ID NO: 65)
GCAGGATATCAGTTGTTTG Reverse for identifying 3002-1 UTR:
                                  (SEQ ID NO: 66)
CAGAATCTTAGAAAGGAGG Forward for identifying introduction of LpLDH,
BtLDH and SeLDH:
                                  (SEQ ID NO: 67)
GCAGGATATCAGTTGTTTG Reverse for identifying introduction of LpLDH:
                                  (SEQ ID NO: 68)
AATACCTTGTTGAGCCATAG Reverse for identifying introduction of BtLDH:
                                  (SEQ ID NO: 69)
ACCTTCTTGTTGTCTAGC Reverse for identifying introduction of SeLDH:
                                  (SEQ ID NO: 70)
ATAACTCTTTCAGCTGGC
```

An experiment was performed on the transformant genotype of which was identified through 50 ml flask culture at 30° C. and 150 rpm. The inoculation OD was 0.1, the medium used herein was YP medium (20 g/L peptone, 10 g/L yeast extract), 6% of glucose was used and uracil 150 mg/L was added.

The results are shown in Table 8.

TABLE 8

Comparison of effect of LDH introduced at g3002-1 (PDC) site

| ID | Lactic acid (g/L) | Yield (g/g) |
|---|---|---|
| LpLDH | 1.1 | 0.01 |
| BtLDH | 4.6 | 0.07 |
|  | 3.2 (sugar concentration 2%) | 0.16 (sugar concentration 2%) |
| SeLDH | 24.5 | 0.39 |

As shown in Table 8, there was a marked difference in lactic acid production due to the change of LDH in the same genome. In particular, the two results that LpLDH substituted at the g4423 genome site of YBC exhibited very strong expression corresponding to the yield of 0.5 g/g or more, but was hardly expressed at the site of g3002-1, and that LDH activity was obtained at the g3002-1 site, comparable to that the case of the g4423 site by changing the origin of LDH to SeLDH, are new phenomena that have not been reported to date.

Example 6: Effect of SeLDH Substituted at Site g3002-1 of YBC1 and YBC5 Strains

In order to verify the high activity of SeLDH at the g3002-1 site identified in the example above, the same genetic manipulation was performed on the strains YBC1 and #26-5 (from YBC5).

The genotypes of target YBC1 and YBC5 are as follows.
YBC1: Δg4423::LpLDH
26-5 (from YBC5) Δg4423::LpLDH, Δg3002-72::LpLDH, Δg2947::LpLDH, Δg1544

The cassette and method used herein were similar to those of Example 5. In the case of YBC5, LpLDH at the target position should be substituted with SeLDH, but the primers were changed as follows in order to amplify the part with low similarity between the two LDH sequences and identify the correct transformant based thereon.

Forward for identifying presence of LpLDH: GCAGGATATCAGTTGTTTG (SEQ ID NO: 71)
Reverse for identifying presence of LpLDH: TTTCAAACCAGTACCACCA (SEQ ID NO: 72)
Forward 1 for identifying presence of SeLDH: GCAGGATATCAGTTGTTTG (SEQ ID NO: 73)
Reverse 1 for identifying presence of SeLDH: GAAGAAGAATACAAAGCACC (SEQ ID NO: 74)
Forward 2 for identifying presence of SeLDH: GCAGGATATCAGTTGTTTG (SEQ ID NO: 75)
Reverse 2 for identifying presence of SeLDH: CACCAGCTTTAACAGTAAC (SEQ ID NO: 76)

The strain constructing by introducing SeLDH at the g3002 position of the YBC1 strain is designated as "YBC2se", and the strain constructing by introducing SeLDH at the g3002 position of the YBC5 strain is designated as "YBC6", and genotypes thereof are as follows.

YBC2se: Δg4423::LpLDH, Δg3002-72::SeLDH
YBC6: Δg4423::LpLDH, Δg3002-72::SeLDH, Δg2947::LpLDH, Δg1544

An experiment was performed on the transformant genotype of which was identified through 50 ml flask culture at 30° C. and 150 rpm. At this time, the inoculation OD was 0.1, the medium used herein was YP medium (20 g/L peptone, 10 g/L yeast extract), 5% of glucose was used for YBC2 and YBC2se, 10% of glucose was used for YBC5 and YBC6, and 150 mg/L of uracil was added.

The results are shown in Tables 9 and 10 below.

TABLE 9

Identification of the effect of SeLDH in YBC1 (w/o pH control)

| ID | Yield (g/g) |
|---|---|
| YBC2 | 0.66 |
| YBC2se | 0.88 |

TABLE 10

Identification of the effect of SeLDH in YBC5 (w/o pH control)

| ID | Yield (g/g) |
|---|---|
| #26-5 | 0.55 |
| YBC6 | 0.76 |

As shown in Table 9 and Table 10, YBC2se located at the PDC gene of the YBC1 strain exhibits a high yield under similar conditions compared to YBC2 in which LpLDH is substituted at the same position. Strong LDH expression of SeLDH in addition to PDC blocking cause great improvement in the lactic acid production compared to ethanol production, resulting in a yield substantially similar to the theoretical yield, in consideration of the reduction in the yield related to the production of ATP required to transport lactic acid to the outside of the cells under acid-resistant conditions. In addition, the strain #26-5, which was imparted with improved productivity but reduced yield, by the conventional adaptive evolution, exhibited a great increase in yield under the same conditions as well. This means that the activity of the LDH, which was reduced by adaptive evolution, was greatly improved through SeLDH strongly expressed at the site of g3002-1.

Example 7: Fermenter Operation Using YBC6 Strain

In this example, the YBC6 strain was cultured in a bioreactor and the lactic acid fermentation performance thereof was determined.

The YBC6 strain was primarily and secondarily seeded in 40 ml and 380 ml, respectively, in mYP medium (10 g/L peptone, 5 g/L yeast extract, 5 g/L $KH_2PO_4$, 2 g/L $MgSO_4 \cdot 7H_2O$, 0.3 g/L uracil), cultured at 30° C. at 200 rpm for 2 days, and all cells were harvested. The cells were inoculated in 1.18 L mYP medium and then cultured at 30° C. At this time, the concentration of each of the components of the mYP medium was adjusted with respect to a volume of 1.7 L including both the additional sugar solution and $CaCO_3$ solution. The culture was initiated at an inoculation OD of 1.74, and 100 ml of 42.33% $CaCO_3$ was mixed with 450 ml of 64.4% sugar solution in separate feeding bottles, and the mixture of sugar and $CaCO_3$ was injected into a bioreactor while the bottle was continuously mixed at 400 rpm with a magnetic stirrer such that $CaCO_3$ was homogenized in the solution. However, the mixture of $CaCO_3$ with a sugar solution was injected in consideration of the fact that it is possible to minimize the increase in $CO_2$ concentration (obstruction of oxygen transfer) due to the introduction of $CaCO_3$ and thereby to improve fermentation performance when injecting as evenly as possible. In commercial fermentation, $CaCO_3$ may be directly injected without mixing with water. However, in a laboratory scale, sterilized $CaCO_3$ was injected as a solution phase. In addition, $CaCO_3$ may be injected at a uniform mix ratio of the sugar and $CaCO_3$ during the entire fermentation process. However, in this fermentation, most of $CaCO_3$ was added within 24 hours after inoculation at which initial strain growth actively occurs, and only the sugar solution was injected thereafter. The injection rate of the sugar and $CaCO_3$ mixture was elevated from 4.5 to 18 ml/hr during the initial 8 hours, and was 22.5 ml/hr thereafter. The culture was performed at an aeration rate of 0.5 lpm and at a stirring rate of 600 rpm during the cell growth phase. After 12 hours, the culture was performed at an aeration rate of 0.35 lpm and a stirring rate of 600 rpm, which are gradually changed therefrom. After 33 hours, the culture was performed at an aeration rate of 0.4 lpm and a stirring rate of 600 rpm.

Figure 6:
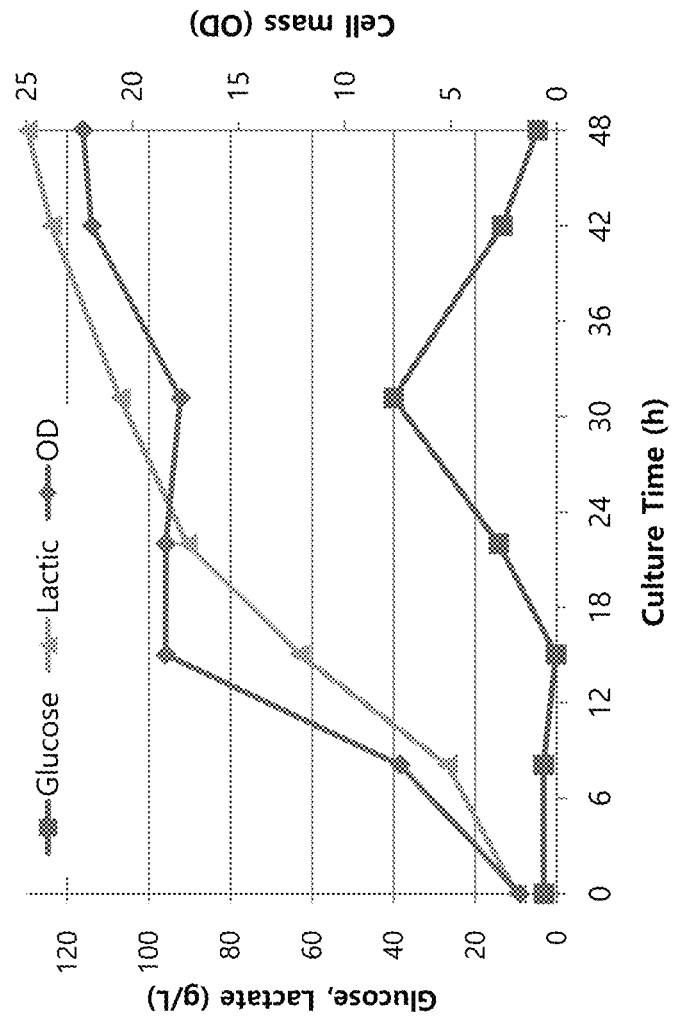
FIG. 6 shows a fermentation profile of YBC6, which is a strain constructed by introducing LDH derived from *S. epidermidis* into the #26-5 strain selected from the strain flora imparted with an improved lactic-acid resistance by adaptive evolution of the YBC5 strain according to the present invention.

The results of fermentation culture using YBC6 strain are shown in FIG. 6.

The concentration of sugar shown in FIG. 6 is the concentration of sugar in the reactor during the process of injecting a mixture of sugar and $CaCO_3$ in a fed-batch manner. Commercial fermentation may be performed in a batch manner in which the total amount of sugar is injected in the initial stage, while $CaCO_3$ is separately injected. In the same way, it is possible to operate and optimize fermentation in a fed-batch or a semi-fed batch in which a part of sugar is injected during fermentation as an appropriate combination with the fed-batch.

The results of culture showed a lactic acid yield of 0.75 g/g a fermentation rate of 2.56 g/L/h and a lactic acid concentration of 130 g/L at pH 3.16, which is the best result among the performance of acid-resistant strains published to date. Cargill's patent relating to acid-resistant strain culture (U.S. Pat. No. 7,232,664) suggests a yield of 0.75 g/g, a fermentation rate of 2.5 g product/L/h, and a lactic acid concentration of 120 g/L as standards for commercialization performance of acid-resistant lactic acid strains. The results of this example achieved the above criteria in all indicators. The example of the U.S. Pat. No. 7,232,664 discloses the total yield of 0.67 g/g, the mean fermentation rate of 0.8 g lactic acid/g-cell/h and the concentration of 114 g/L. The result of the present fermentation showed superior yield and performance than that of this example.

Figure 7:
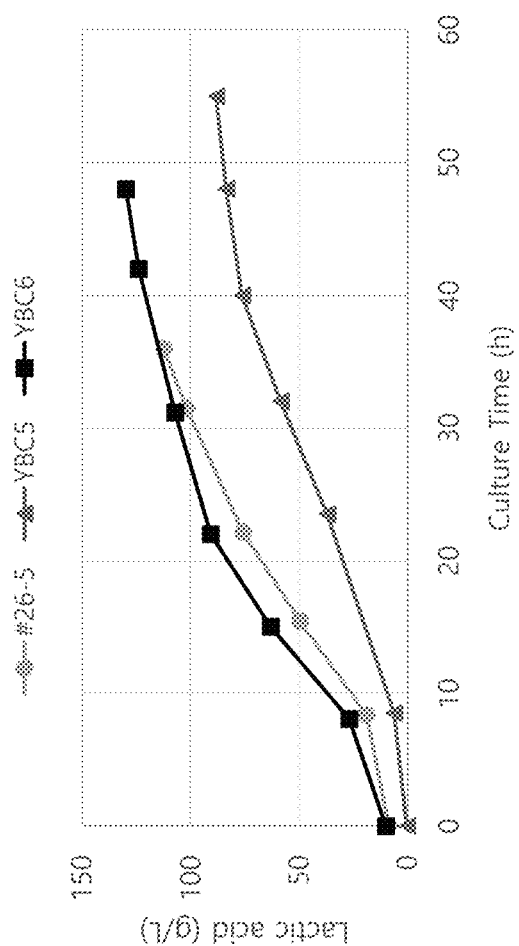
FIG. 7 shows the results of a comparison of the lactic-acid-producing ability among the YBC5 strain, the #26-5 strain, and the YBC6 strain according to the present invention during the fermentation process.

FIG. 7 shows the results of comparison only in the lactic acid production ability among the YBC5 strain and the #26-5 strain and the YBC6 strain, and demonstrates the excellence of lactic acid production of YBC6 due to the combined effects of adaptive evolution with LDH enhancement at the PDC position in the genome.

Name of depository institution: Korea Research Institute of Bioscience and Biotechnology Accession number: KCTC14215BP Deposit Date: 20200615

Although specific configurations of the present invention have been described in detail, those skilled in the art will appreciate that this description is provided to set forth preferred embodiments for illustrative purposes and should not be construed as limiting the scope of the present invention. Therefore, the substantial scope of the present invention is defined by the accompanying claims and equivalents thereto.

What is claimed is:

1. A recombinant strain having lactic-acid-producing ability, wherein the recombinant strain is constructed by deleting a gene encoding a pyruvate decarboxylase from the acid-resistant yeast YBC strain deposited under accession number KCTC13508BP and introducing in said acid-resistant yeast YBC strain deposited under accession number KCTC13508BP a gene encoding a lactate dehydrogenase derived from *Staphylococcus epidermidis* and comprising the sequence of SEQ ID NO: 1 at the position of the gene encoding the pyruvate decarboxylase.

2. The recombinant strain according to claim 1, wherein a gene encoding an alcohol dehydrogenase is further deleted or inactivated by deletion or disruption.

3. The recombinant strain according to claim 1, wherein a gene encoding a glycerol-3-phosphate dehydrogenase that converts dihydroxyacetone phosphate to glycerol-3-phosphate is further deleted or inactivated by deletion or disruption.

4. The recombinant strain according to claim 1, wherein an endogenous gene encoding a lactate dehydrogenase that converts lactate to pyruvate is further deleted or inactivated by deletion or disruption.

5. A recombinant strain having lactic-acid-producing ability, wherein the recombinant strain is constructed by (a) deleting (i) a GPD1 gene, which is a gene encoding an enzyme that converts dihydroxyacetone phosphate to glycerol-3-phosphate, (ii) a CYB2 gene, which is a gene encoding an enzyme that converts lactate into pyruvate, (iii) an ADH gene, which is a gene encoding an alcohol dehydrogenase, and (iv) a PDC gene, which is a gene encoding a pyruvate decarboxylase, from the acid-resistant yeast YBC strain deposited under accession number KCTC13508BP, and (b) introducing in said acid-resistant YBC strain deposited under accession number KCTC13508BP, a gene encoding a lactate dehydrogenase, wherein the gene encoding the lactate dehydrogenase is introduced at the positions of the deleted ADH gene, PDC gene and GPD1 gene, and wherein the gene encoding the lactate dehydrogenase is derived from *Staphylococcus epidermidis* and comprises the sequence of SEQ ID NO: 1.

6. A recombinant strain #26-5 deposited under accession number KCTC14215BP, wherein said recombinant strain #26-5 deposited under accession number KCTC14215BP is constructed by adaptive evolution at a high lactic-acid concentration of a recombinant strain having lactic-acid-producing ability constructed by (a) deleting (i) a GPD1 gene, which is a gene encoding an enzyme that converts dihydroxyacetone phosphate to glycerol-3-phosphate, (ii) a CYB2 gene, which is a gene encoding an enzyme that converts lactate into pyruvate, (iii) an ADH gene, which is a gene encoding an alcohol dehydrogenase, and (iv) a PDC gene, which is a gene encoding a pyruvate decarboxylase, from the acid-resistant yeast YBC strain deposited under KCTC13508BP, and (b) introducing a gene encoding a lactate dehydrogenase comprising the sequence of SEQ ID NO: 1 into the acid-resistant yeast YBC strain deposited under KCTC13508BP.

7. A recombinant yeast YBC6 strain constructed by introducing a gene encoding a lactate dehydrogenase derived from *Staphylococcus epidermidis* and comprising the sequence of SEQ ID NO: 1 at a position of a PDC gene of the recombinant strain #26-5 deposited under accession number KCTC14215BP, the recombinant yeast YBC6 strain having improved lactic-acid-producing ability at a high lactic-acid concentration and suppressed ethanol- and glycerol-producing ability compared to the YBC strain deposited under accession number KCTC13508BP.

8. A method for producing lactic acid comprising:
(a) culturing the strain according to claim 1 to produce lactic acid; and
(b) collecting the produced lactic acid.

9. A method for producing lactic acid comprising:
(a) culturing the strain according to claim 5 to produce lactic acid; and
(b) collecting the produced lactic acid.

10. A method for producing lactic acid comprising:
(a) culturing the strain according to claim 6 to produce lactic acid; and
(b) collecting the produced lactic acid.

11. A method for producing lactic acid comprising:
(a) culturing the strain according to claim 7 to produce lactic acid; and
(b) collecting the produced lactic acid.

\* \* \* \* \*

SEQUENCE LISTING

<160> NUMBER OF SEQ ID NOS: 76

<210> SEQ ID NO 1
<211> LENGTH: 948
<212> TYPE: DNA
<213> ORGANISM: Staphylococcus epidermidis

<400> SEQUENCE: 1

```
atgaaaaaat tggtaaaaa agttgttttg gttggtgatg gttctgttgg ttcttcttat      60
gcttttgcta tggttactca aggtattgct gatgaatttg ttattattga tattgctaaa     120
gataaagttg aagctgatgt taaagatttg aatcatggtg ctttgtattc ttcttctcca    180
gttactgtta aagctggtga atatgaagat tgtaaagatg ctgatttggt tgttattact    240
gctggtgctc cacaaaaacc aggtgaaact agattgcaat tggttgaaaa aaatactaaa    300
attatgaaat ctattgttac ttctgttatg gattctggtt ttgatggttt ttttttgatt    360
gctgctaatc cagttgatat tttgactaga tatgttaaag aagttactgg tttgccagct    420
gaaagagtta ttggttctgg tactgttttg gattctgcta gatttagata tttgatttct    480
aaagaattgg gtgttacttc ttcttctgtt catgcttcta ttattggtga acatggtgat    540
tctgaattgg ctgtttggtc tcaagctaat gttggtggta tttctgttta tgatactttg    600
aaagaagaaa ctggttctga tgctaaagct aatgaaattt atattaatac tagagatgct    660
gcttatgata ttattcaagc taaaggttct acttattatg gtattgcttt ggctttgttg    720
agaatttcta aagctttgtt gaataatgaa aattctattt tgactgtttc ttctcaattg    780
aatggtcaat atggttttaa tgatgtttat ttgggtttgc caactttgat taatcaaaat    840
ggtgctgtta aaatttatga aactccattg aatgataatg aattgcaatt gttggaaaaa    900
tctgttaaaa ctttggaaga tactatgat tctattaaac atttggtt                   948
```

<210> SEQ ID NO 2
<211> LENGTH: 316
<212> TYPE: PRT
<213> ORGANISM: Staphylococcus epidermidis

<400> SEQUENCE: 2

Met Lys Lys Phe Gly Lys Lys Val Val Leu Val Gly Asp Gly Ser Val
1               5                   10                  15

Gly Ser Ser Tyr Ala Phe Ala Met Val Thr Gln Gly Ile Ala Asp Glu
            20                  25                  30

Phe Val Ile Ile Asp Ile Ala Lys Asp Lys Val Glu Ala Asp Val Lys
        35                  40                  45

Asp Leu Asn His Gly Ala Leu Tyr Ser Ser Pro Val Thr Val Lys
    50                  55                  60

Ala Gly Glu Tyr Glu Asp Cys Lys Asp Ala Asp Leu Val Val Ile Thr
65                  70                  75                  80

Ala Gly Ala Pro Gln Lys Pro Gly Glu Thr Arg Leu Gln Leu Val Glu
                85                  90                  95

Lys Asn Thr Lys Ile Met Lys Ser Ile Val Thr Ser Val Met Asp Ser
            100                 105                 110

Gly Phe Asp Gly Phe Phe Leu Ile Ala Ala Asn Pro Val Asp Ile Leu
        115                 120                 125

Thr Arg Tyr Val Lys Glu Val Thr Gly Leu Pro Ala Glu Arg Val Ile
    130                 135                 140

Gly Ser Gly Thr Val Leu Asp Ser Ala Arg Phe Arg Tyr Leu Ile Ser
145                 150                 155                 160

Lys Glu Leu Gly Val Thr Ser Ser Val His Ala Ser Ile Ile Gly
            165                 170                 175

Glu His Gly Asp Ser Glu Leu Ala Val Trp Ser Gln Ala Asn Val Gly
        180                 185                 190

Gly Ile Ser Val Tyr Asp Thr Leu Lys Glu Glu Thr Gly Ser Asp Ala
        195                 200                 205

Lys Ala Asn Glu Ile Tyr Ile Asn Thr Arg Asp Ala Ala Tyr Asp Ile
    210                 215                 220

Ile Gln Ala Lys Gly Ser Thr Tyr Tyr Gly Ile Ala Leu Ala Leu Leu
225                 230                 235                 240

Arg Ile Ser Lys Ala Leu Leu Asn Asn Glu Asn Ser Ile Leu Thr Val
            245                 250                 255

Ser Ser Gln Leu Asn Gly Gln Tyr Gly Phe Asn Asp Val Tyr Leu Gly
        260                 265                 270

Leu Pro Thr Leu Ile Asn Gln Asn Gly Ala Val Lys Ile Tyr Glu Thr
        275                 280                 285

Pro Leu Asn Asp Asn Glu Leu Gln Leu Leu Glu Lys Ser Val Lys Thr
    290                 295                 300

Leu Glu Asp Thr Tyr Asp Ser Ile Lys His Leu Val
305                 310                 315

<210> SEQ ID NO 3
<211> LENGTH: 963
<212> TYPE: DNA
<213> ORGANISM: Lactobacillus plantarum

<400> SEQUENCE: 3

```
atgtcttcta tgccaaatca tcaaaaagtt gttttggttg gtgatggtgc tgttggttct      60
tcttatgctt ttgctatggc tcaacaaggt attgctgaag aatttgttat tgttgatgtt     120
gttaaagata gaactaaagg tgatgctttg gatttggaag atgctcaagc ttttactgct     180
ccaaaaaaaa tttattctgg tgaatattct gattgtaaag atgctgattt ggttgttatt     240
actgctggtg ctccacaaaa accaggtgaa tctagattgg atttggttaa taaaaatttg     300
aatattttgt cttctattgt taaaccagtt gttgattctg ttttgatgg tatttttttg      360 gttgctgcta atccagttga tatttttgact tatgctactt ggaaattttc tggttttcca    420
aaagaaagag ttattggttc tggtacttct ttggattctt ctagattgag agttgctttg     480
ggtaaacaat ttaatgttga tccaagatct gttgatgctt atattatggg tgaacatggt     540
gattctgaat ttgctgctta ttctactgct actattggta ctagaccagt tagagatgtt     600
gctaaagaac aaggtgtttc tgatgatgat ttggctaaat tggaagatgg tgttagaaat     660
aaagcttatg atattattaa tttgaaaggt gctactttt atggtattgg tactgctttg     720
atgagaattt ctaaagctat tttgagagat gaaaatgctg ttttgccagt tggtgcttat    780
atggatggtc aatatggttt gaatgatatt tatattggta ctccagctat tattggtggt   840
actggtttga aacaaattat tgaatctcca ttgtctgctg atgaattgaa aaaaatgcaa    900
gattctgctg ctactttgaa aaaagttttg aatgatggtt tggctgaatt ggaaaataaa   960
taa                                                                 963
```

<210> SEQ ID NO 4
<211> LENGTH: 988
<212> TYPE: DNA
<213> ORGANISM: Artificial Sequence
<220> FEATURE:

<223> OTHER INFORMATION: 5' UTR of g4423 allele 1

<400> SEQUENCE: 4

| | | | | | |
|---|---|---|---|---|---|
| gttaactcag | ttttctctct | ttccctccac | cccacgttac | tctgcgaaca | aaaatacgca | 60 |
| cagaatgaac | atctgattga | ttaatattta | tatattactt | agtggcaccc | ctacaaacaa | 120 |
| accaattttg | aatatttctc | accatcatga | tatttattta | gggcaagaat | ttcatgtaca | 180 |
| tacgtgcgtg | tactgcatag | ttttgttata | tgtaaataac | cagcaatata | tcaccaatga | 240 |
| taaatgctca | gtaatttatt | tggaaccaaa | atagtttcag | taatcaaata | atacaataac | 300 |
| taacaagtgc | tgattataca | acagctgtta | acaacacaaa | cacgctctct | tctattctct | 360 |
| tccctgcttg | ttcgtgtggt | atattcccga | atttgcaatt | tagaaattat | attttttaaa | 420 |
| agaattgttc | tccattttct | ggtagtcgta | agtggcaaat | tggatcataa | gacacaatct | 480 |
| tgttagttcg | actgctaaca | ccagacaaga | ccgaacgaaa | acagaaaaaa | aagataattt | 540 |
| tgttattctg | ttcaattctc | tctctctttt | taaggtatct | ttacattaca | ttacatatcc | 600 |
| caaattacaa | caagagcaag | aaatgaagca | caacaacacg | ccatctttcg | tgattatttt | 660 |
| atcatttcta | tatcgtaact | aaattaacaa | atgctatgtt | tcttaattt | taatgataaa | 720 |
| tctaactgct | accttaattt | ctcatggaaa | gtggcaaata | cagaaattat | atattcttat | 780 |
| tcatttctt | ataattttta | tcaattacca | aatatatata | aatgcaatta | attgattgtt | 840 |
| cctgtcacat | aatttttttt | gtttgttacc | tttattcttt | atccatttag | tttagttctt | 900 |
| atatctttct | tttctatttc | tcttttcgt | ttaatctcac | cgtacacata | tatatccata | 960 |
| tatcaataca | aataaaaatc | atttaaaa | | | | 988 |

<210> SEQ ID NO 5
<211> LENGTH: 961
<212> TYPE: DNA
<213> ORGANISM: Artificial Sequence
<220> FEATURE:
<223> OTHER INFORMATION: 5' UTR of g4423 allele 2

<400> SEQUENCE: 5

| | | | | | |
|---|---|---|---|---|---|
| gttaactcag | ttttctctct | ttccctccac | cccacgttac | tctgcgaaca | aaaaatacgc | 60 |
| acagaatgaa | catctgattg | attaatattt | atatattact | cagtggcacc | cctacaaaca | 120 |
| aaccaatttt | gaatattgtt | caccatcatg | atatttattt | agggcaagaa | tttcatgtac | 180 |
| atacgtgcgt | gtactgcata | gttttgttat | atgaaaataa | ccagcaatat | atcaccaatg | 240 |
| aataaattct | caataattta | tttggaacca | aataatgcaa | taactagcaa | actaagtggt | 300 |
| gattatacaa | cagctgttaa | caacacaaac | atacgctctc | ttctattatc | tcttccctgc | 360 |
| ttgttcgtgt | ggtatattca | cgaatttgca | atttagaaat | tatatttttt | aaagaattg | 420 |
| ttctccattt | tctggtagtc | gtaagtggca | aattggatca | taagacacaa | tcttgttagt | 480 |
| tcgactgcta | acaccagaca | acaccgaacg | aaaacaagaa | aaaataatta | ttctctctct | 540 |
| ttttaaggta | tcttacatta | catatcccaa | attacaacaa | gagcaagaaa | tgaggcacaa | 600 |
| caacacacca | tcatctttcg | tgattatttt | tatcatttct | atcatgtaat | taaattaaca | 660 |
| aatgttaagt | ttattaattt | ttaatgataa | atctagttgc | taccttaatt | tctcatggaa | 720 |
| agtggcaaat | actgaaatta | tttaattcta | ctttcatttt | cttataatttt | ttatcaatta | 780 |
| ccaaatatat | ataaatgcaa | ttaattgatt | gttcctgtca | cataattttt | tttgtttgtt | 840 |
| accttattattc | tttatccatt | taatttattt | cttgtatctt | tcttttctat | ttctcttttc | 900 |
| tgtttaatct | caccgtacac | atatatatcc | atatatcaat | acaaataaaa | atcatttaaa | 960 |

-continued a                                                                961

<210> SEQ ID NO 6
<211> LENGTH: 257
<212> TYPE: DNA
<213> ORGANISM: Artificial Sequence
<220> FEATURE:
<223> OTHER INFORMATION: 3' UTR of g4423 allele 1

<400> SEQUENCE: 6
taagtcattt aatttattct tttagaatat atttattttg tctttatttt tgaaatgtta    60
atagtctttt tttttacttt tgaacaaaaa aaagtaaaat taaaacttat cttatatacg   120
cttttaaaca ttaaactcgt taacgaatta tataatgatt ttatcgaact actttatgtt   180
tttttaatag aataatcttc tttattaata taacttacta cttcttaatc ttgttgtcct   240
ccattcgaaa ctcgagt                                                 257

<210> SEQ ID NO 7
<211> LENGTH: 255
<212> TYPE: DNA
<213> ORGANISM: Artificial Sequence
<220> FEATURE:
<223> OTHER INFORMATION: 3' UTR of g4423 allele 2

<400> SEQUENCE: 7
taagtcattt aatttattct tttagaatat atttattttg tctttatttt tgaaatgtta    60
atagtctttt ttttactttg aaaaaaaaaa aaagtaaaat taaacttatc ttatatacgc   120
ttttaaacat taaactcgtt aacgaattat ataatgattt tatcgaacta ctttatgttt   180 tttaataga ataatcttct ttattaatat aacttactac ttcttaatct tgttgtcctc    240
cattcgaaac tcgag                                                   255

<210> SEQ ID NO 8
<211> LENGTH: 19
<212> TYPE: DNA
<213> ORGANISM: Artificial Sequence
<220> FEATURE:
<223> OTHER INFORMATION: g3002-1 UTR-LDH-fwd primer

<400> SEQUENCE: 8
gcaggatatc agttgtttg                                                19

<210> SEQ ID NO 9
<211> LENGTH: 20
<212> TYPE: DNA
<213> ORGANISM: Artificial Sequence
<220> FEATURE:
<223> OTHER INFORMATION: g3002-1 UTR-LDH-rev primer

<400> SEQUENCE: 9 ataccttgt tgagccatag                                                20

<210> SEQ ID NO 10
<211> LENGTH: 375
<212> TYPE: DNA
<213> ORGANISM: Artificial Sequence
<220> FEATURE:
<223> OTHER INFORMATION: 5' UTR of g2947 allele 1

<400> SEQUENCE: 10
atatattttg gctgacattg taattagatg agatccacaa ttttctttt gtttgactgt     60

```
tcgatatgga aaggtggga tgcactatta ttatattcag aagtttattt gtacagttta    120
aagaacaaat agtggctaat cctatcctcg gactaaaaaa aatcgttcac ttctatccta    180
ctgtaaatct tatgaaaatg atgtaattca tatagttact atattttctt tcttttagaa    240
actttatgat atatatatat atataaaagg actaatcacc caactctcaa attcattaaa    300
aagaaatatg tttctatcat cttctttcct tattataccct cgtctaataa taaaaccaaa    360
caattttctg taaag                                                    375

<210> SEQ ID NO 11
<211> LENGTH: 375
<212> TYPE: DNA
<213> ORGANISM: Artificial Sequence
<220> FEATURE:
<223> OTHER INFORMATION: 5' UTR of g2947 allele 2

<400> SEQUENCE: 11
atatattttg gctgacattg taattagatg agatccacaa ttttctttt gtttgactgt     60 tcgatatgga gaaggtggga tgcactatta ttatattcag aagtttattt gtacagcttg    120
aagaacaaat agtggctaat cctatcctcg gactaaaaaa aattgttcac ttttatccta    180
ctgtaaatct tatgaaaatg atgtaattca tatagttact atattttctt tcttttagaa    240
acttcatgat atatatatat atataaaagg actaatcacc caactctcaa atttattaaa    300
aagaaatatg tttctatcat cttcttttct tattataccct tctctaataa taaaaataaa    360 caacttttctg taaag                                                   375

<210> SEQ ID NO 12
<211> LENGTH: 997
<212> TYPE: DNA
<213> ORGANISM: Artificial Sequence
<220> FEATURE:
<223> OTHER INFORMATION: 3' UTR of g2947 allele 1

<400> SEQUENCE: 12
ttgtgactct atggagttta cctattttat ataccactat atcacaaaaa gtaataacaa     60
cttttcaaat ataatacaat attcaataaa tatatttata tattctaaaa tctacgtttt    120
tctctttctt aaaaaaataa acaaactgac cctttcaatc ttcaatgtga tactttactt    180 atttatttc attacacaga aaggtataaa tatatacata acttaatggt ttattcattt    240
cttcttatta gacaacgtgg ttagttgttg tttaacccat tccaataata aatcagtttg    300
taaataacct tcactgttaa atactttatt aatctctaat gaactagtta aagttttctt    360
cttattatct atcaaagtca tattgtaaat tggtttattt tcttcaaatt ctgtctttaa    420
tttaattatt tcagtaccat tcttaccact atatacgata gattttttcaa catatttctt    480 aaagaaccaa atattacag atagtacaaa atatgtaccg actaaaattt gttgatattt    540
aacgatatta tcatgaacaa atttttttatc aatgatgaaa ctgattgctg caacgatggc    600
agttgaataa ccaattaata atttctgatc aactaattca aaggtttctt catagcctaa    660 tctttttcatg acatcaggta gactttcatt tatagtttgt gatacttcag agatggaata    720
aacgttaacg ggcttactca ttgtgcttta aaggagaatg cggaattaat gagctcttta    780
ctatgtatca gaactcgaac taatgcaaag acaaatggaa taaactagtt acaatatata    840
tgaattttgt ctgttctttt ataatatatt ataatggatt tcccaaattg atgattattg    900
gttcactaag aaaagctagaa agaagatgag atttctcgaa tagtaaaata ttacgttaac    960
atatctgaga ttaaaccgat agtcaatttg tacgtta                             997
```

<210> SEQ ID NO 13
<211> LENGTH: 997
<212> TYPE: DNA
<213> ORGANISM: Artificial Sequence
<220> FEATURE:
<223> OTHER INFORMATION: 3' UTR of g2947 allele 2

<400> SEQUENCE: 13

```
ttgtgactct atggagttta cctattttat ataccactgt atcacaaaaa gtaataacaa      60
cttctcaaat ataatacaat atttaataaa tatatttata tattctaaaa tctacgtttt     120
tctctttctt aaaaaaataa acaaactgac cctttcaatc ttcaatgtga tactttactt     180
atttatttc attacacaga aaggtataaa tatatacata acttaatggt ttattcattt     240
cttcttatta gacagagtgg ttagttgttg tttaacccat tccaataata aatcagtttg     300
taaataaccct tcactgttaa atactttatt aatctctaat gaactagtta aagttttctt     360
cttattatct atcaaagtca tattgtaaat tggtttattt tcttcaaatt ctgtctttaa     420
tttaattatt tcagtaccat tcttaccact atatacgata gattttttcaa catatttctt     480
aaagaaccaa atattacag atagtacaaa atatgtaccg actaaaattt gttgatattt     540
aacgatatta tcatgaacaa attttttatc aatgatgaaa ctgattgctg caacgatggc     600
agttgaataa ccaattaata atttctgatc aactaattca aaggtttctt cataacctaa     660
tcttttcata acatcaggta gactttcatt tatagtttgt gatacttcag agatggaata     720
aacgttaaca ggtttactca ttgtgcttta aaggagaatg cggaattaat gagctcttta     780
ctatgtatca gaactcgaac taatgcaaag aaaaatggaa taaacttgtt acaatatgta     840
tgaattttgt ctattctttt ataataaatt aaatagatt tcccaaattg atgattattg     900
gttcactaag aaagctagaa agaagatgag atttctcgaa tagtaaaata ttaccttaac     960
atatctgaga ttaaaccgat agtcaatttg tacgtta                               997
```

<210> SEQ ID NO 14
<211> LENGTH: 1328
<212> TYPE: DNA
<213> ORGANISM: Artificial Sequence
<220> FEATURE:
<223> OTHER INFORMATION: 5' UTR of g1544 allele 1

<400> SEQUENCE: 14

```
agaaaatagt ttctccgatt aaattttttt ttcaaatcaa atctttattt aagaattggt      60
agtgtatagt agtataatat tgcctaagaa attggagtag tccgtaaaaa atgggacaaa     120
attgttgaaa ttgagcaacc tgaaaatttt atgctggtct caagtagaga aacagacgta     180
gaaccaaaat tgacccaatt tcttgttgcc tttaattggg tcattcataa gaattcaaaa     240
tattttcttt tcccactcac gcgagagata tgcgcacacg atatagttaa taccgcttgt     300
aacaatacgt agatggccaa aaatgaacaa aaggggacac tcctcaaaag aaaaaattgc     360
ttgtttggct gtcttctcca attgaaatat acacacacac cgcggtaaaa aaaaaattga     420
aatggaaatc gcggtgggac aaaagtagca accacaacaa gggaattttc cttactgctg     480
cggcagatcc ttactcatct ctcgaatata tatagcctct tgggtccacg ggcaaaaaag     540
aaataaaaaa aagagaagca acagaaccgc acgcaacgta cgcagtgatc catccatttt     600
ccacaaaatt tatctatttt cttgtctata ttttttacgt acaactaact gatcttcttg     660
tcccctccc cccatttacc cgttaaaatg aaagctgaac aacagaaaat aataattcgc     720
```

```
tctggtggac aaaaaataca agaacaagag agtatcataa ttatgtgggt cacaaatgac    780
cctacaactg tcacctagtt ggtacaaaat ttgaccctca ttctcaaata attactacat    840
ttgggtctgt attaatgcta atatttcaat atatctctat ctatcagtca catacaaatt    900
tatcttcatc ttaaagggac tcacttactc aataatggtc tatctttata ttttttcat     960 acgtatgtat gtacgtagta aagggccatc aatgatccat cttactatta ttattcttta   1020
gttatttcta agcaacaaaa ggtctgtacc acagtttcag tgtcgtcata cctcttcttt   1080
taatttcttt tcggggaggg atgtcttaat gctaacttct gtctcactat taacggtaaa   1140
tcgtattaat ctcaatatat atataaaggg ttgatatttt ccaccgtttt aaaaattatt   1200
cccttgtttc tctattatta attttagact acttatttta attattttc cctttttac    1260 ttattatata tatataacta tatattacca ataataatat aagcaatcac atatatttat   1320
cccattaa                                                            1328
```

<210> SEQ ID NO 15
<211> LENGTH: 1328
<212> TYPE: DNA
<213> ORGANISM: Artificial Sequence
<220> FEATURE:
<223> OTHER INFORMATION: 5' UTR of g1544 allele 2

<400> SEQUENCE: 15

```
agaaaatagt ttctccgatt aaattttttt ttcaaatcaa atctttattt aagaattggt     60
agtgtatagt agtataatat tgcctaagaa attggagtag tccgtaaaaa atgggacaaa    120
attgttgaaa ttgagcaacc tgaaaatttt atgctggtca caagtagaga ataggcgta    180 gaaccaaaat tgacccaatt tcttgttgcc tttaattggg tcattcataa gaattcaaaa    240
tattttcttt tcccactcac gcgagagata tgcgcacacg atataattaa taccgtttgt    300
aacaatacgt agatggccaa aaatgaacaa aatgggacac tcctcaaaag gaaaaattgc    360
ttgtttggct gtcttctcca attgaaatat acacacacac cgcggtaaaa aaaaaattga    420
aattgaaatc gcggtgggac aaaagtagca accacaacaa gggaattttc cttactgctg    480
cggcagatcc ttactcatct cttgaatata tatagcctct tgggtccacg ggcaaaaaag    540
aaaaaaaaaa aagagaagca acagaaccgc acacaacgta cgcagtgatc catccatttt    600
ccacaaaatt tattattt  cttgtctgta ttatttacgt acaactaact gatcttcttg    660 tcccccccc cccatttacc cgttaaaatg aaagctgaac aacagaaaat aataattcgc    720
tctgatggac aaaaaataca agaacaagag agtatcatca ctatgtgggt cacaaatgac    780
cctacaactg taatctagtt gatacaaaat ttgaccctca ttctcaaata attactacat    840
ttgggtctgt attaatacta atatctgtat atctctctat ctatcagtca catacaaatt    900
tatcttcatc ttaaagggac tcacttactc aataatggtc tatctttata ttttatcat    960 acgtatgtat gtacgtagta aagggccatc aatgatccat attattatta ttattcttta   1020
gttatttcta agcaacaaaa ggtctgtacc acagtttcag tgtcgtcata tctcttattt   1080
taatttcttt tcggggaggg atgtcttaat gctaacttct gtctcactat taacggtaaa   1140
tcttattaat ctcaatatat atataaaggg ttgatatttt ccaacgtttt aaaacttatt   1200
cccttgtttc tatattacta atttaacatt acttatttta attattttc cctttttac    1260 ttattatata tataagta catattacca ataataatat aagcaatcac atatatttat    1320
cccattaa                                                            1328
```

```
<210> SEQ ID NO 16
<211> LENGTH: 402
<212> TYPE: DNA
<213> ORGANISM: Artificial Sequence
<220> FEATURE:
<223> OTHER INFORMATION: 3' UTR of g1544 allele 1

<400> SEQUENCE: 16
tccatcatca agaatatata tatataataa agccatccct tttacgaacc tgcctgcatt      60
tgcttaagac cgagcaaaaa aaataaatta caacataacg aaaaaaacaa acaaacttaa     120
gggggagaaa aaaaaataat atcccataac ttacatacac aacatacata aaattaaaaa     180
aataaacatt ttatcaataa ttttttttta agtatatag agctactaat attatagaaa      240
tacagacgca acttaaagaa ctttgttcaa tcttttcaat cttctcagtc ttttctagtc     300
ataataaatt atcaaatgcg aatatttaaa tcaaaattat ataaggggta tatcgtatat    360
atataaattt atcaaatgtg tatatgtatt ttattatgtt ta                        402

<210> SEQ ID NO 17
<211> LENGTH: 402
<212> TYPE: DNA
<213> ORGANISM: Artificial Sequence
<220> FEATURE:
<223> OTHER INFORMATION: 3' UTR of g1544 allele 2

<400> SEQUENCE: 17
tccatcatca aaaatatata tatataataa agccatccct tttacgaacc tgcctgcatt     60
tgcttaagac cgagcaaaaa aaataaatta caatataacg aaaaaaacaa acaaacttaa    120
gggggagaaa aaaaaataat atcccataac ttacatacac aacatacata aaattaaaaa    180
aataaacatt ttatcaataa ttttttttta agtatatat agctactaat attatagaaa    240
tacaaatgca acttaaagaa ctttgttcaa tcttttcaat cttctcaatc ttttctagtc    300
ataataaatt atcaaatgcg aatatttaaa ttaaaattat ataaagggta tatcatatat    360
atataaattt atcaattgtg tatatgtatt ttattatgtt ta                        402

<210> SEQ ID NO 18
<211> LENGTH: 4032
<212> TYPE: DNA
<213> ORGANISM: Artificial Sequence
<220> FEATURE:
<223> OTHER INFORMATION: C2862_g1_i1

<400> SEQUENCE: 18
tctaatattt taatcttttg accaaatatg tttttgtcgc ctattgataa tagaaaaatg     60
taaccttcac aaacaaccct aataccaaga gaacgaaaga tagggtatat atatatcatg    120
aatgaatatc actaacaacg aaatataata ctcactttct cgaggcggcg tccatccata   180
caccgcatac ccattacaag aagccaagtc tgcctgcatt ttttttcttt ttcaataaag    240
aaaagaaaac cggggttttt gcctatttca attatagtta attctccgta gcttaatatc    300
atgttctctc gaaaatgtct tttgtttgca aatacctgca ataagtacaa ataatccggt    360
atgttgaaaa gaacaataaa aaataataag ggccaccgtt acactgtatg gccacacaca    420
ataccgtttg tggtatttcc cgcgtggaac aacaacaact gatttgtttc aaggttgctc    480
tccctccatt ttcacagaat ccaggttctt ggtgggtggc gtgttctggg attcctgtaa    540
tgacaacgcg agacaaagcc aaggagacag aaagggacg gcttctcatc ccatcagtcg     600
cagcaaccgc ggcttcctct agcacgttcc acgctttta tagtggttaa ctcagttttc     660
```

```
tctctttccc tccaccccac gttactctgc gaacaaaaaa tacgcacaga atgaacatct      720
gattgattaa tatttatata ttactcagtg gcacccctac aaacaaacca attttgaata      780
ttgttcacca tcatgatatt tatttagggc aagaatttca tgtacatacg tgcgtgtact      840
gcatagtttt gttatatgaa ataaccagc aatatatcac caatgaataa attctcaata      900
atttatttgg aaccaaataa tgcaataact agcaaactaa gtggtgatta tacaacagct      960
gttaacaaca caaacatacg ctctcttcta ttatctcttc cctgcttgtt cgtgtggtat     1020
attcacgaat ttgcaattta gaaattatat ttttaaaag aattgttctc cattttctgg     1080
tagtcgtaag tggcaaattg gatcataaga cacaatcttg ttagttcgac tgctaacacc     1140
agacaacacc gaacgaaaac aagaaaaaat aattattctc tctcttttta aggtatcttt     1200
acattacatt acatatccca aattacaaca agagcaagaa atgaagcaca acaacacgcc     1260
atctttcgtg attattttat catttctata tcgtaactaa attaacaaat gctatgtttc     1320 ttaatttta atgataaatc taactgctac cttaatttct catggaaagt ggcaaataca     1380
gaaattatat attcttattc attttcttat aattttatc aattaccaaa tatatataaa     1440
tgcaattaat tgattgttcc tgtcacataa tttttttgt ttgttacctt tattctttat     1500
ccatttagtt tagttcttat atctttcttt tctatttctc tttttcgttt aatctcaccg     1560
tacacatata tatccatata tcaatacaaa taaaaatcat ttaaaagggc ccaacaaaat     1620
gtcttctatg ccaaatcatc aaaagttgt tttggttggt gatggtgctg ttggttcttc     1680
ttatgctttt gctatggctc aacaaggtat tgctgaagaa tttgttattg ttgatgttgt     1740
taaagataga actaaaggtg atgctttgga tttggaagat gctcaagctt ttactgctcc     1800 aaaaaaatt tattctggtg aatattctga ttgtaaagat gctgatttgg ttgttattac     1860
tgctggtgct ccacaaaaac caggtgaatc tagattggat ttggttaata aaaatttgaa     1920
tattttgtct tctattgtta aaccagttgt tgattctggt tttgatggta ttttttttggt     1980 tgctgctaat ccagttgata tttttgactta tgctacttgg aaattttctg gttttccaaa     2040
agaaagagtt attggttctg gtacttcttt ggattcttct agattgagag ttgctttggg     2100
taaacaattt aatgttgatc caagatctgt tgatgcttat attatgggtg aacatggtga     2160
ttctgaattt gctgcttatt ctactgctac tattggtact agaccagtta gagatgttgc     2220
taaagaacaa ggtgtttctg atgatgattt ggctaaattg gaagatggtg ttagaaataa     2280
agcttatgat attattaatt tgaaaggtgc tactttttat ggtattggta ctgctttgat     2340
gagaatttct aaagctattt tgagagatga aaatgctgtt ttgccagttg gtgcttatat     2400
ggatggtcaa tatggttttga atgatattta tattggtact ccagctatta ttggtggtac     2460
tggtttgaaa caaattattg aatctccatt gtctgctgat gaattgaaaa aaatgcaaga     2520
ttctgctgct actttgaaaa aagttttgaa tgatggtttg gctgaattgg aaaataaata     2580
agagctctac cgttcgtata atgtatgcta tacgaacggt agcgatcgct ttgtctttat     2640
ttttgaaatg ttaatagtct tttttttta ctttgaacaa aaaaagtaa aattaaaact     2700 tatcttatat acgcttttaa acattaaact cgttaacgaa ttatataatg attttatcga     2760
actactttat gttttttaa tagaataatc ttctttatta ataaactta ctacttctta     2820 atcttgttgt cctccattcg aaactcgaga ggaacaattt ctgagtctct ctcgcaccct     2880
ttcgtacgta ccgttttttcc aatttctttc gggaaacgga actggacgca ttttatttga     2940
ctgttgaaag ggagatttaa tatttatata gagagatata caactaact tataagttta     3000 tacaggctgt tatcacatat atatatat caacagagga ctagctcaat agaataacat     3060
```

```
tagatatgtc gatgctgaac cgtttgtttg gtgttagatc catttcacaa tgtgctactc    3120
gtttacaacg ttctacaggg acaaatatat cagaaggtcc actaagaatt attccacaat    3180
tacaaacttt ctattctgct aatccaatgc atgataacaa tatcgacaag ctagaaaatc    3240
ttctacgtaa atatatcaag ttaccaagta caaataactt attgaagaca catgggaata    3300
catctacaga aatcgatcca acaaaattat tacaatcaca aaattcttca cgtcctttat    3360
ggttatcatt caaggattat acagtgattg gaggtggttc acgtttaaaa cctactcaat    3420
acacagaact tttatttcta ttgaataaac tacatagtat cgatccacaa ttaatgaatg    3480
atgatattaa gaacgaatta gctcattatt ataagaatac ttcacaggaa actaataaag    3540
tcaccatccc taaattggat gaattcggta gaagtattgg aatcggtaga aggaaatccg    3600
caactgcaaa agtctatgta gttagaggtg agggccaagt tcttgtaaat aatagacaaa    3660
ttaacgacta ttttgtcaaa ttaaaggata gagaatctgt aatgtatcca ttacaagtaa    3720
tcaatgggat tgctaattat aatgtattta ttactacatc aggtggtggt tcaactggtc    3780
aagctgacgc cgcaggatta gctattggta aagctttaat tgcattcaat ccattgttaa    3840
agacaagact acatagagcc ggatgtttga ctaccgatta cagacgtgtc gaaagaaaga    3900
aacctggtaa agttaaagct agaaaatcac caacttgggt caaaagatag acgcacacga    3960
tttctttcgt tacatattct tacatatttt aaacatatac attcgtacca tgtaaatatt    4020
aatatcaaca ta                                                        4032
```

<210> SEQ ID NO 19
<211> LENGTH: 3067
<212> TYPE: DNA
<213> ORGANISM: Artificial Sequence
<220> FEATURE:
<223> OTHER INFORMATION: c4821_g17_i3

<400> SEQUENCE: 19

```
caattaactg atggtccatt ctttaacaaa taattttttt tttgttagaa gttatttaa      60 aaggaattaa cagaaaagca atgactgggg tcattaggat tgtcaatata aaagcaacta    120
aactcctaag agtttactgt acgaacggcg ataaggtagt tcatcatact tacttaataa    180
ttacaggaag tgacaataca aaaagaaatc tagttctgga gagaaaacca agggtaagga    240
atgaaacaga actgggaaga gaaggattct tcctgctgtc ctgcgctttt tcctagtgga    300
aatacatgca caaatttttt tttctgatgt atatttcctc tgtgtgaacc acgtagctct    360
gtgaaaaagt atcgtaggct agtttgaatg tggaaaatta gcggggtgg ggccccgata     420 gaggctaaag ttatgttaaa attgtctacg ctagattcac tgaaattaca cgttgaactg    480
gaaaaataat tccccgggt gaatgaaatt tgtcatgcag ctgtaaaacg ggacacagaa      540
aacggcgcat ggtgaaaatt tttcagttgc ttttttggtg gctagtattc aaataatttc    600
tccttgcagc cacatagatg aaaatgaaga agttaaagaa caaaaagatc ccctacaata    660
tagatttgca actacatgca accataatca tggtaacaat tgaacaaaat gcagcagcta    720
aaggtgcaaa ttagtttctt ttgtgcatta atttcgcctg aaataatttt ccttttttt     780 tttttttta tttttttctgg aatcaacatt caaattatct aaagaacctc tgcagaattg    840 ttttatttt cttaaagatc aaccaactta aggaaatttt tttcaaagtt ttgctagtgt      900
tttctctcct ttaacccact tcatccaatg gttattcttg tcgttatgct acgtatttt     960 ccaggcggaa ttgcttttc tgccttgttt tgattattaa atagtttctc cctttattaa    1020
```

-continued

```
taattattcc atgaacaaaa tctcccttc atttgattca gaaatcactg cagattaaag    1080
acactcatgc aagttgaaat tgaattaata aattactttt atttcatgca aagctcaaca    1140
acaaggacaa catgaatgat gaaaattcca aaaagtaact ctttcagaaa taggaaaaaa    1200
aaagatataa aaggtcaacg aatattccaa cttttacaga ataaatttcc tttacaactt    1260
ttcctatttc atatttcatt tcttttgttt attttaaaaa taaaaaacca tacaactaaa    1320
gatttatatt atatctcttt aacaataaca attcagtaaa tatatacttc aatatgtctg    1380
ctgctcctgt tgaagaaaac attaataacg agtctcaaca attgactcca actgcctctg    1440
gctccaactc tgttctatct actccatcta acaaagctga cagagatgaa ctaaaagatg    1500
aagctgaaaa cgctgaagat aatgtcgctg cttttgacga tatgccatta aagccagctt    1560
ccgcttacgt caccgtctcc atcatgtgtg ttatgattgc tttcggtggt ttcgttttcg    1620
gttgggatac tggtaccatt tctggtttcg ttaaccaaac tgattttatt aacagattag    1680
gtcaaaagcg tcacgatggt tctcactact tatccaaggt cagaactggt ttaattgtct    1740 ctatttcaa cattggttgt gctatcggtg gtgttatctt atctaagatc ggtgatgtct    1800
acggtagaag aatcggttta attactgttg ttaccattta cgtcgtcggt ttaattattt    1860
ccattgctac ccaacatgct tggtaccaat atttcattgg tagaattatc tctggtctag    1920
gtgttggtgg tatttctgtt ttatccccaa tgttgatttc tgaagtttct ccaaagcatc    1980
taagaggtcc attagtttcc tgttatcaat tgatgattac tctaggtatt ttcttaggtt    2040
actgtactaa ctacggtacc aagaactact ctaacactgt ccaatggaga gttccattag    2100
gtctaggttt cgcttgggct ttattcatga ttggtggtat gatgtttgtt ccagaatctc    2160
cacgtttctt agtcgaagtt ggtagaaatg aagatgctaa gagatctatt gctgtctcta    2220
ataaggtttc catcgacgat ccatctgtac aagctgaatt agaattatta atggctgctt    2280
ccgaagctga aagattagct ggtaatgctt cctggggtga attattcgct accaagaaca    2340
agattttcca acgtttaatc atggcttgtg ttatccaatc tctacaacaa ttgactggtg    2400 ataactatt cttctactat ggtaccacta ttttcaacgc tgtcggtatg aatgattctt    2460
tcgaaacttc tattgtttta ggtattgtta actttgcttc cactttcgtc ggtatctggg    2520
ctgtttctag attcggtaga agaactctat tattatgggg ttccgcttcc atgactgctt    2580
gtatggttgt tttcgcttct gtcggtgtta ctagattatg ccagatggt gctaaccaca    2640 aggaaaactc ttctaagggt gctggtaact gtatgattgt tttcacatgt ttcttcattt    2700
tctgtttcgc tccaacctgg gctccattag ttttcgttgt ctgttctgaa tctttcccat    2760
tgagagttag atctaagtgt atggctttag ctcaagcttg taactggatc tggggtttct    2820
taattggttt cttcactcct ttcattactg gtgctattaa cttttactat ggttacgttt    2880 tcatggggttg tctatgtttc tcctggttct acgttttctt ctttatccca gaaaccaagg    2940
gtctatctct agaagaagtc gatcaaatgt ggctagaagg tgtcttacca tggaagtctg    3000
ctcaatgggt tccaccatct aagagaggtg ccgaatacga tgccgaagct atggctcatg    3060
atgataa                                                              3067
```

<210> SEQ ID NO 20
<211> LENGTH: 5390
<212> TYPE: DNA
<213> ORGANISM: Artificial Sequence
<220> FEATURE:
<223> OTHER INFORMATION: c4795_g1_i1

<400> SEQUENCE: 20

```
gacaataata aaaaataaag gtgttgaact gtcaacaaaa tacagttaat tgtacggtat      60
gtaattttca tcattcacat cgacttatgt ttatgctgct cctcttcata atctgctaca     120
attaaattgc tctttttttt ttgttatcaa cagaatatat atttcctgag gggggaaaaa     180
agaggtaaga cagttcaatc ttttaacaag ttataagtaa caaggacaaa tgcgtttttt     240
ttgtcaactt ttgattgtat cgcataaaat atttactcca ttgcaaatag aacttattg     300 actataacag taatttcctt tattaataat gaatttattt ctctttatgt atttgcataa     360
taactgggac attttgctc ttgttcagcg gtaaatcgtc tagacgaagc ctatgtatct     420
attaatctat tatagaggtg atgtcccttc gtagtcaata aattctaagt acacatatac     480
atacgtaggg gcactcacac tattatattt attttctttc tttctttat ctggcaatac     540 gatacggaga ccggagaaag aatgttcgtg ggaaaaaaaa acttttttt tttgttctag     600 aaggtttcat tttcaaccag agtaactccg gacaaaaaag ggataccgta aaacccgtg     660 cgagtgagat ttgaattcct atcatatcgc aatttgtcgc aattcatatg gttctttcat     720
tttttcactt acataataaa catttctctt tccccagaat tttttttac ttttatttg     780 acaatagcaa tgaattttaaa ccctgaaata attatattat tgattgatgg agttttcaat     840
acaaagagag agagaaagaa aaagttagaa ttgatatcgt agatggcttt atccacctat     900
tcattcaagt ctgtcagcac ttcatcaggt tagagataag acctaatacg ctggttccac     960
aataattgaa ctaataaatt acactatatt ccttttgtc tctggataaa agatgtatta    1020
tagtttcaag atacatattt gaacgtaca agtaatacaa agttgttaaa accataattt    1080
aataaaaaaa ttctttatgc aacattgatt ggaacgacta caattaaggt tctatatccg    1140
atgcttcaat aatgcgagat tttaagaaag caatatgcct acaagagaat gttaagtaat    1200
ataatcaaga cattttttc ttacaaaagc aaaaaaagt gaaaagtcgg aaatgtctta    1260
agacccgaga atccaggaac cgatgtgaaa aaagtttaat tatcaaatga attaacagt    1320 tattcatacg tacaattaat tcccaatcta atatatattc atatgagtgt agtgtatata    1380
atcttaacta atgcatactt cacttttaat gattacaaaa tgaaacagca ttttaaatct    1440
tattattagc atacccaatc atttaaagta attttatatt tcgaggatag atagtatttc    1500
ttgtcgacat aataacataa gcaaaattct tgtatctcta attaggtaac tcccgctccc    1560
cccccaaaga aaaaacaaac cacttctgca agtttcagtt attaaataat atgggaaagc    1620
gacacattcg gagttttata ttattatcac acatataacg tcatatttat ctataagtgg    1680
taactaatat gccaattttt tacaagaaac aaacgaacac ccatatgtta cggtaatggg    1740
aaacaacata atttgtcaaa tatatggcat atatctatca agttttacct gatatcttca    1800
attcggaaag ttacttgtta tggtaaaaat gaattagctg gcccttaatt tatgacaaga    1860
atgagctatt atctggggta cgtttattta tcgtatacct acttataaga atgtaagaat    1920
aataagtttt gaaagatttg attaagactt tgggaatggt aaaattgtta ataatgattt    1980
attaattact gtcagatatt aaaactccat cgttaccaga agttcattat aatttcaca    2040 tgcttctact aaaatatttt tgttgagctg ttatgcgtgt catttgtgac actgcgatta    2100
tgagtatgtc attcatttaa catcagtttc tccaagttat ttaattttt tagtgtcata    2160 ttgttattac cccaatattg tcatacattt atccccaact aattataata ttctcaataa    2220
ttatagcttg gcgagtaaat cttttcaataa tctgttgaga aaaacctgtc ataaaatatt    2280
acgaatttct tttcaacagg tacaagcaca tgaataatct taactttatt ctctattggt    2340
```

-continued

| | |
|---|---|
| ttaattaaac acttttaaac tgtggaaaca tactaatatg gtttatacag acatgtacgt | 2400 |
| atactccaat ttttatttga aatacatacc ctaatttcag cccttcattt tacgcgtatc | 2460 |
| atcttgaaca gatacaagtt acctaattag gaaatgtaat atcttgaagc caaaaatcta | 2520 |
| ttttttttct ctcttcttcg gaaaacgcgc gatcaatctc tttaccgaat gaggtaatct | 2580 |
| taattacacg aaaaatttc agatatttt ctctctttct cgaacagtgt ttggttaatc | 2640 |
| gaaacataat cgtaaaataa acacataaac cttccgtttg caataccttg ccgtcaattt | 2700 |
| aacacccttt tcatactttt tcaaataatt atattcaact aaaagttaaa aatcagttaa | 2760 |
| ctaacgtatt tttacaacat ttgttaaggg aataatagaa gctatcaaac gttaagttat | 2820 |
| cacacagtta tatcatcaaa caacaatgtc atttgataga ccagaaattt atagtgcgcc | 2880 |
| agttttacaa ggtgttacac caaacgatga tgataacaca gaaattatca aatcctttag | 2940 |
| aaatttatc cttgaattta gaatcgattc acaatttatt tacagagaac aattaagaaa | 3000 |
| tgcattatta gttaagaatt attcattaag tgttaatatg gaacacttaa ttggttataa | 3060 |
| tgaggatctt ttcaaaaaat tgtctgatga accatctgat attatcccat tatttgagaa | 3120 |
| tgcaatcact caagttgcta aaagaatcac tatcctaaat agatctcagg agtctaccac | 3180 |
| aggtaatgga caagcaacag gtgaggatat cgcatctttg attccaccat ttcaattaat | 3240 |
| cctaaattcg aaagctaatc aaattccaat gagagaatta ggttctgaac atgtctccaa | 3300 |
| agttgttaga ttatcaggta ttgttatctc tgcatcagta ttaacatcca gagctacaca | 3360 |
| tttacgtcta atgtgtaaga attgtagaca tacaacatcg atcactgtaa atacattcaa | 3420 |
| ttccattact ggtactcaag tttctttacc acattcctgt ttatctaatg ttcaaactga | 3480 |
| atcaggtcaa gtaagttcca tggaggcaag tgctccacca aaaaattgtg gacctgatcc | 3540 |
| atatatgatt atccatgaag cctctacatt tattgatcaa caatttttga aattacaaga | 3600 |
| aatcccagaa atggtaccag ttggtgagat gccacgtcat ttaagattat catgtgatag | 3660 |
| atatttgaca aataaagttg ttccagggtc tcgtgttaca gtagtcggta tttattccat | 3720 |
| ctataccgct aaaggtgcag gaccaagttc aggtaacgaa ggtggtgtct ctattagaaa | 3780 |
| tccgtatatt aaagtattag gtttacaaac tgatatcgat acaaatactt tctataattc | 3840 |
| tgtttccatg ttttccgaag aagaagaaga agagttttta caactaagta gaaatccaaa | 3900 |
| tatttatgat cttgtcgcta aatctatcgc tccttcaatt ttcggtaatg aggacattaa | 3960 |
| gaaagccatt gtttgtttat tgatgggtgg ttccaagaaa ttattgcccg atgggatgag | 4020 |
| attaagaggt gatatcaacg ttttactact gggtgatcca ggtactgcaa agtctcaatt | 4080 |
| attgaaattc gttgagaaag tctctccaat ctctgtttat acatcaggta agggttcttc | 4140 |
| tgcagcaggt ttaactgcga gtgttcaaag agatccaaca acaagagaat tttatttaga | 4200 |
| aggtggtgct atggttcttg cagatggtgg tgttgtttgt attgatgaat tcgataaaat | 4260 |
| gagagatgaa gatcgtgttg cgatcccatga agcgatggaa caacaaacca tttctattgc | 4320 |
| aaaagcaggt attactacag ttttgaattc aagaacaagt gttcttgcgg cagcaaatcc | 4380 |
| aatctatggt cgttatgatg aaatgaaatc tccaggtgaa atattgatt tccaaacaac | 4440 |
| aattttgtct cgttttgata tgattttcat tgttaaggat gaacatgatg aagcccgtga | 4500 |
| tatctctatc gctaaccacg ttattaatat tcatacaggt cgtgtctcgc aagaacaaga | 4560 |
| agaaatggaa aacaatggtg aagaaataag tatggataaa ttgaagcgtt acattactta | 4620 |
| ttgtagaaga aaatgtgcac caagattatc tgttcaagct gctgaaagat tatcatccca | 4680 |
| attcgttacc attagaaaag aattattaat aaatgaattg aattctactg aacgttcttc | 4740 |

```
aattccaatc actgttcgtc aattagaagc tattattcgt atcactgaat ctttagccaa    4800
attagagtta agtcccgtag ctcacgagag acacgttcaa gaagcaatca gattgtttca    4860
agcatctacc atggatgcag catctcagga tccaatcggt ggtatggatc aacagggaa     4920 ttcaagatct atacttgcag agattcgtga aattgaacaa gaactaaaga gaagattgcc    4980
gattggttgg tcaacatcaa tacaaacatt aagaagagag tttgttgaat ccaatagatt    5040
ttcacaacct gcattagata aagcattata tgcgctagaa aaacatgata ctattcaatt    5100
aagacatcaa ggtcaaaatg tttatagaag tagtatatga tctggtgata acacatgggg    5160
taaagtaatc ttgaatcaaa agtttgtaat attaatacat caatttgtct agattgaaac    5220
atatatatac gtacatacaa ctaatgaata tattctaggc aagagcaaaa ataatacat     5280 agtatatgga tccgattctt atggagattg aagtaaactc aaccagccct atactcttca    5340
atttattctt gagttgtaag ttaaccgaag gacggtcgga acgaacgcag                5390

<210> SEQ ID NO 21
<211> LENGTH: 5128
<212> TYPE: DNA
<213> ORGANISM: Artificial Sequence
<220> FEATURE:
<223> OTHER INFORMATION: c4321_g4_i2

<400> SEQUENCE: 21
attgaaataa ctctttcttt gatacatcac ctaaagacta tcaaacacat ttattaatat     60
taagatttta aaatattaag aaacttttcg tcaaaagtat atttcaaagt ttttttttaat   120 atattcattc agtttaaaaa tctcattaat tcattcatga taatataaga gattttctaa    180
atattttctc acatcatcgt tctacaaaaa taatatatt gcaaaactaa attaaagaag     240
gaattttata attttaagtt ctaactttca actgttttt attgttcaat tttattttca    300
ttaacttttt cacaaaattc tacaagtatt tccttaatga atttaaccgc ttatcatcca    360
tatccaattt ctaaccaatc aacacaatat cataaaactc taatggaaaa tccatcgata    420
ccaaattcaa gtgtagcaac ctcatctatt acaactacgc ccacaaatga tttcaataat    480
gatttacctt caaactctag gagggaatct gaaacaggct ccacaaaggt aacattacca    540
ccaatctcta gtatcatcaa tgctccacaa gaacaacaaa ataaaagtat tagatctgaa    600
atagttgaac ccgaaaactc tacttcttta aggacatctc ctttaacgca gacggatatt    660
caaaattcac agtcaatgaa taatagtact ataactcctg ctggtccagg tattagcact    720
tacgttcaac caatggtaaa ttccagaaga ccttccgcaa cacagcagca aatgaatatt    780
aattatgcta caccaagaaa tggtatggca gtactaggtg gggtttcttc ccaagcaact    840
ccaattggta ccccagggaa tagcccaaac ggtaattatt tagctaatca agcgattata    900
cagcaagaaa atgaagctgc tgcttatgca attcaacaga acaacaatt gcaacagata     960 cagtatcaac aacaagttca agctcaagct caagctccac aacaaggcta ttattatgtt   1020
gttgcaccat ttcaacaaca acaacaagtt caaacgcaag cacaacaaat gccacaaatg   1080
atgccaatgt ctatcactca acaacaaatt gctttccaaa aggctcaagc acaacaggtt   1140
gacgaacaac aggctcagca gcagcatatg cttcaacttg cacaacagca acaacaacaa   1200 gctattttcta catatcctgt tgttgttaat atgccacatc caaatgagat tcaacaacag   1260
caaccgcaac agcaacaggt acggagtccg gaatttgaga ataacgttgt ttatcaagtt   1320
ccaagacaac cagaaggtat aatgaatcaa ggtcaccaa taatggttcc aaccactgct   1380
```

```
attccaacaa gttctcaacc agttcaaaaa ccaacaatga ctgctggtta tgttacatca   1440
gaaggtttaa ttcctgttcc aacaagtatt caatctaatc taagcttagc tgttagatta   1500
cgtaaacaat gcccagtatg tggtaagatt tgttctagac catctacttt gaaaactcat   1560
tatttgatcc acactggtga tacaccattt aaatgtccat ggaagacatg taagaaatct   1620
tttaacgtta agagcaacat gctaagacat ttaaaatgcc atcaaaagaa atcaccaaag   1680
gttactaaag gtggttctaa ttctggtgat gaaaaaaact ctatagacaa tgaaaagaca   1740
attaaggcta ttgaaggggc agtatcatca tctgaaaaac aatcgaaagc tactgatgac   1800
gatgctaaag ctgattcgtt gtcgacagaa attccaaaag aaactaaata actttgctaa   1860
tttgatatta tgcgaactct atattattgc tcaattccga taaacaaaat taatagaagg   1920
aagcaaaaag ggctatctat ataatatttt actacatata aaaatgaata ttcataacta   1980
ttaaacacaa atagaattgt aaagtttcga aaacaggttt ccattaactg ggacaaggat   2040
acgtttctcg gatctgtttg gctgctatat tattaacaat ctatccagtt tccaaaaact   2100
gcacttccct attcataaac tagcatctga ttattttga aagccgattt gagtttcaaa   2160
tcttacttaa tgaaacttta ataatcccct ctgtctctat ctttaagagg ttttgatacc   2220
ataataatct taacaaaagt ccctcatttt caattccgtc aaaattgatt ggttaataat   2280
attcaatgat tgatttgcat atatcgtctc gaatttgagt cttcaagctc actattgtga   2340
catagacaaa atattatctc aaaggataaa gcaaaaaatt aaattgaaat ttcagtaatt   2400
aatcgaatgg tttgttagta attaataatt atgaggtcaa atgaaaacag atcgatactc   2460
gtttcggaaa tgctaagagt aaaccaaaat aaggttttat ttccaaaaaa aggaaagtaa   2520
aaagaaacta tacattgcct attgtggaag gtttagtaaa tctccgaaga acctgcgggc   2580
gagcggatga attttgtttc ctgagaaata aaattttttg atatatctct gtaaatatcc   2640
gtagtactgc tgttgtttcc tagaatattt agaaacatcg aagagaaagg aacgcgggac   2700
aaagaaataa gatttctatg tttagcgtgg gtagtaaggt cacttgtacg tattgttctg   2760
acatcgcata gatatctaca aaattaagtc aatttagaaa agtgatcagc aggtgagaag   2820
atccagtagc caattcatta tttgtgcaca aatttactgc aaaaggttat gtatcttgca   2880
tatccatatc gagacctaat ttaggaattt taatatttta actgtcctca aacttattca   2940
attcatttac ccttctctga ctatttcaaa caaggcactg gaatttctta gataaagaaa   3000
aatataattg caacatttgt ccacattatt gctctgttta acagcgaaaa tcgtgtaaat   3060
tttagtggga aaacataata ttaactacta ccaaattctt tcatgggtac tatcagctta   3120
aggtggaaaa taccaagtgt tcttctatta tctaatagtc cctaagatat ggagggaccc   3180
aagtaagaga tattgaaatg ttccccaaag ctatgcccca cttgaatatg ctttccctt    3240 caagcttcct aaacatgtaa cattcttagt attggataag tgctgactta tataacaagg   3300 ttttctttt aaatccagga tatataaaca aactctaagt aaaaaggtta gagcaccgaa    3360
ctaaacgaaa tcaagaaaga cttcgtttga agcgaattgt atagctcaac caatcaggaa   3420
caatagatca aatatttagt atgatgtgat atattgatgc tactaaaagt taacggaaag   3480
acgaaaatga tatccgatta atcgattatc tcgaatacag taaattatta gaagatgaaa   3540
gataattaaa tttgtgaaac atacctaaat ccaaacacag atcaaatatt agtatgccct   3600
taccacctct taactctttg ttagggtgtt tttagaacaa gctataaatc ataagaggtc   3660
aggtgataag agccactgtg ccgaacctga accgtaagat aatagttgaa gtagtgactg   3720
gaaatagcct ggcccgctat gatctatgta acaagaccag tacacactca caaataggaa   3780
```

```
gttagatacg cacgtgataa gagtgtatgc cttagaagct taagtagata acattgagcg   3840
acaatacaat agtatgtccg ataagagttc cgataagaga acacatgtcc tagttgttct   3900
aataatacaa tagcatatac atgctcgtca acgaggaggt ccctacgtta ggattccttc   3960
cgagtgatta tcaacagtgt ggtatgagac acacgaccag caaataataa agaaagaata   4020
ataataaata aaatataaaa ggacgttaag caagtgctta acgaaagatc caaacagata   4080
tataaaaata agcaatcaag cttaaagata ataattacaa caatcaacac taagattgta   4140
agtgtacata agatacataa tataatataa gaatctacta taaatactct tatcacagaa   4200
aagcgtctaa cacattaact ataactaaga tgattgaatt aactaaacac aaaagacatc   4260
taagacttcg aaagacatcc aagggaatcg aagacatcta cttaatgtag aatctgagaa   4320
tctaggaatc tgagaatcta agaatctgta gttaacatca acaagataca gcttggcact   4380
atcaccaact gaacccatct tagctatgca cacaacatag tctactgtca actctcttaa   4440
ttggaacgaa gaagaactaa gaactaagaa ctacttatga taacttcaga catcttatca   4500
actaagaatc tcgaattatt atactcatga tacagcatag cgtaatgagc aactggatcc   4560
ttatcgtaca agaactatct atcatagaca acgtctcttg taagttccct cgattaatga   4620
aaggaactaa ccaatgactc tttcattcaa taggacaact caataacgac tctcgtgtat   4680
aatctatttc caaacataa attttaacca ccgtaaaaca ccagagccgt tacaaaaaat   4740
tcgaaagttt gattatttgc tattgttaaa tttggaaggt tttctacggc tgtttctagg   4800
cagggagtat taaagataag attatcactt cctaaaacat ttcaaatgag agtaatgtat   4860
tgatatgcat ttgagaatgt acggataata ataatacatc ccatataagt ctaatatatc   4920
aaagaatgat accgtaataa ttcaatcaga ccacatacta aagcttattc tcggtttatt   4980
acgaaaagat atttgtctaa aataagtttt ctaagtattt tgattccatg ttattggcaa   5040
tatatatctc atgaatcaaa tcaagatgtt gcaaatcca ttatgaggtt gttgcaaagt   5100
ccaatatgag gttctaagtt tctatatc                                      5128
```

<210> SEQ ID NO 22
<211> LENGTH: 2759
<212> TYPE: DNA
<213> ORGANISM: Artificial Sequence
<220> FEATURE:
<223> OTHER INFORMATION: c144_g1_i1

<400> SEQUENCE: 22

```
ccattgtcca acactaccaa caataacact aacaccgaag gttcaggggt tgagtccggt     60
gaacacactt tatcgagtat cccacctcaa cataatgcca atacgttctg ttttttttggt    120 ttttattata ttatgtaaat tataaaatct taaatacatg aacgaactga aactcaaatg    180
tgagtccaga tttaccccttt atacacgttg cttttactaa cttaagcttt gatcatcaaa    240
tgaattgtga tttcctaata cttgtgttg tattttttggt accatatttc tgtcacttat     300
gtaaaatgga atatacaata ctactattca attagtgatc agtcagaact ctttgagaac    360
ttgaagtatt cttttccaatc tttcttttca ttctcactct cttctacagg ttttcctctc    420
cttgatgggg gaacccaaga tgcagatttc catggttgta caccttcttc atatagtaat    480
tggatttctt ccaaagacaa accaatcgtt tccggtagaa agaagaaaac atatagaaac    540
atagctacca acaaccgac aaatacgtaa ccatagtaga agtggataga accggtaatg     600
aatggtgtga aaaaccaat caaaaattgc cataaccagt tacatgcggt agaaatcgac     660
```

| | | |
|---|---|---|
| atggctctgg acttgaacct cgaggggaat gattcggcaa ccacaatata agcaacagga | 720 | |
| gcccatgatg ttgcgaagca aaataggtag aaacaggtaa atacaatcat cacattacca | 780 | |
| gcacctttcg aggatggggc actgtcacca tgaggataaa gacatttgac tccgacactt | 840 | |
| gcgaatatga ccatacaggc catcatgcca gctgctccaa ataatagaca tttacgacgg | 900 | |
| ccgatttttgt ccacaactat aacagcaata atagtggaga agaaattcac cgtacccaga | 960 | |
| atgatagaag tctcaaatcc gtcagtaaga cccactgatt tgaaaatagt tgtaccgtaa | 1020 | |
| aagaaaaagt agttttcacc agtaagttgt aaaaacgttt gcactagaat acctgtaatc | 1080 | |
| aaacgctgaa ggatatttga ctcaggtgaa aaaagttcct tccatgaagc ttcaccttgt | 1140 | |
| tcccctttggg caagcacacc ggcgataatt tcttctactt ctccatgtac ccatgcatcc | 1200 | |
| tctggtgaaa tcttgttgat cttggcaata gaagcgcgtg cctcatcatg tctttcctgt | 1260 | |
| tcaaccaagt atcttgggga ttctggaacc aatagcatac caatgatgat aattagggcc | 1320 | |
| cacaaaaagc aaagtccaac agggatcctc cattgtgcag tattattata ctttctggtg | 1380 | |
| ccataaacac tacaataacc taggaaaata ccaaacgtca tgttcaattg atacaatgaa | 1440 | |
| acaagcccac ctctcatgtc tttaggagct atttcagaca aaagcattgg acacaacacc | 1500 | |
| gaacatccac cagcaccgag accataaatg atcttaccga taagtattg gtaccacttg | 1560 | |
| tgatttgaac taatctgaat aattgcacca atcatatata ccaataccac gatgacaatt | 1620 | |
| gctaaccttc tacctaaagt atctgcaaaa cgggcaaaaa gaagacctcc tatagcacaa | 1680 | |
| ccaacactga acattgccac tagaagaccc atacgcacat tactcaagta atattctcca | 1740 | |
| gtactgtgtt tgtaagaacc gaaattcatt ttaaagttgt ccatgttaat gaacccagcc | 1800 | |
| gtaataccac tatcccaacc aggtaggaac cccccaaagg atataggaat acaaagcaga | 1860 | |
| tagatagtaa gataacctag atatcccctc tttggtggtt caatggaatt ccgtttatg | 1920 | |
| acttcattgt cataaacccc atccgaccac tctttttcta caggtggcga gacataaact | 1980 | |
| tcaatattag aggcatcttg aatgtctata ttactatgaa aagatgattg tgaactagac | 2040 | |
| attttttttta ttttaatttt taaagccttt cttttctttt ttttagtta tattattata | 2100 | |
| gaataaaagt ataagaataa atgaatgatg cccattgacc ttgcccttta tatatgatgg | 2160 | |
| tcgaattgca attctatgat agatgatgat aaattcaata gcttatatca tctctttaac | 2220 | |
| ataggttcaa gggaagtaca ctcagggata tgatctgcat tcaaacggtt cggacggtcc | 2280 | |
| agacaattca gacggttcag agtattcgtg gaaagtgaac cggctgctat cattagctaa | 2340 | |
| tactatcctc caaataata cgtcattact ttgggtgaaa tgcattatta gctaaactgc | 2400 | |
| attcattgta cgtcactctc tgtggtacta acaaaccact gtaaaaaaga aaaaaaaacg | 2460 | |
| ccgaattctt tgtgcctgac agattgttgg gatctccacg gatcattttc agcgcccccat | 2520 | |
| gttttgccga atgcataccc cgcccttacg ttgagctttc ataactttaa atttcagtcc | 2580 | |
| ggaggtatttt gttttgagag tgggcctcgc agtgaaaatt ttggaaaagt ttcacacata | 2640 | |
| gttaagttac atttggacct attttcacaa tacaatggaa ctttttttcc aacttttaat | 2700 | |
| atcccttccc ctatacaagg gtaaaatatt ttcatttttt actttccctt cccttttcac | 2759 | |

<210> SEQ ID NO 23
<211> LENGTH: 1217
<212> TYPE: DNA
<213> ORGANISM: Artificial Sequence
<220> FEATURE:
<223> OTHER INFORMATION: c2309_g1_i1

<400> SEQUENCE: 23

-continued

```
cgcaaatttg acaaatggtc attttactcc aatttttttt cttattttga aaaatttccc      60
tgataaacaa aaaaaaaaat tgaattactt ctaaaacgt taatcattta tcctcattgg      120
aagttacttt tttttttcctt ctctgaaacg tgcggagatg atgaggggta aatatttga      180 atttctcttg tttttctttc ttgctgctga catctcacgt ttgacgaaat ggagaacatc     240
agttgccgcg gatccgaaaa gacgattaac taaaaacgcc tcttcattta gttaatcttc     300
ttgctggttt cgcgtctcct tattaccggt tcagctgatt gatattatct cggagatgag    360
caacaaacac cagttgagtt catgattcta tatttgtaaa ctagttttac aatgacatca     420
taaattaaag ggaagaagac aagagttact taagaatctc gagttctgtt tgtttgtttg     480
tttttttaat taagtaatat cgctgagaga tatagttaag attacataaa aaacaactga    540
tacaagaata attaacatta acgacctctc aaccataaag tgaacgtagt ccacttatat    600
tttcatattg cttaactgga ttttcattta gaaattgtac agctcattga atagtcgagt    660
caataattca aattccgatt atttaattac cacacaccct tatatttgat caactgacaa     720
aggacatttc cttagtgaaa cagacataat agccagcaaa tcattccatt gcattttgat    780
taagactcat tttttatcat atattgttac tgtttcagaa aatgtcaact tttccatcaa    840
ttttaatgat ggatattaca gattctaata tatcgatacc tgattcaaac gaccccacaa    900
gaaaggaagt tggtcttaat aaagacattt atgactcgtt tgacaatgaa ccatggttac   960
ataattcatc acaagatatc acacaattga agatgatgaa agttgataga gatctattat   1020
ttcaaattat tatgattgaa gatatttcaa aatctaagca atctcaattc gatgaattaa   1080
gtacacgtat agatcctaaa aatcaacgtg ttgatacttt aagaaattca aagggtccta   1140
aaaaatttga tattgttact caagttgatt tagataatga aatgatact tcaacaacaa    1200 caacaaataa taataat                                                   1217
```

<210> SEQ ID NO 24
<211> LENGTH: 2127
<212> TYPE: DNA
<213> ORGANISM: Artificial Sequence
<220> FEATURE:
<223> OTHER INFORMATION: c3558_g1_i1

<400> SEQUENCE: 24

```
gttttattta ataataataa tatttaatta ttattcactt ctacttcaaa taatattcaa      60
ctagtttcat ttttttaatt tattgaaaac atactttttc cctttggtac aggtacattg    120
caataataat taataaatta acccttagaa ttttatttt gtcgatctaa ataaaaaaag    180
aaattaaatt atacgatata tataaatcga ctatcaattt agatcatttt taattcgctg    240
ttaatttatt aaaaaaatcc ttcaacctgt tgtaaaatta gacaaacata tcatactaat    300
caaaaaatat ttctattaaa atggaagaat tgtattacta tataccaact aatcaacgtc   360
caaataatgg tcaacaaata tcacatgtac aacaacaaca ggtacaacaa gtacaacctc    420
aattagttgc atattatcct tctacaaaata ttataattcc acaacaagaa ttacaacaac    480
aacaactaca gaaacagcga caaagaaatt cacaatcgca tcctcaatta tatccatacc    540
ctcaattaat gtatactaat caattggtaa atccaaggta tactacacta tacagtccaa    600
ttatttctca accaggtaca tcgacagcaa ttcctattac aagtacttct gctacatcaa    660
tatataatga acgttctaat caaataaata cacctattcc tacaatgaca agtaatcaaa    720
taactggttc aattcattat aataacgaaa taaatgtcag tcctacagca gtgacacata    780
```

| | |
|---|---|
| ataatccacc aggtgtacaa ttaccaccat tgtcaagctt ggtgtcacag attaaatcaa | 840 |
| catcccaatc atgtcctgat atttctacat tgacatcaca atcgagttct tcaattaata | 900 |
| caatgaatgc aaacaacgca agagaattta agtctgcagc tacatctatc tcatcagctt | 960 |
| caagtttcaa tgacaataaa aataacactg ctactactac tactaataac catagaaata | 1020 |
| gtataccttta tatacttacc ttttcatcgc agaaagaaga caatcttcac tcggtcacta | 1080 |
| atcataatca atctacacaa ttaccaatta cgaatttccc agtaagagaa ataactccac | 1140 |
| caatctatac aatttcacca aaacaaaata atgcaaatat taataaatta atagttacaa | 1200 |
| atagaaactc aaatgaaaat ttaaatcatt tactaactag aaatgatatc actgtaattg | 1260 |
| aaccagtaag aatgaataat acaaatatta atgatatgaa attaaataag ggcaaaaatg | 1320 |
| gtaaaattcc atcacaacaa agaaacaat gtccaatttg tggtaaaatt tgttcaagac | 1380 |
| cttctacttt aaagactcat ttttaattc atacaggtga taatccattt aaatgttcct | 1440 |
| gggttggttg taagaaaagt tttaatgtta agagtaatat gttaagacat ttaaaatcac | 1500 |
| atcaaagaaa actagaaaaa ttagctaaga aacaagctga tttattaaaa caagaaaat | 1560 |
| tgaaacaaac aaccaacaat aatgacaaga agaaatagat agaaaacagt aatggctaaa | 1620 |
| agatttcatt taaatcaaat caaatatttt cattttactg tcttctactt cttactccat | 1680 |
| agaataaagc atacctaaca aataataatt ttgataatat ccttgataat aataatcaaa | 1740 |
| agaaaataac gaaaatattc ttcattgctc taatagcatt cattattctt tattcacttc | 1800 |
| atctatagat attctaaatt taaataatat gataatctct ttttttttt tttgccttt | 1860 |
| cagatctctt tatgtaaacg acacactcgc catctttcaa caagacaacg cggccagccc | 1920 |
| aaaatttta ttgtcctatt taagcaaagt gtaaactttt cagaagtgac aatgttgaat | 1980 |
| taaataaaaa aaaaggaatg caatttctta aatgaataat ttacacatta attagaaaaa | 2040 |
| aatcttaaat atttttacaaa aaccgaaata aaacttagtt tcaggaataa aagcatagaa | 2100 |
| caatgtaaaa aaatcgtggt tttaatg | 2127 |

<210> SEQ ID NO 25
<211> LENGTH: 5413
<212> TYPE: DNA
<213> ORGANISM: Artificial Sequence
<220> FEATURE:
<223> OTHER INFORMATION: c1715_g1_i1

<400> SEQUENCE: 25

| | |
|---|---|
| ggcgtattca agtatagtc aagaacataa tatattgagg gtgtgtcaat accacattat | 60 |
| agatttagga tatactcgat taagaataat aacaatgggt gcgagttgta aggatcaaaa | 120 |
| gaaagctgtt gctatctgtc ttcagagatc tccttgtgta atgatagaaa gaaatagtcc | 180 |
| tcaaaaatgc atagacgatc caaacttaag caaggatttg ccagaacttt gtatagcaca | 240 |
| aatgaaagca tttctagatt gtaaacgagg gatggttgat atgaccaaaa gaatgagagg | 300 |
| taacgctcct ttatctacag gtaagtacga tgaacaatat gataatttat gcaaagggaa | 360 |
| gttcgatccc agggaagaaa tgcataaatt acaagtttta aattctcaag agaaagaata | 420 |
| aaaggagaa tgaattttg taaataaaat gacaacaacg aaagagatta atattccata | 480 |
| cgtttcataa ttcaaaaatt aatttaagaa tatggttttt atgttataca agatgtatat | 540 |
| aagaatgtgt acataagtac cggtataaat cacaatatct ataaacattg atgtaggatt | 600 |
| atcctgagtt ttaagaagtt aacttctgtg taaaaatatg ggcctagagt ataggatgat | 660 |
| tataccggtt aatcaatata tccttctaaa ttattaatat gcaactgtat aagtctgtaa | 720 |

```
tgaccttggt gattaatatt attttcattt gttatagccg attgcgtaat agtgaaaaaa    780
aaatcttaat agcggatcta tgtcttcctt gctgtcagct caagttctta aagaactagg    840
acaaatacac ttgaaaatcc aactttaatc aaattagatg gaagtaatag ttatatcaat    900
agctagctat agttatattc aaaccaactc tataaaaaag cactaatatt gcaaaatgga    960
tgacgatctg caaaataact aaatgtggt gaatattgtc tctcaacaaa gtctggagca    1020
aaaaattggt gataatgttg aacaactaac aaaacagaaa ttactcgaac aagaaactac    1080
aagattagaa agagctcaga atctatttga caaactgaag gggcagctat cctcattaag    1140
aagaaggctt aataatacga accgaatatc gataaagatc aaattaagga aagagatcca    1200
acagttacag gataaagata ttatcgaggc acggaaagat atcagggaga tatatgatcg    1260
acttagagat ctgaaaaagt cagatgatac aaataccaga gagcaagatg atggtggtag    1320
aagagaaggg gagtcagaaa gagattactt agtgaggaca ggtaagctaa ctgcatttgg    1380
ttcaaaatca ggatttataa tcgatgataa agtaaattct ccagctacaa aaagaataaa    1440
agtggaagat gacgcaatac tcgaatctcc cactactgat gaatatgaga tggcgaatga    1500
acaaatggtt gaaaacataa ctgataactc ttcagaaagc gattacaaac cagataataa    1560
tggggatata tccgaaaatg aggattataa tgaaagcgac ataaatactg aggatgagga    1620
aataataata gaggaaggaa aagttaaagt taatgaagct aatgatgatg gtgatgagtt    1680
aacatatcag aaaagattaa aaaagtggat agcccaaaga tctaaggga gaaaaaataa    1740
caatgaagct ccattacctg agtggcgtaa atcacatcct gaaattcctg atgcaagact    1800
tgatgatatt tttaaaattc ctggtgatat acacccttta ttattcaact atcagaaaac    1860
ttgcgtacaa tggttatacg aattatacca caaggtgca ggtggaataa tcggagatga    1920
gatgggtctg gggaaaacaa ttcaagtgat agcatttctt gcagcgctac accattctgg    1980
gctattaaat ggcccagttt taattgtttg ccccgcaaca gtcatgaaac aatgggtcaa    2040
tgaactccac cattggtggc ctccattccg ttctgtcatt ttgcattcaa tagggtcggg    2100
tatgtcagat aaaagcaaaa tgaaagaaac agaattcgaa gaattgatga tgaattcaaa    2160
cccggatgaa ttttcctacg acgatttcaa gaattctaaa aaggcaaaat ctgccttgga    2220
atcgtctctg catttagaca atttaatacg aagagtggtt gaaaagggtc atattctaat    2280
tacaacatat gttggtctca ggatacattc agaaaagctg ttaaaagtag actgggatta    2340
tgttgtctta gacgaaggcc ataagattag aaatccggat tctgaaatat cattaaccac    2400
aaagaaatta agaactccaa ataggataat tttatcaggt actccaattc aaaacaatct    2460
gaatgaatta tggtctctgt ttgacttcat atatccaggt aagctaggaa cattaccagt    2520
atttcaacaa cagtttgtta tcccaataaa taccggtggc tatgcaaatg ccaccaatat    2580
tcaagttcag actgggtata atgtgctgt tgcgttgagg gatctaattt ccccatatct    2640
actgcgaagg gtcaaaagtg acgtagcaaa ggacttacct cagaagaaag aaatggtact    2700
attttgtaaa ttgacacagt atcaaagaaa taagtaccta gaattcctga actcaaacga    2760
attgaaacaa attaaggtg aagaagaca tgttctatac ggtatcgaca tcttgaggaa    2820
aatatgtaat caccctgata ttctggagag agaggagaag caaaacgaac tcgactatgg    2880
taatcccagt agatctggta agatgcaagt tgttaaacaa ctattattgc tatggaagaa    2940
agatgggaac aaaaccttgc ttttcaccca atctagacaa atgttggata ttctggaaaa    3000
atttgtagca agtggagatc ctgatttgag taatatcagt tatctaagaa tggatggtac    3060
```

```
aactaatatt tcaaagcgac aagctttagt agacaggttt aacaatgagg atattgacct    3120
gtttttatta actaccaagg ttggtggcct ggggataaat ttaacaggtg caaacaggat    3180
tatcattttt gatccagact ggaatccatc tacagattta caagctcgtg aacgtgcgtg    3240
gagaattggc caaagagag aagtttcaat ttatagatta atggtgtcag gctcgataga    3300
ggagaagata tatcacaggc aaatctttaa acaattctta actaataaaa tcttaactga    3360
tccaaaacag aagagattct tcaaaatgaa tgaactacaa gatttattta gtttaggagg    3420
agatgatgga ttagcttcag aagagcttgc gaacgaggtc gagagacata cgcagacact    3480
gaaggaatct aaaactaaac aaagtgatga ctttgaacag gttgccaata tagcaggtgt    3540
ctcgaaatta aaggtttct tttcaaaaga agaaaaagaa gccagtaaaa atgaagatga    3600
aagattaata gcagggttaa tcagcgaaag tggtaactta gaaaatgcca gtactcatga    3660
acaggttgtt ggatctcata tgacatctaa acattctacc aaattaattg caagagaagc    3720
tgaaaaaatt gctgggcagg ctgtcaatgc tattcgtgaa tctagaagaa agacccagaa    3780
atatgatatt ggtaccccaa catggacagg taaatttggt caagctggta aggtcataaa    3840
gaaaaaaata aagccgtcaa agaaaaatgc tctggcatca tcagatatct gaagactat    3900 tcgtgatcgt caaatagaat cgaaaagaa tgaatcgttg aatgacttgg ctgatccaaa    3960
ccgtaaatta atgatgaaga tcgtaaatct tttaaatgaa tcatctcagt ataccttacc    4020
atctgcttct atcattgagg atcttaacat agatgtaaag gataaaaatg ttattatcaa    4080
tgtcagagct ttactaagag ctgttgctaa atttgataaa gtgaaaaaaa tgtggacatt    4140
gaacaatgaa tttgttaata attgagcaaa cttttttccc caaggacaat taaatactag    4200
aggaagaaaa gttagccaca gaaagagaat atatatggat ttgcattatg aatatataaa    4260
tatttaaacc ttaacggaaa ccaaacccctt cagattcggt tacagctaac atcaatttat    4320
tctctagctt ttcttttgag gaatattccc atatacacag ttcgttaaaa catgtgtgtg    4380
caattggcag atcattacta tccctagctc ccaatctgct tatcttaaaa gtcaaggttg    4440
atatacctgt agctggtact ctattagaac tagtaatgaa ttgtaacact ttaccttgca    4500
ttttataatc ccaatttttcc aaaatctccc aaaaccaatt tacaacagaa gtttcattgg    4560
taaaaccgcc ttgatattta gtaacagaac gtaacatttg aaaatcatat tttgtatgct    4620
catcatcccc acataataaa cgttccaatt cttcagaatt aaataggcct atggatttac    4680
aatttgaaaa gactctgctg aatccatcca taaatctttc aaaagacgct gctaccgatt    4740
ttgttagata gaaatcaatc cacaattttta cataatcgga tttatttgac tgagttaccg    4800
ggatattaga gccattcttg caaagttcta ccgtcacagt attcgaacct ttggattttt    4860
tactaccttt attattcgct gttagtttat tatgatatgt ggtttcaaat gtaaggcaga    4920
aaacgtcatt aaaatcatcc ttcgaatatt ctaacatctt taataaattt gaagctgtct    4980
ctggatatag ctctgtgtaa tctgcaaaag ttaacgtttc attgcacatc ttttttataaa    5040 gtgcctttgg gaatgataaa tctaggatat ttccgttaaa cattgccaat gctatgacaa    5100
cacccaacag gtaataatat tcttcttgtg attgaatttt ttcttttgat ttggaagatg    5160
gtacaattgg aaaccaacat aatctactat cctttatatg atcaaacaaa ccagttgtcg    5220
gactgaataa agattttgtt aaaaggataa accattcctt tctcaaacca cccgcatcga    5280
taccaggttc tttaataaat tcaattctta gagatttcaa taaatcacct tgatgctctt    5340
tgataacctt taatgaatca tgggtaatat gatctcttcg tattttaatc ttaaaataaa    5400
cttctatagt ctt                                                       5413
```

<210> SEQ ID NO 26
<211> LENGTH: 2985
<212> TYPE: DNA
<213> ORGANISM: Artificial Sequence
<220> FEATURE:
<223> OTHER INFORMATION: c4733_g1_i1

<400> SEQUENCE: 26

| | | | | | |
|---|---|---|---|---|---|
| tcagctacta | atactggtgc | cacctctgtt | cataaaccag | taggtatcgt | cactccaggt | 60 |
| tatggtttgc | cttattttgc | ctcttcttta | acagagacta | aaaataactt | cttattcaat | 120 |
| gttgctgctt | tatcttatca | agataaaaaa | aatagattag | gtagcgatta | cattactcca | 180 |
| ttatcaatcg | ctaaacaatt | aggctttaac | gttattacgc | ctgtttcaaa | gaaagaatta | 240 |
| gagttaactt | cttttattatc | tgttgcttta | gctactttat | ccaattccaa | ttccactatt | 300 |
| catttattcg | atggtttaac | ttctactcgt | tcattttcaa | ctttaaatag | taacattgtt | 360 |
| aactccgaat | ctttaattgc | taatttagct | aagactctag | gtaatgaacc | atcctttgat | 420 |
| gctatcttaa | agggtttcaa | tgaacaaata | ggtagtcaat | tgacaaagtt | ccaatattct | 480 |
| ggtccttcaa | atccagaggt | tttattcgtt | acttatggta | ctaccgaatc | tgaactattt | 540 |
| agttccgttg | taccaacttt | gtcagttaga | gttccattac | catttgacac | taacgaattc | 600 |
| gttaattcaa | ttccatcaag | tgttaagaag | attgtcatca | tcggtcaatc | attgaatgaa | 660 |
| aatcatgctg | tcccatcttc | cctaagatta | gatgtctctt | cagctttatt | cttccatggt | 720 |
| cgtaaaaata | tttcaattca | agaacatatc | tatcaacctg | attttgcttg | gactactcgt | 780 |
| gaagtatcca | acatcgcaaa | ccaattcgat | gtcaagacaa | tcagtaccgc | tgctcaaact | 840 |
| ggtaagcatg | ctttattta | tctaccagat | gattccaaat | ttattaatat | cccagctact | 900 |
| ttagtcaaga | ctttagcttc | tactactaac | gatattcaat | tctctactaa | attcaataac | 960 |
| tctgttcata | gtggtgcatt | tgaagctgat | attgcagttg | gtaatgttga | aacaggtact | 1020 |
| gcttctgccg | atttcatctt | ggttcaagat | atcaatctat | taaaccatttt | agatatcgtt | 1080 |
| aatgctatta | agggaaatgg | taccattgtt | tatttagcta | atcgtgatat | tactaaaatat | 1140 |
| ccacaacaat | tcatcgctga | tttaatcacc | aagaaaatta | ctttagttat | tgttgaccct | 1200 |
| actgaatacg | aagatgatat | cgattcctta | gttgctttga | ttcaaggtca | attctatcaa | 1260 |
| tctggtttac | aattagctaa | taccaaatt | caatcaaaaa | ttgtatctaa | tttatctcaa | 1320 |
| gaacaaattc | atgatatttt | gaacgctaat | gaggattcag | aagaatatca | attctcaatc | 1380 |
| tttactgttt | caaacttacc | tgaacctgaa | ttctccgaag | aagttcgtga | acagttacct | 1440 |
| tctttcttcc | aagctgattc | attcaaacca | aataatatta | acaacaaca | agctattgtt | 1500 |
| aatgacccac | cttcaattac | ttcaacaatt | actgaattga | ctaaaagatt | agctttcaag | 1560 |
| gaagcatacc | acgttgaaaa | gaaattaaga | ccagatttac | cactaattaa | gaaccacata | 1620 |
| atcaaggtta | agaaaacag | acgtttgact | ccagcagact | acgatagaaa | cattttccat | 1680 |
| atcgaattcg | atatctctgg | tactgattta | acttacgata | ttggtgaagc | tcttggtatc | 1740 |
| catgcaagaa | ataacgaaca | acaagttctg | gaattcttac | aatcttatgg | tgtagatcca | 1800 |
| gaacaaatcg | ttcaagtacc | aaacaaggat | caaccacaat | atattgaatc | aagaactgta | 1860 |
| ttacaagtat | tgttgaaaaa | tctagatcta | tttggtaaac | cacctaagaa | attctacgaa | 1920 |
| tccctaatcc | cattcgctga | agatgaagat | gaaagaaat | ttttgcagga | tttaattact | 1980 |
| ccaggtggtg | cattggaatt | gaaaaatttc | caagaagtcg | aatttattc | atatgctgac | 2040 |

| | | | | |
|---|---|---|---|---|
| atctttgctc | gtttcccatc | agtgagacca | gaattagctg | atttgattaa | tatcattgct | 2100 |
| ccattgaaga | gaagagaata | ttctattgca | tcctcacaaa | agatgcatcc | aaatgaaatt | 2160 |
| catttgttaa | tcgtcgttgt | tgattgggtc | gacaaacagg | gtagaaagag | atatggtcaa | 2220 |
| gcctctaaat | atatctctga | tttacaaatc | ggtcaagaat | tagtcgtcag | tgttaaacca | 2280 |
| tcagttatga | aattacctgc | tgatccaaag | gctcctgtca | ttatgagtgg | tctaggtact | 2340 |
| ggtttggcac | catttaaagc | aattgtcgaa | gaaaaattat | ggcaaaagca | acaaggttac | 2400 |
| gagattggtg | atatcttctt | atacttgggt | tccagacatt | gtagacaaga | atacttatat | 2460 |
| ggtgaagttt | gggaagctta | taaagatgct | ggtatcatta | gtcatatcgg | ggctgctttc | 2520 |
| tcaagagatc | aaactcaaaa | gatttatatc | caagatcgta | tcagagagaa | tttagacgat | 2580 |
| ttgaaggtcg | ctatgattga | tcaaaacggt | tctttcttct | tatgtggtcc | aacttggcca | 2640 |
| gtaccagata | ttacttctgc | tttggaagat | atcattgcag | ctgatgctaa | ggaaagaaac | 2700 |
| gttaaggttg | acttgaatga | agccatcgaa | gaattgaagg | aaacttcaag | atatatctta | 2760 |
| gaagtttact | aattcgttac | atatatattt | atttatgata | catttattta | ataaactttt | 2820 |
| ttttagtaaa | tatttctttt | tttttgttgt | taaaatatag | tacgaatatt | ttttttttac | 2880 |
| ataagactga | ctacagatgt | accatcttgg | aatcttgttc | tgaacactct | gttggcatta | 2940 |
| gtgaacatac | cttccttcaa | agaaacaaca | ataaactgag | cccca | | 2985 |

<210> SEQ ID NO 27  
<211> LENGTH: 2512  
<212> TYPE: DNA  
<213> ORGANISM: Artificial Sequence  
<220> FEATURE:  
<223> OTHER INFORMATION: c4679_g6_i1

<400> SEQUENCE: 27

| | | | | |
|---|---|---|---|---|
| taataataat | aataataatg | atgaaattcc | aatattgatc | gattcaaata | acaatgaaac | 60 |
| taggaatatc | gatacttcta | aacaattacc | tttaacacat | catgaaattg | attttgaaaa | 120 |
| tgatctaact | ttggaagata | gtgatacaga | tatcgatatg | atgatggatg | atgaagatga | 180 |
| tgatgacatt | gaacaaaata | atacaactta | caacaacaca | gtgtttcaag | gtaataattc | 240 |
| ttccaggaga | agaatgcgtg | attattttaa | attcaattta | ttcaattctt | caaatcaacc | 300 |
| aaaggttaca | aacgaatctg | aaattttatt | gaagtcagag | gaaaaggata | caacagcaat | 360 |
| actcccacaa | ttcaatgatc | aattcaattt | aaagaaaaaa | tcctcatttt | ggaaccctaa | 420 |
| gacttcatct | ttcttgaaaa | ggtacaatag | taaaaataaa | gatggcatta | ataacactaa | 480 |
| tattcctgat | atagatgaca | tctcaactag | agatttcgaa | ttacctgatt | tattcgatat | 540 |
| tgaaaatcat | ttagttcagg | actcatcttc | atcctcatta | ttattaccaa | tacaatccgt | 600 |
| agaaccaatc | ttcaaaaata | cgttgaatcc | aatggtcact | atgaaccaag | ttactacaca | 660 |
| attacagcaa | caatcacaaa | ttaattcaac | tgcaacaaat | acaactatgt | catcactcgt | 720 |
| ttcaccttct | tctccagtaa | tgacaattgc | tccctcattg | gtaactacag | atgatatttc | 780 |
| aaataacttc | gtcgaaccaa | ttaaatcaat | gaatccattt | gaacaagata | tgaatttgag | 840 |
| ttatttcgat | attaattcaa | ataatgttct | taacgacaac | acagttgaag | aggaaccact | 900 |
| taaatcagtc | cttgaggaac | caccattagt | agaaaacgag | actccaagaa | aagtcacccc | 960 |
| aactacgccg | gctccttcct | tgactccttc | cttgactcct | caacaaccta | tcaagagaag | 1020 |
| aggttcaaat | actctgccaa | agacaagagg | acgtaaacca | tctttaatcc | cagatgccag | 1080 |
| caaacaattc | tgttgtgact | actgtgatag | aagattcaaa | agacaagagc | atctaaagag | 1140 |

```
acacattaga tcgctgcata tctgcgagaa accattcacc tgtcacatat gtcagaaaaa   1200
tttcagtagg agtgataatt tgaatcagca tatcaagact cattctcacg atgaaacaaa   1260
ttgatctggt tcctctaagc tccttttctg cgctcatata tagagataca tacatataga   1320
tagatatata gactcgtgtt ttaactgata taatgaataa tgataaatca acctttttaa   1380
atttaatgtt tctgaataga gtcatctaaa cgtggttgtg acttctggtc tctgatagtc   1440
tgccgatttt cgctgcaaca gaacaatgag ctaccaaaaa aagagaaagt atgggcgtta   1500
ttattagaat aagaacatgt cgatatctca agtacaacat aatgtgggaa gatctaatat   1560
atccaataac aagaccaagt gctatcaaaa ttgcacattt tatcccaacc caatgtctgg   1620
ttacaacagc aataccgctt atcaattgca actagataga tttctgaaat ctccatcaca   1680
taataatcaa tgttcagatt gtaagaattc aaatccaaca tggtgttcta catcctttaa   1740
tgtatttcta tgttccagat gtgcatcctt gcataagcaa ctactaaata aggacccttta  1800 ttattccaat atcaaatcga tcaaattgga tacgtggtct gatgatgaat tgttcaatttt  1860 catacataaa ccaaatcaat caatcaatag agacatatat actacttcag acaatgcata   1920
tgacttggaa caattaatta aaagaaaata tatggatcct ggactagaag tcggattagc    1980
taaaagaaga gccaatagaa aatatcctct attaacaaat aggagaccaa gagattatga    2040
attaagcaaa tattgtagac atatcaggga aatcgaatca tatgatagga gattcactaa    2100
tgaagataat attgtggaag cattatccat ggctcatggt aatattgata acgccattga    2160
aatcttaaga tataatgatg agtaccttaa ctcaagagac tacagagatg attatgatag    2220
tcgaaacagt agtagatcat cgctatcaga aaacagatat cgcaaccgtc cggacagcaa    2280
ccgcacccca agtttgccaa gaagaccaga taatagtgga ccaaaagatg ctgtatttga    2340
tgggtcattt ggtaacgcta ctacaactac aacaaaagct cccaaggcag ctgtattcga    2400
tggtttatca cctgatgcct tatctaatct ccaagcatct gaatatcaag tacaacagaa    2460
tgaattgatg aaacaacaaa tgttgcaaca acagcaacag caacagcaac aa            2512
```

<210> SEQ ID NO 28
<211> LENGTH: 3243
<212> TYPE: DNA
<213> ORGANISM: Artificial Sequence
<220> FEATURE:
<223> OTHER INFORMATION: c4955_g2_i1

<400> SEQUENCE: 28

```
taataataat aataataata atacaacaat cttaccatct actcatatac ccaattcagc    60
cattaatgat attaatagaa ctgctaccgc tgctacaaca acaacaatta ctaccgctaa   120
gattactact tcaaaatatg atcaatcaaa aattcataat ttaccaagtc caacttgttc   180
cgtatcaggt aataacaaca atgctaatat caaaagcaat agtaataaca acagtaatac   240
taatagtgga gtctctactc cacctgaaga tgtagaacca atgaatttag tttgtaaatg   300
ggataattgt aacaaaatct tcgttcaacc ggaattatta tatcatcatt tatgtcaaga   360
tcatgttggt agaaaatctc aaagaaaattt acaattagat tgtcattggg ataaatgtca   420
aacaaagaca gagaaaagag atcatatcac atcacatatt agagttcata tcccattgaa   480
accatttgct tgttcatctt gttcaaaaaa atttaaaaga ccacaggatt taagaaaaca   540
tttaaagatt catttagatt ctggtaacat tatgaaaagg aaaagggggtc caaaagtcgg   600 ttctaaaaga attaataaga atggtattaa atcaatagat aataaacata ttcaaacagg   660
```

-continued

```
tattgatcaa agatcaagaa gtttaccttc aacaagcttc actaatttac ctcatttaag      720
taatggtttc agaaaattca ttactaatga tattcaatct tatcaacctg tattgactca      780
tagattagat acaagattac aaaatataat gggtcaaact cttactgctg ctcaattaca      840
agaacaacca catttatatc atccaatcga taaaaattta caaggtccta acatgtctag      900
tgaaagagta tctgtttcat cagttatgga tacattacca cgtcatgtag cagctaacgc      960
agcaggtttc ttttcagaat tatctaacaa catggctaat aacacagcat tatatcaaca     1020
tcatcaacaa cagcaacaac aacaacaagc acactcaagt attcaattgc aatcacatcc     1080
acagacttta atcggtaact attctaaatt gccaccattg aatggtgtta catcataccc     1140
aacacaacaa catacaacaa tgattgaaag ttcaatgaat gtcccaacta acaaaatgac     1200
tatgttacca tcaatggcag aagttactgg tctacaacct agataccaac aacaacagca     1260
gcaagcacaa caacctagaa gtagtccaaa tgcaactatc atctcatcat atccaactat     1320
ccaaaacatg cctcaacaac aagttccatt acagggacaa gttatggcaa gacctatgcc     1380
aggtactcaa ttgccatata atttggttgt taatgcaatg cctgttgctg gtagtacaat     1440
gaatatggtt gagaatagat atagtacatt acaaagatca actggtcatt ctagtggttc     1500
tgatgattca gaatctgatt cagaatctga agagattat gaagaagaag atttcgaaga     1560
aagcttggat tttgttaatg ttattagaga ttatttgatg tgtacattat tagaagaaga     1620
atatgatgaa tccgtcgatg ataaaattga ggatttgatt aatgataaat tttggaagga     1680
atcaaaaggt ttgatatcta aatatccaac tattagagtt tgaaagaaat atattaagaa     1740
ttataaataa aaattaattt atgtaatgta tatcaataaa taaatacatg aaataaataa     1800
atataaatct gccacaatat ggaatggaat atgatgtgat gtgtgtacag atgtatatcg     1860
cacaaatgaa ttaatgctaa tgttgtaaaa ttgtgacttt tttactagtg cttttttta     1920 ttgcgggaag gaatgaatat tgttttatgg ttgatgatag aatgtaatgc ttgagttcaa     1980
ctatgaaccg aatgattcat tagactctta ggtaaagaag atgtaactga tctagaattt     2040
gtagcggaac ttgaagatct tacaattttt tcatttgtat tatttgcttc atcattattt     2100
gatgctattg atggaattcc tgtattagaa tcacagtctg attgttcatg ttcatgttct     2160
tctaatggag gtccaacata caattgagat ggtacttgtt caacattatt tggcattgaa     2220
aaattgacga tatgtgtgga atcatttgta ttaactttaa atataaaact attatctctg     2280
ataactcttt catatattct atttcttact acgattactg caactgcaca tggagtagta     2340
ataaaaccaa caactgcacc atatgaaagt ttcattaatt gtggctctgg ataattatta     2400
aaatacctat catgattatt tatttattta ccaattgatg caaagatacc catacaaatt     2460
ggccaaacga agataaataa tgcaacagcg aataacattg ctctaataac tttcctaatt     2520
aaccattcaa taatattaaa atataatttt tcatttggat atttaacaac atgatttctc     2580
caaaatttta aaagggacat cttaggtaaa tcaatatctt tattattact atatttatta     2640
tcatctctat gtctcattac acctgtatta atttcaaaat accattgcat atatcttgaa     2700
aatttatttc ttttaacaat gattgaatta taccaaaaat taacaaacca tgaaggaaat     2760
tcaaatgtat tgtttaaata atcatcataa cctaccatta attcttcaac aacccaagta     2820
acaccaactt gaatgaataa agttaatgca caatcacctg ataatgtatt agggaatgcc     2880
cataatgtaa ctaaatgagg agatttctga tacataccat aagcgatacc aaattcagaa     2940
ccaccaccta taatggcaga acctaatcct tgatataaga atagataaac tattgaaaat     3000
atcaacgggt attttataaa tagtgtaatc atctatcgta agttatgtgt gtctgtgtgt     3060
```

```
gagtgtaatt ttgtgatgat ctgggtttga attaaatata attgtaattt gtttagttta      3120
tagtagtacg tatatgtgag cttatctttt taccaaatca atgaacagtt ttataacgta      3180
tcttctttcc ttctctctta aataaataaa taataataat aatagaattt aaatatgcag      3240
cag                                                                    3243

<210> SEQ ID NO 29
<211> LENGTH: 5008
<212> TYPE: DNA
<213> ORGANISM: Artificial Sequence
<220> FEATURE:
<223> OTHER INFORMATION: c8855_g1_i1

<400> SEQUENCE: 29
cttaagaatt agatatataa ctaaaattaa gttgaaaagt tacgttacat gatgcggata        60
ctacttcaag ctagtgaata attgaattca caatacttgg gggggtacta gaatgggata       120
atacattata gtgtgtggta gttcaaaaat gaattatacc agacggtatg gcatgctata       180
ataggttatc tataaactat ataaatcaaa aaagagatt tttacatgat gatacaaaat        240
acattgctcg aaggtcttgt atcgatgtga gcaatacgat ttctcaatag actacaacgg       300
tatctgattt ttatcttttt tatgtaataa gtacttgttt tacatacttt tttcacttga      360
tattctataa tgaaagttag atgtctattt aaattggcca ttttcgttat tttaaagtac       420
aactgagttt tgattcatag tcattatagt tgtgaatcgg tttccatttc ttgaatgtcc       480
cgatgagctt cttcatattt gcacacagat gcattgtaaa agtacgtttt tatattatag       540
taattacgaa acttttgtga ctagtattta attattttta aaaaaaaaca gtaagaagct       600
gatatcaagt cgtacaataa gaaattctta caacaagga actatgtcta aaagagttag        660
caatactgta cggtataaac acccactacc aatccatcca ctagatctac ctcaattatt       720
tgttcataat ccgatatcat ggacctactg gttgtatagt tacatcacaa gttataatgc       780
atcatcgaca aagatacatg tagatatcac aaaacacaac aacttcatac atatagaagt       840
tagagaacta accgatatga aatatttgtg ggataatgga ttctttggca caggccaatt       900
gtccagaagt gaacctacgt ggtatgaaca acaagcaag aagttccaaa gcagtggcga        960
tgaaaagagc aatggtatca gtttagagcg agtcactaaa ttaagaagac aacaaagagt      1020
tgagttcaag aaacaacgtg aaatagtaga ggagaaattg ttacaactta ggagagaagg      1080
taatttgaca cctgaacaag aagcagagat tcttgaacaa gaaagagaca aactacgtaa      1140
atttaaggat gatcaagttt cattagacag aatggatcaa gatgaagata ttactgaaca      1200
agagactaaa cgactgctat tacagcaatc tgaaatattt gatgaaaatg ataatttatt      1260
gaatttggaa tcactcgaat taatgcctgt agagacgata ttcttaagtt ttgcattacc      1320 tatttagat atatcaccag tagatttcat tttgaagtgt tgctttactg atatatctcg       1380
gtattcagag gaattacaca cattattgat ccaatatgct gcatatcatc attacagatc      1440
tcatggatgg tgtgtacgct ctggtataaa atttggtagt gattatattt tatacaagag      1500
aggtccacca tttcaacacg cagacttttg tataatggta ttagattcta attgttcgaa      1560
accttataca tggtattcta ccattgctag agtatgcggc acggcaaata agacattagt      1620
cctttgctat gtagaacgtc tagagactga agaacaaata ttagaatggt tacaaggggg      1680
acagttaaca aaagttttta acagcttaa ggtcggtgag gttatataca gaagatgggt      1740
agcaggaaga aaccgtgact aataatgtca gatcgatttg aacgactgaa tgaagagata      1800
```

```
atttattact acttggtatt tactatgaat gtttaattat ataagttcaa aggtatataa    1860 ttgtttttttt ttccattata tgaatgcatg catgtgactg tttattctag tctataataa   1920
cctatttacc attgtatgta tctagaaccc aaccacaatc tctcattccc ttgatgtgtg    1980
cttttggtcc ttctaccaga tcgtcataaa ttttgtttat cttctgatca tgggtagctg    2040
gttttgatat acaaacaacc tcttcgtttg gtaggatgca ttttagttgt gatttttggaa  2100 atggacatgg acaatcggac ttcgataata cacattctag cgtaacaggg cataagtagt   2160
ttttacaatc actgtctaat actctgtctt catatggttc taattttgga ggttgttgct   2220
gttgctgttg ttggttgaag ttaaacataa acccttgaac atccagcaat aaaaaaaatg   2280
ctgctactag tatgacttta ttaaatgatc ttaaatagga catattattt ccttctctct   2340
cctggactat tcgataacga cctaatgttc atatatctac ccgtatatac gataaatatg   2400
ataccttgca atcataataa actgtgttat ataaatatat atgtttgtat cctggaacta   2460
gatggttggt tagttaacac agtggcatct cttcgctcca tgttgacatc aaagtggtga   2520
agttcgtggt tagtgatatt ctacgcgtta atttttttcga tttcaacaaa cgcgaaattc  2580
tgttttgatg aaacttctct tttcaataac aacaacaaca aaggttgaaa gtctggtcat   2640
tccatctttg tttcgttttg acattgtata tatcaatatg tgtcaagtcg tgttgtgcag   2700
aggaagaaac aaacgacgat ttagggtaat ttcagtagct gcagaagacg ttgaggagga   2760
tgtattacag gatcgatcaa tataccaacg catataataa gattctcaga gaatcttcaa   2820
atccgtcgac atgccaacta gtcattttg tgtcatgttt gaatatcgat gcactgtgtg    2880
caactaggat gttatccacc cttttcaaga aacaactagt ccaattacaa attgtacctg   2940
tgtttggtta ttctgaatta aaaacacatt ataagaaatt agatgaaaac attaatagca   3000
tagttttggt cggttttggt agttacattg atattgagac atttctagaa attgaccctc   3060
aagaatatgt gttggatacc tcatatagtg aatcgttaat tcaaaaacca gagaataata  3120
catacaaaag atacatttac gtattggata gtcataggcc gtggaatcta gataattttat 3180 ttggttctga cattgtacaa tgtttcgatg atggcacagt ggaagattca ttaggggaac  3240
agaaagaggc atattttaaa ttgatagggc tagaaacagc agcaggagat gataactcgg  3300
aagaagaatc agatgatgag gaaaacacag atgacgatga taacgacgat gatgaggatg  3360
ataatgactc cttagaaaat ggtaagagac tacaccctga tagtataaaa tataagaaac  3420
aagctcgaaa acaaaggagg aaagaaataa gtcgatatga aaatgtactg gaagaatact  3480
actcccaagg tactacagtt gttaattcaa tatcatctca agtctattca ttgatttccg   3540
ctattggtga aactaattta actcaattat ggctagccat cctaggtgca acttcattag   3600
atactacata ctcctcagtt tacaataact tataccccaat tatgcaggac gaagttaaaa  3660
ggttatcacc tgggaatagt tttctcgtat ctgcaacacg ttcaaatggt acagggtctt   3720
cttcaaaaac accagatact ttatctcttg aagttcagcc agattactat ctattttat    3780 tgagacactc ttcattatac gacagtttct attattctaa ttttgttaac gctaaattat   3840
cactatggaa tgaaaatggt aggaaacgac tgcataaaat gtttgcaaga atgggtatac   3900
cattaagtac tgcacatgaa acgtggcttt atatggataa ctccattaaa agagaattag   3960
gaaatatttt ccataaaaat ttagatagat acgggttaca agacatcata agagatggtt   4020
ttgttcgaac atttgggtac aggggatcta taagtgcaag tgaatatgtt gaatcattag   4080
cggcattatt agaagctgga tcaacggtga acagctcaaa tcatagtaat acatctaatt   4140
cccctgggaa atctagtagt aatgataata atagcaatga taatgacgat gatgataatg   4200
```

| | |
|---|---|
| gtgcacaaga agaggatgat gagcaggatg tagcagcagt taaccgtaag aaagcgttgt | 4260 |
| cttccatgga aaatatcaga aaacaatggg tttctaattt ctggttaagt tgggatgcat | 4320 |
| tagacgaaaa gaatatagat atattatctc gaggtattaa gcatgcacaa tttcttcaaa | 4380 |
| aggcaatatt taacaccggt gttactgtcc ttgaaaagaa aatgattaaa catttaagaa | 4440 |
| tatacagatt atgtgtctta caagatggtc cagatctgtc aatttatcag aacccattaa | 4500 |
| cattattgag attagggaac tggttaatag agtgttgtgc cgaggcagaa gataagcaat | 4560 |
| tattacccat ggtattggct tgtttagatg aggatactga cacatactta gttgctgggc | 4620 |
| tttcaccaag atatccaaga ggtttagata atttgaagaa gaaagaacct atattaaata | 4680 |
| actttagtat ggcatttcaa caaatcactg cccaaactgg tgcaaaggtt aaaattgaca | 4740 |
| acttcgaaag ttctataatc gaaatcagaa aagatgattt gtcaccgttc ttagagaggt | 4800 |
| taacattaag tggattgtta tgagatagtt ctgattataa catgaatagt agaatgaaaa | 4860 |
| gagggaaggt tattaaaata atataaaaaa ttaaataaga tagtcatatt cacattacat | 4920 |
| agtcatatac atatttacaa taatttaata tgttagatat tagaacacat cattggagtt | 4980 |
| ttgatgatta taaatattct tttgttaa | 5008 |

<210> SEQ ID NO 30
<211> LENGTH: 3479
<212> TYPE: DNA
<213> ORGANISM: Artificial Sequence
<220> FEATURE:
<223> OTHER INFORMATION: c7636_g1_i1

<400> SEQUENCE: 30

| | |
|---|---|
| gggaaagaag gataatgatg agttccgcca agagaccact tcaagaagtg gataatgagt | 60 |
| tgcttgattt tgcagctcag aatgaggcta atattgaaca tgataaagaa caagccccta | 120 |
| agagaaggaa acgtatttat gaagcgatta cccaatactc catgaacact caagatgagg | 180 |
| caggttctaa ttcaaattta tcttatcctg gttatatcaa gaaggtgaaa ttacgtaact | 240 |
| tcatgtcgca tgaaaatttt gaattagaat tgggtccaca actaaatttc attgtaggta | 300 |
| ataacggtag tggtaagagt gccattctta cggccattac aattggatta ggtggtaaaa | 360 |
| ccagtgatac aaacagaggt actaaattaa cggatttaat aagagaagga accgcgtcaa | 420 |
| ctaagattac attgtattta gataaccgtg gtccaggatc ctacgatcct gagaaatttg | 480 |
| gtgataccat tattattgag agaacaatta gacgtgatag ttccaatgtg tttagtgtta | 540 |
| agaccgaaaa tggtaacgaa gttgggaaca aaaagaaaga tgtccagctt attgttgatt | 600 |
| ttttctccat cccaattata aacccaatgt gtttcttatc tcaggatgct gcaagaagat | 660 |
| ttctgacagc cagtacctca caagataaat accatcattt tatgaaaggt actcttttag | 720 |
| aagatactaa aataaattta gataacgcaa gttctattgt tagtaaagct caagagaata | 780 |
| tgaggttaca tgccggttca ttacaagtac ttaaacagga atataaggac tccaagaaac | 840 |
| tagcgcgtga gttcaataaa acaagtgatc tgaacgaaaa gaaaatgcta ctatgtgcca | 900 |
| agatcttatc tctcgatatc gaggctaata ctaaatccag taatgccgtg aacaggaaaa | 960 |
| ttgtcaataa tgggaaccag ataaaaaatt ttgacaaaag aatcgagaaa cggaaagcag | 1020 |
| atattgaaag atttgtttcg gatcaaaaga aagctgaaga gggtattgaa aatcaaatga | 1080 |
| atataattaa tacaaaagac caagatttta gagctaaaaa agatgaagtt gcaaaattga | 1140 |
| gggctttgta taatgctgaa gaacgtaatc aaactcaaac aaaacaaagt attactgatt | 1200 |

```
gtaaaaacag aattcagctt ttcaataaga aaattgcaaa gttcgaacag aaaatcaatg    1260
aagaaatggg tggggataga gaagcaatga aggagcaact aaagacactg gaaaggaaa     1320 gagacgtagc ccaaggaaat ctttcagcta tgcaaactac attaagggat ctgcaaaata    1380
gggaaaagag cgaatgtgac caacgtaatg ttgaagttcg cactttagaa gatggtattg    1440
cggcaaaaac gtctgaatac aataaaatca agactggtaa taacgatttt ctacttaact    1500
tcgacagaaa aattaatcag ttatttgctg aaattgagcg caataaaaat catttccact    1560
ctatgccaat aggtccactt gggaggtttg taagtataaa acgtgagtat aatcaatgga    1620
cccaaaatat ccagaaattt ctgtcatcga cagtcagctc tttccttgtt acagacttaa    1680
atgacgatcg attattgaga aggataatga aaaaatgtaa tattagaaat attggtgtat    1740
taatttacaa aatgaaaagg ctcgatgttt cttcgtttct agttcgagca tcatatccaa    1800
ccatttacga tgccctcgtc tttgatacce cagaaatgga aagtttattc attgatgtaa    1860
catatttgga aaaagtggtt ttgatagaaa attataaaga ggctaggaat ttcctacaag    1920
gaaatcctgg gagaattcga attgcattat ctttgaggga tcgtaatggt ggttatcagc    1980
tacgtggtgc aaaccagtta gattctgtca aatatgaatc ccagataaaa attaaagttg    2040
gttcttcaaa cgaggataat cttgcatatc tgaaacaaac tattgatgaa gaaaggaaag    2100
agatagaaaa aatcaagaat aagtacgaaa cagttatatt taatacaaga caagagatga    2160
atacgaccaa ccaaacaatg aaacgtttgt cggaagatat taagagaaag ggacatgaga    2220
tcacgcaatt aactgttaaa gctaatgcaa ttgtggatac tgggttactg acatcgatga    2280
acgaagaaag agataagcaa gaaggggcag ttgcagtata tgaggccaca gtaagggaga    2340
tagatgctaa attggatgcg ctccgtgaaa agatacagcc aataaagata agctatgaca    2400
atgcaaaaca cagtcttcgt gaagcaaata aaacattaga tgaacttaaa gcagctgtta    2460
atagccgttc agacaaagta gaaagatata atgctgatat ccagaattgt gagcatgaaa    2520
tagaaaagct atctcaaaag aataaaatcgc tggaacaaaa taagaagtt cttgttaatg     2580 ggatcactaa gcagaagctg agtttggaac aaatttgttc tatggaagaa ttacagaagg    2640
ctaatctacc tgataaaaaa gatgagttga acgtgagat tgataagatt agtaaagaca    2700
taagaagggc agaaaattct attggtatat cagaagaaaa ggtggtccag ctatttaacg    2760
aaagtagggc aaagtataaa gatgcataca gcagattgga gagtctagaa actaccttga    2820
tacaacttca acaatccatc aaagagcgtg taatcaaata taacttaaat gtcaacgaaa    2880
cgttcttaaa ggccaatttg gacttcatcg gatctctgaa aatgagaaag ttaaccggga    2940
aattattctt taagaaggaa gaacatagtt tagagatata tgtttcaaca ccgggtgata    3000
caacggaaag aagtgtagat acttatcag gtggtgaaaa atcgtattca cagatggcac     3060
ttctattagc tacttgggaa ccaatgcgtt cgagaattat tgcccttgat gagttcgatg    3120
tttatatgga tcaagttaat agaaaaattg gtaccggttt aattgtaaat aaattgaaag    3180
acaaggttag aactcaaact atcatcatca cacctcagga tattggtaaa attacggaca    3240
tcaacgattc tggtgttatg attcatagga taaagatcc aaaaagacaa aataattccg     3300
ataatcgtgc aaattagtgt ctttttttag atattttat gacacggtcg ccaatatggc     3360
gtgcatttac ttgtttgttg atgcgacttt ttcgttggaa tttgaatgta atattaaact    3420
atataaattt tataaacggt aaaatatata tatatatcaa attatgagat aaaacaaat    3479
```

<210> SEQ ID NO 31
<211> LENGTH: 3024

<212> TYPE: DNA
<213> ORGANISM: Artificial Sequence
<220> FEATURE:
<223> OTHER INFORMATION: c4682_g2_i1

<400> SEQUENCE: 31

```
aattaactat ttatcaggtt attattatta ttatttaacc cgaataactt tattgaacaa    60
tataaaagat agtatattca actccagtta gtatctcctc tgacatttaa atcattacgg   120
agttttcttc tcttttacct ttttttttac ttttgctttt cctgaccata ttaaacataa   180
cggtgaaaac atacttttac aatattaaac attcctttt gatccaagga gaatataaat    240
aaatacaaaa aaaataccga aagaaataa atcatttcag agttaaagta aatacattat    300
accgattaaa ttgtaagaac atatagatta ataaaacaaa ataaactact aataattata   360
atattccaaa ctccgtcgtt ttgaaatata cactttcttt cttttttta cacagcctac    420
tttgacagta taattaaaga atattaaaat taatcattat cttttttattg ttattatatt   480
tttgcacctt atttcccaac catcccccaa aattatttaa acagcatact ctattaaaag   540
ttttgatata aattaaaaaa aaaaatagtc atttgatctt ttattaataa taataaaaga   600
ataatacccc aaatacataa caaatatgca agctaataaa gaacctgtaa ttgatattac   660
tatacaaagt ggtaacgatg aagtaataat attaaaggga ccacctgaaa ctgctccacc   720
ggtattatta tcaggtatca taacattatc tacatgtgaa actgtaaaag ttaaatctgt   780
ttcattaaga ttaacaggta gaatgactta taatgtaccc attataaata aagataaatc   840
gaaaaaggat aataatgaaa ctatagatca aacaaaagtt aaacgtttat ctgctgatag   900
atggttatat catcataaat gggatgattt tacaatagat aattattttta aaggtttata   960
taaaaattat caaacaaaga cacctattat ggattctaaa aatgttagac atactgtcgt  1020
accgtcacat ccaatagcac aaggtacttc agctccattt aagaatggtt tagcaagacc  1080
aagatcaact acttctttat tatcattaaa gacaaataca aatatttctt cacctttcca  1140
aagaagaaaa tctcatactt tattaaaggg gaaatatgaa ttcccttta catcaatatt    1200
accaggtgat attaacgaaa ctattgatgg tttacctgat acaaatgtaa attattattt   1260
agaagcaatt attgaaagaa ctaatggtaa atctgatctt tattgtagaa aatatgttag   1320
aattgtaaga acaattactc cagatatcgc agaaatttct gaaacggtaa atgttacaga   1380
tacatggatt gatagaattt tttattcgat ttctgttggt gcaaagactt tagccattgg   1440
ttcaaaagtt ccaataaata tttccgtgat tcctttacaa tcagggatta gactaggaac   1500
gattcgaata tcattatatg aaactgcaga atattgcttt aaaggtacaa gaacaaaaat   1560
tgatcgtgtc gtatcaagat tgaaaattga aaatccggaa aaattattag ttaaattaat   1620
taaagacgat aaatttcaag agaaatggga attagatttg ccatttagaa tcccagcaag   1680
tttatctaaa tgtactcaag attgtcaagt tatcaaagaa attagagtaa cacataaatt   1740
taaatgttca atcaattttt ataatgcaga tggacacgta tcaaaattaa aggctaattt   1800
acctgtttgt ttattcattt cagaatttgt accattgaaa gttagacgaa tggaatctac   1860
aacagatttc acttgtatca caaaggatat atcaaaccag attcgtaacg aagatgcaaa   1920
ggaaacaatt tttgaagcag gtcatacagg attagtatct ccacaatatg ataatgaatc   1980
aatgttaccc gtaagagcat taatgaatt attggctcct ccagaatatg aaaaccatgt    2040
ctttgataga agattttgta atgacatgga tgtggaatcc tcaatgttac ctcctccatc   2100
agatgtcgcc ccagatttac taccatacga accaaatgaa gagttgtctg catcaaagat   2160
```

| | |
|---|---:|
| cttaaaggat attgatctag ataattctac tcatagaaga atgagtgatg catcatgtca | 2220 |
| aacaatgcct gaatttgcat ttgctagtat tgatacggca gtagaggaag gactacctaa | 2280 |
| tgaaacaact aatgaacaac aacttattcc caacctacaa aattatacat ttggccaaag | 2340 |
| tcaaacaaac aatagtaatt atagggattc tcgtcataat agtaacgcaa gtaataacat | 2400 |
| tcaaacaaat gatatagata tggaaccatt aaatggtagt gaaatgccac ctccatccta | 2460 |
| tatggaagat gatcatgatc acataagcaa cacaattcca ccgattttg gttctattca | 2520 |
| agacagacct agacggttta gatctacttc actaacaaac acattcacat cagctgattt | 2580 |
| aggaccaatt gctattccag tgccagctca tacaataaat tcatcccaaa atattataag | 2640 |
| atcggtacca caagtctcca gaatgagaaa ttcttctgtt tcttcaaaca atccttttct | 2700 |
| aaatgatgtc attgtatcgg acgcatttgc aactatggta tcagagacaa ttcaaaggtt | 2760 |
| ttcaccaatt gctaactcaa gtagcaattc aagtgaatcg agagatattt ttaactctcc | 2820 |
| aacaaacaat caattatacc acacattttc agagccatat gaaaagttaa ctgcacaaaa | 2880 |
| cgaacgcaga tattcagtca cagagacaat gaagaataat aacaacgatt ttatatcaag | 2940 |
| aaaggatatt ctaactattg aatccagaat ggatcaagta gctatgggtc cagaaaacta | 3000 |
| attaaattca tatttggcaa ttat | 3024 |

<210> SEQ ID NO 32
<211> LENGTH: 2232
<212> TYPE: DNA
<213> ORGANISM: Artificial Sequence
<220> FEATURE:
<223> OTHER INFORMATION: c4154_g1_i1

<400> SEQUENCE: 32

| | |
|---|---:|
| ctgacaataa taaccttttg ttttaaactc accgaagtat ctctttcctt tggttcccgc | 60 |
| cttcctttaa ttgatgtcaa tacgaatgtt atacaagagc ataatttcac gtgcagcaga | 120 |
| caatttcaag aaagtccgtt tataaaaaga aacagaacac agggcactga ttaaagcatt | 180 |
| tgcacaaaat gaaattgtgt gaatctttct tagatggaca gttgcaaaca ctctcaactc | 240 |
| aacgtataac tacatttcag atcattactg gataaaaata cataagttta tgaaaccaag | 300 |
| atattgtcta aatataatga ctaagcagac taccgtcatt cagaaagact tatatatcta | 360 |
| tatataaaga tatacatatc gattcatcca agatttcccc caaatattga attctattaa | 420 |
| cactttcctc aatagcatac cgaactataa cacaaaatgt ctaaagtata tgaattaaac | 480 |
| aacaatatca gtgtaacaca acaacagtta gaccactgga ataaatttct tggcacatta | 540 |
| tcaacaccac aagagattct aagatgggcc atagttacat tcccaggtct atttcaaact | 600 |
| actgcttttg gtttaacagg tttagctacc attgatatgt tatctaagat tcattctcag | 660 |
| gttgaacaat atccgttagt tccattgatt ttcatcgata cattacataa tttcccacaa | 720 |
| actttagatc ttttacaagt tgtacaagat aaatattata aaccattgaa tcaatccatt | 780 |
| aatgtgttca aaccagtaaa ttgttccgat gaaacagagt ttgctaataa gtatggcgat | 840 |
| ttattatggg aaaccgatga ggataaatat gatttcttag caaaagttga acctgctagt | 900 |
| agagcatata aagaattagg tgttaccgct gtgttcacag gtagaagaaa atcacaaggt | 960 |
| gcagctagat ctgaattaaa atttgttgaa attgatgagt tgaataaaat tattaagatc | 1020 |
| aatccattag ctaattggac attcaatgaa gtccagtcat atattcaaga aaataatgtt | 1080 |
| ccgactaatg aattgttgaa actaggttat aagtctattg gtgactacca ctctacccag | 1140 |
| ccagttaagg aaggtgaaga cgaaagaagt ggtagatgga agggcaagac aaaaaccgaa | 1200 |

```
tgtggtatcc atgaaacaag taggtttgct caatttttaa aagataagaa tgaatcaact    1260
aacgaatcaa ctaccactaa agcctagcga agatgacatc ttaaacagag caatgtttat    1320 ataaaccta catattttat agaataattc atgttacaat tactcaagta aactttctgc     1380
caatctgtat acttcccagg atatatatat ttaagtttgt actagggttc atattgacaa    1440
tccgttaggt ctaattttat tttcttcatt tatatccgct ccgtccttag cggaaggtcc    1500
tatctcgctg aagcaacaaa ttaatagaat ataagaaat atattggaag aagatcttga     1560
accacgagga tgatatatac tgccataccc tggttaagag aaggtgttaa caacaaatct    1620
atcacaacta cgttatattt aattgctact ataccacaat gggtaacttt agatttccag    1680
taaagacgaa actaccacct ggtttcttaa atgcaagaat cattagggat aattttaaaa    1740
gacaacaagc agcagagaat gaagtcacca ttaaagcatt aaaatatatt gctagaaata    1800
ctgtacttcc accaaaggca cgtttgcaag cacaattgca acttaatatc atgcctaact    1860
atactaaaat gacacaagtt aagaatagat gtattgcttc tggtacagcc agagctgtaa    1920
taagtgattt tagattatgc agaacacaat tcagagaaaa ggcaagggct ggtgagctac    1980
caggtgtgaa gaaggtgtg tggtaaatcc atattatact gtctagaaat attattttac     2040
accaacattc catgaaaaga aaagtatacc agattgattt tcttatattt taatctaaaa    2100
ttttatatag gacatctggt gtaccatgta catacatata aatacctgtc ataaattttt    2160
gtatattcta ataaacaaac attcgtaaat aacaggattg caatagcagg ctcaagaaat    2220
tgagagataa cg                                                        2232

<210> SEQ ID NO 33
<211> LENGTH: 7626
<212> TYPE: DNA
<213> ORGANISM: Artificial Sequence
<220> FEATURE:
<223> OTHER INFORMATION: c422_g1_i1

<400> SEQUENCE: 33
ataagacata acagtgtagg aaaatgttag gaacataatg aagttctatt tattcataag      60
gttcttcaaa atgttggtat gtagaataga actgtttcgg tcgcctaaga tagacctcta    120
gaaaacgtat gaacttttct gttaaaattg gttgctaatg caccccccac attcattttc    180
ttcattagtc aattgacaga aattgtgtat agccacataa atatgatatt gctataacac    240
agaattacgc cgatattat cgattcctac gttaaatgag tgactcggaa aatatcgtta     300
cttttcagat tcgtttagtt cagtcattcc gagaactttt tatataccag ataaaaaggt    360
gggatgtcta gatcattaga aattcagaaa aagtagattt attgttggct caacaagtgg    420
ctgtaaagaa tatgatatcg acgattatat aatgagttac tgttaaatgt gaccgtatct    480
cttttcttgt ttgactccgg taattgggct ataatttaat tataatatat ttagtcggca    540
ttgtattatg gtatagaatg gagggttaag agaaaaattg tgaacatata tagctaagcc    600
aacagaattt aaatgatata gaaaaatgaa tattctcgtc aacgacataa attgtagcag    660
tcttccaccc caagtcattg ccaaatgtga aatgtatttc ttttttactt caaaattaca    720
gtataaaaag gcaatttaat ataacttaag tttaattgat gaaatcatca gctaacattt    780
ggctagtttg aaacctgaaa ataaccaatc tttcaaagat atataatggc attgattctg    840
aaaaacgact atatcacttt atggtgttga ctttcaaata tttttgggaa aagaattttc    900
tgagtaacgc aaagtagtgt caaattttga gagtgtatta ccaactacga ttagtctctg    960
```

```
aaaatggata taaattgtga agaagtcggt tatttacgcc taagtgaagt cgataacatt    1020
tcgaagtcgt gtctttcttg gttattggtt atattaacac gatttctgtc ctctatggta    1080
caagcccata ttatacgtat taagtatttc gatttatcag gtccaagaag atttcagcag    1140
agcttgtctg atataatagt tgttgttaac catgttactt aaccatatcg gtctcttcta    1200
tcttaaaaat aatagtctta aatacattat agcgttccaa acatatccat atcttattat    1260
gaattattgt ttacatatta tttagtacaa caataatatg taattcggga ttttcagaag    1320
taaacatatt tgtaaaaatt atgataaagt cacagctaaa aaaaaaaaac atttatttca    1380
cttcgaggaa acaacgaat agcgctcgct caactttgtt tatgaaattc atatggtaaa    1440
cgtacgcaat gtctttcatc tctttgataa ggtatatctt taattaactt ccaacaatca    1500
aacagttgtg ataattatac ttttttgaca atatatataa acctaggtca tagtcattgt    1560
tgttgtataa cactttgtaa cataggtagg gtcgaacatt cctatttgt tgtcacattc    1620 gcatagttca tgagaaaatg aaaactgacc aatcagacga gagataatta aactcacaaa    1680
aatgtattac taagcacagc aacgatcgga aaaattaaga aaaatattc cagttgtgta    1740 attcttgcta gcgcacctct ttttgttgat gtcatgcata ttgcaataaa gaatgaaaat    1800
attttccagc ggcgttcctg tttttttaaa tatatatata taaaggcgat cttttggtt    1860 tactgctaac tactattcaa ttcattcctt cagttatgag tttagaaaaa tttgctattt    1920
aatttcagaa caagttataa tcatagcacc atatttagat aaacttttct ctgatatttt    1980
taccttctga catgatatag ttctaatagg tagaaggttt cacaagatag taatatttga    2040
gatatatttt atttatacaa gcaaggtgaa gtcggtatgc tatttataca atttggtgga    2100
tttatattag acatttattg caacaatgaa gaatcataat ccgatctgct ttataccttt    2160
agaatcgatg caaatctata gttgtggttt accgatgaat gttttggtct cttttagtta    2220
attcatatgt tcgtaatagt gaacatctca taacgataaa atgctcgaac catacaaata    2280
ttaagatagt acgagtatga accatatatt tcgagagtac attatctacc atgtatccca    2340
ttaggctatt ttgtcgatta ttgttatgct gattttgcct gttaatagcg attcttcact    2400
tttcactatg taaaatccgt aaaatcacca tatcaaaaga ttagcaatca ggcacgcggt    2460
atgattgctc agtaaatcca attattattc agtataacaa gagcgatctc gttccttcca    2520
ataggatgat attgtcctct ctaaaattaa tgaatacctc gatgattgtg ctgtcatgtg    2580
ccatttcaat tttgtctttc gaggcattat aatttccgac aacaagttag gaaggatcgt    2640
tgttagtcgc accgggaaaa aagtgtgggt aaaacagatg gccaaaaaaa aaaaattgg    2700 taagcacttc gtagtaagac ctttgcggaa ctcagtgtat atgtatacgt caacagatgt    2760
aaatagctat gaacgaaaga taatggcaac tgggaatact ggacggcaag taaccgaaat    2820
ttgctcacgt tatgagaaat taagtgtaat caacttacac actaaaacgt atatgctaag    2880
actgaaatca agaattcaca atgatagctg ttacagtatc agtcctttac acaaccacac    2940
tttcatgtta ttgaagagtt cgaatcgcaa tgattgtaac ccagaatgat gactgttgca    3000
aataagagta cggcatgtta aaattaacga agttttataa caatatatat ataccgaa      3060 aagaaagaca gttttgttca actaaatacg cttatgcatg ctctcattca tatttcaata    3120
ccaagttcgt gtttttttt ggttgactaa taattttctg agtataacca gaagtaatca    3180
tcaactcaat gtcgaataat ctattccaat tgctcttgaa gcatacagag tctgatatag    3240
attgcaacgt ttttaccaca gctgacctta aggatgactt accacaaaca gtttctcaat    3300
tactgaatag aaatgatcct ttcgctcaag ttaaagaaaa tatcaaacca aataaactga    3360
```

```
atgtcgtatt cacagatgaa ttgacattat taagggcatt gcctcatttg accagtttaa    3420
aagaacaacg tttagtcatc aatgttaaca tcggtcataa cgattactca gtcgtgtcta    3480
cattaaaaga tctaaatatt gttactttga tatctaacga ttataactct gctctcaaga    3540
atattaacgt cgctaattct gttgccttta actcttctac tacagtattg cactttatca    3600
actacagaaa gtgcaccaat gatttgcagg atatcaaaga aaatgaatta ctaccggtta    3660
gtttaatcaa taatggccaa ttacaatctg aagacaatat gctatccgaa ttaaacaatt    3720
tttcattgtc tcctacttca tcagaagatg catctgttgc tgttatcaac ttatctcctt    3780
atggaaagga attttctaga tatttgccat ctcaagtctc acttattgat atcaacattt    3840
atagaccatg ggatattgat caacttttaa ctctttttgt cccttctatc agaaagattg    3900
tgattgttca aggcgctagt gcagatgatg atggtgaaca atctcatgct tttgatccat    3960
tgttgttaga tttttttcagt gattttaata aattggtcga agaaaagatt gaccaattga    4020 tttttatcaaa agtaggctta atttccatct gtgatataaa agactcctta gaaattattg    4080
tttccaacgc tgttaaggat gctccaaatg ctcatctatt tgtaggtaaa ccggtcgatg    4140
gtattaatgg taaatattcc agttctattc tttcttcgat tgatcaccaa cgtactttcg    4200
aaagttctta tcagggtt ctgcaacaat tattttcttc aaatttgaat attttaaacg    4260
aatttcagag tgattctatt gtggctaatt ctccggaata cggctttggt tatctgttga    4320
attcagataa cattcgtgaa aagttggttg aaaatgctag aagcttactt gacttcactt    4380
ccttcaaaga tataccagct gctgatgcca ctaatttggt taagcttttg tcaaaatgga    4440
ttgattgcaa ccgctcttca aagagtacca ccgaagagtc gaacgaaatt tctactgcta    4500
tttttaatat ttttaagagt tatccggaat gtcaatcaat caagacattc ttagaaatat    4560
ctgatgatat cgaagattac ttatttaaat caaactggtt aattggttct gatgcttggt    4620
catatgatgt aggcaactcg ggtgttcatc aagttttaag ttcaaagaag aatataaata    4680
tgttaatcat tgattcagaa acttcctcca ctataaaacg aaacaagtct cactcaaaga    4740
aaaatattgg tttgtatgct atgaatttcc acactgtata tgtcgcttcc gttgctgtct    4800
attcatctta tactcaactg ttaacttcat tattagaagc tgcgaaattc aatggtcctt    4860
ctgttgtcgt tgcctatcta ccttatgaaa ctgaaaagta cacccccagtc gatattttaa    4920 aggaaaccaa aattgccgtt aattctggat attggccatt gtacagatac gatccatcta    4980
ttgaagatga taatgaagct ttccaacttg actcttctgt tattagaaag gaactccaag    5040
acttcctaga ccgggaaaac aagttgacat tattaacgaa gaaagaacct ggaattgaga    5100
ccactgttga acaatctgtt tcagatgcta ttgctaaaaa aatggaatta agaaacaagg    5160
ctgccttaca tcaactactt aatggtttgt caggacctcc gttacatatt tattatgcat    5220
ccgatggtgg taatgcttca tctcttgcca atcgtttggc taatagagct actgcaagaa    5280
acttaaacgc tacgtctcta tcaatggaca ctattgttat ggatgaatta tcaggcgaag    5340
aaaatgttgt ttttattacc tccacggctg gtcaaggtga atttccacag gatggtaaaa    5400
cattctggca agaactaaaa atggcaggac aagctgatct atcaagtatt aggttctcgg    5460
tatttggttt aggtgattcg aaatattggc caagaaggga gattctcgt tacttcaata    5520 aaccatcaaa agatttattt tccaaattac aatcactcgg tgccgatcca tttgttccac    5580
tgggcctagg tgatgaccaa gaggataatg ttatgaaac tgcgtattcc atatgggagc    5640
aacaattgtg ggttgaactt ggtgtggata agattgaagt tgccgacgaa ccaagagaac    5700
```

```
tgactgccga agatgtcaaa ttacaatcca atttcttacg tggtacatta gcagccgatt    5760
tagtaaatga agaaactggc aacattacta atgaaaatac acaaattgcg aagttccatg    5820
gtttgtacat gcaagatgat agagatatta gagccactcg caaagaacaa ggtttagaac    5880
cattatatgc attcatggct agagttagaa cccctcatgg tactgcatct cctgagcagt    5940
ggttattact tgataaatta tctgacgaaa ctggtactgg tactattaaa ttaactaaca    6000
gggctacttt ccaactgcat ggtgtattaa agaaagatat taagcataca atcagatcga    6060
tgaactcgtt actaatggat actctagctg gttctggtga tgttaataga gatgttatga    6120
tatctgcaat tccggaaaat aagaaagtac atgatcaatt ggtttctatt ggtaaacaga    6180
tatctgagta ttttttgcca aagacgactg cttatcacga aatttggtta catggtgttg    6240
acgaacgtga cgatgaccca acctggccta ccatttacga aatagaaaaa gaaggtccaa    6300
gaaagaagaa gacaatggtt agtggtaatg ctctggtaga cgttgaacca atatatattccc    6360 cggtttatct tccaagaaaa ttcaaagtca atattgccgc acctccatat aacgatgtcg    6420
atgtttggtc aagtgatgtt ggtttaatat caattattaa tcaagatact caagaaattg    6480
aaggtttcaa tctattagcg ggtggtggta tgggtacaac tcacaacaac ataaagacat    6540
ggcctgatac tggtaaaatg ctaggttttg ttactccaga caatgttatt aaagccattg    6600
agagtgtatt aattttttcaa agagataatg gtgaccgtac aaaccgtaaa cacgcacgtt    6660
taagatacac tatcgacaca gttgggtttg aaaactttaa aaatattgtt gaagaaagac    6720 tagttttttga tttcaaacca ccaagagatt atactatcga ttccaatgtt gacaaatttg    6780
gttgggtcaa agacgaaagt ggtctgaacc atttcacaac ctttattgaa atggtagag    6840 ttctagatgc tcctggtatg aatcaaaaga caggtctgag ggaaattgcg aagtatatgc    6900
aattgaagaa atgcggtgag tttagattaa ccggtaacca acatatcatt attagtaaga    6960
tacaagataa ctatctacca gaattaaaag aattgctaaa acagtttcaa ttggataacc    7020
ttcaattgtc aggattgaag ttatcatcct catcgtgtgt cggtttccca acttgtggtt    7080
tagctatggc tgaatcagaa agattttttcc ccattattat tacagaaata gaagaaacat    7140
tggaagattt tggtttacgt cacgattctg ttgtattaag aataactggt tgtggtaatg    7200
ggtgttcacg cccatggtta gctgaagttg ctttgatagg taaagcccca aatgtttaca    7260
atattatgct aggtggtggt tatcacggta acagattgaa caaactgtac agatcaaatg    7320
tcaatgataa agacatctgt ggtattctaa agcctttgtt taagcagtgg gcacttgaaa    7380
gatatgaagc tgaacacttt ggtgactttc taattagaaa agatataatc aaggaaacta    7440
cagaaggaaa atatttccat gataatgttg cccaggaagc ctattaatta ttttttttat    7500
ctatttgtat atttatattt atttatttat ctatttacta aaaagaatat tattattcta    7560
aagtacgtga tcttcggtat atagtttaaa atcagttgaa tgactacatc atttttttt    7620 aagagg                                                              7626
```

<210> SEQ ID NO 34
<211> LENGTH: 1418
<212> TYPE: DNA
<213> ORGANISM: Artificial Sequence
<220> FEATURE:
<223> OTHER INFORMATION: c3775_g2_i1

<400> SEQUENCE: 34

```
ttatcagtat atgctgttaa taagcaaaga tatatcggtt gtgtgtgaac tacacataat     60
tatacgttga ttatcaatgg aaatagaatg agacttatcc gacatcggtt ttccagtgaa    120
```

```
aatatattgc ccccttagtgc ctctccgata tcatagatat gttgcctaaa gccagtgatt    180
gttgactcac atacagacac accctattct tgaattgcct atcgcttatc atttacaata    240 taccccctgga cctcatttcc tatccttttt tgccccacta ttagccagga aaaaatgatt    300
tactgtttga acaatcccgt cttcgcaaat catatattca cccacattcc cgaaaactcg    360
gaaaactatt tcttgcggta aggcaatgaa aatgaggaac agaaccactt cggacttcga    420
cggccgttcc ttcggccggt ttggcaccaa attttttcgag aagcaaaaaa gaaacgaagg    480
aaacagaaag agaggggcag agacgaaaaa tggaagaaaa aaagcaatt ccacgcacat    540 tctacgaggg ggtctctgtg aaggagtgtc cgatgatttc cgattactta cataagtggc    600
attatgagat tcctactgat tttaattcaa taagcaaaaa aaaatttttcg tcgagaataa    660 tgaggaggga tagatatgtg ccaaatttgt tgttttgaag ataagtattt gagacatata    720
taaaccgagt taaaattggt atatgattag aatagttcct gctgttcctg ttcctttctg    780
gtaatgaggc gaaccaaaga atcatagctt ttaaaaataa aaacaaacaa aatgtacagc    840
gagggaactg ataagacttc cgaaatccgt gaaatttat tattgaacgg tttctaaaaa    900
taatgactaa ggtggactga caccaaattt tgcataagta ataatattat taaacaagtt    960
ttagaagaca tggtatatct cataactaca taacatttac acatatataa tctaatacat   1020
ataacatata ctggaatatt cgtgtttctt taattatttt tttatccttt attaatttat   1080
tatgtatggt ctctataaaa tatatatcat gatgatgcat taattaatgt tattcatttc   1140
cccgcgttta gttgttcaga taacttgcct tgagcgatta gtgccgcagg agcatccatt   1200
acaggtaaca tgatttcaat cattctaatg gtagagtttt tctggaaatt tttatcgtta   1260
gttaactttc tccattctcc tactgtggat actctataag tttcataatc tgtggccccg   1320
aagacaggca atagttgtaa atgatcccaa ctttggactg cattatatgc agcatcgggt   1380
ccgtggatta atctttcaat agtatacccca tcattatt                         1418

<210> SEQ ID NO 35
<211> LENGTH: 2172
<212> TYPE: DNA
<213> ORGANISM: Artificial Sequence
<220> FEATURE:
<223> OTHER INFORMATION: c4997_g1_i1

<400> SEQUENCE: 35
agacagacag tcacatttgg taactgttct ttaaccgttt gagatatgta cacatgtatg     60
tgaacattat taagattcct gtcctcttag atacataata tataaatagg gatacgtata    120
ctctgtaaag tgggatctta caagagagtg agagagagag caacagaata aaaaaaaaag    180
gtacacacac agtatcagtt gagcataacg atgggggcta tcacacagaa accaagagac    240
atatatgaga agaaagatgg tgatgatcat ttaaatacga tgaaccatga gcgttatgag    300
tgtccgcatc cggattgtaa taaaagtttc tcaaggcagg aacatttagg tagacataaa    360
ttaaatcatt ggccaaaaga aatttttcact tgtaattatt tatttcctga gactaaatta    420
ttatgtggta aaacatttgt taggaaagat ttattagtaa ggcatgaaaa agagacatact    480 aaggagaaaa atagattaca tgcaaaggag attcaccaa ctgctacaaa tgtaactacg    540 gaaagaaag ttgtcaagaa aagacaatcc aagaagaaac agcaacagca agggaaagat    600
attcaaaatg ttattccaga gtcaaatgcg gatgattcag gtatgggaac atcaaaaata    660
aagaataaga aaaaaaatat aactaaaaga ttaagcacta aaattgatag agtcgcttcc    720
```

| | |
|---|---|
| gttccaataa gtttgaaaaa tgatgataat actacaacaa caagtaatgg aatgaattat | 780 |
| ccaacaagta gtaatttgaa tcaaaataaa ttaaattcaa agagtttatt aaatatgact | 840 |
| agtttgaatg ataataactt aggcacagct acatttttcg gtaatggacc aggacaatct | 900 |
| tcaaatatct tcgattggtt atgggctcct gaacctaaaa gcaaattaaa cgatacaaca | 960 |
| agtatgaata ttcagaacaa ttctggtttg aatcaaccat ttaatgttat gtcgcagcaa | 1020 |
| cagatgcctc aacagcaaca acaacaacaa cagatattgc ttccgaatgg tacttacca | 1080 |
| ttacatttac aacagtattc tccattagat actacgaata ataatcataa taataataac | 1140 |
| aatttaccat taagtccaga atgaataaa acatataatg ttggtaacaa ttccaatatt | 1200 |
| gttgtattcc cagtacaaga ggtacaaatg gattattcag atgaaagaag attcccaata | 1260 |
| acacaatcaa tgaataataa tagtagtatt gtacatactg ttacaatgag tccaactcaa | 1320 |
| caatatatg atacaagtca tacagggact ttaccaacac atcattcaac tgtcaataac | 1380 |
| aacaacggta taactactat tggaactaaa aaatttggtc gtagacgtaa attaacaaca | 1440 |
| atcgataaaa attcaccacc aaaggattta tccactgtga ttaacgccga aagaaatta | 1500 |
| ttattaccat tgacacaaac aacattagca aattctaaaa taaatactgt aattaataat | 1560 |
| cctttaccaa ataaagatcg taggatatca atagatgcag aaattgttaa tggtaatgaa | 1620 |
| aatattaaaa atgacgacac taggggtaat aataataata gtacaaacga taataacgag | 1680 |
| gaaacaaaga atgttactga tcgtctaagt gtcaattata ttcttctatg aatgttgtgt | 1740 |
| attggaagat ctgcattatt atccatctgt aaaaaatttg gattaagct tcccttttt | 1800 |
| tttcacatct gccataccat catcatcatc atcatcatcc cctttgtaac atatttattt | 1860 |
| caatatatag atatatcaaa ttttttcat aaaacgaaaa gcaaatgat aactacatcg | 1920 |
| ctatttcat tgattcaact caacaatttt tggattaaac tttcacgaca tcattacatc | 1980 |
| attgttttgc atatgtcacc ttctcacttg cttgttgaca ccattaaacg gtaactcaac | 2040 |
| attgatgaaa tgaaatttgg accaacagaa ctagcctcgc ctcattattc aaaggaacag | 2100 |
| ggaaaggcat ggaaggagcg gaggggaaca gcaagagaga actcctcttc ctcttcctct | 2160 |
| tcctcttcct ct | 2172 |

<210> SEQ ID NO 36
<211> LENGTH: 4720
<212> TYPE: DNA
<213> ORGANISM: Artificial Sequence
<220> FEATURE:
<223> OTHER INFORMATION: c7526_g1_i1

<400> SEQUENCE: 36

| | |
|---|---|
| aattttgac ttgtaattaa acatggtcag atctctggat gttatgtcat ctttttcac | 60 |
| cttgagtata tatattatat aaagaaaaca taaaacgtat caaggacttt agtagtttgt | 120 |
| ctcttttcac tggtttctat atttgaaaca ctttttattt cacttaatat tgccctcatt | 180 |
| ttatttttt attgtgtgct ttgagttaaa gtaaataaga aaccatttca acggaatctc | 240 |
| cgaactttcg aaaaacaaag acagaagaag taacaatgac tgcaacttct gatgcatcat | 300 |
| tgaaacaaac tctctatggg tttgctgcaa gagatccatt aaataaatta tactacacta | 360 |
| cattaaacaa aggtcaaaat actaaggatt caattccaga tgttgctgtt caattattaa | 420 |
| atgataacga tccatttgct acaatttggg aaaatgtctc tgaaacattg actacagtat | 480 |
| tcactgcgca acaaactttg ttgaaaagtt taccctcatct atttcaattg gaacagaaac | 540 |
| caatcatcat taatatcgat ttatccttac aagattattc tattatttct gctatcaagg | 600 |

```
atttgaatat tgttacttta gtatcaaatg acggttcttc tgctattgct catgctcaat    660
tagctagtaa cattgctttta caaagacaaa tcccagtatt ccatttcatt aactattcaa    720
taatcgataa atcaggtgaa atcattccag atttccaaga aatagaacaa tcccaagaaa    780
taaccaaaga cgacaacgaa gaagaggaag aagaagaaat ttccttggaa caatatttaa    840
ctgaacaaaa aatacaatct tttgatctat tagcacaagg ttctaatcca tctgtcgcaa    900
ttgtcaatct ttctcaatac tcaaaggaca ttgcctcagt attaccaaat accgcctctt    960
taattgatgt taagatttac aggccatgga acattcaaga actgttacaa ttgattgcac   1020
cttccgtctc taagattgtt gttattcaag gttcctacaa ggataattat actacagttt   1080
ctcaatcatt cgatcctttc ttattagatt tcttctccga ttttcaaaaa ctggtcgaaa   1140
gaaacatcga tcatgtaatc ttaactaaag taggtgaatt accaattgat gctattcatg   1200
actcattaga tatcatcatt aataacgctc ataagaaaa tccagatcaa aacttatatc   1260
taggtaagcc ataccacgaa caaattcaaa ataaagaata catcgatttg attcattcct   1320
ctgttaagaa tgttctaaaa ttagaagaag cttatttgaa ggttctaaga caattattct   1380
ctagtaattt acaaatttta aatgaatatt caaatgatac tgttaatggt aacactcctg   1440
aatatggttt tggttactat ttaaaacaag atcaaactcg tgaacgatta attaatttaa   1500
tcaaatcttc attagatgtc tctcttttcg ctggtgtttc taatggatca gcagtagttg   1560
aaaacttatc caaatggtta aaattcaatg aatctcttga tgatcaacaa gttgaagaag   1620
ctaacgttat tgctcatgat atctttgaaa ctttactagc taataaatct aacgacacaa   1680
ttgctaaatt cttatccgtt gcttctactg aggacgcttt cactttcaaa tcacattggt   1740
tagtcggttc ggatgcttgg tcttatgatt taggcaactc tggtgtacat aacgttttat   1800
catcaaagaa aaacattaac atgttattaa ttgattctga accatacact gctaagaaca   1860
aaattgctca taagaaaaat gttggtctat atgctatgaa ctatcataac gtctatgttg   1920
cttctgttgc tgtctattcc tcttacactc agttattaac tgcaatgctt gaagctaaca   1980
aattcaatgg tccttcttta attctagcct atttaccata ttcagaagaa tcaaatacac   2040
cattagatgt tctaaaggaa actaaagttg ctgttgaatc tggttattgg ccattataca   2100
gatatgatcc aagtaaagag gatgaagatg atgaaactca tggtttcaca ctagattctt   2160
ccgtcattaa gaaagaattg caagacttct tagaccgtga aaacaaattg actctattga   2220
ttaagaaata cccaatcgtt gctgacaata ttaagaattc tgcaagtgat accattacaa   2280
gaaaacatga tgctagaaat aaagctgctt tagatgaatt gcttgatggt ttatctggtc   2340
cgccattaca catctattat tcttcagatg gtagtaattc tatcaattta gctactcgtc   2400
tatgcaaacg tgccgtcgct agaggtttaa agctaccgt attatcaatg gaacaagtta   2460
tcgtcgacga attaccaggt gaagaaaatg ttatcttctt tacatctacc gctggtcaag   2520
gtgaattccc acaagacggt aaatcattct gggatgaatt aaaggcttct accatagatt   2580
tggctggttt gaatgtatct gttttttggtt taggtgactc caaatattgg ccacgtaagg   2640
aagatgctcg ttactacaac aaaaccttcta aggatttagc tgctaaatta gaggttcttg   2700
gtgctaactt tattgtccct ctaggtttag gtgatgatca agatgctgat ggtttccaag   2760
aaggttatca agcttgggaa ccaaaattat gggaggctct aggtgttgac aacgtcgatg   2820
ttccagatga accaagacca tggaacaatg aagatatgaa actcaactca gatttcttaa   2880
gaggtaccat tgttgaaggt ttaaacgacg agtccacttt agcaattcat ccatacgatc   2940
```

```
aacaattgac taaattccat ggttgttata tgcaagatga tcgtgatatc agagatatcc    3000
gtaaggctca aggtttagaa cctttattta gtttcatgtc aagagttaga ttaccaggtg    3060
gtaaagccac tccagaacaa tggttggctt tagataaaat tgcaagtgaa gtcggtaatg    3120
gtactatgaa gatttctaca agagcaactt tccaattaca tggtattcta agaaggatc     3180 tgaaacatgc tatcagaggt atgaattcta ctttaatgga cactttagct gcctgtggtg    3240
atgttaacag aaacgttgtg gttactgctc ttccaaccaa tgctaaggtt ttcaaccaag    3300
tatctcagat gggtactgat atttctgaat atttcttacc aaagacaact gcttatcatg    3360
aaatttggtt acaaggtacc gacgaacgtg atgatgatct aaactggcca caaattttcg    3420
agaatagaaa ggaaggtcca accaagaaga agactttagt aagtggtaat gcattagtcg    3480
acgtcgaacc aatttacagt aatgtttatt taccaagaaa gtttaaggtt aatattgcag    3540
ttccaccata caacgacgtt gatgttttct ctattgattt aggtttaatt gctattgtta    3600
atccagatac acagattatt gaaggttaca acttatatgc tggtggtggt atgggttcta    3660
ctcacaacaa tactaagaca tatccaagaa ctggttctga ttttggtttt gttaaaccag    3720
aagatgttat tcctgctatt caagctgtta tgattatgca aagagataat ggtgatcgtc    3780
aagatcgtaa acatgcccgt ttaaagtata ctattgatga tattggcgtt cctcaattca    3840
aggctatggt tgaagaagaa tggggtaaga agtttgaacc atctagacca tacgaacaat    3900
ttatttctaa ccacgattac ttcgggtggg ctaaggatga gactggtcta aaccattata    3960
cttgtttcat tgaaaatggt agagttgttg atactcctga attacctcaa aagactggtt    4020
tagttaagat tgctaaatta ctacaaaaga ataaatctgg tcattttaga ttaactgcta    4080
ctcaacatgt tttgatttct gatattgaag ataaggactt ggatgaagtc aagaagatct    4140
taaagcaata caaattagat attacagaat tgagtggtat tagaattgct tcttcatcat    4200
gtgtcggttt accaacttgt ggtttagcta tggcagaatc tgaacgttac ttacctgtct    4260
taattgatga aatcgaagag gtcctagaag aatttggtct acgtcatgat tctattgtta    4320
tgagaatgac aggttgtccg aatggttgtt ctcgtccatg gttagcagaa attgctttaa    4380
tcggtaaagc tccacatact tacaacttaa tgctaggtgg tggttactat ggtcaaagat    4440
tgaacaaatt gtacagagca tcagtcaagg atgatgatgt tattggtatc ttaaagccaa    4500
tatttaagag atgggcttta gaaagagaag aaggtgagca tttcggtgat tttgttgttc    4560
gtgttggtat tatcaagcca actttagaag gtaaatattt ccacgatgat atcgctgaag    4620
acgcttatta gaggaacggc gtctattatt ttcatgtata tgtatattta taaatattta    4680
tttcacaact tatttatttt aactattaat tctttaaaat                          4720
```

<210> SEQ ID NO 37
<211> LENGTH: 953
<212> TYPE: DNA
<213> ORGANISM: Artificial Sequence
<220> FEATURE:
<223> OTHER INFORMATION: c10116_g1_i1

<400> SEQUENCE: 37

```
caaatatttt gaaaagtgtt agttaatact tattcaaact aactcatata catccctaac      60
aatcaaagac tcacttacat aatgaagatc ctaacatccg aagaaattaa tgctcatagt     120
gcctatactt taaaaggtgg tgcattaggt gccgttatag gtttagctgg ttcagctgca     180
ttatttaaat tcttaccaaa aagattccca ggttttaaac caagtcaaat ggcatggtct     240
gctaagactg cattatttat tactcctcca acttattta cagctatttg tgcagaagaa      300
```

```
gcatctaata gatttgatgc tttgaaatat tccggttcat atatgtcaga tgaagctcta    360
gagagacaag cagcttggga taaattatca aagaaggagc aaatggttga aactttaaat    420
aataataaat ataaaattat tacaggttta tgggctgctt cattatatgc atcatgggaa    480
attattaata gagataaaat tatgaatgct actcaaaaag ctgttcaagc aagaatgtat    540
gcacaattta ttactgtaat attattatta tgttcagttg gtttaagtac ttatgaaaag    600
aaattaaatc cagataaagc taaacattta gagagtcaac gttgggctaa tgctttaaaa    660
gctgctgcag aacaagaaaa gatggcagat gcacaaacta ctttctctaa tgaagaaaga    720
agagatgcaa agattttcaa atatgattaa tctgttttgt ttgtttgttt gcataatatt    780
attattacca tttactatc acgcaatgcc atattttata cattttatac acaatccaac     840
tttcctccca aatttatttg aacatctata tttatgaact tctattttt ttaattcctg     900 tttcacttac tcaatcttat ttaatgactt tattctcgta taaaaaaata caa            953
```

<210> SEQ ID NO 38
<211> LENGTH: 5517
<212> TYPE: DNA
<213> ORGANISM: Artificial Sequence
<220> FEATURE:
<223> OTHER INFORMATION: c2453_g4_i1

<400> SEQUENCE: 38

```
cacagctttg gataatgtta ccagtgatga tctgtataaa aatacgtaat ttgaaaagat     60
gagcttacat gttgtgagaa gagctgctct gcccttaaac taagaaacaa caattgtcga    120
caacagtatt cctttgatcg aaacaagaaa atgtcagttg aaactttgat atactggtca    180
attgaattaa taatataaca caaagaagag tattcctatc gtaaaccatt agttagatcc    240
caaaggaaga ttgattatca tgcccaactt taagatgtac atttagtttc aattaagtta    300
tattaagagt tgtaatttca agatattcac cctatgccga attaacatat tcggagtagt    360
cgttaagatc aatactactc tgtaggtgac taaataaatc tgttctacgt aattaactct    420
cccagaaatt ccggagtaat cacaaagaag gaagatatgg ttatcggaat ttcaattgac    480
ctgtcagatg gttgaaatat tagattagta aaccaaaaca atctcacaca tacatcaatt    540
aaatctcaat tgagtattaa taagttaatc aatagataaa ttcaaaaata tgtcccttat    600
aatcaaactt ttcgagatca agtttttcat caacctttga atacgactcg gcgagcggct    660
aatttctatt cgcggatcgg taaggaacgg aattacttca agttcacata aaagaaataa    720
gaaagtgtct tgtttacaga acgatcagtt ataatacaac taaatggttg caaaaaatac    780
tagattaaaa ccaaaaaaaa aagaagaaat aactggggca agccgggaat cgaacccggg    840
acctcccgca ccccgagcgg aaatcatacc tctagaccac gtgcccttga aatttcaaat    900
cttgaaattt tgttgggtca ttatatacgg gagctgaaat tcgggtaata ccgaaatatt    960
ttaaatggta ttatccgatt tattcattag tatcttaatc tgataaatgg tctagtattt    1020
tctcgagcta ttattgtatc ttagtattca aaagatgatt agatatatga ggaaattatg    1080
gaacaaaaag gaaatttca acgtttcac taatatgtaa aataatttgt gacaccgttt       1140
cttctaataa ttttaaataa agaaacatct gataatgttt gatgcaaaag tagtggacat    1200
cgtcctttga caacactgtg aaactgatat tcttaaaaat tgtcaaatag acccatatca    1260
aatttatcat gattaaatcg ctggatcaat acacagggtc atataattag tctgatttga    1320
atatcaatct gcttcatgtc ttatcttcgc aaaccaaaat ttagttatta atggattaaa    1380
```

```
actgtatatt tataccatct aacaacagaa tgtttggttt aaactatagg gtatcattaa    1440
actcaattat taataataaa aaaagagaa tttagtatct taaatgtatt aataataatc    1500
ttagatcggt aaacattgtc aataaagagt gaattgcatt aataaattag gtcaacaact   1560
tagctattat taataggtcg ataggtgaag aaggacaata atagtttaat attttagtat   1620
attttgaatt gaaatgggaa aactggatgg gaatgatatt gaatgtgggt acatcctaca   1680
gtaatggtaa tattatcaga attaccacaa gttgaacaaa tcacgtagac tatttctagc   1740
gctatatacc tcacaatctg taatataagt ctacaagtgt tcgtctatgt catgattcga   1800
taccacggaa aagaatagat caatagaaag tggtaacaat tatctgggac tgtcttggag   1860
atatcagacg tcccattcat cttgaatttg aaacatatat ctctccgtaa caattcgaaa   1920
ttgtcactaa tggaagcaga aactcagata ccaaacacat cttttgagta acacaattat   1980
ggttctttga cggaagattt attattccaa aattaagagg ggattttgat ttaaaaatgt   2040
caacattatt taataagaac atatccaatt caaatcctta acaatagcta atagaaactg   2100
ctctaagacg tgtattatat aaacccagag aaagttaaaa tatgtccttt tacaacttag   2160
aagttctcga aacgctaata attacctgtt cttctgaagc tgctaaacga atctagaatt   2220
gatttgttaa ccaaaaaagg aacacaaaca cttgtgaaac ttgtataata tgtgtaatta   2280
tccggaattt tacagtttga attagctctt tatgttaaga acaacattaa ccctttttat   2340
tctgtattcc ccactaattc cccagacaat aaggttagtt ctccattggc ctgcatctcc   2400
cacagaatat aacacaggag attaaataat ccgcgtaata tatcaagata tccatatgga   2460
aaaatatgac aagacagtct cttcagcgtg ctttcttggt tgataaatgt caacaggctt   2520
ttgttcaaat aaggaaaccg gagtaaacaa cacgaattag gtattgaact aaaacaggaa   2580
cttcaaaata aaaccgaacc ccttcatcta cccacgttaa tgaacagagt tgaacgatca   2640
tatattcatt tggaataaat ttctccacat ctattaagtt acggattaaa taaatggaac   2700
atctccaatt aataacattt ccttaattaa tgccagggag tcggaattat gtttacttat   2760
ttcaggagtt aacagaatta ttttttcaatc gtggaaataa gaaagctcgg aacatttatt   2820
tctcaattgc atattagcta agaaaaagta atggcgaaaa gaaaaaaacg gagaaatttt   2880
tttattgaag tcttggatag gcggaatgat ttgtaaagtt gtcatagaaa actaattaag   2940
ttttgagaag gtatctagca ttgctcaact tataggtac gctttggaag aattaaaaca    3000
aattaacttt acgtagtagc tccgacattg ttctggcatt gactttatca aaatcgcata   3060
ttggaacaat caattagggt cttctgtgcg ctttagacat taccaacaaa ttccaacgga   3120
accctacaaa gtgtggggga agaagagtaa ttgttgcctt ttcctctctc aagcaagtgt   3180
gtaatcaaac acacctttta gctaattcac tctccgcgaa gtttaaatat gaagtttttc   3240
cacctatttt caaattcaat tcccaacatc caaaatttat tcctttacaa gatcacaca    3300 ggttattaca ttaggaattg cttttttttt tttttttct tctttccccc ccaagattgg    3360
tgatttgcct tccagattgg aaattattta cgcaaggaat agctgcagaa gcaaggagta   3420
aaatgtcgca gtcaatagtt ttcccgcccc gcgttttttc tccggcgatt ttatctccgc   3480
ttgtactatg ttatctttgg agaatgctat tccaagagt ttcggaaaaa catttatgaa    3540
aagaaataat atcaaaaact gtatgcgaag ataacgttgt aggatatatt tctacgatgg   3600
aacactgtgc cccgcgaatt ttaaagatgc aaaacaataa ctacagatct atctgagaat   3660
atatcatggc acgaccccca ccccataaca ttgcttctgc attagtttct cttttccccg   3720
tctcggaaaa atatattcgt ttttccgaac aaacaaaaca tttcatgtac gtatattcct   3780
```

```
tcatgttcaa tagtagctta tgtaacaatt tgttcggtat cctattgata ctttagcgaa    3840
atatattcaa ttgtgtgtat ggtatgacag atgtcaagat atatatatat atatataaaa    3900
ggaagaaact ttcccattct agactaaaga cattcattta atggtttggt tctttcgttt    3960
tccacctttc cccttcgttt gtcaatctgt cattgaaatt taaacaatc tcaattagta    4020 acactagtat acaatcgttc acaataatta ttgtactgta caattattat tattattttt    4080
ttaagaaagg tcaccaagat taaatataat ttcagttttg aaaggtactc aattgtaaga    4140
aaaagtaata taatataata accaaaatga gtgttaatcc ccaaactaaa tttccagctg    4200
ataacaatga tagaccattt agatgtgagc tttgtcatcg cggctttcac agactcgaac    4260
ataaaaaaag acacgttaga acacataccg gagaaaaacc gcacggatgt cagttccccg    4320
gatgtaacaa atttttcagt agaactgatg aattaaagag acattcgaga acacatattg    4380
gtacatctca aagaaagact aggaagataa ttccaaagaa taatagtgag actcaaattt    4440
catcaaaacc aattactatc gctgcttcaa agaaagtgat taaaaaggag ataagtacac    4500
ctccaaagac atatactgtt ccatcattaa catcattatt acatcatgag actacaccaa    4560
tgtcttcacg taaattatta gctggttcca catcacttga aagaccgatt tcaagaacaa    4620
tgtttcctcc aagtatacag aaagtttccc ctatgagtga aaatagttct gctgaatcat    4680
ccataccgaa ttctccaatt tctcaaaata attctatatc gacatctagt agttcattgt    4740
ccttaaattc attacttaac agtaatgtta acaataacaa taatcaaatg tcatctgtat    4800
catctgtatc atcatattca gatggtagtt tcaattattt agatacatca ttaaaattat    4860
caagtaaaag acgtgcagat ttccaaattg tttcagaaga aaatgatgca gatagcactg    4920
gtagtagtaa tataagattt aatagtaatc aaccgaattc tattcaatta ccaccaatta    4980
aatctatatt agctaatatc aataatttca ataatggaat gatatcatcc caacaatata    5040
ctcgtgcatc tacataccaa caacaagcat aatttcatcg ataggtaacg atgaaatcaa    5100
caatcataac cacatactag tatatacttc tatacataca cacatacata cattcataca    5160
ttcattcata actaatcaac gaacattaaa cattcatcat ttgacaaaaa tcacttgtcc    5220
tcttattcaa atagttccca gatcctgctt acataataat atctgtcggc aatctttatt    5280
atgaaattca cttaccgaca tggaaaccgc ccaccaacaa acaatactgg aaaagtccgt    5340
ccttattata aaataaaaaa attgtttgcc gtttcatttt ttaatttatg cgcatctttt    5400
ttttcttttt tttttgtttc gtacgtaaag aatttcggga agatcctacc attccgtccg    5460
acgtgatgat ccgggtaacg tgtgttttgt tctattcgcc cgcgcgcccc ccacttc      5517
```

<210> SEQ ID NO 39
<211> LENGTH: 2495
<212> TYPE: DNA
<213> ORGANISM: Artificial Sequence
<220> FEATURE:
<223> OTHER INFORMATION: c8818_g1_i1

<400> SEQUENCE: 39

```
gaaaaattta ttaaatatta ataagtcttc tgtgtttgtt ttttttttggc ttttctaata     60 cttatagttt tatttgcctc atgattgatt gattccgtac ttttctctat ttctcctgag    120
gtatagtatt atattaatac tgatatatat ataaggtg ataaatttttc ttgattctag    180 aaatattcat tgtgtcaaaa tcagatcact aacagcatcg atttccaatg atgagtattt    240
ctgatatacc gccagcttta tcaccgattt caagtactac ctcgattcaa ggtttacaaa    300
```

-continued

| | |
|---|---|
| cttcaatgaa taataataat aatagtaata atcatattaa taattcagga acaaattctg | 360 |
| tatcaacttc accacatgct tattcattgg atagatatca tgaaccatct tcgaatgaaa | 420 |
| aatttaaacg taatgggaat tcttcttcat caaataataa taataataat aacggtttag | 480 |
| gtaatacaag taaaaatatg tcattaccac cgatttcatc atttgataat ttgattcgtg | 540 |
| ccgctgagaa acaatatgct tctacaagta ataataatac tgctgcaatg gatcagtcac | 600 |
| aggtatcatt atctgctact gcaagtatga cttcattacc attaagtaac aatactaaca | 660 |
| atgttctatt acatccgcta caacaaggtg taatgactcc agtgggttca agaactaata | 720 |
| tgttaagtta tcaactatct actgaacaaa gacatagagc tcctatcact agaagtatac | 780 |
| tacaacatcc accaagtgca actactacag atgctcgttc cgaatcaaat cgttctttac | 840 |
| ttgcatcccc atcagattca atgtcaagaa caagtgtaag tagtagcagt agcagtacaa | 900 |
| gcactagtac tacagccagt aaatcaatag taggtgatta taaactaggt ggtccacaat | 960 |
| ctcaggaacc accactgagt ctgacaactt caactacaac aaaggtaaca aaaccaagaa | 1020 |
| agaagaaaca atgtccaatt tgtcacaatt attacgctaa tttatcaact cataaatcaa | 1080 |
| ctcatttgac ccccgaggat agacctcata gatgtcccgt atgtgaacga ggcttcgctc | 1140 |
| gtaataatga tctaattaga catagaaaga gacattggaa ggacgaattg atgtcgccgg | 1200 |
| cgacatctac aaataatgga tcctctaagg ataaatcaaa tatcaattct caagcgttat | 1260 |
| cgaaacaatc acaattgaga tcattacatc aaattaaagg aactttaaa tgtccattca | 1320 |
| attcaaattt gattaaattg gatatggagg tatatccaca taagaataag atattgccgt | 1380 |
| tcgagacatc gaattgtcat caaactggtg tattttcaag atgcgataca tataagaatc | 1440 |
| atttgaaagc gttacatttt gaatatccac caggtacaaa aaaaaaggat agaggaatcg | 1500 |
| ttcctgggaa atgtaaacat tgtggtgcaa aatttgaaaa tgttgatacg tggttaaata | 1560 |
| atcatgttgg taaaaattgt ggttacatat atcattgatt tgtacatata tatattttt | 1620 |
| ttttgtaaag ttatataaga tgcattattt ttttttaat ttttaattt ttaattaatt | 1680 |
| ttgaatgagt ggctgagtct cgaaccatta caatattcat atcattgaga taattcgatg | 1740 |
| ggaacgcggt ataatttgta taaggtacaa taggtttcgg gtagaaacta tgttcaatac | 1800 |
| cttgagaaaa ttcaagattc agactagtac ttatatacca acaaccaaat gctttctgta | 1860 |
| tatttgagat catattttta aggatattaa aggatttgaa atcatctgaa gtatttagat | 1920 |
| acgatagatt atcaattatt ataccgtcca atgaacaatc ggcagcattt gttccatacc | 1980 |
| gtatcggaca ttctttattt aatgtcacta ttggattagc gttaactcta ccaaggaaac | 2040 |
| aaattaaccc ttcaattgtc gaaatttctt tactgttaac gtaccaatat ttgatatttg | 2100 |
| caaatcgggt ctcctccaat gtttgtctcc atatagatat gatatcaata ataagaattg | 2160 |
| caccggtgtt ccctgtttca taatttcgta gtaataattg tctcttatat tcattcattt | 2220 |
| tgaaatccgg ttcaattaaa tgcattgaat acttcggagt agtagttgca tcggacacat | 2280 |
| cttgaagatt taatgaatgt ggtactgtat ggtagtattg ggataacgga tattctttac | 2340 |
| aatgtttcaa tatttccatc tttattttga gttgttatac tgttcaatat tatcactttc | 2400 |
| actgatgttt gaactcacgg ctcttatatt ggaaaacaaa tcttgcgcat cgatcgcgac | 2460 |
| atactgaaaa acaaaagatt ttaaataatc atgag | 2495 |

<210> SEQ ID NO 40
<211> LENGTH: 1779
<212> TYPE: DNA
<213> ORGANISM: Artificial Sequence
<220> FEATURE:
<223> OTHER INFORMATION: c4613_g5_i1

<400> SEQUENCE: 40

```
tgtgaaaatg attatcgggg ggcagaaagt aacgaagaga taaacaggaa tgtctgattt      60
caattgggaa aatattggaa aagtgtattg agacaaaaga gagagagaga aggaatatat     120
atataaggga atcaatatct tttttgttgt tgctaatgtg tgtattggaa tttatttttt     180
ctatatttat tgaattttga tattttattt atgtatatat gtcgtttgag gaaatccatt     240
cctaaacaag gaccgtttac tgaaagaacc taaggttggt ttttttttgc ttttaattac     300
atctagttgt taacttttct tactgataaa gttaatcttt ccgatggttc ataccaacca     360
ccgttagcag aaggacattt agcaacagtt gcataattat aatcactggt gaaagtatat     420
gaccaacctg gtgtaatagt tgtcttttgt tgtgtagatt ttctaaaagt tgaataatat     480
gttactgcac tagttggata tttcatagac caagttgtcc ttgtgacagt tgtatttggt     540
tgcatttgca ttggagcaaa tctacttacg cctgtttgta aagtatatgg tacagtgaat     600
gaagcactat caattgaatc tgaaccacct tgatcaggta aattatattg tgcagttgga     660
gcttctgtac ctgaataagt attagtacca acggtacctg ccatattttt caattcaaat     720
ctaggactat aatgaattgc ataattatta ctattaacta aaccattaat ttgaaggaaa     780
aattgacctg agccaacaac agaacttgaa aaggtaacat tataattata taatgttgta     840
tcttcaccat cattactagt actagtttta aattctgcag gacttaattt attttcaata     900
gtatatggac aattcattgc agtatttgga cctgtacata atttaatttt gaataatgta     960
acatctgtga ttgttggata atctgtatta tcagaaaatt gaatcggaat ggtgacttca    1020
ccagaacttg gtttataact ggtaccttct tccggtccaa caatagagat atcacccatt    1080
gtaaagagac ataattgtgc taacacaaca ataactgatt ggaataacat tttttttgct    1140
ttctattgta aaatacgtga ttttgatatt aagctaacga aagaaataaa gattcgatac    1200
tcgttctgaa ctgttttatc ttatatacta gacctgttaa ctgatacgac gtaccttgta    1260
gagtttactt gtattaaacg tcaacaaatt tcttctcact tatattcagt ttgctgagcc    1320
tacatttaca tctatgttta ctccctcagc atataaaatt tctcactgca ggaaagcgag    1380
aaacagtttt ttcctcttga cagatcgcgt aaaaatatct gatttgtgac ttggcacagt    1440
gtggtgtacg gttttctccc accacgagaa gttctcaacg atcagctcag ctggaactga    1500
cactcttgat taaagcaacc catatgttat ctacatcgtg ctactattat atatacggtc    1560
atacatagct atttatagtt ggactttgtc gtaacatcga tattgatgtt ccgtatgtat    1620
gtacatagta aaatttgcaa cttttgctct atatttttat catcttgtac gtagtagcaa    1680
ttaccgttca agagcgcgtt cggaccaaca aaaatttggg acaccgggct ggaacccaaa    1740
gagaaaaaac aacgagatta ttgattggcc ttctgagca                          1779
```

<210> SEQ ID NO 41
<211> LENGTH: 3714
<212> TYPE: DNA
<213> ORGANISM: Artificial Sequence
<220> FEATURE:
<223> OTHER INFORMATION: c4552_g7_i1

<400> SEQUENCE: 41

```
tatatatata tatatatata agagcttgca atattgtatt gtgtgaaaat attgaattta     60
tatttatatt tctttacctt tactcaactc tgtcaaatac atacacacac acacatatac    120
```

```
atacatatat atataaatat acttacagaa atatggtgga acaatatagt gttattgttg    180
gtaaagcaga aaatgaacat gaaactgcac caagaagaaa tagtagattt aagaaggctc    240
ccttagtgag accaattggt atgaaatgta atacagttta tgaattctta gttgaaattt    300
ttaataaaaa taaatcaggt caagcaatgg gttggagaga tacaattgat attcatgaag    360
agattaaaat tattaataaa gttattgatg gtaaaaatat accaactgag aaaacttggt    420
tatattatga aatgtcacct tataattata atagttataa tgaattaatg gatattatgc    480
atgatttagg tagaggttta attaaaatgg gtttaaaacc tgaatctgaa gataaattac    540
atattttcgc ttcaacttca cataaatgga tgaaaatgtt tttaggtgca caatctcaag    600
ctattccaat tgttaccgct tatgatactt taggtgaatc tggtttaact cattcaatgg    660
ttcaaactgg tacaaatgca gtatttacag ataataatct tttatcaaaa ttaatcaatc    720
ccttgaagaa agccacagaa attaaataca ttattcattc tgaaaagatt aatccaaagg    780
ataaagaca aaatggtaaa atgtttaaag ttgctaatga cgcaattgaa aagattaaag    840
aaattagacc agatattaaa attttcactt ttgatgaaat tattaaaatg ggtcaagatt    900
caaaacatga aatcgatatt catcctccaa ctcctgaaga tttatgttgt atcatgtata    960
cttcaggttc aacaggtgat ccaaagggtg tcgtattaaa acattcaact gtaacagcag   1020
gtatcggtgg tgtcggtagt acagtttatg gtttcatggg tccagaagat agtatcattg   1080
cattcttacc tttagcacat attttcgaat tagtcttcga attagaatgt ttctattggg   1140
gtgctaccat tgggtatggt accgttaaga cactttcagc tcaatcaatg cgtaattgtc   1200
aaggtgattt acaagaattt aaaccaactt taatggtcgg tgtcgcagct gtatgggaaa   1260
ctatcagaaa gggtattctt gcacaattaa gtcaacaacc agctattgta caaaaatt    1320
tctggacagc ctataataca aagactactt tgaaaaaatt ccatttacca ggtggtgacg   1380
ccattggtag attaatcttt aaaaaagtta agaagctac aggtggtcgt ttgaaattta   1440
tgtgtaatgt tggttctcca attagtttag acgctcaagt cttcttatct aatattttat   1500
gtccaatgtt aattggttac ggtttaactg aaactgtcgc taatactact gttactcaac   1560
ctgatagatt tgaatttggt gtagcaggtg atttagctgg taccattacc gctaaattag   1620
tcgacgttga agaattaggt tatttcgcca aaaataatca aggtgaatta tggttaaagg   1680
gtgcttgtgt cttaccagaa tattacaaga atcctgaaga acagaaaag gctttaacta   1740
aagatggttg gttcaagact ggtgatatcg cagaatggac cgctaatggt catttaaaga   1800
ttattgatag aaagaagaat ctagttaaga caatgaatgg tgaatacatt gctttggaaa   1860
aattagaatc tatctataga tcaaacaaat atgttatgaa catttgttgt tacgctgatc   1920
aaactaaagt taaagctgtt ggtattgtcg tgcctgtatt cccacaatta gctaaattag   1980
ctgtatctct aggtataatg aagcaaggtg aagatgtgga acaatatgtt gacaatccaa   2040
agttggccaa tgctgtatta gccgatatgt taaaaactgg tagagatcaa ggtttagcag   2100
gtattgaact attacaaggt gttgttctat ttgatgatga gtggaccccca gagaatggtt   2160
atgttacttc cgcacaaaaa ttaaagagaa aggatatctt acacgctgtt caaaagagag   2220
ttgataaggt ttatctaaca aaataaattt aatccgtcac ttcatcttc gcataattaa   2280
tcactaccca tatattccta aacacatttc ttttattaac ctccccattt aactcattca   2340
tatcatgtta acgatttctc gttaggaata acattttaa gatacatttg tttatccatt   2400
tgtaaaaaca aagaaacat tttaaaaagt ttcaattcat attagcattc acttataatt   2460
ataataagtt tttcaagttt tttttttact ttacgtactt atatagaaac aagaataaaa   2520
```

```
aaaagtaata tcaataataa aaaaagattt atcccaattt tgaaactaca aactattatt    2580
atttcaatag atgagcgatt aaatgggaca atgactctat gacttcttgg cccgtatacc    2640
attcatgttc caaaataatt catactttcc actcgaacca atacatatca ataccaacac    2700
aaaagagagg tcctccaaag cacataaaac attaaatcat ttcaacatgt aactatccaa    2760
aaaagtaatc aatttcacca aatgatagct ttcaaataca tatccatcac atatcaacat    2820
tcaaacaagt atcaagtcat agcatattca ataaataaaa acaaccaaaa ttcaaagaat    2880
gataccttaa atttgaatca ttaatattgc aaagttatgg aaatgaaagc tttgaaacaa    2940
tataacgacg cacagtaacc ttctataagc ttacaatcat aaggatgaaa aactcataga    3000
tatgaatcgt aagtgaatct tgtctgaata cgaaacctat gactctttct tgtttgaaac    3060
acgtatgata cggacagtat gcattgagaa aaatccaggt tgattgacta tttctgaata    3120
atcacaattg aatgttgaaa ctataatgca aacgactagg agaataaaaa tctcagttgt    3180
ggatacagta tagcagtatt tgattacgag acattctttc gtgagatcaa atcttatatg    3240
gtttggaata caaaccatat acagcagtcc atcaataaat aattagttac ccctttta aa    3300
agaaagaaca agataatcca agagttttaa aatgaagtta ttgacatgga ttggtctttt    3360
atagttggcg tctcattgat gacttcaaaa ttttggaagc ttcccgcttc ccgctgaaaa    3420
gttgaaaaat ttttcgagat gtaagggtaa cgttcaaaat gattagaacg ttaggttata    3480
acgaatatcg aacaacaaag taacaagtga tgtcagaaca tttggagggt gaaccatata    3540
taccgattgt tttgctattt attagacatt acaaattgaa cgtgtctcta aataagtact    3600
atatacagaa ttccataatg cacattgttc agtatccttc tctacatttt ttgaatgttt    3660
tggattgact ttacattcga acgctgtaat agaagcgtaa ttccaaggtt tggc          3714
```

<210> SEQ ID NO 42
<211> LENGTH: 6997
<212> TYPE: DNA
<213> ORGANISM: Artificial Sequence
<220> FEATURE:
<223> OTHER INFORMATION: c5170_g1_i1

<400> SEQUENCE: 42

```
tcgggtgaat atatgttcca acacattatg acactgcgga acaattgatg cccaaattat     60
gtgggataa gcctatatag tggtcttgga ataggacatt caagaatatg acatattaat    120
taaatcatcc aattcggaat cgtatgaaac agagtcttga gaaatcgaac ttctgcataa    180
atattttctt ccgagggaga ggaagaacaa acatctgcat aacaatatta cattttaata    240
aaaccgacca aaacaacact gagactaaat aatgatcaac tagctagaca aagaagttct    300
gttagttacg aactgtttga aacaattctt gctgcgtggt ctctataata cagttcgacg    360
aatatatttg gttccgccat tgtattgtac agcgttccca tacccgatca acatgcaaaa    420
aagatattca aactacagtc ttacaaaccg accacacctt cacaaagcat tgtttatatt    480
tttagacatt ccaaaactgt tgacatttta taactaatag atcaattaag cttggaagga    540
ctgtcattca atattcaaca gattgttcca atataaagaa gtgaatatac attaaaagaa    600
aaaaaagaa ttataattac aaaagatatt tagttattaa tctatattag gtggtggcta    660
atttatataa taaaaattag tcataaatag aaatataaaa cattatagaa cgagatcatt    720
cactcgaatt aaaatgacag gaaaaatgtc gatcgttctt tatgttggaa aggaaaaacg    780
gaatcataaa gattagttgt tttggattac attagcaatt gaattagatt ccgaatagtt    840
```

```
cattgctcca aattaaatga aaaaaagaag tcttttagga aagacaaata ttacttctta    900
aatgagaaca tcctcttata cattggctta tcatccgtta aggctgcatc aacatcataa    960
ttagcgtctc ttcttgcagc tgggacccag gagcctgact tccatggtag aacaccttct   1020
aaccacattt cgttaacttc atctaaggta agacccttag tttctggaac gaagaagaaa   1080
acaaaagggg ctgcaaaaat catacatccc ataaagacgt acccgtaaca gaaaccaata   1140
gcaccagcaa tgaaagaggt aaagaatgaa attaagaaat tccataacca attggaaccg   1200
gcagaaagag ccatacccct tggctttgac t ctcagtggaa aattttcggc tgcaacaatc   1260
caagcaattg gagcccaagt acaaccgaag gagaaaatga agaaacagga gaagacaatc   1320
atacagttac cagcacccct tgatgatggt tcactcttac cgttagggta taatctcttg   1380
acaccaacag atgcgaacac aacgaaacaa caaaccatgc agatagcacc ccataataaa   1440
caggtacgac gtccaaatct atcgacaata tacaatgctg ggaatgtgga gaagaaagcg   1500
acgacaccaa agacaattgc tgtttggtat gtatcatcta aaccgacagc tttaaaaata   1560
gtagtaccat aatagaagaa atagttacaa ccacttaatt gttgcaaaga gttaatgata   1620
cagcacatga ttaaacgatg cagaatctta cccttt ggtg aaaacatttc tggccaactg   1680
gcggtaccac tagctctttc agcctcaata ctagctgcaa taatatcgac ttctctttga   1740
acaccaggat cttcagcact aactttattg gaaatggcaa tggattttt agcttcttct   1800 actctaccaa catccattag ataacgagga gattcgggga caaaaagcat agcacatgcc   1860
ataaataatg cccaagcaaa tgataaacct aaaggaactc tccattgaac agaatttgaa   1920
taacccttag taccataatt agtacaatca ccaaggaaaa tacccatcgt acacattaat   1980
tgaaaaaagg aacctagagt accacgtaaa tgttttggag cgacctcagt tagcagcata   2040
ggggagaaaa ttgacatccc accgacacca gtacctgcga caattctacc aataaagtat   2100
tggtaccact tatcaataga agcgatctgg atcacaatac caataatata aataaaagcc   2160
gtgactgcca aggccttctt acgaccaact ttattggcga tgtcacctaa agtaatacaa   2220
ccgattaaac ccccaatgtt gaatatagaa acgattaaac ctgttctaac attggaaaag   2280
tagaaactcc catctttacg tctagaggca aacctcttaa cataatcagg gtgggctaag   2340
aaaccaccaa tcgtacctgt atcccatcct gagatgaaac caccaaatgc aattaaaata   2400
caccagaatg tgataccaat atatgcactc ccaggtttaa ttggaatttc gacctccagg   2460
ttcccaatat cttctaaact attatcggta gcaccgttat cggtttctaa tttatgactg   2520
tctgctgtta gtcttgagtg tgcatctccc tccccagatt gtgatggatt cgtgcttgta   2580
aacgtggagt cggctggact tccgtctata atattttgtt cagacattat taaatattaa   2640
ttttctagat gtcagacaat tagtaaagca aatgaaaaaa aaaaattgtt ttgttatttt   2700
ttttgattaa ctatatttta tgttatatgt tataataaac tgaaattttg caataaaaaa   2760
tgattaaaaa tacgaagtga agtaaaagag aaaataataa tgatagtgat agtttcaaat   2820
caatttatga atgagaatat aatttctttt tatattaaag ttatattaga aagttatgaa   2880
aaagaaaata aaaattgaag aaataaataa taatattgat gtctaagacg tttcatgata   2940
gacatattct aggatgatca tttcaacaga attcatcct actatattca aagcaaatta   3000
gattacttat ttttgcatga aataaagtat cttgctgcag tatcaacatt ttcttcgcat   3060
ttttgtggaa agagaacatg ataactaata tttcaaagac ccacatatgt tcgagtgtca   3120
agatgtttca caagtttaga tgagaagata agatgacaat atcctttgaa tatattagca   3180
tgaaataagt tattactgta caaaagcaag gattacaggg taaaccttaa ttgttggttg   3240
```

```
agtgacgtta tattttcata aggttgacga ggttttctat acttctaccg gaataggaac    3300
tattataacg tgttcgtata ataacctttc taagacagta attttaaaaa taaataaaaa    3360
agagcagaag cgaaaggcaa ctgtattttc acaaaaacaa tattcacaaa tcccccctct    3420
tgaaccccct tcactactat tgaaagcaac ttcatattgt gatggttggt agatattttc    3480
tgaattatat ttcttagaaa tacaattgcg ctattatcat ctaaggagta ccaatgtggg    3540
gcatgcatta tgaatgcggg gtttacgctt tcatgtgaaa tagcagggtg aataataaaa    3600
catagcttcc tttttctcct atatgcaact gtaaatgaac gcaatttgca ctatatcgat    3660
ttcctaatta ttacaattgt ttttgtagct gtaccttatc tgcatcagtg gagcttaaaa    3720
agaaaaaaaa aagttaaatc gtcaatccat aacacgactg tgctacgcta tgatcagtgg    3780
gagaaatttc atgaaatgat tatttcatct acaacaatat accacgttat ggaacgttat    3840
gcagaaatcc gataaaatgc acattaattt attatctaat gtctctattg ttttagaaca    3900
actgaatcat aatattgttg aaagcggttg aagagtacac agtatcatac atccatcttt    3960
ttttagcact attgcatagt tatactgtta ttaccaaaat atctgaataa cttacgtcaa    4020
agatatttca aaaagaaag gaaaaaaaa aaaagacat gaaggagca tttggaacac    4080 gcaattttga atctaaataa catagaggca gctggtagca ccacttactc gaaaatatta    4140
gcacaatatt taaataccg tgcactactt ggaatataca gtaaaatgag atacaaactc    4200
gtataaacta gtcatgtttt gtacttcata ttaactacaa acaaatattt gataataatt    4260
atacatccgt acagatatga cagcccagaa tacatgtgat tgttagttat cgctgaaaaa    4320
tctaactgtt gaacttggtg atcatggtcc gtaagattat tacttaatct ggagagggga    4380
aggtgaaata agaatatggt tgtaccgtat tttgtattag ttactgtaaa ttattgcggg    4440
gataataacc ttaatgctaa agttttctta gagattcctc caatgaacga aagagaaaa    4500 catgaaggaa ctcctctgtc gtatggtaaa agcaaggata gttttcttac attgttaatt    4560
ttaacatcga acccatctta aacgtgaaaa ttttgtgcct agtaaatact cttaatagta    4620
aatagagctt aaataacccc tatagatttt tctatcacat ttatgattta gggtagtaga    4680
aaattaacct agaaagaaca tgtgttgtta caactggaac ctgaaacata tattacaagg    4740
ataatatcag gtatctcatt gacgttattc tcctaaattt actgcacaat aaagaatatt    4800
aacttacaga atcaaatgtc cagaacttga ggagatgtcc cgttatatca aacttaaaaa    4860
aattctaact taaggctctt agcgtatcct gataattaaa agtttatttt aatcaaacga    4920
acgcaaataa ttaccatcct aaataggaaa cgcacgtcag tatcgtgatg tgcgctcttg    4980
tttctttacg tacgtacact attctcctac atgctaagac ccgtacgctg ttcttctcat    5040
atttgtttat ttcgataaaa tagggagaca catcttttg cacaggaatg ccgcacgtag    5100
atcataattt ccccgggaaa tgccgaaatg gcaaaaaagc aacgacgatg tgcagtgagt    5160
gataaacgtc gtttctttt tttcagcaaa gaaaagcaac tgccgtaaat ctttagttcg    5220
agataccaca gagagaactg caatgcattt aacgcagata tcctgtgcga gcgtacgttc    5280
aagacgctat tatgcatgtt tgctccgaat ggtggggtag cgtgaagaat gttttccttt    5340
aaataaagat tcttaaacat gttagaggta attttcttac gacagggcca gaacaagatt    5400
ttgctgtctc gatgacaagg cagtgaaata agagacggaa caaaaatttc atacagaaca    5460
gtaagccaag actgctctcg tagtcacttt tttctatttt ctataatgtt tatcagaatt    5520
tgaggatgaa aacctacctt tttgaaaagt ttaaggataa taccacatgc tgacgtatat    5580
```

```
attccccaca acacttgata atttcttatt gtttattaag gggtaccatt aaatcacaga    5640
taaagaacag cgctatccgt tatttggtaa taagtataac atcgccatct gtgaggtggg    5700
atgctcaaaa cgactattag ataaattttt aggtacttca tatttggaaa gtggtcccat    5760
attatcatct gcttcagtgg actcactttg atcccatcat agagtgaagg acaaagtatt    5820
atcgagtata ttcacgactg tcacgaactt aaatcacata cattgtacta ttatttcaag    5880
taatatagta caacaactga ttggaataaa tgaattgcat cacatcagtt gagtgcgttt    5940
tttatgtttt tatataatcg ctattttcat atattacttt aagaaataaa aaaaatataa    6000
aagggctcct aatttcaaca tattcatgat tttaatttac ctgttgccat ttatttagtt    6060
tacatctttt agaaagttat ttctatataa acaaaaaaat tataatatca ataattactt    6120
ttttaaaaca ttaacaaaca acaaacaact gcattatgag tgctccaaag aaatttctac    6180
tttttggtga ttctattact gaatttacgt atgaaccaga tcaatggtgt ttaggtcctg    6240
ctttgcaaaa cgtttatgcc agaaagatgg atattatcca agagggttac attggttaca    6300
attcacgttg ggctctacat atccttcctg aattattaga tggtattgga aaggtcgatt    6360
tagcttatgt tttcttcggt actaatgatt gtatgccaag tggtcaattc gctgttcctc    6420
ttgaagaata cttagacaat atgaagaaga ttgtcacatt aatgactgct agaggtatta    6480
aggtcattgt tattggtacc tctttgattg agttagatag atggaacgaa ttaaatccat    6540
ctgaaaatgc cactggttta attcgtaaca ctgaatccca aaagttcttc ggtgacaaat    6600
taagagagtt atgtaaacaa gaaaactacg tctttgttga cttatacaag aagtttaccg    6660
aacttggtgg tgcagaatgg aagagtttat taaggatgg tttacatttt aatagtttcg    6720
gttacaaaat tttctatgat gaattattgc gtgtaattaa agaaaattac ccagaattcc    6780
atccttctaa catgcactat caatatccag aatgttacat tattgacagg gacatgaaga    6840
acttggtcat ttaatgagat tacatagtaa accaaactat ccatgacgca aaattattat    6900
tatttactac cctttttact tatccttta cttaatgatt tatactctgg tttcgatact    6960
agatattttt ttcccaatcc taattttact tctttgc                            6997
```

<210> SEQ ID NO 43
<211> LENGTH: 2575
<212> TYPE: DNA
<213> ORGANISM: Artificial Sequence
<220> FEATURE:
<223> OTHER INFORMATION: c2749_g2_i1

<400> SEQUENCE: 43

```
gtaaaatatg tcatattttc aacgtcccca aatggtgcag gaactgctcc cagtgtattg      60
ttcaatttcg gaaatatatt atcagttctt tgaccatttc ggaaataaca atttgatcat     120
ttgctctggt acacgtaata atcttaagaa ttatcgttga aagcctcaaa cttaactttc     180
ggccgaaatg cctcacttgg aatggtgatt aagtgatgag aaagaagaaa cgataacaat     240
aatcaaatat ctccgaactc ttcggccgaa caacacacag agagatgatc gtacaggaac     300
catacagatg agaaactgtt tccatgcaga tcttttcgat ttacttaatt aacaaaagat     360
tttcataaat tcttcattcc gcataaaaaa gggagagaac acttagatat tcaggttatc     420
ttattgaaaa atttatata aagacgacga atattttcaa atatttcaag tttcaattaa     480
ttctcttgct tctctttct gtataaaata atataataat ttcgacaact tataagggta     540
aaacactcat ataaaacaaa aactgcaatt attttaacta tttcattata aaaaaaatgg     600
cttatccaga aacttttca ggtatcgcaa tcctagataa caaggattac actcatccga     660
```

```
agaaggttga cttcgaacca aaggtgtttg gcgatcacga tattgactta aaggtcgaat      720
gttgtggtgt ctgtggttca gatcatcata tggcctgtgg tgcttggggt gaatccgtta      780
agccaactgt tctaggtcac gaagttattg gtaccgtcgt taaattaggt ccaaaatgta      840
acacaggtct aaagatcggt gaccgtgttg gtgttggtgc tcaagctttt gcttgtttgg      900
aatgtgagcg ttgtaagtct gacaacgaac aatattgtag aaagggtgtt tggactatcg      960
gtgctcctta tgctgatgga tattccagta aaggtggttt tggtaactat gttagattac     1020
atgaacattt tgctgttcca attccagaag gtttagattc cgctacaatt gctccattat     1080
tgtgtggtgg tatcactgtt tactccccat tattgcgtaa tggttgtggt ccaggtaaga     1140
aagtcggtat catgggtatc ggtggtattg gtcacatggg tatcatgtta gcaaaagcta     1200
tgggtgcaga agtgtatgca atctctagat ctaacgcaaa gaaggatgat tccttcaaat     1260
taggtgcaga tcattatatc gctaccaagg aagagccaga ttgggccact aaatatgatg     1320
acactctgga tttagttgtc atttgtgccg gttcattgac agatattgat tttaatgttt     1380
taccaaaggt tatgaaaatc ggaggtaaga ttatttctat agctgcacca gatgcctctg     1440
aaaagttaga aatgagtccg tttggtttgt taggtgtctc tattgccaat tctggtattg     1500
gttccgtcaa agaaatcaag caattactac aattagccaa ggataaggat atcaaaccat     1560
gggttgaaca agttccaatg ggtgaagatg ctttaggtca agttttttgct agaatggata     1620 agggtgatgt cagatacagg tttaccatgg ttgactatga caaggtcttt taatttaaaa     1680
caatagttta ccattgatca gtcatgactc tttatgaaac gctacatcct aaataaata      1740 gctaaactaa ttatttatat acatatatat atatattgac atacttataa tgtacattac     1800
atattaccat tccatatagg aatgtcattc gaagtattgt tttgcaaagt gatacattgt     1860
aaactgagct aataaaatgt attttgaaaa tccctatcat ttttcaaagg tctgtaaacg     1920
atgaaaagat aaacagaagt acgaataacc gaacatttgg aattctaatt atgtcgtact     1980
gtttttaata atgcattata ttttgtacac catatgatgt tatatttcaa gaaggaaacg     2040
gcgtgacata aagtttgaag ggacggtatg ttatgtatgt gcttaaagtt taattaatta     2100
cctatggaaa tgaatttaat tttggtagtg atcaagcatg atagctccat tggtgacaac     2160
agaactttat gtcttccgca actgctaaaa tgtatctaaa ggtcgaatcg ttcaatcttg     2220
ataacattta aactgtgttc agcaactgca atgaattcgg tatgtcatct gattcagttt     2280
aatggtcgtt caatatgggg tcaacgaatt tttaacttga cagacaaaca tatgataata     2340
tacgaactag ttacgtctct tgtaagggtt ataaagagga gcaggtatca tctactgttt     2400
ttaatcacta ttgttctttt gtttacacgg ttttttacatt ttgtcttctc ctggacatct     2460
tacaaggcga taaaaatatt atatttcact tgtataaaaa aaaaaatatt tccaaaaaaa     2520
aaggaataat atttttatat ttacatcttg tagtttatat acatgtaatt taaac          2575
```

<210> SEQ ID NO 44
<211> LENGTH: 412
<212> TYPE: DNA
<213> ORGANISM: Artificial Sequence
<220> FEATURE:
<223> OTHER INFORMATION: c2564_g1_i1

<400> SEQUENCE: 44

```
tttaattaat ttattttctt ataattatta ttcttttttct tttttttgcta ataaaccaaa       60 gagaattaca tttactcata attattttca tcaactatgt cagaatattt agatttagtt      120
```

```
aaaagaggtg gtaacgaagc cttaaaggtt aacggtccag ccaaggctga tttccacatc    180
acagacaggg gttcagattg gttattcacc gtcttctgta tctacacttt tgcctgtatt    240
gttgctattc tattaatgtt tagaaaacca gcaaatgaaa gatttgttta ctatactgta    300
atccttccat atgcttgtat ggctgtcaac tacttcacaa tggcttccaa tttaggttgg    360
gctccagtcg ttgctttata caaccgtcac agagtctcta ctcaaactac tc            412
```

<210> SEQ ID NO 45
<211> LENGTH: 677
<212> TYPE: DNA
<213> ORGANISM: Artificial Sequence
<220> FEATURE:
<223> OTHER INFORMATION: c2992_g1_i1

<400> SEQUENCE: 45

```
ggtttatctg aaggtggtaa cgttatcgtc cctgattctg aacatatttt ctacggtatc     60
attgatttaa tttacttatg tttcttacct gccgtttggt tagttttcgt ctcctatgtc    120
ggtttagaca agatgggtct agacacccct ggtgccccat ctgatttgga accattacca    180
actgtcgctt ccactactag tgttgcctca aagaaatctg aatcatcctc cgctggtgaa    240
ggtgaagaaa agaagaagtc caagtcacca ttgaacaagt taagaagtc caagaaggct     300 gacgaagaat aaatttaatt tagctttctt tgcctaattt tttttttttt caataaatga    360
aatacgatca ccctttttt aaatccctta atgtgtttat attttttgt tactattatt     420 attcaactct aatttccttc tataagaaga acaaaaata tcatatatcc cccacactca    480
agtagaatct tttgaaaaga ttcactacaa acgtatatcc attacccct aattattatt    540 tcttaatgtt taatattctc aatttttttt ctctcacaca ctatactaaa ggaaactttt    600
taattaaaat ttccaattca tcattaatat ccaataaaaa aaattgttta atttttctat    660
ttaaagtttc ttctata                                                    677
```

<210> SEQ ID NO 46
<211> LENGTH: 2141
<212> TYPE: DNA
<213> ORGANISM: Artificial Sequence
<220> FEATURE:
<223> OTHER INFORMATION: c4074_g1_i1

<400> SEQUENCE: 46

```
tctctaagta ctacgtacat agtgataaac gggcacgtgc gtcacgtgat attgtgatgc     60
agggcacgtg acatggcgtc ataaaaatcc gaacttcaaa gggaaaaggc gttttaacg    120 accaaaagca gaagcaacaa tttggcaaag taaaccagaa gttatatatg cttgtgttat    180
tcgttactgc taccgttatt atagagcgct ggtgctatcc tcatttgtat atgtatgtat    240
gtacatactg ctttgtgcct ttcttttggg tttggcccac ttcataaaca cagtcagatt    300
ttgcactgtc actcaccacc acagtcagca gtagcaccgt ctgttgttct tattattgcg    360
caaacaataa gtcgatgaat ggaaataata tcgcattta tattcaagta tataaggccc    420
gttaaacgat aacagatcaa tcttgatgag aaaggagcca ggtttcttct attttcaata    480
ttgttctttc ttccaactga tataactcat caatcataca attcataatg cctgcaccac    540
atggaggaca attacaagat cttgttgcaa gagactacga aaagcgtgac aatctttttac    600 aagaagctac caatgccact ttaaaacaat ggatcctaac tgaacgtcaa ttatgtgata    660
tcgaactgat cctaaatggt gggttctctc cattaactgg gttcctatcc caaaaggatt    720
atgactcagt tgtactaacc agtcgtttat ccgatggtac cttatggcca atgccaatta    780
```

```
ctctagatat taatgattcc aacttcacag attccattaa atccggtgac agaattgtcc    840
tatcacaaaa cggtgagatt ccaattgcga tcctaaccgt ttcagatatc tggcaaccag    900
ataaatccat cgaagccaag aatgtcttcc gtggtgatcc agaacatcca gctattaaat    960
atttgtttga aaccgctggt gatcactacg tcggtggttc attagaatgt attcaattac   1020
ctatccatta cgactaccca ggtcaaagac gtactcctgc acaactaaga gcagaattcg   1080
attctcgtca ttgggataga atcgttgcat tccaaactag aaatccaatg catagagcac   1140
acagagaatt aacagttaga gccgctagag aaactaacgc taagatcttg attcaccctg   1200
ttgtaggtct aactaaacct ggtgatatcg atcatcacac cagagttcgt gcttataacg   1260
aaattgttaa aagatacsst gctggtatgg ccctgctatc attattacca ttagccatga   1320
gaatggctgg tgatcgtgaa gctttatggc atgcaatcat tagaaagaat tatggtgcta   1380
atcatttcat tgtcggtaga gatcatgcag gtccaggtaa aaactcaaag ggtgtagatt   1440
tctacggtcc ttatgatgct caagagttag tcgaatctca tcgtgatgaa ttacaaatca   1500
ctgtggttcc attcagaatg gttacttatt taccagatga ggacagatac gctccaatcg   1560
atacagtcga tactaccacc acaagaactt taaacatcag tggtactgaa ttaagacgtc   1620
gtttaagagt aggtgcctct atcccagaat ggttctccta tccagaagtt gttaagatcc   1680
taagagaatc caacccacca agaccaaaac aaggttttgc catttcttta ttatctgacg   1740
acatacctgt ttcaactaat caattatcca ttgcattgtt atctatcttc ttacaatttg   1800
gtggtggtag atactataag atccttgaac gtgacgatta cactgatgat ctattagttg   1860
aattgattaa cgatttcgtt aaagccggta ctggtctaat catcaaaaga gacgtcccag   1920
taaagaacct aaccaacgtt tacactgttg gtaagaccga tgacgcagac attaagatca   1980
atgaaactga tggtacagta tttgatatcg ttcaaagagt tgtcttattc ctagaagaca   2040
acggttacat caatttctaa tccctcatat ataatataca tataaaaaaa taatgataaa   2100
aatgtttctt tctgtaaaat aaatcaataa ttcaagtttc t                       2141
```

<210> SEQ ID NO 47
<211> LENGTH: 5350
<212> TYPE: DNA
<213> ORGANISM: Artificial Sequence
<220> FEATURE:
<223> OTHER INFORMATION: c4925_g1_i1

<400> SEQUENCE: 47

```
attaaacaaa aagaaaagag aaaatagtag ataaaagtat ttccatcatt tcacgaataa     60
ttccccttt taaaaattta taaaacacct tctcccttt ataaccttct ttaactaaca     120
aacaaacaaa taaacaagaa aagatggact taactccaag aattgtttat aagaattacg     180
tattcaatga gagtgcaaac tattcccaat acggtaataa tatgattgcc caacatcaac     240
caggtatgca accggtaaat gtaaattatt tacctttacc aaacgttcca ataataactt     300
atcgtaataa tgatggttcg attaatgcta cagctgctgg ttcagctgtt tcttcaactg     360
caccaggtgt gtatccaagt tattatcaac cagctattgc tgcttctgct tcccctcctt     420
atcaatttaa tgctaatatt cctcaaacta cctttatga cactcaacaa caacaacaaa     480
ctgtcaataa taataataat aacacacttc cacgtgttaa ttctggctca aattttagat     540
tgccatctat ctccagtatt atggggtcaa ataacaacat taacaatacc agtactaaag     600
ctacaaacaa tgatgtcatg attgatcatg catttgaaaa taataaggat aattattctt     660
```

```
caagtaaatc ttcaccaatt acacctagaa ataacgttat ggttatggtt gctaatccat    720
tagttctatc aaatgtagta acaccgattt atcaacaaaa gattcctgca ggtcctttga    780
caccaccaat gtcagttcct cattctccaa tgtcttctga aggtattgaa aataaagttt    840
ccgccgatgc tgagaatact actacgcctt cggctggtag acaatcggct ttaaagatta    900
ccgaagttaa gccagaaaga aaatctagaa gaaagaagtt tatttgtgat ggtattggta    960
aacatttaag tccagaagtt agacaaaaaa aagaatgtcc aatttgtggt aagaaatgtt   1020
ccagaccttc aactttaaag actcattatt tgattcatac aggtgataat cctttctgtt   1080
gtactagacc tggttgtaat aaaagtttta atgttaagag taatttgcaa agacacatta   1140
gaagtcacga taagaaacta tcgaaaactt taaaacaatc aacacaaatt ccgattcagt   1200
taccatgtcc acatatgtac taaggaaggg tgctccaaat gaggaaacat aaaaagagag   1260
gatgaaaaaa aaagaggat tgaaatagga aattgagaaa caaacgtaca aattggcaat   1320
aatcaagaaa aaattgaaaa tgaggagaac atgcatacta atgcgcctaa aaaggaatga   1380
cgctactgga aaccaaaatc ggatgaatat aaaaatggat ccttaaaagt ttttagccgt   1440
aaagaatatt ttgttgaata actttaaga aagttttta agtttagaca ttagaggttt   1500
gaagtatcat gataaagtgg tcattgaatt agtcagtgca aagtcaaata tatttataat   1560
tgtgttaatc aactatattc tgtattgttc cgaaaggagt atcatataag gctgtgcact   1620
aagatgtcta aaatttaagt ttcaagtttg agattttcct tttcattgtt ctggtttcca   1680
taattaaagt ttcaggaatc acatttctct actttcgttt ttctgttctt atcattaaaa   1740
tccgtttttt gtttatttca tttttataat aaagtttgtt atacttcaat atatcctttc   1800
aacccctccc tttcatttga atttgctaca taataacaa taataatag aatatatacg   1860 taattgaaat tcaattcaaa taaattcaca ttcaaaattt ttaataatct gaaaatcaag   1920
gataagtaaa tgaggtactg taccttacat taaaagttgc tagatggact gaaggattgt   1980
tgttgaagat cctattgttt tgggatactg tattgttccc gatgatacta ttgttttgca   2040
ccattgtatt gttatccata ttacctttt ggtaattgtt gagcttgcca cactttcgat   2100
aaccatgcaa attaaacttt gttttagcag gcattttga tcaggggcag tacgtactcg   2160
aagtgacaaa ctttattcgt tatcaagtaa ggtatcatat ttaatgataa cagactagaa   2220
taaatgtttt ttgaataata catcccacta accttaagtt ctcacttgca atagagtcga   2280
tgagatactt cgcgtatgtt acgaatactt caagataatc ctgataattt tttccctttt   2340
tttttgagga gactccaatg aaggtcattg gaaattcttt ttactgccag ttccctttt   2400 atttttaca catttatgtg cccttcgag actgattatt cctcatttt ttggattttt   2460 gagttctaag ttataacctc cttgcttagg gacatttaag ttgaagactt tctatcattt   2520
aacaattaaa tggttttcaa tcacttataa agatgagtaa gctaagttat atggctagac   2580
ttttcaaacg accccacctc atcgataaag tcaatcgaat cttcttttct tctttgatgc   2640
aaaagtgatg atgtcagatt atactttct ttataattct tctgtcattt taatcattct   2700
actgcttttt attgaatcta gttctcagtt ttctctacgt acaggcttta tgcagatatt   2760
aatccttcta catatcttcg gagactattg tgaattgaaa gcaaggaaa cacatagaga   2820 ctattttgcc acttgctttt gcgagacatc ggtatctaac ggttttcatt ttttcggac   2880 ccaggatgac agcgtaggaa atgcacctgg accctttca cgcacgaagc acataacgga   2940
tattgttttt ttcttcaact tcttaaaagc cgatgtaatt attatagaaa taatatttt   3000 actatggggt ttttactcgg aatttaaat attgcttaat cgcagatctt aaatttttat   3060
```

-continued

```
gtccattttt acaacaagtg ggtctaaaaa ttttcaccca atacgtattt tttcctgctt    3120
ggtattatcg gagatttta cgttttgaat tagaagcaaa aaaaatttt ttcgatcaga     3180 ggaatacaga ggtaacagta cttcttgta aaatgaatct ggagaatttg tttggaattt    3240
atcacaaaat ttacgtaccc cactttattt acgtagctga atctaaagtc tttgaaatga    3300
tactgtgcat atatgatgta gtttctatct catcgaagaa gtattattat tattagtaat    3360
gatctgatat gtggctagat ttacggagtt aaaagacttt aaaattaata tagtaaacta    3420
ttactattca atactagaag taataatatc catgcacatg cttcattttt atgctatatc    3480
ttaatgatat cattataaca tatctcaatg atatcattat aatgctaacc ctcaaaactt    3540
taaactcgaa ttgagagtag aaagttagcg ataactatg tagtatgtta taacctttat    3600
agtttatcaa acaatgacg aaatatttag taatttattt ccttgaagga aattaattat    3660
gattaataaa tccaaaaata atattgatca acagtaacca gggaccttcc taaagcaaaa    3720
aaagaaaaac aacagctagg caaacatcga attttcgtca ttagttcgtc aataaggatt    3780
attgaccgaa caagaaaaaa aagaaaatta tagttgatga accaataatg accaaatatt    3840
aagaaactgt catcggttac aatttccccc aagtaaattg aaaggtgttt cttgccgaaa    3900
catcaaaaag caaaaaaaa actacgtact gaaagatcga taggctggaa ttcaatttaa    3960 ttaaaaaaa aaaaaagca aacaactgtt gcgtcactat aaatcacacg tacaaagaac    4020
aatggtattt ttctaagttt aaagaacaac gaaaaaaaa ttgtttgagg aggagcggca    4080 gtcttttca cagaacaata aagacataat attatgaatt atgcacaccg tactttgtac    4140
attgtgtcca tatgtgaaat aaaatagatt tactccagaa ttcttgggta gtagtgtttg    4200
atattacgac tatactttt ccttcttaaa actattggaa acatcgaaaa taattgtatc    4260
acaatatcaa attggtaaca aatcgttgag gaaagatatc ttaaagtttt agtaaaaagg    4320
tgcaacttga ttgaaaaaga aataagacag aatatttttg ccaagtttag gagacattta    4380 gaaagaaat tcttttttca agactcaacc aaaagaaaga agaacaggtt ctgcgaaagc    4440
atcatgtttt aatttcatta gttgtgtacg gtaatttgtc ttttcaaatt ttttttacgc    4500
tcaaccccaa taaaataaaa aaagatcatc ttagatagga ggatgtgaca cttgtccagc    4560
tttgtgtgga ttttactca agaattattt taactaaaat aaatatattt tagatgcaaa    4620
tttttactgc cgtttctttt tgttgtctt gttcgctctt tctattcttc tattacagta    4680
aatcttggta gtcacacttt taaaggaaca aataaacttt aatagaatca tgtttaattc    4740
agaaagatgc gctgcaacat tggtctccga aatttcattg aggaaattcc gatgatcttt    4800
aattcctctg tcagaaattt gaaagaacta cgtaaatttc ttgtaggccg cttttttttt    4860
gttacaataa gtaaaatgga gaaaactatg gagaattaca gaagcgaaaa aaaaacccaa    4920
aatctttatt ctaaatttat gagtatgtat agtttttttt cctgatactg cttttagttc    4980
tttctcccat gatcagttag gaacgacata catttacgtc tatttaccc ttttaagtga    5040 cttacagcga aaaatgcgta ataggatttg tacaataaat atatcgcttt tttcagttaa    5100
ttaatttgtt cttcctgcat taaataaaag ggtaattacc gtagcattaa attgattttt    5160
tattttttta cagataatat gtcgaagtta tattacgtat ttacatataa cgataattcc    5220
tcgtgtttcc aaaggaagtc cgcaagtcga gtttaccatt tagtaaaaaa tttatataat    5280
gattggaaat ttaataatca agttcgtttt ctactacctt ttaaccacta tattataata    5340
tcatattgta                                                          5350
```

<210> SEQ ID NO 48
<211> LENGTH: 3493
<212> TYPE: DNA
<213> ORGANISM: Artificial Sequence
<220> FEATURE:
<223> OTHER INFORMATION: c4569_g1_i1

<400> SEQUENCE: 48

| | | | | | |
|---|---|---|---|---|---|
| atctatcaat | tctcttaaag | aacccatgta | cagtacgtaa | gttgacggta | cttgacttgt | 60 |
| tcattccttg | gattaacttg | ttttccattg | ctataataac | aacaacttca | tcattatgta | 120 |
| tcttttaatc | ccttcttgct | tcttttagtg | aacaagttat | attatgaaga | agataatgat | 180 |
| gattgattga | ttgattactt | tgtggcgtta | acaagagaaa | atctactatt | tgatgatgat | 240 |
| gatataataa | actacctgtc | atcgcaaatt | ttaattcaac | attccataat | aacctctaag | 300 |
| aagccaaaaa | aacaaagttt | aaaatgtttt | ccgggaaacg | taaaaggtct | attaagagag | 360 |
| agagatggca | gtaatgataa | tttatatgat | caaattgatt | aaatttaact | tatatacaca | 420 |
| tcgcgtcatt | taaattttgt | ttcttctttt | taatcttctt | aacattctcg | tttacatcta | 480 |
| tccatatata | tatatataac | aaatatttta | ttgtaaatta | aaataaattt | gttgatccct | 540 |
| tgaaatatca | tttctattta | gtttacattt | ttatttattt | tattcattcg | acatctcaat | 600 |
| atatttaaag | atcttctttt | agtttgataa | ataaaaataa | ttagaagcaa | tcataattat | 660 |
| tatattacca | aggatcatat | cgttctatat | tgaagaagcg | acaggaaagg | agagaagaaa | 720 |
| aaaaagaaa | aaagaaaat | acttttttag | ataatctatt | gtgtgcgtga | cttctaccgg | 780 |
| aaaattctta | tttgataata | ataataaata | caatcatcat | catatcccaa | cgtaaggaga | 840 |
| tacaaaagga | aaacacacta | ttattatata | agaagtgtc | atattatttt | agcttatttt | 900 |
| tttcacatta | tatcccttgg | aagactatac | ttcatttaat | ttaattaatt | aaaaactagc | 960 |
| caaatcaaag | gaattacaca | tatacataac | actgccaaag | taaaaaaaaa | aatgcatgaa | 1020 |
| acgttagggc | aggtcatttg | gatcgctgtt | aaacctatta | ttaaaattta | tttaattatt | 1080 |
| ggtgtcggtt | tcggtctttg | taaaatgggt | atcttaacag | ctgatgcaac | aagaagtata | 1140 |
| tcggatattg | ttttaactgt | tcttttacca | tcttttatcat | ttaataaaat | tgttggtaat | 1200 |
| atcgaagata | atgatattaa | attcgttggt | atcatttgtt | taacgtctgt | tttaattttc | 1260 |
| ggtacaggtt | tatttttgc | ctacgtaatt | aagaaaactt | tacctgtacc | aaaagcttgg | 1320 |
| ggtggtggta | tcctagctgg | tggtatgttc | ccaaatattt | cagatttacc | aattgcttat | 1380 |
| ttacaaactt | tagatcaaag | ttcaatgttt | acaacagaag | aaggtaataa | aggtgttgct | 1440 |
| aatgttatta | ttttcttagc | aatgttctta | ttctgtgtct | tcaatttagg | tgggttccgt | 1500 |
| cttattgaaa | atgatttcaa | ttacaaagat | gaagaaagtg | gtgttagaga | gaatgaatta | 1560 |
| caagataatg | ataattcatc | aaatgtttcc | ccattagatt | ctatcccaga | agaagcagat | 1620 |
| gaagagaaaa | atggtttaca | tacttcttct | tcgtcatctg | gtttaagtaa | aaaatctcaa | 1680 |
| tctgttgtca | atggtgaaaa | aataatatt | agtagtaatt | cagctactcc | atctgcacat | 1740 |
| aatattccaa | ttaacaataa | taaagctgtt | aataatggtt | cagaagataa | catggaaaac | 1800 |
| tcaactgata | tgatgatttt | aggtgacatg | catatggaag | atgacttagg | taatgaagaa | 1860 |
| caatccgttc | aatcatctat | tgctacctct | attaactctc | aagtttctgc | aggtgattat | 1920 |
| aaccgtgaat | taggtattcc | agctgcaaga | agaactttaa | gtcaaccagt | tgcttacacg | 1980 |
| gaggaagaac | atagttcctt | aggtcgtcgt | caaacttaca | gtcaatacag | tgtaaattca | 2040 |
| aatctaaatt | taactcctgt | tagatcatta | gataagcgtg | atttaccatc | tgaaggttta | 2100 |

-continued

```
gacgatattg ttagagaata ttctaatgtt gatcaatatg gtggtagaag acaatctgtt      2160
gttggttctt tacaaaatga tgatgggtca atcaatgatc aagcttctca tatgtcaagt      2220
ttacaaaaaa ttagatcatc taatttaact aagattttaa cctcagatgc tactgttagt      2280
aagaaggata ttgaagaatc tggtggttct ttaccaaaat gtattcaaaa gttcccatta      2340
actccattca ttgttttctt cttaaagaat tgtttaagac cctgttctat ggctgttatt      2400
gctgctttaa caatcgcatt tatcccttgg gttaaagctt tattcgttac atcaagtcat      2460
actccacata tcagacaagc tccagatgat caacctgcat taagtttctt catggatttc      2520
accagttatg tcggtgcagc ttctgttcca ttcggtttaa ttctattagg tgctacttta      2580
ggtagattaa agattaagaa attatatcca ggtttctgga atcagctgt cttattagtt       2640 ttcttgagac aatgtattat gccaatcttc ggtgtcctat gggctgatcg tttagttaaa      2700
gcaggttggt tagatagaca aaaggatgaa atgttattat tcgttatgac cattaactgg      2760
gctttaccaa caatgactac tttaatttat ttcaccgcaa gttatactcc attagactgt      2820
gaagatccga ttcaaatgga atgtacggct ttcttcttaa tgttgcaata tccattattg      2880
gttgtcagtc taccattcgt tgtcacatac tacttaaagg tctacttgaa gaagtaggaa      2940
aaataataat cagtaatttt aaaattaata cacaaacgtt acaaaacgta acctcaagtc      3000
aatatattcc catttatgt ttctttcttt aatcatacgg tcgttttta attaagatcg        3060 catttcattc aatctcataa ttcataatca tcatattagt taattcatac cttttttttt      3120
attatgtcat taaaaaaaaa ttataatgat gcttatttga attgaataaa tttgaaaact      3180
ccagcacctt tttttatatc cctaatggat aatccacaat catcagttat attttgatgc      3240
atgcataccg atctttatta aatcttaaca aaaaattcca gaaagaagt atctctacta       3300 acctgatatt tcaagtgaaa agttataata acaatagttt aaagaataaa caaatatata      3360
ataattcata atttcatcat atataaaaac gcctccaatg agcacttaat cgttgggact      3420
tttaatattt aaaaaaaata ataataaaaa aaatatataa taaaatataa taaaaaatat      3480
tttaaataag tta                                                         3493
```

<210> SEQ ID NO 49
<211> LENGTH: 5210
<212> TYPE: DNA
<213> ORGANISM: Artificial Sequence
<220> FEATURE:
<223> OTHER INFORMATION: c1919_g1_i1

<400> SEQUENCE: 49

```
attcaagaaa agaaacaaaa acgaatgtcc ctctttattt ttatcctgcg gaattaagtt       60
agagaaatta aattcccctt actctaacgg tattttgtgt gtaggaaatc aataagtgaa      120
aaaataattg ataaaatatt ttgcatatct cagataatct gaaggcatgg caatttttat      180
ttttgttaca taagattact aaaccaagga aagacaaatc aaagttttag attaacaaca      240
aatgaaaact gggtagctct cagcgaaccg agaatggaaa gttacctgtg ttcactttta      300
actcgcacaa ttaattgttt tgcggctttt gaattgttgc atttttggaa gacaagaatt      360
tcagtcccag taaattctct gtaccaaaaa tctaaatttc ttgtcaaagc gaggaaaata      420
aagaaaaatt ccgcgtttgt gttccatata tttactaagt aactcccgta ttgaggttcg      480
gaaatgttag atcttataat attagaagac aaggggaaac aatgtatca tcaggcttct       540 ctctaagttc tttagagaaa tttatcagaa ggtgcttatt atttatattc cttatattac      600
```

```
taggatacga aattcccaca tgtaaccttg aaaaaagcat agatgcagtg agtttcttaa    660
ttattcatat ggtggggag gtctcataat ccactttaaa ataactttgt ttccctatca    720
aattttcaac aattttttgtt catttattat gctatatcat tcaacccttta ttttttgtta   780 caatgaagcc tctctattca ttaagacgtt tcccaaaga gtccagatat tgaagcagat    840 acctttttaaa ataaacattg ctttcctgct ttatcaagga acacctattg tcttgttatt    900
ttctgtgtta ggtattcatg taccagatca tttaattaaa ctataaagtt ttaaatatat    960
tccgtgcggt gattctcctc gagattttca aagatacgca aaataaattc atgtcttaag   1020
tgattaaatt ttttagtgca aagaaaatat agggtaaaat taaagttctg attattttgt   1080
cgtagtacct gctttaactg gcgggactcc cctgatcttg caagacaata gtacgcacta   1140
ttgtctatga aatctttgaa atttccgcag aaattgctta ttaaactatg ttcttctcga   1200
tgtttttcaa tattttcatt accttctttg ctgcgcagta gtgttaagga agaatatatc   1260 ttttttttgca ctaacattta ttactacaat tcaccagctc atcgtgcccg ctgaatttat   1320
gctacatgaa gtgctatttt caatctctac caaacattga tatgcctgtg gtggtgttgt   1380
tgatgcttct acagtttaat tttaatctac atgatcagct gagagtacag caggatcatt   1440
ttttgttttt ctaaataatt gcgtatgaat tttaattttta atttgatgca ttaaagaatt   1500
catcacaatt atatatagtt gttcttagca tcacccactc tcacgggaat attgtgttaa   1560
ctagttggaa tacaattata cttttcagtt aaaatttact gctttctata tgttctaca   1620 gatgatgaag aaaaaaatac aacacagaaa aagaaaagc acagcatcaa caataacatg   1680
aagagaaaat tctaccaatt catctgattt atattatata aatatatctg ttcttaagtg   1740
ccacaattta ttatgcttat tttaataatc tagaatactg aacttttcctt gtatttgaat   1800 aaagggctta atcaacttcc ttactgatat aataatatat tcttagaaca attatacaag   1860
cagaccattt cacctaacaa tctcatctct caaacattcg tgaaataatc attgcaataa   1920
tcaccacatt ggaaacatat aagagattcc ttcttttttc ttcgtttatc agagacaaca   1980
tattcttcat taataaaaat tattaaggtc gttgaattca ttacgactaa aaatcatcaa   2040
ccaatattcg ggttagcata atccataatc atagtcattt agttcaattc atatacaatc   2100
actgaataat attcctagtt gattgatttc attcccaatt ttaacattta ttttttctcta   2160 tacatatact accttgttat aaaaatttag agatagattg gaaaatcaat agcatttgtc   2220
agtaattcaa tctacgttttt taaatttcca ataacgttaa attttagaa gttaatggca   2280 aacagtccaa cattattgca ttactaaagc attgttaatt aattgtgaac aacaataaaa   2340
tatatattta tattaacaac cgtcaattat tacactcgat ttgcagttaa acgaaaagga   2400
aaaattaatc tggaatacaa acctcaagat ttcaaaataa gtactttcaa aaaaagaaaa   2460
cagaatcaat tgtaatagtt tgtaaacata tcataatttt atcataaatc gtatgcattt   2520
tcaaacagat atcaggacca attcttttta agatatctaa gcaactttga acttaatata   2580
atttctcaca cacatacacg agaaaacaca cctacaagac aaacaagaaa ccctttttaga   2640 agaacacctc acataaaaca tgtcaaaaaa tgttaaagct aaaagcaaaa taagaataa   2700 ggacaaaaag acacggagta ataacaatac tacatgtaca agtaaagatg atgaattgga   2760
aaataaaatt cacataaaga atttcagatg ggaccctaag gaaagtgtag aattccctgt   2820
atcatatcta agtccatcta tcgtcaaact aacaaatagt ccattagacg attatcagag   2880
atccttcttc agttacgcac tgttggatga taaggaactt gatctgaaca tcgagtatac   2940
gacttaccga acaagtatcg ctgaacaatt catttcaccc atttatcaaa caaaacaaaa   3000
```

```
gcgttccaga agaaatggaa gacattctgg tggacatagg agatcaaaac atttactaga    3060
atgttttgaa taccaacttc caaatctaag acagtcattt actgaagaag atggaatcat    3120
aagtccagga aacggtacgc cgtctcccga atcattaata gaaatctaca ggaaaaattt    3180
atgtcttgat agaccaaatg tttatgtcct tgacggaata atcatcaata gcatagaaga    3240
agaatctaaa acttcatcag caggctctga aacaaatagt gacgataaag atacggcgag    3300
caactcaact gaaactagtg acgataaagc attacaaagt tctgacagcc gtgacgcaaa    3360
ccttgaaaat gtagtggaac ccgaaatccc attgttaaaa gataataaat cagacagtat    3420
cagttattca ttaacaaaaa atcaaaaatt taggctacaa aagatggatc acaattctga    3480
gaaaaatcaa aagattataa acccaaacaa ttgcattata tggacattcg aaggtgggta    3540
tgttttttta actggtatat ggagactata ccaagatgtg atgaaaggac tgataacaat    3600
accacgcaaa aattgccatg ataataaaat attacaggaa ctatgtgctg ttgaattcaa    3660
aaatgtttta tcgcatacag ttttcaatat cacaattgat tcagatggta aggtacaaca    3720
ttcgaaaaag aggagttacc cagaatcact aggaaccaat agtcagatag atggtcttga    3780
aacagagcct aatgataaca cggctgatac aacattcgat attttagaag agttcaataa    3840
gttattttcg caatctaaat ccaaatatac tgatctccat tggaattctt taccaagcac    3900
actgagacat gaattgtttg aaagtttcaa agtacatttg atcaaagaaa gaatgttcc    3960 ggctaatttc tttaatggct tcgatatgac tcaattgatt caccgtattc gtggtggtta    4020
tattaaaata caaggaacgt ggattccaat ggaaattgcc aaatctcttt gtattaaatt    4080
ctgtttccca atcagatatt ttttagttcc aatatttggt cctgatttc cagatcagtg    4140 tgctaattgg tttctagata agcaagaaga aaatgttaat gtggtaaaca gtgacacatc    4200
gcacgacatc tcttatagtc ctataactaa gaagagactc cgttctttac caaagttatc    4260
ccagacgtct ttgacagatg gtgatcactt attccatcaa caatatcctt accggtatgg    4320
aaaacaggaa aacagttcac atgttccaat gaacgaccaa ggtttgaatc aacaggcata    4380
tactcaatat ccaaatatta cagatggaaa ttatacgcaa caagcagtga cgtattcaca    4440
aaatattaaa caatatcccg atagaaataa tatagataac gtgcagaaga agctggatgt    4500
ccagaacaga ccacatcttc cacatatcac taacttaatt aactcattaa atggatcgcc    4560
aactcctaga gagaatccgc catcaaggga ggcttttccg caaggaccac aattacagaa    4620
cacaccaaat atcgaaccaa gtaccaatgt gtcaataaat caaaccccac acgaaaatat    4680
gacaagagct attagtcaac cagtttatgc gatgtctgga cattttgata atgctccaag    4740
tcctgcttat catcaccctg tccaatatgg tggcccaact gtattcgagt cctatagtaa    4800
ggagaatgtg aataaccaat atggtggaca tattgtatct gtacccgcta cttcatatcc    4860
acaagttaat cctattatgg gtcacgatcc aaatatgtat gttagaaatc aaatggttcc    4920
acagcaagtt agacaaattc cgacacctgg ccaggttgta tatattaata aaccccaca    4980 gataatgcat cagcaggtac tacctacaac tattgaacaa ccaaatcaaa taccgataca    5040
ccaactaggt ccacaatatg cagtattaga ggatggaagt agagtacctg ttaattctaa    5100
tagtcaagtt gttatggtgc aacctcgat gcaacctcaa attttgccgc aatatgccaa    5160
caatcctgtg attatcgctc ctgctaataa taataacaat aacaataaca    5210
```

<210> SEQ ID NO 50
<211> LENGTH: 2404
<212> TYPE: DNA

<213> ORGANISM: Artificial Sequence
<220> FEATURE:
<223> OTHER INFORMATION: c2966_g3_i1

<400> SEQUENCE: 50

| | | | | | |
|---|---|---|---|---|---|
| gtccaatgga | gagttccatt | aggtttatcc | ttcgcatggg | ctctacttat | gattggtgcc | 60 |
| atgttcttcg | tcccagaatc | tccacgttat | ttaatggaag | tcggtaagac | tgaagaagcc | 120 |
| aagagatcca | tctctacttc | taacaagatt | tctgttgatg | atccagctgt | tcaaagagaa | 180 |
| gctgatacca | ttgccgctaa | cattgaggcc | gaaagagctg | caggtagcgc | tacttgggct | 240 |
| gatatgttct | ccaccagagg | taaggttgtt | caacgtctat | taatgtgttg | tatagttcaa | 300 |
| tctttacaac | aactgaccgg | ctgtaactat | ttcttctatt | acggtactat | tgtcttcaag | 360 |
| gctgtcggtt | taaacgattc | ttatcaaact | gctattgttt | tcggtattgt | caattttgca | 420 |
| tctagttttg | tttcactgta | tgtcgttgat | agattcggtc | gtcgtgcttg | tctaatgtgg | 480 |
| ggtgccgccg | ctatggtctg | ttgttacgtt | gtttacgctt | ctgtcggtgt | tactagacta | 540 |
| tatccaaatg | gtaagaacga | ggcaacttcg | aaaggtgctg | taattgtat | gattgtcttc | 600 |
| tcatgtttct | tcatttttg | ttttgcttgt | acttgggctc | ctatctgttg | gattgttgtc | 660 |
| tctgaaactt | cccactgaa | gattaagcca | aagggtatgg | ctttagctaa | cggttgtaac | 720 |
| tggttatgga | atttcttaat | ttcttcttc | accccattca | tcactggtgc | tattaacttc | 780 |
| tattatggtt | acgttttat | gggttgtatg | gtctttgcag | tattttacgt | tttcttctgt | 840 |
| gtcccagaaa | ccaagggttt | aactttagaa | gaagttaacg | aaatgtggga | agatggtgtc | 900 |
| ttaccatgga | aatctacatc | ttgggttcca | gctgccaaga | gaggtgccga | ctacgatgcc | 960 |
| gatgctgcta | aggtcgataa | caagccaatg | tacaagaaat | tcttctaaac | aggagtactt | 1020 |
| taatgaaaca | ttgttagatt | ctttaaattc | ataccacatg | caatatctct | ttcctatttt | 1080 |
| atccatcttt | tttttatttc | cagtttagct | gttttttcaa | ttcatgactt | tttggtattg | 1140 |
| taagaattct | tcaaagaact | aacaattaaa | tatctaataa | cactttgtct | tttcataatc | 1200 |
| attcgaattt | taatttactt | tttaacctaa | cttaatctat | atatacacaa | tacaaaattt | 1260 |
| attttatcat | aaaacacgaac | atagttatat | agtattatct | actggaaaca | aaacaagtct | 1320 |
| cttagtctga | cgaagattcc | tcctggaggt | aactagaggg | ctttctgtat | tacactaaca | 1380 |
| caatctattt | ctgagttttc | aacgtgttta | accaactgta | gacaatcctg | atgtattgtt | 1440 |
| tgtcaaatat | taatattaat | ccaataggta | atttcgggaa | aacaaattta | gttattcccg | 1500 |
| acgtattgtt | tgttaattac | aatagtagta | taatagacaa | tctcgggaaa | ataaccttag | 1560 |
| ataattttga | cttattgctt | gtttaaataa | tacaataggt | cgtatcctgg | aaaacatcta | 1620 |
| ctttaagtta | ttccgcacgt | tatcgtgaca | ttaagataag | cggatagatc | atttctatcc | 1680 |
| tcctgattcc | attaacggtt | tgatcaagcc | actttgataa | ttcccttttcc | agattttgtt | 1740 |
| aaaatgagtg | ttttgtaaa | gtatttttat | taattatgtg | ctatatatat | ttgcacttta | 1800 |
| tataagatat | atattaaatt | taaaggattt | aggtcataaa | aacgtaaaat | aaggaaaaaa | 1860 |
| aggtaaagag | agctcattga | aggcattaaa | taaaaagtag | gatgattctg | cctatcttgt | 1920 |
| tatttgtttt | gaatctattc | tagaataccc | tttggaccag | tactaccgta | tgggtaaatt | 1980 |
| tctggttctg | gagcatttgg | accttcgacg | tagtttagta | atggagtaaa | gatatcccaa | 2040 |
| ctgacatcta | attcatcatc | tctgacataa | ttagctctgt | tacctaggaa | agcatctcta | 2100 |
| attaatcttt | cgtaagcttc | tggaacccag | tccttagcgt | acttcttgga | gtaagtcata | 2160 |
| tctaaagaga | cttgatgaac | gttatcaacg | aaacctggag | cagtagtgtt | gaaagtcatg | 2220 |

```
tagatcttac gttctggatg gaattgaatg acgaattcat ttggagtaca accagcaaac    2280
ataccactta ctttcttctt gtatttcatt ctaatttcaa ctctatcttc atctaaaccc    2340
ttaccagctc tcatgacaat tggaacgcct tcccaacggt cattgtgaat atccatggtg    2400
attt                                                                 2404

<210> SEQ ID NO 51
<211> LENGTH: 6125
<212> TYPE: DNA
<213> ORGANISM: Artificial Sequence
<220> FEATURE:
<223> OTHER INFORMATION: c6180_g1_i1

<400> SEQUENCE: 51
cacagagaca gtattagttc tggtctgagt agtttacact tacctagtta cgttatcttt      60
acagaaagat ggagaacgac gattcaaaat tatctgcgat tggtaccaca gaggcccaaa     120
ataccacact gaaaagtaaa tcagaagctc aaaaagttaa gaaaccaaaa tcaaagagac     180
ataaaccaat aagatcatgt tccttttgca ggaaacgtaa gttgaaatgt gaccaaaaga     240
aaccgatatg ctcgagttgt aaatcaagag aactttcaga atgtatctat gcagagaatt     300
caaatagcgg gaatagccca gctaatagca tatcaaatga ttcaagatct agacaaagta     360
gtaatatgaa aagagattct cctggtagtg ccatgtcagg agttgcagaa tattctacag     420
cccctttgag aaacttattg tcaaccatgc aattcccacc aatggaaatt tgtaataata     480
ataattcacg agattcttct gaaaagcaat caagcccaac tacaagtcac ttctcctttt     540
atgatgatcg tctaacgaca gctgttccaa atattacaca tagtatcgct gctagtaatg     600
ctcaaaatac tacaggaaat acaaaatctg atgtagacga acaaatacca aatccattca     660
gaaattatta ttttatacaa tgcaaggata ccggtagaac catatcatat ggtcctacct     720
cgttacgtac ttttatcatg agaaataact ggggttttaa ggataaatat attcaattat     780
ggaaaaagat taaattagaa agaaataatt ggaagaaaaa atatatgact aacaaaaata     840
atgaacttga cttaattgag cttgatctag gtaactcggt atcgatttta aatgatgtgt     900
tgccatgtct acctgattat gattctataa agagctatat caatgatttt tttgatgaca     960
agaattcaaa cctttatgag tgtaatacat tcttagacaa aaggaaaatc ctctatgatt    1020
tagagtttag tttattcaa aatagagtag gtaatattat ccagctgaaa ccaacagaca    1080
agaaaaatta ttacaagatt gccgttattt taatgatttt agtatttaca aaattcagac    1140
aaaatattcc ggttcaaata ttgagattga tgacatattt gacaggttta gtatccccaa    1200
agactagtta tattgaaaaa tcgcagtttt tattacaaca ggttttttat atatcatatt    1260
ttgcgcaaaa gggtgatgaa acaagtctga taggaataat gtctcagctg actacaagca    1320
caatgacatt aggtttacat ttaaatatta gagagattta taagaatagg gagataatgg    1380
taggaagttg tgaatctatt gaaaatttat ggacctgggt attatatttt gattttgaat    1440
tatcattgag aataggaaaa ccattagata tccccttga ggtattcaat gaaattaatt    1500
tccaagatga taatagtttg gcattatatg gtgatgtaat gaataatgaa ttcggtttaa    1560
acagggatga tacgagacca gagttttgta tgatgccgaa atcattatca tctttactaa    1620
ataatagccc tggtacaacg aaccaaagtg gaccaaaatt tccatcttca acgaaaccca    1680
gaataagaga ttttacaaag gagaaatcct tctttggtaa aatgagaagg ttccttttct    1740
tggtcagacc aatgcttggt gaattttata agaagacggg tacccctaag cttgttgaac    1800
```

```
atgggcaagt tctttta aaa tttttggaag atgaattgaa accaatcaaa tatgctacag    1860
atccggattt gatatctgaa ttaacctttg gtgatctccg tttaacatta acgattttag    1920
atatcataac tattttttac tcggttggtt ttgtactatt gaatcatcga tctctaatat    1980
tgaaaaatat ttcaattcaa actcacctat tgacatttgc aattttcaaa aatttcgtca    2040
accactgttt caaattagat gaaaaatatt tcccagagat gatccatcca tcttataata    2100
atctaacccc ttatttgact gcctgtttag gcatttcatt acacccggta ttgcaatcac    2160
ttggtgtatt ctatgcgttc ttcttttta aggcaacatt atttgaaaac ggtatatttg    2220
tttcatatga tatgaccgag gttgaatggg atatgtcttc attcaatgtt ccaactgaca    2280
aatccatctc attgatcact actttcaata tgtacaagaa gatatttgaa gattggataa    2340
gttatgataa gcaaaataaa agaggcttcc aattaaaaaa tcttattcta agatcatatt    2400
caggattaat cttaattaca ctagaaaaaa cctatagaat cattgtcgaa aaggctctag    2460
agtatagaaa aaagattgaa acctcattaa tgactgaagg tggatctaat aaaagagaaa    2520
ataaaaaggg tgtagaaatg tgtgacgagt accgctactc atctaatcct ccaagattag    2580
aagtggactc agttgatggc tcagttggta gtcccggacc cattggcgca agacaagcat    2640
atcatagtta tttacagtac caagtacaac ttcaagaaca aaatcagata ttgggacttc    2700
gtaaacacat cgaatcatta aaagagaagg atagaaatag attgaatctg acaaagggac    2760
ctatgaggaa tattggcaat ggtctcaaca ttgatccaaa ttataatatg gcaggcgtta    2820
acggttatgc tgcggcagct gactctaatg atgcaaatga tggtcatacg atttcctctg    2880
agaatggtgg accaacaatc atctccagca caggtgaaaa gatatcagct tcagaaacag    2940
aaatggcaca aaaattagtt gatgatttct ggtcaagtta taatactggt tgggaaaagt    3000
tgttaaatga ttcggactca cttttccaaa attttgaaga tgaattaaag aatggtatgg    3060
accatccttt tgatttgcaa taaccgaaaa caaaacagtc catagagttg gtgcctcaca    3120
tatataagat ggattttcct atctgcaagg tgtaccctta tgctctacta cccctttgaa    3180
acaataacat tgtaacttct ttcaaaagtg tgtcattcgg atcatttct catgagacga    3240 ttgtccctta ttgtttgcgt aaagggatt taagggtaca acaggaacat ctcttttata    3300
aatttataga gagcacatta tgtaaataca aaaagtggaa gaagatgctt ctatatatat    3360
ataaataagt agataatttt atgttaaatg ataagtgtct gatgttcttt ggtttttgtt    3420 ccttta aact gtgatgaaac caaactgggc atatctgata gtaatttaat tttgaagatg    3480
tctccacagg ttcaccacaa ggagtacacg ttacaagacc tactagataa gtttcaatac    3540
gtcagagacc ttgattctaa tcctgaaaca aagattatct ctctacttgg gacagttgat    3600
tcacagtccg ctatattgac tgtagagaag acacatttca ttcataatga gaccattaga    3660
aagcagtcta ttcatccccc ttggactaga attaactctt acagaaattc aaactcaaat    3720
aacgaatatc atcctgtaaa gaagcatgat aatgagatta tgatggtatc agatgaggag    3780
ctggggataa gaaagccttc tgctacggag tttttatcttc tgaacggagt tgtcgatttg    3840
aaggaactaa cttcaaatgg gaactattat tgggcgttag cattaatcaa agagaatatt    3900
gatgagaatc ctactgccaa gatcagcttt atatggccag caacgacgt gcatataaga    3960 aggtatgatc aacagaagtt gcaccttgtg aaggaaactc cggatatgta tcaaaggatt    4020
gtcaaaccat tcattactga aatgacttct ggtcacaaat tggattgggt gtacaagatg    4080
ctatacgaaa acacagagga cagcagggtc atatacaagc aatacaatga attacagaag    4140
gatgatgcat tcatcctatt accagacacg agatgggatg gtcagacttt ggaatccctg    4200
```

```
tatcttgtag ctttaatgta tagagacgat ataaaatcta ttagagactt tagacctgaa   4260
catagagatt ggttaatccg gataaataag ttattaaaat cggtcatccc accttgctac   4320
aattatgcgg tgcatgccga tgagttacgc atctttattc attatcagcc gtcatactat   4380
catttgcata tccatgtagt tcatatcaaa catccaggac taagtggagg actccatgat   4440
gggaaagcaa ttcagataga tgacgctatt gagcatctga cattcctagg tgcaaatggt   4500
tggatggatg catgcattac atacactatc ggtgaaaatc atccactatg gttaaagggg   4560
ttaaaagatg aagttcaaaa gcaactaaaa gaggcaaatg ttcaggaacc accaccgata   4620
attaacagtc tgtattccct agagaaaact acacgaattg gggcacgagt ctcattatga   4680
tgactatccc ttatccattt ttacaggctg ttatttgatg ttcttatgta aacgtatatc   4740
tatctctggt acctctcaga atttttttgt tgccatcaga taaggattag aaacggtacc   4800
tttatgggtt catatctata gtctatattc taagtattta taaggatagt tttcatgata   4860
ttatcacatt gttttgattc agccaatgta atcattcagg tacatttaaa ttctggtcta   4920
agtatagatg aatggactga acttcttgtt gattttccg ccaagttcct ctaaagcgag   4980
agcacttctt gaagtatcta tcactaaaaa aaaatatttg aactttaaga cacagttcaa   5040
aagaacaact tgagaagagg aggaaaaggt tcaaggttg accaacaaaa taacaagaag   5100
atatacagat tactaaacaa agtcaaaata tgtcgacaca ggaatttgga atgtcgcacg   5160
ttagatcttc atctgtatca ttattagcgg aagcaacctc cggagctggc tctgcaggaa   5220
tcaattcgat agaggataaa ctaactagaa ttgaaatata taagaaccct accgattatg   5280
aggatacttt ggcaaaattg attgaatcag ttgataagtt ccatccaaat atgaaatatg   5340
cccaagattt gatacaggca gatttttgatt tatttacctc tctggagaca tttgccaaat   5400
atgatgaaat tgataataaa ttgaatttgc tagaagataa gcgtacagct attggtgacc   5460
aaacgaagga tatacttgag attttgaatg aatgtcatga tgatctaaat aatttaccaa   5520
gtttagagca agttgaattc gaaaagaaaa caatattgga acaaagacaa aaagttaact   5580
cgacgatatt gttagattat gccactaaat tatccaaatt tacaaagata ccgcctacat   5640
ttgataaagg tactattgga ccgaataatt ttgtttggcc aggtgatgat gccttaagaa   5700
gaggtatgct agcaatggca tctttgaaca gtgataaatt gaccagaata gcaggagaat   5760
cagatacaaa tgcaaacaca aatcctacgt tagaaaccat ggaaattagc actgaagaga   5820
ataatgaaaa taccagtgat tcagcagatc aaaagcaaga caatactgat gatagaagag   5880
gttcgtttgt atttaatggt aacgataaac cgcatacaag cgaaagaaag gaacagagtg   5940
ataatgaaga catagattta gatctagatt tgttcaatcc tgatgaattt taaaagaaga   6000
aaatatccag gcatttgagg gtatcttgat tctttatttc ttatatatgt gtatatatat   6060
tttataacgt caatttttt tttcataaac cattagaatg ctgtaaacag gggtatcggt   6120
ccctg                                                               6125
```

<210> SEQ ID NO 52
<211> LENGTH: 4808
<212> TYPE: DNA
<213> ORGANISM: Artificial Sequence
<220> FEATURE:
<223> OTHER INFORMATION: c494_g1_i1

<400> SEQUENCE: 52

```
aactgccggc ctgtcaaatc gagtgaaaaa aaaagagatg tataatggaa ataagaagta     60
```

```
aacagtaaca cgcacaccta attgaagata acttgatccg gttaacagga acatttctaa    120
ctttataact agtgaatatc aacgacagtt taaactaaaa aacgacacaa ctctttgaat    180
acccaacatg tctgtgttaa aagcattaag ggggcttcca ttacaccctg atacaattac    240
attaattgaa cgtaacattc tatcaaaccc gaaaacgaaa cctgagtatc aattacaact    300
tcatcaatta ttagaaaggt atgagagtgc taggaaaata acaacaaaaa acaaaaccat    360
cgaacaaata atttacacat catatttcca atggtttaat actgtcccac cttatttgaa    420
agtgtttgag acacgatatg atgatttaca taattattgg cccattgata aggactcaga    480
tcacattcat gatagaaaag taccaatgtt aagagacctt tggttaaaga acgatgaccg    540
cgcagtagat tatacgttgg aatacatgct aaaacaagac tcatgttgcc caacagatat    600
ttttgaacct atatttgggc aatttcaatt tataatgaaa aatccacaaa tacagagacg    660
taagattggt aagacttcta gaattccaat attactgctg ccgttaaatg ttctaggtga    720
agatatcgcc gcgtgtcgat ccaacaactt attgcgaaga caaatcaatg aagtaagaag    780
aatattagtt gttgataatc cgatattaga tgctaatgtg gctgaacaat tgctacaatt    840
atcgaataat tatgcacaggt caatggagag aaaggtgtcc agaaggtatt atcttacatc    900
aaaacttgga tatacttgga tcaaaccaaa tagtaatgag tcaaacgaaa atgacaataa    960
tggtaagcct cagttatcga ccctaactgg tgatgcattc acatcagggt tggagttgcc   1020
tcaatttgca tccttcacgt gaatttctga gtaaaaacgt gaaaatcacg tgccattgtg   1080
ctgttttttca aacttttatc tccgactttt ttattgccca attcccacca tctcggccga   1140
aacaatgcaa ctcccacatt tctccggaga gggtgaaaca agcgcagaga ctgctattat   1200
tcacaaggaa cagcgcgtta tttaacggcg gtggtggcgg tggtggtagt ggtgtgttcc   1260
gcgtgtgcca cagttcttgt cgttgcattt agataagcat aatgaggaag aatcttctta   1320
atgcggcgac agtaaatcca ttaacatttt tcacaatgac acacatgaac cacattatca   1380
ttctgcttag ggggaccagt cctgtttgcc agcttaatac attttgaagc cactactgtc   1440
tgagacaaat aattctagat ttgaaggatt gtcatggaaa taaattttat caagaacgat   1500
tgttagtaat acgaatgaca aatcttaaag gaaactaata tataaagaat gatcaaacga   1560
tttgaaaatc tcaattcgaa tgtatttctt atctttaaat tttacttccc acttgttaat   1620
aataaagcca ttcatacgaa ttacatattc ataatcaaaa aacaaaattg agatcatata   1680
ttatttcact tatctgaact atctctaata tatatttata tattaccgct tttttttttt   1740
tacaaaaaga gactgtcacc acatatttca acataaaagg cttggcaagt atagtttatc   1800
taccttaaag ttttttgttcg atttatctct aattgttcgc tattcatttt aaaagtcaat   1860
ttcaacatga ctaactatcc agaagacaat caacatcaat tcgatgaaat cgaagaaact   1920
ttagaattac cagattacgg tagtaacaac agttttaacg gagatgcaga tttagacgat   1980
ttagaacaag aatataatca atacaaagat gaagaattcg ctaatccatc ctccaataat   2040
aataataata atattcaaaa tactagtaca agtaacgaca caataaaata ttcaaaaaac   2100
tttgacgaat ccaaattaaa tgctaaaatt agtcaaattt cttcttaaa cgattctggt   2160
gtcgaaagta ataataccaa taatattaat attccatcat ttcacgaaca tagtctatct   2220
ctacgtgaat attaccgcca tgatttaaaa gaatatttca gttggaaatc agcaggtaat   2280
tactgtcttt ccatcttccc tgttgttaaa tggttaccac attacaacta tatatggttc   2340
attcaagatt taatcgcagg tatcacaatc ggttgcgttc tagtgccaca atctatgtca   2400
tatgctcaaa ttgctacgtt accaccacaa tatggtttat actcttcgtt catcggtgca   2460
```

```
ttcgtttatt cacttttgc aacatcaaag gatgtctgta ttggtccagt tgccgtcatg    2520
tctctagaga cagctaaggt cgtcgctaga gtcactgaga aattgtctag tgatactgat    2580
attaccgctc caattatcgc tactacacta gcgttcttat gtggtgtaat tgctttaggt    2640
ggtgggttat taagattagg tttccttgtt gaattaattt cattaaatgc tgtttcaggg    2700
tttatgactg gttctgcatt aaatatcatt tgtggtcaag ttccatcatt gatgggttac    2760
agttcaaaat taaacactag acaatctact tacaaagtta tcattgctgc attgaaacat    2820
ttaccagata ccaaattgga tgctgtattt ggtttaatcc cattattcat tttatatact    2880
tggaaatggt ggtgtaacaa catgggtcct aagcttgctg aaagacattt cggtagaact    2940
aaaccaagat taaatttcta tcttcaaaaa ttttatttct acgcacaagc ttgtagaaac    3000
gctatcgtta ttatagtttt cacttgtatt tcatggtcta ttactagagg taagactaaa    3060
gctgaaagaa agatcaaaat attaggtgct gtgccttctg gattgaaaga tgttggtgtc    3120
tttgaattac gtgatgattt aatgtcaaaa attgctcctg aattaccagc ttctgtcatt    3180
gtcttattat tggaacatat ctcgattgct aagtcatttg gtagagttaa tgactataag    3240
attgttccag atcaagaact aattgctatt ggtgttacta atctattggg tactttcttc    3300
atggcttatc ctgctacagg ttcattttca agatctgcat taaaggctaa atgtgatgtc    3360
aagactccat tctctggtgt tattagtggt gcttgtgtgt tattggcatt gtactgttta    3420
acaagtgcct tctttttcat tccatcagct actttatctg ccgttattat tcatgctgtc    3480
tctgatttaa ttgcttctta tcacacaaca tggaatttct ggaaaatgaa tccattagat    3540
tgtttatgtt tcattgttac agttttcata actgtctttt cgtctattga aaatggtatc    3600
tatttcgcca tgtgttggtc agctgcctta ttgattttga aggtaacgtt cccagccggt    3660
aaattcttag gttacattca aatcgctgaa gttgttaatg gtaatattgt caatgatcca    3720
tcaatcactg tatctgagcc ggtctctgaa aatgaggaag atccagaagt caataagaaa    3780
tcttcaacat ttaataaatt taaaggtaaa atgtttcat catctggtaa atctgcttct    3840 acaaagaat tcaacagtga tgaatacaaa aagaatttat atgaaacaat gaatgaaagt    3900
gaaactaatg acagtactgc taaattgaac tactacacca aatgggttcc attcgatcat    3960
gcatatacca aagaattaaa cccggattgt aatattattg ctcctccacc tggcgtcatt    4020
gtttacagat taactgacag ttatacatat ttgaattgtt caagacattt tgacatcatc    4080
tttgatgaag ttaagaaaca aactaagaga ggtaaattaa ttcaacattc gaagaaaacc    4140
gatcgtcctt ggaatgatcc aggtccatgg gaacctccaa cgttccacag agctctaatt    4200
aagaaaggta acaatttttt ctcaagaaat aaatctggta atggtgagga tactactgaa    4260
gtagatatcg atgcaaatgt atctttggat aacaatacaa ttgtggatga acgtccatta    4320
ttaaagatca tttgtcttga tttttcacag gtttcacagg tcgatgcaac tgcattacaa    4380
tcactagttg atctaagaaa agccatcaat aaatatgctg atagacaagt tgaattccat    4440
tttgcaggta ttacatctcc atgggtcaaa agaggtttag aaaatatgaa attcggtaaa    4500
gtcaatgaag aattcagcga tgaatctatt attactggtc atactagtta tcatctagcc    4560
agatctcaag aaaagtcaga tgattcaagt aatcttgatg attcatttga agatttagaa    4620
agtagaaaga cttatcaaat taatgttgct acaggtacta atttaccgtt cttccacata    4680
gatattcctg atttctcaca atggaatatt taaaacgtta atttagtcat acatatgttt    4740
tacatatatc actatataca tattctataa taatatcaat atcaagataa aataatacaa    4800
``` ttacaaag    4808

<210> SEQ ID NO 53
<211> LENGTH: 3437
<212> TYPE: DNA
<213> ORGANISM: Artificial Sequence
<220> FEATURE:
<223> OTHER INFORMATION: c2966_g2_i1

<400> SEQUENCE: 53

```
gtccaatgga gagttccatt aggtttatcc ttcgcatggg ctctacttat gattggtgcc    60
atgttcttcg tcccagaatc tccacgttat ttaatggaag tcggtaagac tgaagaagcc   120
aagagatcta ttgctacttc taacaaggtt tccattgacg atccagctgt caccgctgaa   180
gctgaattga ttgctgccgg tatcgaagcc gaaagagctg caggtagtgc ttcttgggct   240
gatatgttct caagtaacgg taaggttgtt caaagattaa ttatgtgttg tatgctacaa   300
tgtctacaac aattgactgg ttgtaactat ttcttctact acggtaccat tattttccaa   360
gctgtcggtt taaacgattc ttatcaaact gctattgttt tcggtattgt taatttcgcc   420
tctacattcg ttgcattcta cgtcgttgat agattcggtc gtcgtgcttg tctaatgtgg   480
ggtgccgccg ctatggtctg ttgttacgtt gtttacgctt ctgtcggtgt tactagacta   540
tatccaaatg gtaagaacga ggcaacttcg aaaggtgctg gtaattgtat gattgtcttc   600
tcatgtttct tcattttttg ttttgcttgt acttgggctc ctatctgttg gattgttgtc   660
tctgaaactt tcccactgaa gattaagcca aagggtatgg ctttagctaa cggttgtaac   720
tggttatgga atttcttaat ttctttcttc accccattca ttactggtgc tattaacttc   780
tattacggtt acgtcttcat gggctgtatg gttttcgctt acttctacgt cttcttctgt   840
gtcccagaaa ccaagggttt aactttagaa gaagttaacg aaatgtggga agatggtgtc   900
ttaccatgga aatctacatc ttgggttcca gctgccaaga gaggtgctga ctacgatgct   960
gaagctacca aggtcgatga taagccaatg tacaagagaa tgttctctag aaagtaaaca  1020
gatagataat taattatttt ttatccttct gtcttttttac aattttaatg aatagaaata  1080
taaactcaaa cacatatttc aaatagtatt atgattttat gattttttc ccttcttta   1140
caaaaatgat agattgcatg ttttaacaaa aattctttct attgtttcgt tgttttgaca  1200
aaaaaaatcc tttcttttat gatacacgca attttctaac ttaattttaa tatcaacttt  1260
tttaataata ataataattt cttttttaact tataatatcg ttttcttctc aataataatt  1320
atgtaaataa tatatatatt atttgtttcg aacctgctat tatattttaa aaatagatgg  1380
atagcaccgt gccattatca tcacaacttt gaacaataaa accaatatcg aatcttcctg  1440
agttgaataa atccctcatt ttcacatagc aaaaaattat tcaaaattaa tccacataat  1500
actttctttg tctcccccgg attatctcca ttttatgcgt cataccacca aagcaaacag  1560
aactccccgc cataatgcat ccggaaaaaa tgataaattg cttattatct tttcttttttc  1620
tttgcgatgt ctcggaattt ctctttcggg accggattaa ttttcaaatt tcttttttttt  1680
tgagaaccag aatcacggaa caagataatg gcatgtcgat gatcatttaa tcgaaaatct  1740
gttactaaaa accgactgca gtctctccaa caagaatact tgtatctcct aaaatgttct  1800
ggatgattcc aatatcgata tccacacata ttaaacaaat ttatttgtgt ctttctaaat  1860
ctccatatttt gtacagagag ttaaataatg gggttacatg agaatactgt ggggatggac  1920
attatggtac gtattgattc ataaaagttg ctaaattaat cgacttatca ctcagtgatt  1980
ggaaagaatt ctgttttttaa ccgattcact ccttcattaa ggtgcaggtc aatcatcaac  2040
```

```
taatttctgg agaaattaaa ctcaagcacc gagaatttcc aaaatttacc acggttagta    2100
tcgacgattg gttcgttgaa aaggtacagt tcaaacttaa aaaggaaccc ggtgaacacc    2160
tatcatgtag tccggtaatg gtcttctaat gctaggtact gagattgttc tttctagatg    2220
cggtatattg tacatttta cgatatttga tttcaatgtt aatctccttt tattgttact    2280
taaagattac aattgggtct ttaatttcat cacaataccg ccgtcgtcac tcctaggttc    2340
cttactgtgc cccacgacgg tctcaaaatg gggaaactgc aaaatactta ttattaaaat    2400
cttcattcat acgactgcca tctaatttaa attcgcttac attaaattat tctgacaaat    2460
gatgcaacag acgccttcat ccaccccgga ttaatgtttc ctaacttatc tttaaacaaa    2520
aattatgaga tatttaattt taaaatctgg ggtatataaa ggtaagaaat aacgaatcat    2580
attgataatg tcaaattatt attttccaaa tcattttcc ctttaaagtc tctttatatc    2640
agaagttcaa tatactaata aataattaca aatatttatt aacacaaaca aaaagagcat    2700
ttcaaaaatg actgaaacaa attctgttca tgagttggaa aacacaaacg ctttgcctat    2760
taactctgac agtaatacag atactcaatc aaacagtgct tcactaacag attcaaggaa    2820
acaagaattc ggtaatcaag agctagaagg taccgatgga aatcaagaag atttagatat    2880
tccaatcaaa gctgcctctg cttatgtcac catctctatc ttctgtgtta tgatcggttt    2940
cggtggtttc atttcaggtt gggatactgg taccattggt ggtttcttag cccatcctga    3000
ttatttgaaa agatttggtt ccaaacataa ggatggtact tactacttct ctaacgtcag    3060
aactggttta gtcgtctcta tttcaacat tggtggttta atgggttgtt taatccttgg    3120
tggtctagct aacagaatcg gtcgtaagat ggctctagtc gctgtcactg ccatttacat    3180
ggttggtatc gttattcaaa ttgcttccat taacaaatgg taccaatact catcggtag    3240 aattatctca ggtatgggtg tcggttctat ctctatgttt tccccaatgt tactatctga    3300
agttgctcca aagcatttaa gaggtacttt aggttctatt tatcaattaa tgtgtacctt    3360
cggtattttc ttaggtgatt gtactaatta cggtactaaa gcttactcta attctgtcca    3420
atggagagtt ccattag                                                  3437
```

<210> SEQ ID NO 54
<211> LENGTH: 2198
<212> TYPE: DNA
<213> ORGANISM: Artificial Sequence
<220> FEATURE:
<223> OTHER INFORMATION: c849_g1_i1

<400> SEQUENCE: 54

```
gtttatcatc tttctgatat ttagaaagaa ggaataaaaa gaaaatgta acatatgtta      60 aaggttgttt tcttattcca cgatcagaag ttaaaaactt taaatatatt gtacctccct    120
cttactacat catcaactat ggagatacta gaaagtttgt tcacgtaatc attttcttaa    180
gaatctgaac gcgttgttct tttttttct ttttctttct tttggtattg aacgttgcga    240
acaatatact gcagggagta gttagtattc ttttttccat atcttacttt cttccttatt    300
tataactgca gtgctatgct gcattgccag agaaaattac cgaccattca tgtgaggtac    360
cgaatagctt gaaaagtcag aaaccttgaa gaccggatgt caagtatgt tgttcttatt    420 ttttttaaga tttttctttt ttattttaa tctgttgcaa agaattgaag aaactagagg    480
tttccttctt gattatcaca tatttattcc atttaaaatt atgcaatatc ctttggaaaa    540
acccagagta catgtttgtg catatcctt tgtgggtatt tttcacccga aaatatatat    600
```

```
ccttaataat aaagttataa ctataatgtt gcatgcaggt tttattgtta acatgtacat      660
tctattttac aaatagcaat taaatccagc ttgtttacgt gcctcaaaaa caaatacagc      720
aaagaaaaaa aatagtattt gactaatgca gtttctgagt gaaaatgatg aaaaatatca      780
tatatataaa cagaacaaga tcttaaatat ttcaataatg gggatgccgg tttatcgaat      840
agataatctt atccgtagta attaatttta cttatataat atcccgtaaa ctagataaaa      900
gataatttt  ggttaatatt ataagtgaca atcatcatcc gcttacacat tagaaaagtt      960
attccaaaat tcaaactata agaggacaac aaaaacaatt atatgtattt gtcaaacgtt     1020
ttagtagtta tatatctgta atactatttt attcaaaaga aattcgggga aatataatca     1080
cattatgaaa ggtaataaca aaattacaaa agatagaaac acatcaaagg gtcaatcgag     1140
ttacttagag actttgttgt catcggaagt gacgacaagt ttagacacaa caccattttt     1200
ttgtaatatt ttgacaaatt tatatgaaaa tgttcaactt gatggttcaa ctcacaaatc     1260
tggagttgtt tctgatacaa gaacggttct attacatcaa catcaatttg atggtatctg     1320
cgggtctaat gaagatgaag ttcctaatac ggagcaatct ataacaagcg aattaaaaaa     1380
ttctactcca gattctcgag gccgtgagag tatatcttct tggaaccatt ctactttaac     1440
aaattattca ccactttttt tggaaccaag atcatattcg agcatgagtt cacaatcgtc     1500
attatatgaa gaaatacac  aacaagaaat gcattccaaa aatgaaaccc agatcaatgc     1560
aaactccaaa agtgtacaag attatatatc ttcatatatg gacctaacaa cagatactag     1620
aatttatgat tcaatatcac catcgtattc atcattatta gaaatttctg ataatattac     1680
aaattctagt actaaaaaag acagcgctga aaattcatct accaaaagaa atgggagcat     1740
atctaaatca aatttcccaa aaggcgtcat acatgaatgt aatctatgtg gtaaaagatt     1800
ccaaaggccg tctacattgg agactcacat gaacgttcac tcaggtgaaa agccattttc     1860
atgtcccttt ttagattgta aaaaattatt taatgcaaga tcaaatatgc taagacattt     1920
aaagatgcat ttcaagttag gaaaagggaa atatttgtta ccaaatggcg agatatcatc     1980
tgagaaacct acagctaagc aattagtatg ctttactaac cctgcagcta gcaaagttac     2040
atgagaaact gtccacaaat tttcgaagtc ataatgcatt tcatccatga gtttgatata     2100
tgtgcaacat atctagtttg tcacaaaaca tccagtactt atattcatat atatatatat     2160
aacaacacca ataaatatat tctaatttttt attcttca                            2198
```

```
<210> SEQ ID NO 55
<211> LENGTH: 2430
<212> TYPE: DNA
<213> ORGANISM: Artificial Sequence
<220> FEATURE:
<223> OTHER INFORMATION: c2966_g1_i1

<400> SEQUENCE: 55
cccaaatact tatataatat tttctccatt gtcacaagaa ctttcaattt gtattctcat       60
ttagaaatat aacaaaggac acaaattgta taagtattca ttttgacaac aaaagagcta      120
tgctactgga cattttcttt cttttttctt tttgattcaa aagatatcgg cacctaatca      180
ggagacattc atcgtctcct tgttagttca agacaataaa tacttactag ttaccccaga      240
tatatatgtt cattacccca gatataattt acaaccatca tgcatatttc acactagaac      300
ttcatttaac aaatccttga acatacgtaa ggaagtaaaa aaaaaagtta ccccttaaag      360
gacggtccta tcttcttttc ttttaaata  acaaatacgta aaaaggactt cacgtacatg      420
tattaaccccc gcaaaataac attcaataac gattgttcaa ggagttataa cagacaccag      480
```

-continued

```
attacaatat ccattaattg ttcgaagtga cacgagccgg tataaacaaa taaattattt      540
actctgccga attgtcattg accatcctct ggtggtccca gatgctgatg ctgttgttgg      600 cccccctcc atagaacaac taataattag ataccgactt ccccacactc atgcgtcacc       660
cactgattta acggaccgaa gttgaatagg aagaggaag aaattctttc gaccgttcag       720
tggcgtgaca ccgacagcca aaccgttcaa tcaaaaaatg aagccgttaa ttcgattcta      780
ctaacaatcc ccagtacaat cccaccggta gcgtgggggt gagtaatacg gtgtgtctat     840
cagtaacagc ggggcgatct ttttttttt tttcactttt ctttcatcgg tgaatatttc       900
ctgtcctgat gtcccgatta ggacattccg caccgcctgg cccgtacgca atattgttac      960
cgcgtacgca tggtactacg tggcgttgtt acagcgggtg ccccgccccc gcgttgctgc     1020 tttttcggg ggcgagctta atagcttaaa gtttctttt gtgcgaggct gcttaccaaa      1080
tgagggcaga aagaaagaaa agaaatcaaa aaaaaagcaa ccacccacga tcacatgccc    1140
gttctcgagg agtttgttag agaattgact tatggaatac ttcaacaaga atacgaatat    1200
catcaattct atgaaaaatg tatctcacgg tgtctcggtg aaattgttat gtcctgcata    1260
taacagtgtc agcagaaacc gagggaaaca tatcgttact cctactactt cgtcgtaacg    1320
tgtccttgaa agaaattaac aaaaaacaag gaaataattc accgacttga tctttctttc    1380
tctctgttcc tctggtgaaa ttatggagaa ttctttgttt ttgttatgtt ggaagtgaaa    1440
agaaattctt tcatatcaat gcagttcagt tgactagtga aacaagtata ttcaaaattg    1500
taacgtttgc tactttttg atttagttat tttaggaatg tttatttggt ttctggaaac    1560
atataaatac agcaacgata tcaactcaat tttaaaattc aattcaatct tgtctctctc    1620
tttttttaat tcatacttat ttttttttctt taactataa aaaacccatc aataataact    1680
aataacatta tttaataaat atattcaata tgtctgaagc tcaggttgat cctcaaaacg    1740
agcatccaga aactaatgca atgccttctt catctgacaa caactctgtc ttaactgccg    1800
actccaacaa agtcgacaat gacatgaaga tggaaggtga aaactctagt caagatcaaa    1860
tggttgttga tattccaatc aaaccagctt ccgcttacgt caccatttct atcttctgtg    1920
ttatgatcgg tttcggtggt ttcatcgccg gttgggatac tggtaccatt ggtggtttct    1980
tagcccatcc tgattattta aagagatttg gttccaaaca taaggatggt acttactact    2040
tctctaacgt cagaactggt ttagtcgtct ctattttcaa cattggtggt ttaatgggtt    2100
gtttaatcct tggtggtcta gctaacagaa tcggtcgtaa gatggctcta gtcgctgtca    2160
ctgccattta catggttggt atcgttattc aaattgcttc cattaacaaa tggtaccaat    2220
acttcatcgg tagaattatc tcaggtatgg gtgtcggttc tatctctatg ttttctccta    2280
tgttactatc tgaagttgct ccaaaacatt taaggagtac tttaggttcc atgtatcaat    2340
taatgtgtac cttcggtatt ttcttaggtg attgtactaa ttacggtact aaagcttact    2400
ctaattctgt ccaatggaga gttccattag                                       2430
```

<210> SEQ ID NO 56
<211> LENGTH: 2873
<212> TYPE: DNA
<213> ORGANISM: Artificial Sequence
<220> FEATURE:
<223> OTHER INFORMATION: c2749_g1_i1

<400> SEQUENCE: 56

```
tttttttttt tttttttttt tgaatatatt aaatagaata tttcgatgtt attagaattg       60
```

```
ataaaccttt cctcaagata tctttaatgc aataacttct tagtttctga tatctgaaac      120
tactagttac aaaaatgcat atctgaaact actagttaca aaaatgcata tctgttgtta      180
gaaatatttg acttagccac attgcactta gcttatatat gtcacataga aagtatcctt      240
gttttagaag tatttgcatt ttagatacat tgatatagtg attattttga agctaggtca      300
tcactaatag gtgattaatt aatgaaatga ttgtttcggc cgaaactttt ttgtagcctg      360
tcacgtgcac ttcggattta acaaagaaaa aaggatttac tacgtacaat atagtgttgg      420
gagttgcctt tattgaagtt actttgacta aattatattt ttatttctga ctattttccg      480
aagtagctgc tattttcatc cattagaaac aagagcaaca aacaattata gctggtggag      540
gtaatgctat tcctgtctac gtacatccat ttcacagaat tatgcttcaa ttgcgattct      600
tcttaatgaa gaccaagtaa atatcgtgac ttgaatagtt gcacgtttaa gctctacata      660
ccatatagca gtatctttgt tagcttggcg gtgtcatatt atatgcgatg acaatacata      720
cttggcaact gggggatact attaaagatc aaggaggcgt aaaatacatc cctactaata      780
ttattactat tatgttgttt ttgtgataac ctattcagaa gtgattttag ggatgctgct      840
ttgacgctcc gtacagttga aggttaacag tctaagttga catgtggcta tacaatatcc      900
ttgtttaaga gattaattca acgaactctt gatgaaataa tcaatcattc gagatttggt      960
ataaaactgt cggccgaata atttccaacc aaagcctctt cttctccgtc ggagatatct     1020
tctactacgg ccaatttaca gtagaaaaaa aagaaacgg aatcacattt tatatttacg     1080
taggttccag aatatctgtt tccggcacag aaacaactgt acgacagaaa atagcaaaga     1140
tgcctttctc cgagaagaat cctccttcgc ttaaataatt gaaaaattta ttaaggattt     1200
gcttgataca aagccaaggt tctctctgtt ctgttatgtg attgtcttgg aagtataagg     1260
agattcaatg agctttttca aggatgaaaa tgattaatat ataaaggcaa cgaattccta     1320
tgaaatgttt cgatgttatc tagatgtttt cccagttttc ttttttgtttt tcgctaaagg     1380 gtcaacgata aataaatatc acaattataa caaatatggc ttatccagaa aatttctcag     1440
gtatcgcaat cgtagataac aaagattata ctcatccaaa gaaagttgat ttcgaaccaa     1500
aggtctttgg cgatcacgac attgatttaa aggtcgaatg ttgcggtgtc tgtggttcag     1560
atcatcataa ggcctgtggt gcgtggggtg aaaccgttaa acctactgtt ttaggtcacg     1620
aaattattgg taccgttgtt aaattgggcc caaaatgtaa ttccggtcta aaaattggtg     1680
accgtgttgg tgtaggtgct caagcattcg cttatttgga ttgtgaccgt tgtaaatctg     1740
ataacgaaca atattgtaga aagtgtgttt gggccatcga ttcagcatat gccgatggtt     1800
accgtagtaa aggtggtttt ggtaactatg ttagattaca tgaacatttt gctgtcccaa     1860
ttccagaagg tttagattct gctaccattg caccattatt atgtggtggt gtcactgttt     1920
actccccatt attacgtaat ggttgtggcc caggtaagaa agttggtatc atgggtattg     1980
gtggtatcgg tcacatgggt atcttgttag caaaagcaat gggtggtgaa gtatacgcaa     2040
tctccagatc caacgcaaag aaggaagatg cctttaagtt aggtgccgat cattatattg     2100
caaccaagga agaaccagat tggactacta aatatgatga taccttagat ttagtcgtca     2160
tctgttcagg ttcttttaact gatattgatt taaatgtttt accaaagaca atgaaaattg     2220
gcggtaagat tgtttccatt gctattcctg aagcttccga gaaattagac atgagcccat     2280 ttggttttgtt aggtgtctct attgctaact ctaatattgg ttccgttaag gagatcaaac     2340
aattactaca attagctaag gataagaata tcaaaccttg ggttgagcaa gttccaatgg     2400
gcgaagattc cttaggtcaa gtctttgcta gaatggataa aggtgacgtc agatacagat     2460
```

```
ttactatggt cgattatgac aaggtctttt aaaggatgat ttagtatatt cttctgaaaa    2520
aattatcact tttcatatta tatatatata acgttcataa tctactatta ttcaaaaaaa    2580
aatattcttc aataattatt atgagtttat ttacactaaa tacaaaatga aacgtgtata    2640
cagaaattct aaagactttc aagatataat atggccaagt agaattgtgt ccaattactg    2700
gaaactgaaa ttacactgtg tgctatcctt aagtgtataa ttcttcatag taaaaggaaa    2760
taatttcaat atgcaatagt aagtttaata aaccctacac tatatattgt gacttatata    2820
taatatatat aacatttcta ttactatggt tatgtaccta ataactaa aac             2873
```

<210> SEQ ID NO 57
<211> LENGTH: 1837
<212> TYPE: DNA
<213> ORGANISM: Artificial Sequence
<220> FEATURE:
<223> OTHER INFORMATION: c7728_g1_i1

<400> SEQUENCE: 57

```
agagaatata gtgggtatga cttaagtgtt gtgaagcgtg ttacatgact tttacaatgt      60
aagcaggtaa tgttttcaga ttttggatat tatctacaga atttcttgat cattattgca     120
tattatcctg agcaatattg ataatttctt aaatcagctg gtaatccagc actttaatag     180
ttgggataca gggacatagg aagtagaaat ataatgcggt tgtttctacc cctataatta     240
gactgcacgt cagtactctt gtctcttttt gttgagaaac aagtcattaa ccccgaaagt     300
tttagtcaac agatgcggga gccctaagaa actgtcaagt tataaacaga tgatcggtaa     360
cgaagtagaa agggaaatta caatatttaa gaagataaca ttatcttaaa ggttcctttt     420
ttggtttaag ttgtcacttg taaacgagag agctagttgt cctttatat tgactgtaac      480 acttcaaccc ttcagaaaga tgagtaccaa acaaagatg cagaaaagat cagttaataa      540
aaattcgaac aacattgaaa tcaacgatga cgataaaaca ttgaagaagg ttgtaactca     600
taccacatca accaaacgta agctttacac atggcacgaa atacctgatt ggcagaaaga     660
taatgaatat atccatggtg ggtacgtgaa agaaactaat agtttcactg aatgcatcaa     720
tagtttattc tatattcaca atgagactgt caatatttac agtcacttaa ttcctggttt     780
gatctcctta ggactagtta ctattgacaa atactgtgtt cctaaattca atactacagc     840
aataacagat tatcttttca ttgatttatt cttccttggt gcatttgctt gtctgacgat     900
gagtagtaca ttccattgtc ttaagagtca ttctccaggt gttgccaaat ttggtaataa     960
attagattat ttaggcattg ttgtattgat ttcaacttca atggtaagta ttctttatta    1020
cggcttctat gataattctt ttatgtttta tttgttctca ggaattacat tgatgttcgg    1080
tagcgcatgt gctatcgtta gtctagatga gaaatttcgt acgagggaat ggcgtcctta    1140
tagagccgcc atgtttgtta tgtttggact ttcagctttt ctgccaatag gagcaggtct    1200
catttattac ggttcccatg aaacttggac tagagttcaa ttaaaatgga ttattttaga    1260
aggtgtattt tatatatttg gtgcatttct gtacggaggg agacttcctg aaaagtaccg    1320
tcctggtcac tatgatattt ggggtcattc tcatcaaata ttccatgtct tagttgttgt    1380
tgctgcattg tgccacttaa cgggtcttat tgaaagttac agatatgtcc acacatatat    1440
gattccatta atgatgcaag catgaatttc tattcttcaa agacagtttc catattttg     1500 tatttctgt ctgtaattgc taatgggaca ctactatata ttaccataat gttagcgtat    1560
ctagcgtatt atttataact tatagaacta gttattgatt tatacgataa acaatatatc    1620
```

| | |
|---|---|
| tattaatatt actgaaatac tatttgtgta tcttctaagt acaatcattt agcatttttg | 1680 |
| gtgccctaaa atttgtaact ttggtattct caccctacat ggagttaatc cgttgatcaa | 1740 |
| atcagctata gatgtcttaa tgaataagtt aatcacaaat acatttaata acaaattgat | 1800 |
| ttcaatcagg gttaaaatta aaaaaaaaaa aaaaaa | 1837 |

<210> SEQ ID NO 58
<211> LENGTH: 996
<212> TYPE: DNA
<213> ORGANISM: Bos taurus

<400> SEQUENCE: 58

| | |
|---|---|
| atggctactt tgaaagatca attgattcaa aatttgttga agaagaaca tgttccacaa | 60 |
| aataaaatta ctattgttgg tgttggtgct gttggtatgg cttgtgctat ttctatttg | 120 |
| atgaaagatt tggctgatga agttgctttg gttgatgtta tggaagataa attgaaaggt | 180 |
| gaaatgatgg atttgcaaca tggttctttg tttttgagaa ctccaaaaat tgtttctggt | 240 |
| aaagattata atgttactgc taattctaga ttggttatta ttactgctgg tgctagacaa | 300 |
| caagaaggtg aatctagatt gaatttggtt caaagaaatg ttaatatttt taaatttatt | 360 |
| attccaaata ttgttaaata ttctccaaat tgtaaattgt tggttgtttc taatccagtt | 420 |
| gatatttga cttatgttgc ttggaaaatt tctggttttc caaaaaatag agttattggt | 480 |
| tctggttgta atttggattc tgctagattt agatatttga tgggtgaaag attgggtgtt | 540 |
| catccattgt cttgtcatgg ttggattttg ggtgaacatg gtgattcttc tgttccagtt | 600 |
| tggtctggtg ttaatgttgc tggtgtttct ttgaaaaatt tgcatccaga attgggtact | 660 |
| gatgctgata agaacaatg gaaagctgtt cataaacaag ttgttgattc tgcttatgaa | 720 |
| gttattaaat tgaaaggtta tacttcttgg gctattggtt tgtctgttgc tgatttggct | 780 |
| gaatctatta tgaaaaattt gagaagagtt catccaattt ctactatgat taaaggtttg | 840 |
| tatggtatta agaagatgt ttttttgtct gttccatgta ttttgggtca aaatggtatt | 900 |
| tctgatgttg ttaaagttac tttgactcat gaagaagaag cttgtttgaa aaaatctgct | 960 |
| gatactttgt ggggtattca aaagaattg caattt | 996 |

<210> SEQ ID NO 59
<211> LENGTH: 2850
<212> TYPE: DNA
<213> ORGANISM: Artificial Sequence
<220> FEATURE:
<223> OTHER INFORMATION: g3002-1 allele 1 5UTR

<400> SEQUENCE: 59

| | |
|---|---|
| tcaaaaaaaa ttctttggaa gaagaaggat cattgcaata ataatgaaat aaaaagttca | 60 |
| acagttgtag tttgtacttg agctattgga caatcattac cactttcata aaaagtcacc | 120 |
| aaattaaaga gttaacaaaa atcgtgaacg aactggatta agtttctaaa ttacgttgaa | 180 |
| gatagattta ccgaaatgaa aattatgtca tctttctcta caaatttcgg atgtaattac | 240 |
| agttttactt tgattaagaa caaaatatac atgttagggt tggtaatcac tttaatgggt | 300 |
| ctttgattgt tatctattag ataatacagt aattaatttt caggccacac ttttatcat | 360 |
| cagcatacca agaaaactca agagatatgt gacctgttgc atgaggaaga tttcggatat | 420 |
| gagcacgcaa ttcatttaat gagatgtatg tattaagaag gtaaaattca atagagaatg | 480 |
| cagtttatac ttttagaagg ggtcaccaat tcaaccccaa attaaatgat ttagaaattc | 540 |
| aatattattt cactagaaca attcaagcaa tgagtttctt ttatttctag attctattta | 600 |

```
ttctttcctt tcattaataa ataacaaata aatgctttta ctgttcaaaa aatatgtttc    660
cattacagtg atatattgaa ttagaaatat gacctatgct aattgaggtt tacttaattc    720
aaacatgaat aattcaaatt aagggagtac agttgatgaa aggaatattc tcagtttaga    780
attgttatta acaatatata gttaatagct gcacacccct tttctttatg catatatatt    840
ttcaataaaa gtaattacat aaccacccct taatgagttt ctcgaaattg ttataattta    900
aatttatttg tatataaaag agacgaaccg aattatagta gaaaaactg aaagttgttc     960 aaaaagtgtc cctgctaaaa aattagcata caaatttgta aattcaaatg gataaataac   1020
aaataaatcg atgtaccgat agaatgcaca tgagtgacat gtctcagtat tttagaatag   1080
aagatagttg attaactaaa taaaggggat aataattttt ttaccatttc acatcagaaa   1140
aataggaaaa aatgataata ttccttgatt tgattttctc cgagaatcga attatgaccc   1200
cactataata tagtgacagc ttcgacatga cttccgaaaa agaaaatatt tcgtaaattc   1260
cctgtatagt gagtgaatct aaagcaacca actagcaaaa ccaacgtcaa gaataccat    1320 gaaaagttta agaatacaag acctgctcca acccttttt cgtttgtttg ttcagccgtt    1380
cggtacaatt tacgagtttt cataaattat gcaaattaac agtttaccca tcgtgtcttt   1440
gtataactct cactcatcct tcggactctt accgctgctc taattacgta gtaatggatc   1500
aatttctatt gacctttatt taattagaat gattttgtga cgttttttt tcttagctta    1560 aaaaatacta cgtgcatttt gctaagagcg acggtagaaa cttcaccata gaaaaatatc   1620
tattttagct gtaagaaggg tatttcttct catggttgac aagaaagtaa ttgactggct   1680
ctgtgaaacg ccggttaaga gtatttggtg agccctccag ttatattctt tcaacgtgca   1740
tcagacggtt catacaaaca tggccaaaga aatcgtgtag tagtagcatt catttatctg   1800
tgccttgggc ttcttctttg atgaaataat ggaaaaaaaa gaaatgtgcg cttgctgtgc   1860
ctgacttctt agcttccacg aaaaaatacc cagcgtccac aattaatttc tttttttat    1920 ttatttatct ggagaacatc tgagtaaaaa aaaaagcggg aagagccaga aatatcgtat   1980
ctctttgaac aggaaattca taaattatgc atttattcat tttctcaaag atttaataaa   2040
aaaacaaaca aacttgaact atgtatattc ttcgcgctgt tttagttccg catatatccc   2100
actcacatta tttttttttt ctctcgtcgc ttcatccaaa ttcgctctgt gtattttatt   2160
atctctttcg gttatttcaa ttttttgcat aatttattca aaactcttaa atttcgaaaa   2220
aatttccacc cataaaaatt attttaattg atccagtaaa attgttgcac agatcgtaaa   2280
tgaaaaatta ttcacatcga tatcgtcttt gttgtaattt tgaatcgtta acaagaaatt   2340
tgttacttga cagcaggata tcagttgttt gttagagaaa ttataagcaa aaaaaaattc   2400
tcaaatttca cgaaagtcaa acagagttag atcaaattta ataatcatca acaggaaaac   2460
aactattttc tgcggataat ttacagtatt cacaatttgc tctcaaagga gtttgtggg    2520 caaatatttc tctttgtgat tgtttaaggg cagaaaaaag taagttgata gaataaaaat   2580
attaacaatt gatgatgttg atgtttgttt gatgtcagtt tggttgtttt actgcataaa   2640
gattgagagg actaagatca tcaaaatgag aaaattttt cttttcagt ttacgtatct    2700 gaattaatct tttttttta atatataagg aacagattgt tttcctattt gaatgaatt     2760 ctccgtttgt aaattttctc tgttaattgt ttttctctat ttcttgtcaa ttctaagata   2820
accatcctat tcaattatac acatccaatc                                    2850
```

<210> SEQ ID NO 60

<211> LENGTH: 2850
<212> TYPE: DNA
<213> ORGANISM: Artificial Sequence
<220> FEATURE:
<223> OTHER INFORMATION: g3002-1 allele 2 5UTR

<400> SEQUENCE: 60

| | | | | | |
|---|---|---|---|---|---|
| tcaaaaaaaa | ttctttggaa | gaagaagaat | cattacaata | ataataaaat | aaaaagttta | 60 |
| acagttgtgg | tttgtacttg | agctattgga | caatcattgc | cactttcata | aaaagtcacc | 120 |
| aaattaaaga | gttaacaaaa | atcatgaacg | aagtggataa | agtttctaaa | ttacgttgaa | 180 |
| gataaattta | ccgacattga | aattatgtca | tctttctctt | caaatttcgg | atgtaattac | 240 |
| agttttactt | tgattaagaa | caaaatatac | atgttagggt | tggtaatcac | tttaatgggt | 300 |
| ctttgattgt | tatctaatag | ataatacagt | aattaatttt | caggccacac | ttttatcat | 360 |
| cagcatacca | agaatactca | agagatatgt | gacctgttgc | atgagaaaga | ttttggatat | 420 |
| gaacatgcaa | ttcatttaat | gagttgtatg | tattaagaag | ttaaaattca | atagagaata | 480 |
| cagtttatac | ttttagaagg | ggtcaccaat | tcaaccccac | attaaatgat | ttagaaattc | 540 |
| aatattattt | cactagaaca | attgaagcaa | tgagtttctt | ttatttctag | attttattta | 600 |
| ttctttcctt | tcattaataa | ataacaaata | aatgcttta | ctgttcaaaa | actatgtttc | 660 |
| cattacagtg | atatattgaa | ttagaaatat | gacctatgct | aattgaggtt | tacttagttc | 720 |
| aaacatgaat | aattcaaatt | aagggagtac | agttgatgaa | aggaatattc | tcagtttaga | 780 |
| attgttatta | atgaaatatc | gttattagtt | gcacacccct | tttctttatg | catatatatt | 840 |
| tccaataaat | gtaattacat | aaccatccct | taatgagttt | ctcaaaatgc | ttatgatcta | 900 |
| aatttatttg | tatataaaag | agacgaaacg | aattatagta | gaaaaaactg | aaagttattc | 960 |
| aaaaatcgtc | cctgctaaaa | attcagcata | caaatttgta | aattcaaaag | gatatatcac | 1020 |
| aaataaatcg | atgtaccaat | agaatacata | tgggtggcat | ttctcagtat | tcgagaatag | 1080 |
| aagataattg | attatttaaa | taagggggat | aattattttt | ttaccatttt | acaacagaaa | 1140 |
| aataggaaaa | aatgataata | ttccttaatt | tgatttttct | cgagaatcga | attatgaccc | 1200 |
| cactataata | tagtgacaac | ttcgacatga | cttccgaaaa | agaaaatatt | tcataaattc | 1260 |
| cctgtatagt | gagtgaatct | atagcaccca | actagcaaaa | ccaacgtcaa | gaaataccat | 1320 |
| gaaaagttta | agaatacagg | atctgctcca | tcctttttt | cgtttgtttg | ttcagccgtt | 1380 |
| cggtacaatt | tacgagtttt | cataaattat | gcaaattaac | agtttaccta | tcgtgtctt | 1440 |
| gtataactct | cactcatcct | tcggactctt | accgccgctt | taattacgta | gtaatggatc | 1500 |
| aatttctatt | gacctttatt | taattagaat | gattttgtga | cgttttttt | tcttagctta | 1560 |
| aaaaattcta | cgtgcatttt | gctaagagcg | acggtagaaa | cttccaccata | gaaaatatc | 1620 |
| tattttagct | gtaagaaggg | tatttcttct | catggttgac | aagaaagtaa | ttgactggtt | 1680 |
| ctgtgaaacg | ccggttaaga | gtatttggtg | agccttccag | ttatattctt | tcaaaatgca | 1740 |
| tcagacggtt | cataccaata | tggccaaaga | aatcgtgtag | tagtagcatt | catttatctg | 1800 |
| tgccttgggc | ttcttctttg | atgaaataat | ggaaaaaaaa | gaaatgtgcg | cttgttgtgc | 1860 |
| ctgacttctt | agcttccacg | aagaaatacc | cagcgtccac | aattaatttc | ttttttttat | 1920 |
| ttatttatct | ggagaacatc | tgagcaaaaa | aaaaagcaag | aagagccaga | aatatcgtat | 1980 |
| ctctttgaac | aggaaattca | taaattatgc | atttattcat | tttctcaaag | attcaataaa | 2040 |
| aaaacaaaca | aacttgaact | atgtatattg | ttcgcgctgt | tttagttccg | catatatccc | 2100 |
| actcacatta | tttttttttt | ctctcgtcgc | ttcatccaaa | ttcgctctgt | gtattttatt | 2160 |

```
atcactttcg gttatttcaa ttttttgcat aatttattca tttctgttaa atttcgaaaa   2220
aatatccacc cacaaaaatt attttaactg atccagtaaa attgttgcac agatcgtaaa   2280
tgaaaaatta ttcacatcaa tatcgtcttt gttatatttt tgaatcgtta acaagaaatt   2340
tgttacttga cagcaggata tcagttgttt gttagagaaa ttataagcaa aaaaaaattc   2400
tcaaatttca cgaaagtcaa acagagctag atcaaattta ataataatca acaggaaaac   2460
aattaatttc tgcggataat ttacagtatt cacaatttgc tctcaaagga aatttgtggg   2520
caaatatttc tctttgtgat tgtttaaggg cagaaaagag taagttgata gaataaaaat   2580
attaacaatt gatgatgttg atgtttgttt gatgtcagtt tggttgtttt actgcataaa   2640
gattgagagg actaagatca tcaaaatgag aaaattttt cttttcagt ttaaatatct    2700 gaattaatct ttttttttta atatataagg aacagattgt tttcctattt gaatgaatt    2760 ctccgtttgt aaatttttc tgttaattgt ttttcttat ttcttctcaa ttctaaaata    2820
accatcccat tcaattatac acatccaatc                                   2850
```

<210> SEQ ID NO 61
<211> LENGTH: 922
<212> TYPE: DNA
<213> ORGANISM: Artificial Sequence
<220> FEATURE:
<223> OTHER INFORMATION: g3002-1 allele 1 3UTR

<400> SEQUENCE: 61

```
taaaaaagct gaaaaagatc ttttaattaa tatttttac gttccatttt ttcatcatac    60
atatcataca tacatcatca ctttataaaa tttaatgaaa tagaatattt attcttttaa   120
tatttatttt tcggctatat taattaaatg ttatgcattt tgttacgtat ttattttatt   180
tacatggtat ttatttaatt gagagcattt gccttatttg ccaaatttaa agaatcatcg   240
atcgaatcat taccatacct cctttctaag attctggtcg cgattgttg aattgcccat    300 acttcttcct catccaattc caatggtttc ttttcatcgt tgataatttg cagctcctta   360
acgcgattaa gtaatttagc ttttaaacga agaagcagcc ttcttcttaa gaaattttca   420
tctctcttaa cagatgctcc acttacatct tctggtactt taagttcttc ggagatactg   480
tttaataatc tcacagcttc caactgtata tatatctcag aggtgtaatc atgcgcagta   540
atagtggaag catcgaattc tcctgcacat aaacttttca aaaattgatc caatacacgt   600
tctttcaatt ccaaagtgaa tccagtcttc ctattaaaat tatgaaccaa ttggaacata   660
tacagccatg atttgcgtga atatacttga catcccaatt gtttagaata tttaccgtcg   720
tattccaata cgaaattttg gcatgttttcc aatagttccg aagttttat aggatctgca   780 ttccatctgg ccttagtggc tgctttaata aaaccttgat acattaatcc aatcgtatat   840
acggagacaa atttcttgcc attatcttta gcctcttgga gtgccattgt ttgcttgtct   900
aaataatctg acgtacgtga ct                                           922
```

<210> SEQ ID NO 62
<211> LENGTH: 922
<212> TYPE: DNA
<213> ORGANISM: Artificial Sequence
<220> FEATURE:
<223> OTHER INFORMATION: g3002-1 allele 2 3UTR

<400> SEQUENCE: 62

```
taagaaagct gagaaaaatc ttttaattaa tatttttac gttccatttt ttcatcatac    60
```

-continued

| | |
|---|---|
| atatcataca tacatcatca ctttataaaa tttaatgaaa tagaatattt attcttttaa | 120 |
| tatttatttt tcggctatat taattaaatg ttaagcattt tgttacgtat ttattatatt | 180 |
| tacatggtat ttattcaatt gagagccttt gccttattat ccaaatttaa agaatcatcg | 240 |
| ctcaaatcat taccgtacct cctttctaag attctggtcg cgatttgttg aattgcccat | 300 |
| gcttcttcct catccaattc aaatggcttc ttttcatcgt tgataagttg caactccttc | 360 |
| acacggttaa gtaatttagc ttttaaacgg agaagtagtc ttcttcttaa gaaattttca | 420 |
| tctcttttaa gagatgctcc acctacatct tctggtactt taagttcttc cgagatactg | 480 |
| tttaataatc tcacagcttc caactgtata tatatctcag aggtataatc atgcgcagta | 540 |
| atagtggaag catcgaattc tcctgcacat aaacttttca aaaattgatc caatacacgt | 600 |
| tctttcaatt ccaaagtgaa tccagtcttc ctattaaaat tatgaaccaa ttggaacata | 660 |
| tacagccatg atttgcgtga atatacttga catcccaatt gtttagaata tttaccgtcg | 720 |
| tattccaata cgaaattttg gcatgttttcc aatagttccg aagttttttat aggatctgca | 780 |
| ttccatctgg ccttagtggc tgctttaata aaaccttgat acattaatcc aatcgtatat | 840 |
| acggagacaa atttcttgcc attatcttta gcctcttgga gtgccattgt ttgcttgtct | 900 |
| aaataatctg acgtacgtga ct | 922 |

<210> SEQ ID NO 63
<211> LENGTH: 19
<212> TYPE: DNA
<213> ORGANISM: Artificial Sequence
<220> FEATURE:
<223> OTHER INFORMATION: primer

<400> SEQUENCE: 63
gcaggatatc agttgtttg                                              19

<210> SEQ ID NO 64
<211> LENGTH: 18
<212> TYPE: DNA
<213> ORGANISM: Artificial Sequence
<220> FEATURE:
<223> OTHER INFORMATION: primer

<400> SEQUENCE: 64
atagagaagc tggaacag                                               18

<210> SEQ ID NO 65
<211> LENGTH: 19
<212> TYPE: DNA
<213> ORGANISM: Artificial Sequence
<220> FEATURE:
<223> OTHER INFORMATION: primer

<400> SEQUENCE: 65
gcaggatatc agttgtttg                                              19

<210> SEQ ID NO 66
<211> LENGTH: 19
<212> TYPE: DNA
<213> ORGANISM: Artificial Sequence
<220> FEATURE:
<223> OTHER INFORMATION: primer

<400> SEQUENCE: 66
cagaatctta gaaaggagg                                              19

```
<210> SEQ ID NO 67
<211> LENGTH: 19
<212> TYPE: DNA
<213> ORGANISM: Artificial Sequence
<220> FEATURE:
<223> OTHER INFORMATION: primer

<400> SEQUENCE: 67
gcaggatatc agttgtttg                                                   19

<210> SEQ ID NO 68
<211> LENGTH: 20
<212> TYPE: DNA
<213> ORGANISM: Artificial Sequence
<220> FEATURE:
<223> OTHER INFORMATION: primer

<400> SEQUENCE: 68
aataccttgt tgagccatag                                                  20

<210> SEQ ID NO 69
<211> LENGTH: 18
<212> TYPE: DNA
<213> ORGANISM: Artificial Sequence
<220> FEATURE:
<223> OTHER INFORMATION: primer

<400> SEQUENCE: 69
accttcttgt tgtctagc                                                    18

<210> SEQ ID NO 70
<211> LENGTH: 18
<212> TYPE: DNA
<213> ORGANISM: Artificial Sequence
<220> FEATURE:
<223> OTHER INFORMATION: primer

<400> SEQUENCE: 70
ataactcttt cagctggc                                                    18

<210> SEQ ID NO 71
<211> LENGTH: 19
<212> TYPE: DNA
<213> ORGANISM: Artificial Sequence
<220> FEATURE:
<223> OTHER INFORMATION: primer

<400> SEQUENCE: 71
gcaggatatc agttgtttg                                                   19

<210> SEQ ID NO 72
<211> LENGTH: 19
<212> TYPE: DNA
<213> ORGANISM: Artificial Sequence
<220> FEATURE:
<223> OTHER INFORMATION: primer

<400> SEQUENCE: 72
tttcaaacca gtaccacca                                                   19

<210> SEQ ID NO 73
<211> LENGTH: 19
<212> TYPE: DNA
<213> ORGANISM: Artificial Sequence
<220> FEATURE:
<223> OTHER INFORMATION: primer
```

```
<400> SEQUENCE: 73
gcaggatatc agttgtttg                                              19

<210> SEQ ID NO 74
<211> LENGTH: 20
<212> TYPE: DNA
<213> ORGANISM: Artificial Sequence
<220> FEATURE:
<223> OTHER INFORMATION: primer

<400> SEQUENCE: 74
gaagaagaat acaaagcacc                                             20

<210> SEQ ID NO 75
<211> LENGTH: 19
<212> TYPE: DNA
<213> ORGANISM: Artificial Sequence
<220> FEATURE:
<223> OTHER INFORMATION: primer

<400> SEQUENCE: 75
gcaggatatc agttgtttg                                              19

<210> SEQ ID NO 76
<211> LENGTH: 19
<212> TYPE: DNA
<213> ORGANISM: Artificial Sequence
<220> FEATURE:
<223> OTHER INFORMATION: primer

<400> SEQUENCE: 76
caccagcttt aacagtaac                                              19
```